(12) United States Patent
Eckert et al.

(10) Patent No.: US 7,960,504 B2
(45) Date of Patent: *Jun. 14, 2011

(54) INHIBITORS OF HIV MEMBRANE FUSION

(75) Inventors: Debra M. Eckert, Cambridge, MA (US); David C. Chan, Arcadia, CA (US); Vladimir Malashkevich, Belmont, MA (US); Peter A. Carr, Somerville, MA (US); Peter S. Kim, Lexington, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 1284 days.

This patent is subject to a terminal disclaimer.

(21) Appl. No.: 10/987,687

(22) Filed: Nov. 12, 2004

(65) Prior Publication Data

US 2005/0221294 A1 Oct. 6, 2005

Related U.S. Application Data

(63) Continuation of application No. 09/746,742, filed on Dec. 21, 2000, now Pat. No. 6,841,657, which is a continuation of application No. PCT/US99/17351, filed on Jul. 30, 1999.

(60) Provisional application No. 60/094,676, filed on Jul. 30, 1998, provisional application No. 60/100,265, filed on Sep. 14, 1998, provisional application No. 60/101,058, filed on Sep. 18, 1998, provisional application No. 60/132,295, filed on May 3, 1999.

(51) Int. Cl.
 *C07K 14/15* (2006.01)
(52) U.S. Cl. ...... 530/300; 530/324; 530/350; 424/185.1
(58) Field of Classification Search .................. 530/300, 530/324, 350; 424/185.1
 See application file for complete search history.

(56) References Cited

U.S. PATENT DOCUMENTS

| | | | |
|---|---|---|---|
| 5,444,044 A | 8/1995 | Jiang et al. |
| 5,464,933 A | 11/1995 | Bolognesi et al. |
| 5,656,480 A | 8/1997 | Wild et al. |
| 5,780,221 A | 7/1998 | Schumacher et al. |
| 5,840,843 A | 11/1998 | Jiang et al. |
| 6,150,088 A | 11/2000 | Chan et al. |
| 6,506,554 B1 | 1/2003 | Chan et al. |
| 6,747,126 B1 | 6/2004 | Eckert et al. |
| 6,818,740 B1 | 11/2004 | Eckert et al. |
| 6,841,657 B2 | 1/2005 | Eckert et al. |
| 7,053,179 B2 | 5/2006 | Root et al. |
| 7,226,598 B2 | 6/2007 | Eckert et al. |
| 7,402,396 B2 | 7/2008 | Chan et al. |
| 7,504,224 B2 | 3/2009 | Root et al. |
| 2001/0047080 A1 | 11/2001 | Root et al. |
| 2002/0077284 A1 | 6/2002 | Eckert et al. |
| 2003/0082525 A1 | 5/2003 | Root et al. |
| 2003/0099935 A1 | 5/2003 | Chan et al. |
| 2004/0044183 A1 | 3/2004 | Eckert et al. |
| 2004/0213801 A1 | 10/2004 | Wild et al. |
| 2005/0053917 A1 | 3/2005 | Chan et al. |
| 2006/0014139 A1 | 1/2006 | Root et al. |
| 2008/0269462 A1 | 10/2008 | Eckert et al. |

FOREIGN PATENT DOCUMENTS

| | | |
|---|---|---|
| WO | WO 94/02505 | 2/1994 |
| WO | WO 96/40191 | 12/1996 |
| WO | WO 98/32848 A | 7/1998 |
| WO | WO 00/06599 | 2/2000 |
| WO | WO 0040616 | 7/2000 |
| WO | WO 01/03723 A1 | 1/2001 |
| WO | WO 01/44286 A2 | 6/2001 |
| WO | WO 02/24735 A2 | 3/2002 |
| WO | WO 02/24735 A3 | 3/2002 |

OTHER PUBLICATIONS

Rabenstein M (Biochemistry 34(41), 13390-97, 1995).*
Suzuki, K., et al., "An Isoleucine Zipper Peptide Forms a Native-like Triple Stranded Coiled Coil in Solution," *Protein Engineering* 11(11):1051-1055 (1998).
Preliminary Amendment, U.S. Appl. No. 11/976,764, filed Mar. 11, 2009.
Office Action, dated Apr. 3, 2009.
Reply filed Jun. 30, 2009, U.S. Appl. No. 11/976,764.
Office Action dated Nov. 5, 2009, U.S. Appl. No. 11/976,764.
Office Action (RR), dated Sep. 24, 2002, U.S. Appl. No. 09/746,742.
Reply to RR filed Mar. 23, 2003, U.S. Appl. No. 09/746,742.
Supplemental RR, dated Jun. 6, 2003, U.S. Appl. No. 09/746,742.
Reply to Supplemental RR filed Aug. 29, 2003, U.S. Appl. No. 09/746,742.
Office Action, Bonafide Attempt Letter dated Nov. 17, 2003, U.S. Appl. No. 09/746,742.
Reply filed Dec. 11, 2003, U.S. Appl. No. 09/746,742.
Office Action dated Mar. 10, 2000, U.S. Appl. No. 09/746,742.
Reply filed Jul. 12, 2004, U.S. Appl. No. 09/746,742.
Notice of Allowance, dated Aug. 24, 2004, U.S. Appl. No. 09/746,742.
Office Action (RR), U.S. Appl. No. 09/668,072 dated Aug. 21, 2002.
Reply filed Dec. 19, 2002, U.S. Appl. No. 09/668,072.
Office Action dated Mar. 19, 2003, U.S. Appl. No. 09/668,072.
Reply filed Sep. 19, 2003, U.S. Appl. No. 09/668,072. Notice of Allowance dated Dec. 2, 2003, U.S. Appl. No. 09/668,072.
Office Action, U.S. Appl. No. 10/395,817 dated Jun. 30, 2006.
Reply filed Sep. 29, 2006, U.S. Appl. No. 10/395,817.
Notice of Allowance dated Jan. 12, 2007, U.S. Appl. No. 10/395,817.
Notice to File Corrected Application Papers dated Feb. 13, 2007, U.S. Appl. No. 10/395,817.
Replacement Drawings filed Mar. 15, 2007, U.S. Appl. No. 10/395,817.
Communication from Examiner dated Apr. 16, 2007, U.S. Appl. No. 10/395,817.
Office Action (RR), U.S. Appl. No. 09/364,497 dated May 17, 2001.
Reply to RR filed Jun. 18, 2001, U.S. Appl. No. 09/364,497.
Office Action dated Sep. 11, 2001, U.S. Appl. No. 09/364,497.
Reply filed Feb. 11, 2002, U.S. Appl. No. 09/364,497.
Office Action (2nd RR) dated May 22, 2002, U.S. Appl. No. 09/364,497.

(Continued)

*Primary Examiner* — David Lukton
(74) *Attorney, Agent, or Firm* — Hamilton, Brook, Smith & Reynolds, P.C.

(57) ABSTRACT

Inhibitors of HIV membrane fusion and a method of identifying drugs or agents which inhibit binding of the N-helix coiled-coil and the C helix of HIV gp41 envelope protein.

12 Claims, 45 Drawing Sheets

OTHER PUBLICATIONS

Figure 5A:
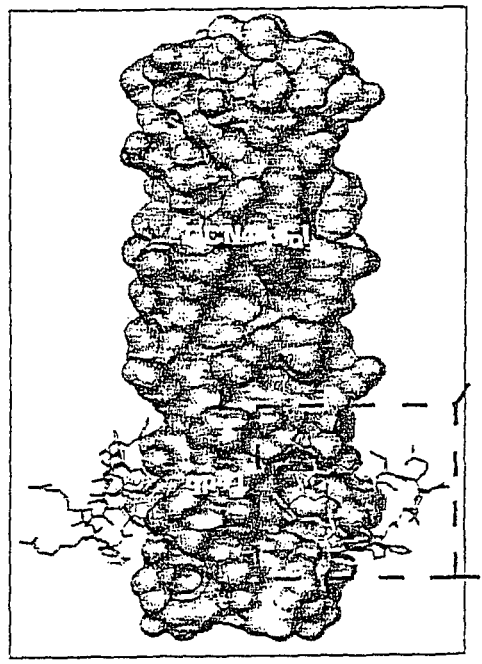

Reply filed Sep. 23, 2002, U.S. Appl. No. 09/364,497.
Office Action dated Mar. 12, 2003, U.S. Appl. No. 09/364,497.
Reply filed Sep. 12, 2003, U.S. Appl. No. 09/364,497.
Office action dated Jan. 14, 2004, U.S. Appl. No. 09/364,497.
Interview Summary dated Mar. 4, 2004, U.S. Appl. No. 09/364,497.
AAF filed Mar. 12, 2004, U.S. Appl. No. 09/364,497.
Advisory Action dated Jun. 2, 2004, U.S. Appl. No. 09/364,497.
Notice of Allowance dated Jun. 29, 2004, U.S. Appl. No. 09/364,497.
Office Action (RR), U.S. Appl. No. 09/738,945, dated Jun. 3, 2003.
Reply filed Sep. 2, 2003, U.S. Appl. No. 09/738,945.
Office action dated Nov. 17, 2003, U.S. Appl. No. 09/738,945.
Reply filed May 17, 2004, U.S. Appl. No. 09/738,945.
Office Action dated Sep. 22, 2004, U.S. Appl. No. 09/738,945.
Reply filed Feb. 22, 2005, U.S. Appl. No. 09/738,945.
Notice of Allowance dated Apr. 11, 2005, U.S. Appl. No. 09/738,945.
Office Action (RR), dated Sep. 24, 2003, U.S. Appl. No. 10/173,570.
Reply dated Oct. 24, 2003, U.S. Appl. No. 10/173,570.
Office Action, dated Jan. 28, 2004, U.S. Appl. No. 10/173,570.
Reply, dated Jul. 26, 2004, U.S. Appl. No. 10/173,570.
Office Action, dated Dec. 20, 2004, U.S. Appl. No. 10/173,570.
Notice of Appeal, dated Mar. 16, 2005, U.S. Appl. No. 10/173,570.
Office Action (RR) dated Jun. 4, 2007, U.S. Appl. No. 11/151,598.
Reply filed Jul. 5, 2007, U.S. Appl. No. 11/151,598.
Office Action dated Sep. 13, 2007, U.S. Appl. No. 11/151,598.
Reply filed Mar. 12, 2008, U.S. Appl. No. 11/151,598.
Office Action dated May 30, 2008, U.S. Appl. No. 11/151,598.
Reply filed Sep. 2, 2008, U.S. Appl. No. 11/151,598.
Notice of allowance dated Oct. 20, 2008, U.S. Appl. No. 11/151,598.
Office Action (RR), U.S. Appl. No. 09/062,241, dated Dec. 4, 1998.
Reply filed Apr. 22, 1999, U.S. Appl. No. 09/062,241.
Office Action, U.S. Appl. No. 09/062,241, dated Jul. 15, 1999.
Reply filed Jan. 17, 2000, U.S. Appl. No. 09/062,241.
Office Action dated Mar. 3, 2000, U.S. Appl. No. 09/062,241.
Reply filed May 3, 2000, U.S. Appl. No. 09/062,241.
Notice of Allowance dated May 22, 2000, U.S. Appl. No. 09/062,241.
Office Action (RR), U.S. Appl. No. 09/484,925, dated Mar. 27, 2001.
Reply filed Aug. 27, 2001, U.S. Appl. No. 09/484,925.
Office Action, U.S. Appl. No. 09/484,925, dated Nov. 8, 2001.
Reply filed Feb. 8, 2002, U.S. Appl. No. 09/484,925.
Notice of Allowance dated Apr. 22, 2002, U.S. Appl. No. 09/484,925.
Office Action (RR), dated Apr. 8, 2003, U.S. Appl. No. 10/200,007.
Office Action (RR), U.S. Appl. No. 10/680,853, dated Sep. 25, 2006.
Reply filed Nov. 27, 2006, U.S. Appl. No. 10/680,853.
Office Action dated Feb. 21, 2007, U.S. Appl. No. 10/680,853.
Reply filed Aug. 20, 2007, U.S. Appl. No. 10/680,853.
Notice of Allowance dated Feb. 22, 2008, U.S. Appl. No. 10/680,853.
Notification of Transmittal of the International Preliminary Examination Report (IPER) with IPER, PCT/US99/17351, mailed Oct. 31, 2000.
Notification of Transmittal of the International Search Report (ISR) or the Declaration with ISR, PCT/US99/17351, mailed Jan. 18, 2000.
Written Opinion, PCT/US99/17351, mailed Apr. 5, 2000.
Office Action, 2,338,022, dated Jan. 3, 2007.
Reply, 2,338,022, dated Jul. 3, 2007.
Supplementary Reply, 2,338,022, dated Aug. 3, 2007.
Office Action, 2,338,022, dated Jan. 2, 2008.
Reply, 2,338,022, dated Jul. 2, 2008.
Office Action, 2,338,022, dated Jul. 2, 2009.
Office Action, 99937691.6, dated Mar. 21, 2006.
Reply, 99937691.6, mailed Aug. 30, 2006.
Office Action, 99937691.6, dated Feb. 6, 2008.
Reply, 99937691.6, mailed Jun. 6, 2008.
Office Action, 99937691.6, dated Jun. 18, 2009.
Reply to Request for Examination, 57886/01, dated Apr. 10, 2002.
Reply, 57886/01, mailed Nov. 25, 2003.
Office Action, 57886/01, dated Dec. 24, 2003.
Reply, 57886/01, mailed Jan. 5, 2004.
Office Action, 10-2001-7001273, dated Dec. 19, 2005.
Notification of Transmittal of the International Preliminary Examination Report (IPER) with IPER, PCT/US01/29637, mailed Feb. 17, 2003.
Notification of Transmittal of the International Search Report (ISR) or the Declaration with ISR, PCT/US01/29637, mailed Jan. 22, 2003.
Office Action, 2001292944 dated Apr. 21, 2004.
Reply, 2001292944 dated Jul. 5, 2005.
Office Action, 01973355.9 dated May 26, 2006.
Reply, 01973355.9 mailed Dec. 4, 2006.
Office Action, 01973355.9 dated Sep. 21, 2007.
Reply, 01973355.9 mailed Jan. 24, 2008.
Office Action, 01973355.9 dated Aug. 12, 2008.
Reply, 01973355.9 mailed Feb. 6, 2009.
Office Action, 01973355.9 dated May 5, 2009.
Reply, 01973355.9 mailed May 20, 2009.
Official Action, 2005225063, dated Sep. 20, 2007.
Reply dated May 7, 2009, 2005225063.
Further Official Action, 2005225063, mailed May 15, 2009.
Reply dated May 25, 2009, 2005225063.
Notification of Transmittal of the International Preliminary Examination Report (IPER) with IPER, PCT/US00/34194, mailed Apr. 11, 2002.
International Search Report, PCT/US00/34194, mailed Jul. 10, 2001.
Written Opinion, PCT/US00/34194, mailed Dec. 14, 2001.
Requisition by the Examiner, 2,395,291 Canada, mailed Feb. 4, 2008.
Response to Requisition, 2,395,291 Canada, filed Aug. 1, 2008.
Office Action, 2,395,291 Canada, dated Jul. 24, 2009.
Office Action, EP 00986475.2, dated Aug. 22, 2003.
Reply to Office Action, EP 00986475.2, mailed Feb. 27, 2004.
Office Action, EP 00986475.2, dated Dec. 3, 2004.
Reply to Office Action, EP 00986475.2, mailed Jun. 7, 2005.
Office Action, EP 00986475.2, dated Jun. 30, 2006.
Reply to Office Action, EP 00986475.2, mailed Oct. 19, 2006.
Communication under Rule 51(4) EPC, EP 00986475.2, mailed May 22, 2007.
Reply to Communication, EP 00986475.2, mailed Sep. 5, 2007.
Office Action, JP 2000-562395, dated Sep. 3, 2009.
Reply, Canada 2,338,022, filed Jan. 4, 2010.
Supplemental Reply, Canada 2,338,022, filed Apr. 19, 2010.
Reply, EP 99937691.6, dated Dec. 8, 2009.
Supplemental Reply, EP 99937691.6, dated Mar. 1, 2010.
Office Action, Canada 2,423,004 dated Dec. 10, 2009.
Reply, Canada 2,423,004, filed Jun. 10, 2010.
Reply, Canada 2,395,291 filed Jan. 21, 2010.
Office Action, Japan 2000-562395, dated Apr. 13, 2010.
Muller, K.M., et al., "Protein Fusions to Coiled-coil Domains," in *Methods in Enzymology* 328, Thorner, J., et al., eds., (Academic Press USA), pp. 261-282 (2000).
Lupas, A., "Coiled Coils: New Structures and New Functions," *TIBS* 21:375-382 (1996).
Eckert, D.M., and Kim, P.S., "Design of Potent Inhibitors of HIV-1 Entry from the gp41 N-peptide Region," *PNAS*, 98(20):11187-11192 (2001).
Manchester, M., et al., "Identification of temperature-sensitive mutants of the human immunodeficiency virus type I protease through saturation mutagenesis," *J. Biol. Chem.*, 269(10):7689-7695 (1994).
Moschella, F., et al., "Administration of different antigenic forms of altered peptide ligands derived from HIV-1 RTase influences their effects on T helper cell activation," *Hum. Immunol.*, 64:1-8 (2003).
Chen, et al., "Mutations in the leucine zipper-like heptad repeat sequence of Human Immunodeficiency Virus Type 1 gp41 Dominantly Interfere with Wild-Type Virus Infectivity", *J. of Virology*, 72(6):4765-4774 (1998).
Kliger et al., "Inhibition of HIV-1 Entry Before gp41 Folds into its Fusion-Active Conformation", *J. of Mol. Biol.*, 295:163-168 (2000).
Miller, M.D., et al, "A Human Monoclonal Antibody Neutralizes Diverse HIV-1 Isolates by Binding a Critical gp41 Epitope," *PNAS* 102(41):14759-14764 (2005).
Baum, Rudy, "Virus-cell Fusion Targeted for Drug Development," *C&EN* (1996).
Blacklow, Stephen C., et al., "A Trimeric Subdomain of the Simian Immunodeficiency Virus Envelope Glycoprotein," *Biochemistry*, 34(46):14955-14962 (1995).
Blake, James and Li, Choh Hao, "Adrenocorticotropin. 47. Synthesis and Biological Activity of Adrenocorticotropic Peptides Modified at the Tryptophan Position," *J. Medicinal Chem.* 18(4):423-426 (1975).

Borchardt, Allen et al., "Small Molecule-dependent genetic selection in stochastic nanodroplets as a means of detecting protein-ligand interactions on a large scale," *Chem. & Biol.* 4(12):961-968 (1997).

Bullough, Per A. et al., "Structure of influenza haemagglutinin at the pH of membrane fusion," *Nature* 371:37-43 (1994).

Caffrey, Michael et al., "Three-dimensional solution structure of the 44kDa ectodomain of SIV gp41," *EMBO J.* 17(16):4572-4584 (1998).

Cao, Jie et al., "Effects of Amino Acid Changes in the Extracellular Domain of the Human Immunodeficiency Virus Type 1 gp41 Envelope Glycoprotein," *J. Virology* 67(5):2747-2755 (1993).

Chabala, John C., "Solid-phase combinatorial chemistry and novel tagging methods for identifying leads," *Curr. Opin. Biotech.* 6:632-639 (1995).

Chakrabartty, Avijit et al., "Aromatic Side-Chain Contribution to Far-Ultraviolet Circular Dichroism of Helical Peptides and Its Effect on Measurement of Helix Propensities," *Biochemistry* 32:5560-5565 (1993).

Chambers, Philip, et al., "Heptad Repeat Sequences are Located Adjacent to Hydrophobic Regions in Several Types of Virus Fusion Glycoproteins," *Journal of General Virology*, 71:3075-3080 (1990).

Chan, David C., et al., "Evidence that a Prominent Cavity in the Coiled Coil of HIV Type I gp41 is an Attractive Drug Target," *Proc. Natl. Acad. Sci. USA* 95:15613-15617 (1998).

Chan, David C., et al., "Core Structure of gp41 from the HIV Envelope Glycoprotein," *Cell* 89:263-273 (1997).

Chan, David C. and Kim, Peter A., "HIV Entry and Its Inhibition," *Cell* 93:681-684 (1998).

Chen, Yee-Hsiung et al., "Determination of the Helix and β Form of Proteins in Aqueous Solution by Circular Dichroism," *Biochemistry* 13(16):3350-3359 (1974).

Chen, Benjamin K. et al., "Distinct Modes of Human Immunodeficiency Virus Type 1 Proviral Latency Revealed by Superinfection of Nonproductively Infected Cell Lines with Recombinant Luciferase-Encoding Viruses," *J. Virology* 68(2):654-660 (1994).

Chen, Charlie L. et al., "One Bead-One Compound Combinatorial Peptide Library: Different Types of Screening," *Methods in Enzymology* 267:211-219 (1996).

Chen, Chin-Ho et al., "A Molecular Clasp in the Human Immunodeficiency Virus (HIV) Type 1 TM Protein Determines the Anti-HIV Activity of gp41 Derivatives:Implication for Viral Fusion," *J. Virology* 69(6):3771-3777 (1995).

Cole, James L. and Garsky, Victor M., "Thermodynamics of Peptide Inhibitor Binding to HIV-1 gp41," *Biochemistry* 40:5633-5641 (2001).

Delwart, Eric L., et al., "Retroviral Envelope Glycoproteins Contain a "Leucine Zipper"-like Repeat," *AIDS Research and Human Retroviruses*, 6(6):703-706 (1990).

Doering Don S. And Matsudaira, Paul, "Cysteine Scanning Mutagenesis at 40 of 76 Positions in Villin Headpiece Maps the F-Actin Binding Site and Structural Features of the Domain," *Biochemistry* 35:12677-12685 (1996).

Dutch, Rebecca Ellis et al., "Paramyxovirus Fusion Protein: Characterization of the Core Trimer, a Rod-Shaped Complex with Helices in Anti-Parallel Orientation," *Virology* 254:147-159 (1999).

Eckert, Debra M., et al., "Inhibiting HIV-1 Entry: Discovery of D-Peptide Inhibitors that Target the gp41 Coiled-Coil Pocket," *Cell* 99:103-115 (1999).

Eckert, Debra M. et al., "Crystal Structure of GCN4-p1$_O$1, a Trimeric Coiled Coil with Buried Polar Residues," *J. Mol. Biol.* 284:859-865 (1998).

Eckhart, Leopold et al., "Immunogenic Presentation of a Conserved gp41 Epitope of Human Immunodeficiency Virus Type I on Recombinant Surface Antigen of Hepatitis B Virus," *J. Gen. Virol.* 77:2001-2008 (1996).

Edelhoch, Harold, "Spectroscopic Determination of Tryptophan and Tyrosine in Proteins," *Biochemistry* 6:(7):1948-1954 (1967).

Fass, Deborah et al., "Retrovirus envelop domain at 1.7 Å resolution," *Nature Structural Biology* 3(5):465-469 (1996).

Fass, Deborah and Kim, Peter S., "Dissection of a retrovirus envelope protein reveals structural similarity to influenza hemagglutinin," Current Biology 5(12):1-7(1995).

Furuta et al., "Capture of an early fusion-active conformation of HIV-1 gp41," *Nature Structural Biology* 5(4):276-279 (1998).

Gallaher, William R., et al., "A General Model for the Transmembrane Proteins of HIV and Other Retroviruses," *Aids Research and Human Retroviruses*, 5(4):431-440 (1989).

Harbury, Pehr B. et al., "Repacking protein cores with backbone freedom:Structure prediction for coiled coils," *Proc. Natl. Acad. Sci, USA* 92:8408-8412 (1995).

Harbury, Pehr B. et al., "Crystal structure of an isoleucine-zipper trimer," *Nature* 371:80-83 (1994).

Hirsch, Vanessa M. And Johnson, Philip R., "Pathogenic diversity of simian immunodeficiency viruses," Virus Research 32:183-206 (1994).

Hooft, Rob W.W. and Vriend, Gert, "Errors in protein structures," *Nature* 381:272 (1996).

Jiang, Shibo et al., "A conformation-Specific Monoclonal Antibody Reacting with Fusion-Active gp41 from the Human Immunodeficiency Virus Type 1 Envelope Glycoprotein," *J. of Virology* 72(12):10213-10217 (1998).

Jiang, S. et al., "A screening assay for antiviral compounds targeted to the HIV-1 gp41 core structure using a conformation-specific monoclonal antibody," *J. Virol. Methods* 80:85-96 (1999).

Jiang, Shibo et al., "HIV-1 inhibition by a peptide," *Nature* 365:113 (1993).

Jones, T.A. et al., "Improved Methods for Building Protein Models in Electron Density Maps and the Location of Errors in these Models," *Acta Cryst.* A47:110-119 (1991).

Judice, J. Kevin et al., "Inhibition of HIV type 1 infectivity by constrained α-helical peptides:Implications for the viral fusion mechanism," *Proc. Natl. Acad. Sci. USA* 94:13426-13430 (1997).

Kilby, J. Michael et al., "Potent suppression of HIV-1 replication in humans by T-20, a peptide inhibitor of gp41-mediated virus entry," *Nature Medicine* 4(11):1302-1307 (1998).

Kliger, Yossef et al., "Mode of Action of an Antiviral Peptide from HIV-1," J. Biol. Chem. 276(2):1391-1397 (2001).

Kozarsky, Karen et al., "Glycosylation and Processing of the Human Immunodeficiency Virus Type 1 Envelope Protein," *J. Acquired Immune Deficiency Syndromes* 2:163-169 (1989).

Kubinyi, Hugo, "Combinatorial and computational approaches in structure-based drug design," *Curr. Op. In Drug Disc. & Dev.* 1(1):16-22 (1998).

Kuntz, Irwin D., "Structure-Based Strategies for Drug Design and Discovery," *Science* 257:1078-1082 (Aug. 1992).

LaCasse, Rachel A. et al., "Fusion-Competent Vaccines: Broad Neutralization of Primary Isolates of HIV," *Science* 283:357-362 (1999).

Lam, Kit S. et al., "A new type of synthetic peptide library for identifying ligand-binding activity," *Nature* 354:82-84 (1991).

Lambert, D.M. et al., "Peptides from conserved regions of paramyxovirus fusion (F) proteins are potent inhibitors of viral fusion," *Proc. Natl. Acad. Sci. USA* 93:2186-2191 (1996).

Letvin, Norman L., "Progress in the Development of an HIV-1 Vaccine," *Science* 280:1875-1880 (1998).

Li, Zhe, et al., "Anti-malarial Drug Development Using Models of Enzyme Structure," *Chemistry & Biology*, 1:31-37 (1994).

Lu, Min, et al., "A Trimeric Structural Domain of the HIV-1 transmembrane glycoprotein," *Nature Structural Biology*, 2(12):1-8 (1995).

Lu, Min and Kim, Peter S., "A Trimeric Structural Subdomain of the HIV-1 Transmembrane Glycoprotein," *J. Biomol. Structure & Dynamics* 15(3):465-471 (1997).

Malashkevich, Vladimir N. et al., "Crystal structure of the simian immunodeficiency virus (SIV) gp41 core: Conserved helical interactions underlie the broad inhibitory activity of gp41 peptides," *Proc. Natl. Acad. Sci. USA* 95:9134-9139 (1998).

Meng, Elaine C., et al., "Automated Docking with Grid-Based Energy Evaluation," *Journal of Computational Chemistry*, 13(4):505-524 (1992).

Muster, Thomas et al., "Cross-Neutralizing Activity against Divergent Human Immunodeficiency Virus Type 1 Isolates Induced by the gp41 Sequence ELDKWAS," *J. Virology* 68(6):4031-4034 (1994).

Muster, Thomas et al., "A Conserved Neutralizing Epitope on gp41 of Human Immunodeficiency Virus Type 1,"*J. Virology* 67(11):6642-6647 (1993).

Nautiyal, Shivani and Alber, Tom, "Crystal structure of a designed, thermostable, heterotrimeric coiled coil," *Protein Science* 8:84-90 (1999).

Nolte, Alexis et al., "Mirror-design of L-oligonucleotide ligands binding to L-arginine," *Nature Biotechnology* 4:1116-1119 (1996).

O'Neil, Karyn T. and DeGrado, William F., "A Thermodynamic Scale for the Helix-Forming Tendencies of the Commonly Occurring Amino Acids," *Science* 250:646-351 (1990).

Purtscher, Martin et al., "Restricted antigenic variability of the epitope recognized by the neutralizing gp41 antibody 2F5," *AIDS* 10:587-593 (1996).

Reimann, Keith A. et al., "A Chimeric Simian/Human Immunodeficiency Virus Expressing a Primary Patient Human Immunodeficiency Virus Type 1 Isolate *env* Causes an AIDS-Like Disease after In Vivo Passage in Rhesus Monkeys," *J. Virology* 70(10):6922-6928 (1996).

Richman, Douglas D., "Nailing down another HIV target," *Nature Medicine* 4(11):1232-1233 (1998).

Rimsky, Laurence T. et al., "Determinants of Human Immunodeficiency Virus Type 1 Resistance to gp41-Derived Inhibitory Peptides," *J. Virology* 72(2):986-993 (1998).

Ring, Christine S., et al., "Structure-based Inhibitor Design by Using Protein Models for the Development of Antiparasitic Agents," *Proc. Natl. Acad. Sci. USA*, 90:3583-3587 (1993).

Root, Michael J. et al., "Protein Design of an HIV-1 Entry Inhibitor," *Science* 291:884-888 (2001).

Schumacher, Ton N.M. et al., "Identification of D-Peptide Ligands Through Mirror-Image Phage Display," *Science* 271:1854-1857 (1996).

Shuker, Suzanne B. et al., "Discovering High-Affinity Ligands for Proteins: SAR by NMR," *Science* 274:1531-1534 (1996).

Singh, Mona et al., "LearnCoil-VMF: Computational Evidence for Coiled-coil-like Motifs in Many Viral Membrane-fusion Proteins," *J. Mol. Biol.* 290:1031-1041 (1999).

Tan, Kemin et al., "Atomic structure of a thermostable subdomain of HIV-1 gp41," *Proc. Natl. Acad. Sci. USA* 94:12303-12308 (1997).

Tarrago-Litvak, Laura et al., "The reverse transcriptase of HIV-1: from enzymology to therapeutic intervention," *FASEB J* 8:497-503 (1994).

Tucker, Thomas J. et al., "Development of Nonnucleoside HIV Reverse Transcriptase Inhibitors," *Methods in Enzymology* 275:440-472 (1996).

Tyagi, Sanjay et al., "Multicolor molecular beacons for allele discrimination," Nature Biotechnology 16:49-53 (1998).

Weissenhorn, Winfried et al., "Assembly of a rod-shaped chimera of a trimeric GCN4 zipper and the HIV-1 gp41 ectodomain expressed in *Escherichia coli*," *Proc. Natl. Acad. Sci. USA* 94:6065-6069 (1997).

Weissenhorn, W. et al., "Atomic structure of the ectodomain from HIV-1 gp41," *Nature* 387:426-430 (1997).

Weissenhorn, Winfried et al., "Crystal Structure of the Ebola Virus Membrane Fusion Subunit, GP2, from the Envelope Glycoprotein Ectodomain," *Molecular Cell* 2:605-616 (1998).

Wild, Carl et al., "A synthetic peptide inhibitor of human immunodeficiency virus replication: Correlation between solution structure and viral inhibition," *Proc. Natl. Acad. Sci. USA* 89:10537-10541 (1992).

Wild, Carl T. et al., "Peptides corresponding to a predictive α-helical domain of human immunodeficiency virus type 1 gp41 are potent inhibitors of virus infection," *Proc. Natl. Acad. Sci. USA* 91:9770-9774 (1994).

Williams, Kelly P. et al., "Bioactive and nuclease-resistant L-DNA ligand of vasopressin," *Proc. Natl. Acad. Sci. USA* 94:11285-11290 (1997).

Youngquist, R. Scott et al., "Generation and Screening of Combinatorial Peptide Libraries Designed for Rapid Sequencing by Mass Spectrometry," *J. Am. Chem. Soc.* 117:3900-3906 (1995).

Malashkevich, Vladimir N. et al., "Core structure of the envelope glycoprotein GP2 from Ebola virus at 1.9-Å resolution," *Proc. Natl. Acad. Sci. USA* 96:2662-2667 (1999).

Ferrer, Marc et al., "Selection of gp41-mediated HIV-1 cell entry inhibitors from biased combinatorial libraries of non-natural binding elements," *Nature Structural Biology* 6(10):953-960 (1999).

Jiang, Shibo et al., "Development of HIV Entry Inhibitors Targeted to the Coiled-Coil Regions of gp41," Biochemical and Biophysical Research Communications 269(3):641-646 (2000).

Yang, Xinzhen et al., "Characterization of Stable, Soluble Trimers Containing Complete Ectodomains of Human Immunodeficiency Virus Type 1 Envelope Glycoproteins," J. Virol. 74(12):5716-5725 (2000).

Bahbouhi, B., et al., "Effects of L-and D-REKR Amino Acid-Containing Peptides on HIV and SIV Envelope Glycoprotein Precursor Maturation and HIV and SIV Replication," Biochem. J. 366 (Pt. 3):863-872 (2002).

Benkirane, M., et al., "Antigenicicty and Immunogenicity of Modified Synthetic Peptides Containing D-Amino Acid Residues. Antibodies to a D-Enantiomer Do Recognize the Parent L-Hexapeptide and Reciprocally," J. Biol. Chem. 268(35): 26279-26285 (1993).

Corigliano-Murphy, M.A., et al., "Synthesis and Properties of an All-D Model Ribonuclease S-Peptide," Int. J. Pep. Prot. Res. 25:225-231 (1985).

Kramer, A., et al., "Stepwise Transformation of a Cholera Toxin and a p24 (HIV-1) Epitope Into D-Peptide Analogs," Prot. Engin. 11(10):941-948 (1998).

Levy, R.B., et al., "T Lymphocytes Can Recognize Determinants Unique to Neuropeptides of Guinea Pig Myelin Basic Protein Containing a Single D-Isomer Amino Acid Substitution," J. Neuro. Res. 25(1):29-38 (1990).

Weng, Y., et al., "Mutational Analysis of Residues in the Coiled-Coil Domain of Human Immunodeficiency Virus Type 1 Transmembrane Protein gp41," J. Virol. 72(12):9676-9682 (1998).

Richman, Douglas, D. et al., "Rapid Evolution of the neutralizing antibody response to HIV type 1 infection," *Proc.Natl.Acd.Sci., USA* 100(7):4144-4149 (2003).

Butto, S., et al., "Dual infection with different strains of the same HIV-1 subtype", *AIDS* 11(5):694-698 (1997).

Fahey, J.L. and Schooley, R., "Status of immune-based therapies in HIV infection and AIDS", *Clin. Exp. Immunol.l*, 88:1-5 (1992).

Eckert, D.M. and Kim, P.S., "Mechanisms of Viral Membrane Fusion and Its Inhibition," *Annu. Rev. Biochem.*, 70:777-810 (2001).

Rudinger, "Characteristics of the Amino Acids as Components of a Peptide Hormone Sequence," Peptide Hormones (Ed. JA Parsons, Jun. 1976) pp. 1-6.

Bowie, J.U., et al., "Deciphering the Message in Protein Sequences: Tolerance to Amino Acid Substitutions," Science, 247:1306-1310 (1990).

Chang, Ding-Kwo, et al., "Proline Affects Oligomerization of a Coiled Coil by Inducing a Kink in a Long Helix," *J. Structural Biol.*, 128:270-279 (1999).

Poumbourios, P., et al., "Human Immunodeficiency Virus Type 1 Envelope Glycoprotein Oligomerization Requires the gp41 Amphipathic α-Helical/Leucine Zipper-Like Sequence," *J. Virology*, 71(3):2041-2049 (1997).

Bernstein, H.B., et al., "Oligomerization of the Hydrophobic Heptad Repeat of gp41," *J. Virology*, 69(5):2745-2750 (1995).

Miller, M.D., "A Human Monoclonal Antibody Blocks HIV Entry by a T20-Like Machanism," Abstract presented at the 13th International HIV Drug Resistance Workshop, Jun. 8-12, 2004, Tenerife, Canary Islands, Spain.

Joyce, J. G., et al., "Enhancement of α-Helicity in the HIV-1 Inhibitory Peptide DP178 Leads to an Increased Affinity for Human Monoclonal Antibody 2F5 but Does Not Elicit Neutralizing Responses in Vitro," *Journal of Biological Chemistry* 277(48):45811-45820 (2002).

Office Action (Restriction Requirement), U.S. Appl. No. 12/321,300, mailed Sep. 21, 2010.

Reply filed, U.S. Appl. No. 12/321,300, Nov. 22, 2010.

\* cited by examiner

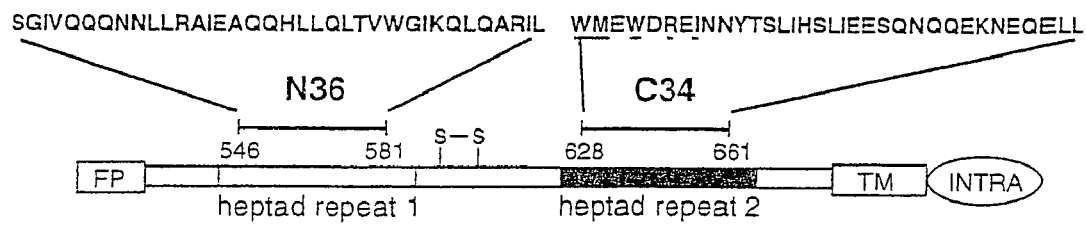
Figure 1: HIV-1 gp41 Structure and Peptides

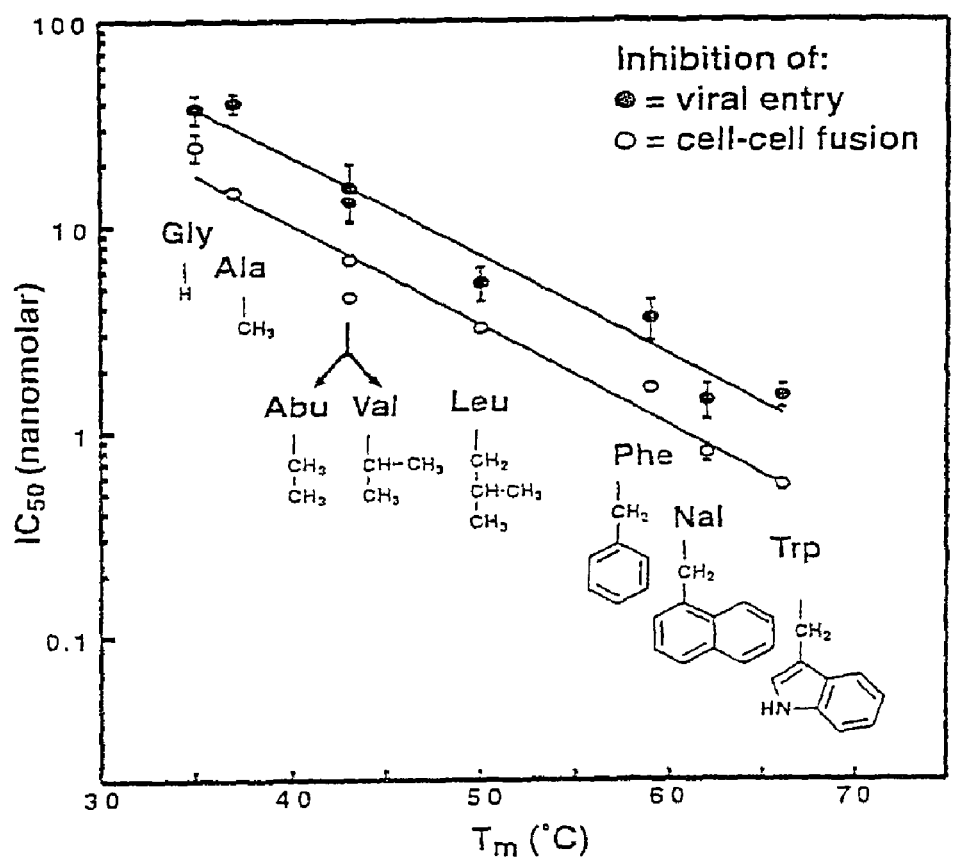
Figure 2: Correlation of C34 Inhibitory Potency With N36/C34 Stability Figure 3: D-peptide Sequences

```
D10pep1  :       Ac -      G A C E A R H R E W A W L C A A - CONH2
D10pep1a:    Ac - K K      G A C E A R H R E W A W L C A A - CONH2

D10pep3  :   Ac - K K      G A C G L G Q E E W F W L C A A - CONH2

D10pep4  :       Ac -      G A C D L K A K E W F W L C A A - CONH2

D10pep5  :   Ac - K K      G A C E L L G W E W A W L C A A - CONH2
D10pep5a: Ac - K K K K     G A C E L L G W E W A W L C A A - CONH2

D10pep6  :       Ac -      G A C S R S Q P E W E W L C A A - CONH2
D10pep6a :   Ac - K K      G A C S R S Q P E W E W L C A A - CONH2

D10pep7a:    Ac - K K      G A C L L R A P E W G W L C A A - CONH2

D10pep10:    Ac - K K      G A C M R G E W E W S W L C A A - CONH2

D10pep12:    Ac - K K      G A C P P L N K E W A W L C A A - CONH2

Consensus Sequence              C X X X X X E W X W L C
```

Where:
G = glycine
A = alanine
C = cysteine
D = aspartic acid
L = leucine
K = lysine
E = glutamic acid
W = tryptophan
F = phenylalanine
R = arginine
H = histidine
S = serine
Q = glutamine Figure 4: Mirror-Image Phage Display with the D-IQN17 Target
1. Perform rounds of phage selection to identify binders to D-IQN17.
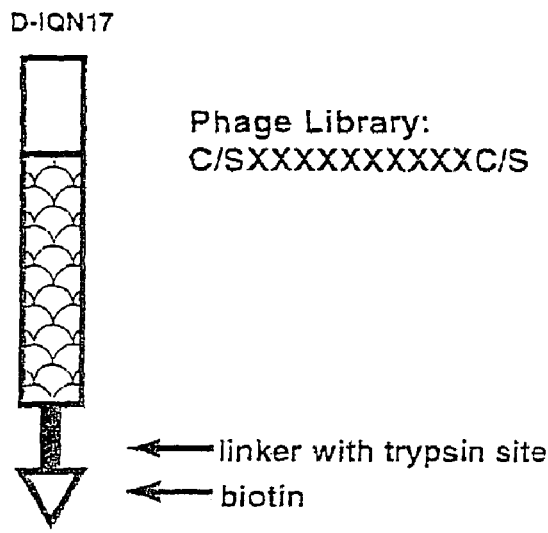
2. Sequence individual phage clones
3. Test for specificity of binding. Determine if the phage bind to the gp41 region of D-IQN17.
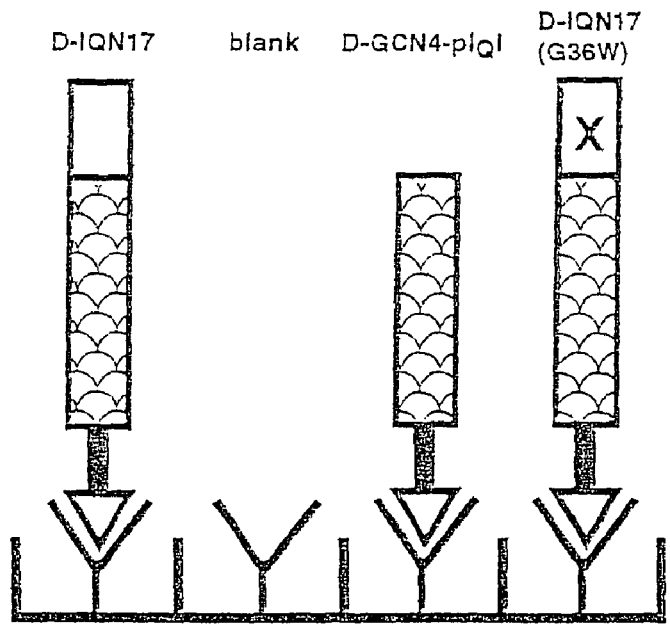
4. Synthesize D-peptides.
5. Assay anti-HIV activity of D-peptides.

Relationship of D-peptides to IQN17

Syncytia Assays

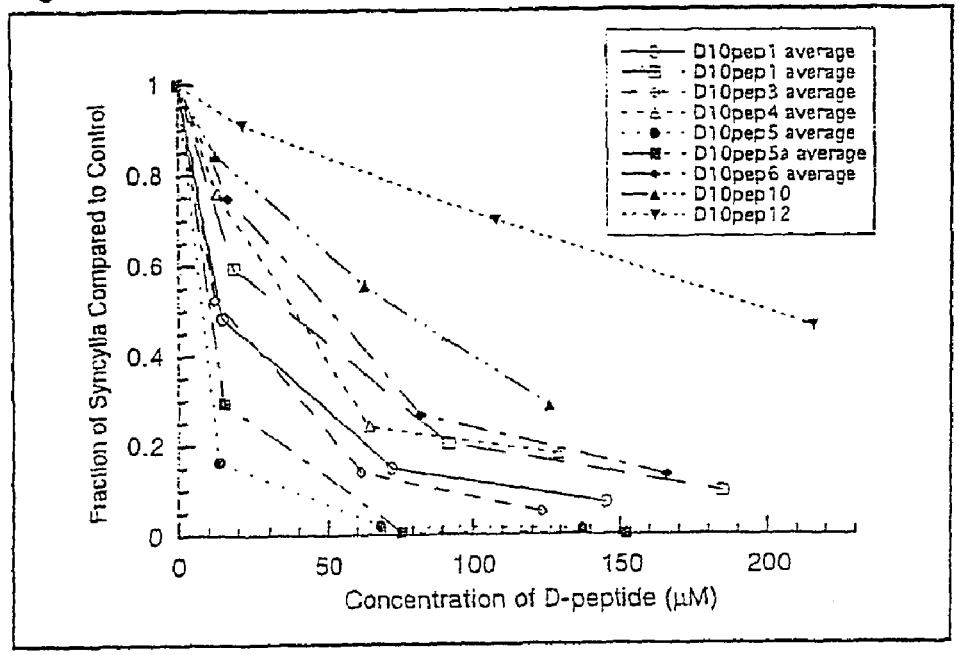

Figure 6A

Figure 6B: IC$_{50}$ Data for D-Peptides:

| D-Peptide | Approximate IC$_{50}$ Value (from one or more experiments) |
| --- | --- |
| D10pep1 | $2 \times 10^{-5}$ M |
| D10pep1A | $3 \times 10^{-5}$ M |
| D10pep3 | $1 \times 10^{-5}$ M |
| D10pep4 | $3 \times 10^{-5}$ M |
| D10pep5 | $3 \times 10^{-6}$ M |
| D10pep5a | $6 \times 10^{-6}$ M |
| D10pep6 | $3 \times 10^{-5}$ M |
| D10pep7a | $4 \times 10^{-5}$ M |
| Dpep10 | $6 \times 10^{-5}$ M |
| Dpep12 | $2 \times 10^{-4}$ M |

D10pep3, D10pep4, D10pep5 show anti-viral effects with IC$_{50}$ values of less than $1 \times 10^{-4}$ M.

```
REMARK   3
REMARK   3 REFINEMENT.
REMARK   3   PROGRAM     : CNS 0.5
REMARK   3   AUTHORS     : BRUNGER, ADAMS, CLORE, DELANO,
REMARK   3               : GROS, GROSSE-KUNSTLEVE, JIANG,
REMARK   3               : KUSZEWSKI, NILGES, PANNU, READ,
REMARK   3               : RICE, SIMONSON, WARREN
REMARK   3
REMARK   3  DATA USED IN REFINEMENT.
REMARK   3   RESOLUTION RANGE HIGH (ANGSTROMS) : 1.50
REMARK   3   RESOLUTION RANGE LOW  (ANGSTROMS) :10.00
REMARK   3   DATA CUTOFF            (SIGMA(F)) : 0.0
REMARK   3   DATA CUTOFF HIGH         (ABS(F)) : 646169.44
REMARK   3   DATA CUTOFF LOW          (ABS(F)) :   0.000000
REMARK   3   COMPLETENESS (WORKING+TEST)   (%) : 94.6
REMARK   3   NUMBER OF REFLECTIONS             : 13549
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE            (WORKING SET)  : 0.214
REMARK   3   FREE R VALUE                      : 0.245
REMARK   3   FREE R VALUE TEST SET SIZE    (%) : 10.1
REMARK   3   FREE R VALUE TEST SET COUNT       : 1362
REMARK   3   ESTIMATED ERROR OF FREE R VALUE   : 0.007
REMARK   3
REMARK   3  FIT IN THE HIGHEST RESOLUTION BIN.
REMARK   3   TOTAL NUMBER OF BINS USED             :   6
REMARK   3   BIN RESOLUTION RANGE HIGH       (A)   : 1.50
REMARK   3   BIN RESOLUTION RANGE LOW        (A)   : 1.59
REMARK   3   BIN COMPLETENESS (WORKING+TEST) (%)   : 96.1
REMARK   3   REFLECTIONS IN BIN    (WORKING SET)   : 2008
REMARK   3   BIN R VALUE           (WORKING SET)   : 0.233
REMARK   3   BIN FREE R VALUE                      : 0.270
REMARK   3   BIN FREE R VALUE TEST SET SIZE  (%)   : 9.8
REMARK   3   BIN FREE R VALUE TEST SET COUNT       : 219
REMARK   3   ESTIMATED ERROR OF BIN FREE R VALUE   : 0.018
REMARK   3
REMARK   3  NUMBER OF NON-HYDROGEN ATOMS USED IN REFINEMENT.
REMARK   3   PROTEIN ATOMS            :   0
REMARK   3   NUCLEIC ACID ATOMS       :   0
REMARK   3   HETEROGEN ATOMS          :   0
REMARK   3   SOLVENT ATOMS            :   0
REMARK   3
REMARK   3  B VALUES.
REMARK   3   FROM WILSON PLOT           (A**2) : 21.6
REMARK   3   MEAN B VALUE      (OVERALL, A**2) : 29.7
REMARK   3   OVERALL ANISOTROPIC B VALUE.
REMARK   3    B11 (A**2) :  3.61
REMARK   3    B22 (A**2) :  3.61
REMARK   3    B33 (A**2) : -7.22
REMARK   3    B12 (A**2) :  1.74
REMARK   3    B13 (A**2) :  0.00
REMARK   3    B23 (A**2) :  0.00
REMARK   3
REMARK   3  BULK SOLVENT MODELING.
REMARK   3   METHOD USED : FLAT MODEL
REMARK   3   KSOL        : 0.394054
```

Figure 7A

```
REMARK   3    BSOL           : 58.3445 (A**2)
REMARK   3
REMARK   3  ESTIMATED COORDINATE ERROR.
REMARK   3    ESD FROM LUZZATI PLOT        (A) : 0.18
REMARK   3    ESD FROM SIGMAA              (A) : 0.09
REMARK   3    LOW RESOLUTION CUTOFF        (A) : 5.00
REMARK   3
REMARK   3  CROSS-VALIDATED ESTIMATED COORDINATE ERROR.
REMARK   3    ESD FROM C-V LUZZATI PLOT    (A) : 0.20
REMARK   3    ESD FROM C-V SIGMAA          (A) : 0.12
REMARK   3
REMARK   3  RMS DEVIATIONS FROM IDEAL VALUES.
REMARK   3    BOND LENGTHS                 (A) : 0.012
REMARK   3    BOND ANGLES            (DEGREES) : 1.5
REMARK   3    DIHEDRAL ANGLES        (DEGREES) : 15.7
REMARK   3    IMPROPER ANGLES        (DEGREES) : 1.00
REMARK   3
REMARK   3  ISOTROPIC THERMAL MODEL : RESTRAINED
REMARK   3
REMARK   3  ISOTROPIC THERMAL FACTOR RESTRAINTS.    RMS     SIGMA
REMARK   3    MAIN-CHAIN BOND              (A**2) : 0.956 ; 2.0
REMARK   3    MAIN-CHAIN ANGLE             (A**2) : 1.503 ; 3.0
REMARK   3    SIDE-CHAIN BOND              (A**2) : 1.853 ; 3.0
REMARK   3    SIDE-CHAIN ANGLE             (A**2) : 2.676 ; 3.5
REMARK   3
REMARK   3  NCS MODEL : NONE
REMARK   3
REMARK   3  NCS RESTRAINTS.                         RMS   SIGMA/WEIGHT
REMARK   3   GROUP  1  POSITIONAL            (A) : NULL ; NULL
REMARK   3   GROUP  1  B-FACTOR           (A**2) : NULL ; NULL
REMARK   3
REMARK   3  PARAMETER FILE  1  : protein_rep_d.param
REMARK   3  PARAMETER FILE  2  : CNS_TOPPAR/water_rep.param
REMARK   3  PARAMETER FILE  3  : CNS_TOPPAR/ion.param
REMARK   3  TOPOLOGY FILE   1  : CNS_TOPPAR/protein.top
REMARK   3  TOPOLOGY FILE   2  : CNS_TOPPAR/water.top
REMARK   3  TOPOLOGY FILE   3  : CNS_TOPPAR/ion.top
REMARK   3
REMARK   3  OTHER REFINEMENT REMARKS: NULL
SEQRES   1 A  214  ACE ARG MET LYS GLN ILE GLU ASP LYS ILE GLU GLU ILE
SEQRES   2 A  214  GLU SER LYS GLN LYS LYS ILE GLU ASN GLU ILE ALA ARG
SEQRES   3 A  214  ILE LYS LYS LEU LEU GLN LEU THR VAL TRP GLY ILE LYS
SEQRES   4 A  214  GLN LEU GLN ALA ARG ILE LEU ACE DLY DLA DCS DLU DLA
SEQRES   5 A  214  DRG DIS DRG DLU DRP DLA DRP DEU DCS DLA DLA CL  WAT
SEQRES   6 A  214  WAT WAT WAT WAT WAT WAT WAT WAT WAT WAT WAT WAT WAT
SEQRES   7 A  214  WAT WAT WAT WAT WAT WAT WAT WAT WAT WAT WAT WAT WAT
SEQRES   8 A  214  WAT WAT WAT WAT WAT WAT WAT WAT WAT WAT WAT WAT WAT
SEQRES   9 A  214  WAT WAT WAT WAT WAT WAT WAT WAT WAT WAT WAT WAT WAT
SEQRES  10 A  214  WAT WAT WAT WAT WAT WAT WAT WAT WAT WAT WAT WAT WAT
SEQRES  11 A  214  WAT WAT WAT WAT WAT WAT WAT WAT WAT WAT WAT WAT WAT
SEQRES  12 A  214  WAT WAT WAT WAT WAT WAT WAT WAT WAT WAT WAT WAT WAT
SEQRES  13 A  214  WAT WAT WAT WAT WAT WAT WAT WAT WAT WAT WAT WAT WAT
SEQRES  14 A  214  WAT WAT WAT WAT WAT WAT WAT WAT WAT WAT WAT WAT WAT
SEQRES  15 A  214  WAT WAT WAT WAT WAT WAT WAT WAT WAT WAT WAT WAT WAT
SEQRES  16 A  214  WAT WAT WAT WAT WAT WAT WAT WAT WAT WAT WAT WAT WAT
SEQRES  17 A  214  WAT WAT WAT WAT WAT WAT
CRYST1   41.829   41.829   84.817  90.00  90.00 120.00 P 3 2 1       6
ORIGX1      1.000000  0.000000  0.000000        0.00000
```

Figure 7B

```
ORIGX2         0.000000   1.000000   0.000000        0.00000
ORIGX3         0.000000   0.000000   1.000000        0.00000
SCALE1         0.023907   0.013803   0.000000        0.00000
SCALE2         0.000000   0.027605   0.000000        0.00000
SCALE3         0.000000   0.000000   0.011790        0.00000
ATOM      1   CA  ACE A    0      26.930    7.813  -22.925  1.00 54.89       A
ATOM      2   C   ACE A    0      26.773    9.004  -22.017  1.00 54.85       A
ATOM      3   O   ACE A    0      25.855    9.820  -22.124  1.00 54.90       A
ATOM      4   N   ARG A    1      27.749    9.121  -21.117  1.00 54.75       A
ATOM      5   CA  ARG A    1      27.815   10.229  -20.165  1.00 54.58       A
ATOM      6   CB  ARG A    1      27.625   11.568  -20.887  1.00 54.64       A
ATOM      7   CG  ARG A    1      27.841   12.790  -20.010  1.00 54.10       A
ATOM      8   CD  ARG A    1      27.657   14.085  -20.800  1.00 54.18       A
ATOM      9   NE  ARG A    1      28.177   15.253  -20.086  1.00 54.02       A
ATOM     10   CZ  ARG A    1      29.470   15.495  -19.970  1.00 54.03       A
ATOM     11   NH1 ARG A    1      30.395   14.654  -20.312  1.00 53.79       A
ATOM     12   NH2 ARG A    1      29.843   16.587  -19.206  1.00 53.77       A
ATOM     13   C   ARG A    1      26.752   10.087  -19.074  1.00 54.54       A
ATOM     14   O   ARG A    1      27.042   10.224  -17.884  1.00 54.51       A
ATOM     15   N   MET A    2      25.518    9.809  -19.480  1.00 54.42       A
ATOM     16   CA  MET A    2      24.445    9.671  -18.515  1.00 54.44       A
ATOM     17   CB  MET A    2      23.074    9.796  -19.202  1.00 54.68       A
ATOM     18   CG  MET A    2      22.749    8.736  -20.238  1.00 54.76       A
ATOM     19   SD  MET A    2      21.345    9.252  -21.275  1.00 55.63       A
ATOM     20   CE  MET A    2      22.189    9.658  -22.823  1.00 55.29       A
ATOM     21   C   MET A    2      24.557    8.360  -17.755  1.00 54.51       A
ATOM     22   O   MET A    2      24.073    8.249  -16.629  1.00 54.42       A
ATOM     23   N   LYS A    3      25.208    7.372  -18.362  1.00 54.34       A
ATOM     24   CA  LYS A    3      25.383    6.082  -17.702  1.00 54.29       A
ATOM     25   CB  LYS A    3      26.212    5.139  -18.581  1.00 54.05       A
ATOM     26   CG  LYS A    3      26.527    3.786  -17.956  1.00 54.04       A
ATOM     27   CD  LYS A    3      27.727    3.853  -17.018  1.00 54.12       A
ATOM     28   CE  LYS A    3      28.108    2.469  -16.513  1.00 54.37       A
ATOM     29   NZ  LYS A    3      29.332    2.493  -15.656  1.00 53.92       A
ATOM     30   C   LYS A    3      26.097    6.344  -16.384  1.00 54.33       A
ATOM     31   O   LYS A    3      25.779    5.740  -15.353  1.00 54.60       A
ATOM     32   N   GLN A    4      27.064    7.255  -16.426  1.00 53.94       A
ATOM     33   CA  GLN A    4      27.811    7.626  -15.236  1.00 53.69       A
ATOM     34   CB  GLN A    4      28.845    8.699  -15.580  1.00 54.21       A
ATOM     35   CG  GLN A    4      29.861    8.974  -14.477  1.00 55.15       A
ATOM     36   CD  GLN A    4      29.621   10.285  -13.732  1.00 55.56       A
ATOM     37   OE1 GLN A    4      29.532   11.354  -14.343  1.00 56.19       A
ATOM     38   NE2 GLN A    4      29.533   10.209  -12.403  1.00 55.66       A
ATOM     39   C   GLN A    4      26.828    8.182  -14.212  1.00 53.19       A
ATOM     40   O   GLN A    4      26.972    7.953  -13.006  1.00 53.10       A
ATOM     41   N   ILE A    5      25.832    8.918  -14.705  1.00 52.58       A
ATOM     42   CA  ILE A    5      24.817    9.523  -13.853  1.00 51.70       A
ATOM     43   CB  ILE A    5      23.826   10.380  -14.687  1.00 51.71       A
ATOM     44   CG2 ILE A    5      22.643   10.812  -13.831  1.00 51.41       A
ATOM     45   CG1 ILE A    5      24.547   11.611  -15.246  1.00 51.48       A
ATOM     46   CD1 ILE A    5      23.646   12.569  -16.017  1.00 51.33       A
ATOM     47   C   ILE A    5      24.051    8.467  -13.060  1.00 51.26       A
ATOM     48   O   ILE A    5      23.650    8.700  -11.920  1.00 51.09       A
ATOM     49   N   GLU A    6      23.864    7.300  -13.662  1.00 50.54       A
ATOM     50   CA  GLU A    6      23.146    6.214  -13.013  1.00 50.01       A
ATOM     51   CB  GLU A    6      22.789    5.148  -14.043  1.00 50.43       A
ATOM     52   CG  GLU A    6      22.141    5.721  -15.289  1.00 51.26       A
ATOM     53   CD  GLU A    6      22.045    4.703  -16.400  1.00 51.68       A
```

Figure 7C

| | | | | | | | | | | |
|---|---|---|---|---|---|---|---|---|---|---|
| ATOM | 54 | OE1 | GLU | A | 6 | 23.016 | 3.931 | -16.557 | 1.00 52.29 | A |
| ATOM | 55 | OE2 | GLU | A | 6 | 21.019 | 4.682 | -17.116 | 1.00 52.25 | A |
| ATOM | 56 | C | GLU | A | 6 | 23.995 | 5.606 | -11.904 | 1.00 49.32 | A |
| ATOM | 57 | O | GLU | A | 6 | 23.475 | 5.210 | -10.859 | 1.00 49.24 | A |
| ATOM | 58 | N | ASP | A | 7 | 25.302 | 5.527 | -12.129 | 1.00 48.32 | A |
| ATOM | 59 | CA | ASP | A | 7 | 26.178 | 4.970 | -11.113 | 1.00 47.23 | A |
| ATOM | 60 | CB | ASP | A | 7 | 27.543 | 4.626 | -11.703 | 1.00 47.92 | A |
| ATOM | 61 | CG | ASP | A | 7 | 27.450 | 3.585 | -12.788 | 1.00 48.33 | A |
| ATOM | 62 | OD1 | ASP | A | 7 | 26.526 | 2.741 | -12.729 | 1.00 48.43 | A |
| ATOM | 63 | OD2 | ASP | A | 7 | 28.310 | 3.605 | -13.690 | 1.00 48.94 | A |
| ATOM | 64 | C | ASP | A | 7 | 26.344 | 5.920 | -9.926 | 1.00 46.09 | A |
| ATOM | 65 | O | ASP | A | 7 | 26.283 | 5.481 | -8.773 | 1.00 45.71 | A |
| ATOM | 66 | N | LYS | A | 8 | 26.551 | 7.209 | -10.201 | 1.00 44.57 | A |
| ATOM | 67 | CA | LYS | A | 8 | 26.703 | 8.195 | -9.129 | 1.00 43.01 | A |
| ATOM | 68 | CB | LYS | A | 8 | 26.959 | 9.598 | -9.708 | 1.00 43.49 | A |
| ATOM | 69 | CG | LYS | A | 8 | 25.895 | 10.076 | -10.695 | 1.00 44.78 | A |
| ATOM | 70 | CD | LYS | A | 8 | 26.423 | 11.125 | -11.702 | 1.00 45.38 | A |
| ATOM | 71 | CE | LYS | A | 8 | 26.698 | 12.490 | -11.068 | 1.00 45.64 | A |
| ATOM | 72 | NZ | LYS | A | 8 | 27.153 | 13.499 | -12.069 | 1.00 45.55 | A |
| ATOM | 73 | C | LYS | A | 8 | 25.413 | 8.171 | -8.318 | 1.00 41.20 | A |
| ATOM | 74 | O | LYS | A | 8 | 25.419 | 8.346 | -7.098 | 1.00 40.61 | A |
| ATOM | 75 | N | ILE | A | 9 | 24.302 | 7.935 | -9.002 | 1.00 39.40 | A |
| ATOM | 76 | CA | ILE | A | 9 | 23.015 | 7.859 | -8.333 | 1.00 37.29 | A |
| ATOM | 77 | CB | ILE | A | 9 | 21.872 | 7.859 | -9.358 | 1.00 37.14 | A |
| ATOM | 78 | CG2 | ILE | A | 9 | 20.600 | 7.251 | -8.759 | 1.00 37.06 | A |
| ATOM | 79 | CG1 | ILE | A | 9 | 21.631 | 9.303 | -9.812 | 1.00 36.95 | A |
| ATOM | 80 | CD1 | ILE | A | 9 | 20.801 | 9.440 | -11.066 | 1.00 36.89 | A |
| ATOM | 81 | C | ILE | A | 9 | 22.927 | 6.638 | -7.418 | 1.00 36.07 | A |
| ATOM | 82 | O | ILE | A | 9 | 22.450 | 6.756 | -6.292 | 1.00 34.70 | A |
| ATOM | 83 | N | GLU | A | 10 | 23.389 | 5.478 | -7.887 | 1.00 34.23 | A |
| ATOM | 84 | CA | GLU | A | 10 | 23.353 | 4.260 | -7.074 | 1.00 33.04 | A |
| ATOM | 85 | CB | GLU | A | 10 | 23.884 | 3.013 | -7.847 | 1.00 32.87 | A |
| ATOM | 86 | CG | GLU | A | 10 | 23.890 | 1.705 | -6.991 | 1.00 33.10 | A |
| ATOM | 87 | CD | GLU | A | 10 | 24.287 | 0.417 | -7.747 | 1.00 33.56 | A |
| ATOM | 88 | OE1 | GLU | A | 10 | 24.327 | 0.442 | -8.999 | 1.00 34.07 | A |
| ATOM | 89 | OE2 | GLU | A | 10 | 24.542 | -0.630 | -7.084 | 1.00 32.41 | A |
| ATOM | 90 | C | GLU | A | 10 | 24.244 | 4.556 | -5.878 | 1.00 32.53 | A |
| ATOM | 91 | O | GLU | A | 10 | 24.009 | 4.069 | -4.779 | 1.00 32.14 | A |
| ATOM | 92 | N | GLU | A | 11 | 25.259 | 5.380 | -6.100 | 1.00 31.82 | A |
| ATOM | 93 | CA | GLU | A | 11 | 26.165 | 5.731 | -5.018 | 1.00 31.36 | A |
| ATOM | 94 | CB | GLU | A | 11 | 27.409 | 6.445 | -5.536 | 1.00 33.18 | A |
| ATOM | 95 | CG | GLU | A | 11 | 28.358 | 6.833 | -4.423 | 1.00 35.22 | A |
| ATOM | 96 | CD | GLU | A | 11 | 29.105 | 5.643 | -3.822 | 1.00 36.93 | A |
| ATOM | 97 | OE1 | GLU | A | 11 | 28.488 | 4.580 | -3.575 | 1.00 38.03 | A |
| ATOM | 98 | OE2 | GLU | A | 11 | 30.322 | 5.774 | -3.579 | 1.00 38.85 | A |
| ATOM | 99 | C | GLU | A | 11 | 25.456 | 6.621 | -3.998 | 1.00 30.15 | A |
| ATOM | 100 | O | GLU | A | 11 | 25.556 | 6.377 | -2.798 | 1.00 28.89 | A |
| ATOM | 101 | N | ILE | A | 12 | 24.737 | 7.640 | -4.471 | 1.00 29.09 | A |
| ATOM | 102 | CA | ILE | A | 12 | 24.017 | 8.533 | -3.550 | 1.00 28.34 | A |
| ATOM | 103 | CB | ILE | A | 12 | 23.301 | 9.675 | -4.325 | 1.00 28.74 | A |
| ATOM | 104 | CG2 | ILE | A | 12 | 22.206 | 10.281 | -3.501 | 1.00 28.70 | A |
| ATOM | 105 | CG1 | ILE | A | 12 | 24.327 | 10.743 | -4.701 | 1.00 28.84 | A |
| ATOM | 106 | CD1 | ILE | A | 12 | 23.932 | 11.603 | -5.890 | 1.00 29.69 | A |
| ATOM | 107 | C | ILE | A | 12 | 22.985 | 7.725 | -2.761 | 1.00 27.83 | A |
| ATOM | 108 | O | ILE | A | 12 | 22.802 | 7.948 | -1.560 | 1.00 26.46 | A |
| ATOM | 109 | N | GLU | A | 13 | 22.312 | 6.790 | -3.423 | 1.00 27.40 | A |
| ATOM | 110 | CA | GLU | A | 13 | 21.313 | 5.965 | -2.762 | 1.00 26.92 | A |
| ATOM | 111 | CB | GLU | A | 13 | 20.579 | 5.087 | -3.805 | 1.00 28.34 | A |

Figure 7D

| | | | | | | | | | |
|---|---|---|---|---|---|---|---|---|---|
| ATOM | 112 | CG | GLU A | 13 | 19.760 | 5.937 | -4.810 | 1.00 29.72 | A |
| ATOM | 113 | CD | GLU A | 13 | 19.080 | 5.119 | -5.900 | 1.00 31.77 | A |
| ATOM | 114 | OE1 | GLU A | 13 | 19.671 | 4.107 | -6.331 | 1.00 33.64 | A |
| ATOM | 115 | OE2 | GLU A | 13 | 17.960 | 5.495 | -6.327 | 1.00 32.24 | A |
| ATOM | 116 | C | GLU A | 13 | 21.975 | 5.110 | -1.678 | 1.00 26.36 | A |
| ATOM | 117 | O | GLU A | 13 | 21.411 | 4.912 | -0.597 | 1.00 25.75 | A |
| ATOM | 118 | N | SER A | 14 | 23.179 | 4.629 | -1.950 | 1.00 26.17 | A |
| ATOM | 119 | CA | SER A | 14 | 23.899 | 3.792 | -0.999 | 1.00 26.31 | A |
| ATOM | 120 | CB | SER A | 14 | 25.184 | 3.224 | -1.625 | 1.00 26.71 | A |
| ATOM | 121 | OG | SER A | 14 | 25.954 | 2.470 | -0.695 | 1.00 30.07 | A |
| ATOM | 122 | C | SER A | 14 | 24.246 | 4.626 | 0.221 | 1.00 25.81 | A |
| ATOM | 123 | O | SER A | 14 | 24.079 | 4.149 | 1.339 | 1.00 25.13 | A |
| ATOM | 124 | N | LYS A | 15 | 24.753 | 5.840 | 0.009 | 1.00 24.70 | A |
| ATOM | 125 | CA | LYS A | 15 | 25.091 | 6.713 | 1.151 | 1.00 25.41 | A |
| ATOM | 126 | CB | LYS A | 15 | 25.805 | 7.971 | 0.672 | 1.00 26.20 | A |
| ATOM | 127 | CG | LYS A | 15 | 27.256 | 7.762 | 0.285 | 1.00 29.07 | A |
| ATOM | 128 | CD | LYS A | 15 | 27.875 | 9.077 | -0.220 | 1.00 30.97 | A |
| ATOM | 129 | CE | LYS A | 15 | 29.328 | 8.914 | -0.603 | 1.00 32.08 | A |
| ATOM | 130 | NZ | LYS A | 15 | 29.547 | 7.749 | -1.502 | 1.00 34.63 | A |
| ATOM | 131 | C | LYS A | 15 | 23.824 | 7.102 | 1.938 | 1.00 24.45 | A |
| ATOM | 132 | O | LYS A | 15 | 23.862 | 7.279 | 3.171 | 1.00 24.50 | A |
| ATOM | 133 | N | GLN A | 16 | 22.708 | 7.254 | 1.247 | 1.00 24.12 | A |
| ATOM | 134 | CA | GLN A | 16 | 21.450 | 7.586 | 1.904 | 1.00 23.82 | A |
| ATOM | 135 | CB | GLN A | 16 | 20.396 | 7.815 | 0.834 | 1.00 25.71 | A |
| ATOM | 136 | CG | GLN A | 16 | 19.229 | 8.643 | 1.232 | 1.00 29.64 | A |
| ATOM | 137 | CD | GLN A | 16 | 18.543 | 9.230 | 0.004 | 1.00 32.26 | A |
| ATOM | 138 | OE1 | GLN A | 16 | 18.015 | 8.498 | -0.817 | 1.00 34.89 | A |
| ATOM | 139 | NE2 | GLN A | 16 | 18.569 | 10.556 | -0.135 | 1.00 32.74 | A |
| ATOM | 140 | C | GLN A | 16 | 21.027 | 6.447 | 2.838 | 1.00 23.67 | A |
| ATOM | 141 | O | GLN A | 16 | 20.584 | 6.681 | 3.979 | 1.00 22.84 | A |
| ATOM | 142 | N | LYS A | 17 | 21.160 | 5.214 | 2.365 | 1.00 22.83 | A |
| ATOM | 143 | CA | LYS A | 17 | 20.798 | 4.057 | 3.179 | 1.00 22.59 | A |
| ATOM | 144 | CB | LYS A | 17 | 20.939 | 2.756 | 2.357 | 1.00 22.86 | A |
| ATOM | 145 | CG | LYS A | 17 | 20.340 | 1.539 | 3.055 | 1.00 26.69 | A |
| ATOM | 146 | CD | LYS A | 17 | 18.837 | 1.579 | 2.932 | 1.00 29.27 | A |
| ATOM | 147 | CE | LYS A | 17 | 18.177 | 0.937 | 4.051 | 1.00 31.75 | A |
| ATOM | 148 | NZ | LYS A | 17 | 16.686 | 0.870 | 3.940 | 1.00 34.25 | A |
| ATOM | 149 | C | LYS A | 17 | 21.718 | 4.015 | 4.406 | 1.00 22.31 | A |
| ATOM | 150 | O | LYS A | 17 | 21.261 | 3.747 | 5.515 | 1.00 21.02 | A |
| ATOM | 151 | N | LYS A | 18 | 23.001 | 4.306 | 4.223 | 1.00 21.81 | A |
| ATOM | 152 | CA | LYS A | 18 | 23.909 | 4.302 | 5.374 | 1.00 21.74 | A |
| ATOM | 153 | CB | LYS A | 18 | 25.348 | 4.540 | 4.964 | 1.00 24.04 | A |
| ATOM | 154 | CG | LYS A | 18 | 26.029 | 3.321 | 4.401 | 1.00 27.30 | A |
| ATOM | 155 | CD | LYS A | 18 | 27.381 | 3.712 | 3.863 | 1.00 29.23 | A |
| ATOM | 156 | CE | LYS A | 18 | 27.972 | 2.592 | 3.025 | 1.00 30.50 | A |
| ATOM | 157 | NZ | LYS A | 18 | 29.290 | 3.010 | 2.472 | 1.00 33.57 | A |
| ATOM | 158 | C | LYS A | 18 | 23.500 | 5.376 | 6.378 | 1.00 20.62 | A |
| ATOM | 159 | O | LYS A | 18 | 23.565 | 5.138 | 7.577 | 1.00 19.85 | A |
| ATOM | 160 | N | ILE A | 19 | 23.062 | 6.531 | 5.887 | 1.00 19.99 | A |
| ATOM | 161 | CA | ILE A | 19 | 22.655 | 7.636 | 6.762 | 1.00 19.98 | A |
| ATOM | 162 | CB | ILE A | 19 | 22.406 | 8.926 | 5.914 | 1.00 20.09 | A |
| ATOM | 163 | CG2 | ILE A | 19 | 21.554 | 9.944 | 6.682 | 1.00 20.80 | A |
| ATOM | 164 | CG1 | ILE A | 19 | 23.756 | 9.499 | 5.464 | 1.00 21.49 | A |
| ATOM | 165 | CD1 | ILE A | 19 | 23.669 | 10.495 | 4.296 | 1.00 21.18 | A |
| ATOM | 166 | C | ILE A | 19 | 21.400 | 7.221 | 7.517 | 1.00 20.44 | A |
| ATOM | 167 | O | ILE A | 19 | 21.282 | 7.452 | 8.735 | 1.00 20.23 | A |
| ATOM | 168 | N | GLU A | 20 | 20.459 | 6.569 | 6.836 | 1.00 20.24 | A |
| ATOM | 169 | CA | GLU A | 20 | 19.230 | 6.149 | 7.503 | 1.00 20.43 | A |

Figure 7E

| ATOM | 170 | CB  | GLU | A | 20 | 18.223 | 5.608  | 6.484  | 1.00 | 22.94 | A |
|------|-----|-----|-----|---|----|--------|--------|--------|------|-------|---|
| ATOM | 171 | CG  | GLU | A | 20 | 17.766 | 6.671  | 5.499  | 1.00 | 25.51 | A |
| ATOM | 172 | CD  | GLU | A | 20 | 16.926 | 6.108  | 4.378  | 1.00 | 29.04 | A |
| ATOM | 173 | OE1 | GLU | A | 20 | 16.961 | 4.873  | 4.177  | 1.00 | 30.40 | A |
| ATOM | 174 | OE2 | GLU | A | 20 | 16.243 | 6.901  | 3.691  | 1.00 | 30.73 | A |
| ATOM | 175 | C   | GLU | A | 20 | 19.533 | 5.109  | 8.576  | 1.00 | 20.88 | A |
| ATOM | 176 | O   | GLU | A | 20 | 18.917 | 5.127  | 9.645  | 1.00 | 20.23 | A |
| ATOM | 177 | N   | ASN | A | 21 | 20.478 | 4.220  | 8.321  | 1.00 | 20.53 | A |
| ATOM | 178 | CA  | ASN | A | 21 | 20.820 | 3.212  | 9.328  | 1.00 | 21.87 | A |
| ATOM | 179 | CB  | ASN | A | 21 | 21.694 | 2.117  | 8.720  | 1.00 | 24.15 | A |
| ATOM | 180 | CG  | ASN | A | 21 | 20.875 | 1.155  | 7.872  | 1.00 | 25.28 | A |
| ATOM | 181 | OD1 | ASN | A | 21 | 19.676 | 0.980  | 8.099  | 1.00 | 28.26 | A |
| ATOM | 182 | ND2 | ASN | A | 21 | 21.505 | 0.549  | 6.870  | 1.00 | 26.78 | A |
| ATOM | 183 | C   | ASN | A | 21 | 21.500 | 3.854  | 10.527 | 1.00 | 21.75 | A |
| ATOM | 184 | O   | ASN | A | 21 | 21.269 | 3.444  | 11.674 | 1.00 | 21.80 | A |
| ATOM | 185 | N   | GLU | A | 22 | 22.335 | 4.853  | 10.274 | 1.00 | 20.99 | A |
| ATOM | 186 | CA  | GLU | A | 22 | 23.007 | 5.548  | 11.369 | 1.00 | 20.36 | A |
| ATOM | 187 | CB  | GLU | A | 22 | 24.059 | 6.516  | 10.825 | 1.00 | 22.89 | A |
| ATOM | 188 | CG  | GLU | A | 22 | 24.914 | 7.169  | 11.901 | 1.00 | 25.86 | A |
| ATOM | 189 | CD  | GLU | A | 22 | 25.515 | 6.170  | 12.882 | 1.00 | 27.97 | A |
| ATOM | 190 | OE1 | GLU | A | 22 | 26.121 | 5.158  | 12.444 | 1.00 | 30.05 | A |
| ATOM | 191 | OE2 | GLU | A | 22 | 25.376 | 6.411  | 14.118 | 1.00 | 31.29 | A |
| ATOM | 192 | C   | GLU | A | 22 | 21.952 | 6.294  | 12.187 | 1.00 | 19.79 | A |
| ATOM | 193 | O   | GLU | A | 22 | 21.988 | 6.264  | 13.445 | 1.00 | 18.87 | A |
| ATOM | 194 | N   | ILE | A | 23 | 21.003 | 6.951  | 11.518 | 1.00 | 18.92 | A |
| ATOM | 195 | CA  | ILE | A | 23 | 19.955 | 7.670  | 12.254 | 1.00 | 18.60 | A |
| ATOM | 196 | CB  | ILE | A | 23 | 19.012 | 8.388  | 11.244 | 1.00 | 18.79 | A |
| ATOM | 197 | CG2 | ILE | A | 23 | 17.672 | 8.764  | 11.880 | 1.00 | 20.11 | A |
| ATOM | 198 | CG1 | ILE | A | 23 | 19.739 | 9.598  | 10.701 | 1.00 | 20.45 | A |
| ATOM | 199 | CD1 | ILE | A | 23 | 19.060 | 10.223 | 9.539  | 1.00 | 22.51 | A |
| ATOM | 200 | C   | ILE | A | 23 | 19.163 | 6.687  | 13.118 | 1.00 | 19.09 | A |
| ATOM | 201 | O   | ILE | A | 23 | 18.807 | 7.006  | 14.260 | 1.00 | 18.74 | A |
| ATOM | 202 | N   | ALA | A | 24 | 18.903 | 5.479  | 12.617 | 1.00 | 18.44 | A |
| ATOM | 203 | CA  | ALA | A | 24 | 18.153 | 4.517  | 13.420 | 1.00 | 18.86 | A |
| ATOM | 204 | CB  | ALA | A | 24 | 17.824 | 3.257  | 12.573 | 1.00 | 19.39 | A |
| ATOM | 205 | C   | ALA | A | 24 | 18.947 | 4.136  | 14.665 | 1.00 | 18.66 | A |
| ATOM | 206 | O   | ALA | A | 24 | 18.343 | 3.966  | 15.757 | 1.00 | 19.32 | A |
| ATOM | 207 | N   | ARG | A | 25 | 20.272 | 4.028  | 14.548 | 1.00 | 18.57 | A |
| ATOM | 208 | CA  | ARG | A | 25 | 21.111 | 3.667  | 15.709 | 1.00 | 19.19 | A |
| ATOM | 209 | CB  | ARG | A | 25 | 22.552 | 3.343  | 15.287 | 1.00 | 20.85 | A |
| ATOM | 210 | CG  | ARG | A | 25 | 22.674 | 1.959  | 14.627 | 1.00 | 23.87 | A |
| ATOM | 211 | CD  | ARG | A | 25 | 24.108 | 1.536  | 14.429 | 1.00 | 25.32 | A |
| ATOM | 212 | NE  | ARG | A | 25 | 24.759 | 2.294  | 13.376 | 1.00 | 27.13 | A |
| ATOM | 213 | CZ  | ARG | A | 25 | 24.672 | 2.019  | 12.075 | 1.00 | 27.60 | A |
| ATOM | 214 | NH1 | ARG | A | 25 | 23.955 | 0.979  | 11.641 | 1.00 | 28.92 | A |
| ATOM | 215 | NH2 | ARG | A | 25 | 25.296 | 2.806  | 11.214 | 1.00 | 27.79 | A |
| ATOM | 216 | C   | ARG | A | 25 | 21.083 | 4.819  | 16.722 | 1.00 | 18.69 | A |
| ATOM | 217 | O   | ARG | A | 25 | 20.942 | 4.592  | 17.940 | 1.00 | 17.93 | A |
| ATOM | 218 | N   | ILE | A | 26 | 21.201 | 6.041  | 16.221 | 1.00 | 17.83 | A |
| ATOM | 219 | CA  | ILE | A | 26 | 21.184 | 7.222  | 17.080 | 1.00 | 16.94 | A |
| ATOM | 220 | CB  | ILE | A | 26 | 21.369 | 8.479  | 16.225 | 1.00 | 17.99 | A |
| ATOM | 221 | CG2 | ILE | A | 26 | 20.943 | 9.741  | 17.006 | 1.00 | 19.34 | A |
| ATOM | 222 | CG1 | ILE | A | 26 | 22.821 | 8.537  | 15.796 | 1.00 | 19.88 | A |
| ATOM | 223 | CD1 | ILE | A | 26 | 23.144 | 9.567  | 14.721 | 1.00 | 21.83 | A |
| ATOM | 224 | C   | ILE | A | 26 | 19.876 | 7.301  | 17.857 | 1.00 | 18.02 | A |
| ATOM | 225 | O   | ILE | A | 26 | 19.875 | 7.580  | 19.055 | 1.00 | 17.73 | A |
| ATOM | 226 | N   | LYS | A | 27 | 18.752 | 7.069  | 17.191 | 1.00 | 17.60 | A |
| ATOM | 227 | CA  | LYS | A | 27 | 17.450 | 7.137  | 17.853 | 1.00 | 17.90 | A |

Figure 7F

| | | | | | | | | | | |
|---|---|---|---|---|---|---|---|---|---|---|
| ATOM | 228 | CB | LYS | A | 27 | 16.330 | 6.994 | 16.805 | 1.00 19.01 | A |
| ATOM | 229 | CG | LYS | A | 27 | 16.266 | 8.210 | 15.876 | 1.00 22.27 | A |
| ATOM | 230 | CD | LYS | A | 27 | 15.275 | 7.984 | 14.711 | 1.00 24.03 | A |
| ATOM | 231 | CE | LYS | A | 27 | 13.860 | 7.664 | 15.161 | 1.00 24.41 | A |
| ATOM | 232 | NZ | LYS | A | 27 | 13.173 | 8.848 | 15.714 | 1.00 27.04 | A |
| ATOM | 233 | C | LYS | A | 27 | 17.326 | 6.097 | 18.969 | 1.00 18.17 | A |
| ATOM | 234 | O | LYS | A | 27 | 16.767 | 6.388 | 20.013 | 1.00 18.33 | A |
| ATOM | 235 | N | LYS | A | 28 | 17.871 | 4.896 | 18.775 | 1.00 17.00 | A |
| ATOM | 236 | CA | LYS | A | 28 | 17.788 | 3.867 | 19.790 | 1.00 17.21 | A |
| ATOM | 237 | CB | LYS | A | 28 | 18.244 | 2.503 | 19.223 | 1.00 18.92 | A |
| ATOM | 238 | CG | LYS | A | 28 | 17.288 | 1.982 | 18.164 | 1.00 24.56 | A |
| ATOM | 239 | CD | LYS | A | 28 | 17.833 | 0.732 | 17.464 | 1.00 26.88 | A |
| ATOM | 240 | CE | LYS | A | 28 | 16.950 | 0.371 | 16.260 | 1.00 28.84 | A |
| ATOM | 241 | NZ | LYS | A | 28 | 17.284 | -0.938 | 15.592 | 1.00 31.36 | A |
| ATOM | 242 | C | LYS | A | 28 | 18.618 | 4.257 | 21.016 | 1.00 17.36 | A |
| ATOM | 243 | O | LYS | A | 28 | 18.169 | 4.066 | 22.165 | 1.00 17.54 | A |
| ATOM | 244 | N | LEU | A | 29 | 19.794 | 4.835 | 20.793 | 1.00 16.84 | A |
| ATOM | 245 | CA | LEU | A | 29 | 20.642 | 5.234 | 21.912 | 1.00 16.41 | A |
| ATOM | 246 | CB | LEU | A | 29 | 22.077 | 5.529 | 21.453 | 1.00 16.26 | A |
| ATOM | 247 | CG | LEU | A | 29 | 23.050 | 6.048 | 22.515 | 1.00 16.76 | A |
| ATOM | 248 | CD1 | LEU | A | 29 | 23.062 | 5.096 | 23.701 | 1.00 16.47 | A |
| ATOM | 249 | CD2 | LEU | A | 29 | 24.450 | 6.201 | 21.885 | 1.00 17.67 | A |
| ATOM | 250 | C | LEU | A | 29 | 20.023 | 6.429 | 22.606 | 1.00 16.92 | A |
| ATOM | 251 | O | LEU | A | 29 | 20.027 | 6.503 | 23.859 | 1.00 16.36 | A |
| ATOM | 252 | N | LEU | A | 30 | 19.447 | 7.343 | 21.820 | 1.00 15.57 | A |
| ATOM | 253 | CA | LEU | A | 30 | 18.818 | 8.519 | 22.424 | 1.00 15.77 | A |
| ATOM | 254 | CB | LEU | A | 30 | 18.401 | 9.501 | 21.298 | 1.00 15.65 | A |
| ATOM | 255 | CG | LEU | A | 30 | 17.717 | 10.780 | 21.696 | 1.00 17.55 | A |
| ATOM | 256 | CD1 | LEU | A | 30 | 18.557 | 11.504 | 22.722 | 1.00 16.71 | A |
| ATOM | 257 | CD2 | LEU | A | 30 | 17.552 | 11.602 | 20.399 | 1.00 18.10 | A |
| ATOM | 258 | C | LEU | A | 30 | 17.659 | 8.067 | 23.288 | 1.00 16.42 | A |
| ATOM | 259 | O | LEU | A | 30 | 17.466 | 8.604 | 24.399 | 1.00 17.55 | A |
| ATOM | 260 | N | GLN | A | 31 | 16.903 | 7.053 | 22.862 | 1.00 16.79 | A |
| ATOM | 261 | CA | GLN | A | 31 | 15.816 | 6.564 | 23.692 | 1.00 18.13 | A |
| ATOM | 262 | CB | GLN | A | 31 | 14.945 | 5.593 | 22.886 | 1.00 21.45 | A |
| ATOM | 263 | CG | GLN | A | 31 | 14.119 | 6.358 | 21.834 | 1.00 24.92 | A |
| ATOM | 264 | CD | GLN | A | 31 | 13.196 | 7.437 | 22.424 | 1.00 26.81 | A |
| ATOM | 265 | OE1 | GLN | A | 31 | 12.913 | 8.459 | 21.786 | 1.00 28.75 | A |
| ATOM | 266 | NE2 | GLN | A | 31 | 12.713 | 7.207 | 23.648 | 1.00 29.86 | A |
| ATOM | 267 | C | GLN | A | 31 | 16.319 | 5.958 | 25.008 | 1.00 17.24 | A |
| ATOM | 268 | O | GLN | A | 31 | 15.655 | 6.092 | 26.038 | 1.00 17.79 | A |
| ATOM | 269 | N | LEU | A | 32 | 17.494 | 5.307 | 24.987 | 1.00 15.77 | A |
| ATOM | 270 | CA | LEU | A | 32 | 18.070 | 4.755 | 26.209 | 1.00 14.63 | A |
| ATOM | 271 | CB | LEU | A | 32 | 19.314 | 3.932 | 25.911 | 1.00 16.13 | A |
| ATOM | 272 | CG | LEU | A | 32 | 19.015 | 2.574 | 25.275 | 1.00 18.58 | A |
| ATOM | 273 | CD1 | LEU | A | 32 | 20.291 | 1.961 | 24.770 | 1.00 20.70 | A |
| ATOM | 274 | CD2 | LEU | A | 32 | 18.337 | 1.698 | 26.315 | 1.00 22.17 | A |
| ATOM | 275 | C | LEU | A | 32 | 18.449 | 5.895 | 27.140 | 1.00 13.68 | A |
| ATOM | 276 | O | LEU | A | 32 | 18.258 | 5.774 | 28.357 | 1.00 13.31 | A |
| ATOM | 277 | N | THR | A | 33 | 18.980 | 6.991 | 26.600 | 1.00 13.42 | A |
| ATOM | 278 | CA | THR | A | 33 | 19.348 | 8.081 | 27.500 | 1.00 12.96 | A |
| ATOM | 279 | CB | THR | A | 33 | 20.236 | 9.134 | 26.820 | 1.00 13.48 | A |
| ATOM | 280 | OG1 | THR | A | 33 | 19.530 | 9.745 | 25.733 | 1.00 15.60 | A |
| ATOM | 281 | CG2 | THR | A | 33 | 21.567 | 8.508 | 26.358 | 1.00 15.01 | A |
| ATOM | 282 | C | THR | A | 33 | 18.124 | 8.742 | 28.117 | 1.00 13.65 | A |
| ATOM | 283 | O | THR | A | 33 | 18.159 | 9.169 | 29.285 | 1.00 12.67 | A |
| ATOM | 284 | N | VAL | A | 34 | 17.038 | 8.838 | 27.345 | 1.00 13.20 | A |
| ATOM | 285 | CA | VAL | A | 34 | 15.804 | 9.410 | 27.863 | 1.00 13.88 | A |

Figure 7G

| | | | | | | | | | | |
|---|---|---|---|---|---|---|---|---|---|---|
| ATOM | 286 | CB | VAL | A | 34 | 14.708 | 9.498 | 26.773 | 1.00 14.31 | A |
| ATOM | 287 | CG1 | VAL | A | 34 | 13.380 | 9.811 | 27.382 | 1.00 15.35 | A |
| ATOM | 288 | CG2 | VAL | A | 34 | 15.096 | 10.517 | 25.710 | 1.00 15.04 | A |
| ATOM | 289 | C | VAL | A | 34 | 15.326 | 8.526 | 29.041 | 1.00 12.55 | A |
| ATOM | 290 | O | VAL | A | 34 | 14.997 | 9.016 | 30.131 | 1.00 13.43 | A |
| ATOM | 291 | N | TRP | A | 35 | 15.354 | 7.210 | 28.857 | 1.00 13.04 | A |
| ATOM | 292 | CA | TRP | A | 35 | 14.946 | 6.289 | 29.908 | 1.00 13.11 | A |
| ATOM | 293 | CB | TRP | A | 35 | 14.988 | 4.861 | 29.319 | 1.00 14.19 | A |
| ATOM | 294 | CG | TRP | A | 35 | 14.672 | 3.785 | 30.334 | 1.00 15.43 | A |
| ATOM | 295 | CD2 | TRP | A | 35 | 15.610 | 3.101 | 31.191 | 1.00 15.26 | A |
| ATOM | 296 | CE2 | TRP | A | 35 | 14.860 | 2.165 | 31.963 | 1.00 15.57 | A |
| ATOM | 297 | CE3 | TRP | A | 35 | 16.990 | 3.196 | 31.393 | 1.00 15.49 | A |
| ATOM | 298 | CD1 | TRP | A | 35 | 13.454 | 3.258 | 30.609 | 1.00 17.15 | A |
| ATOM | 299 | NE1 | TRP | A | 35 | 13.553 | 2.281 | 31.572 | 1.00 17.80 | A |
| ATOM | 300 | CZ2 | TRP | A | 35 | 15.459 | 1.324 | 32.905 | 1.00 15.31 | A |
| ATOM | 301 | CZ3 | TRP | A | 35 | 17.600 | 2.355 | 32.349 | 1.00 16.17 | A |
| ATOM | 302 | CH2 | TRP | A | 35 | 16.815 | 1.437 | 33.090 | 1.00 14.74 | A |
| ATOM | 303 | C | TRP | A | 35 | 15.869 | 6.429 | 31.141 | 1.00 13.13 | A |
| ATOM | 304 | O | TRP | A | 35 | 15.418 | 6.409 | 32.278 | 1.00 12.76 | A |
| ATOM | 305 | N | GLY | A | 36 | 17.176 | 6.556 | 30.893 | 1.00 12.50 | A |
| ATOM | 306 | CA | GLY | A | 36 | 18.118 | 6.668 | 31.998 | 1.00 12.50 | A |
| ATOM | 307 | C | GLY | A | 36 | 17.887 | 7.936 | 32.817 | 1.00 11.58 | A |
| ATOM | 308 | O | GLY | A | 36 | 17.917 | 7.875 | 34.042 | 1.00 11.70 | A |
| ATOM | 309 | N | ILE | A | 37 | 17.656 | 9.084 | 32.174 | 1.00 11.85 | A |
| ATOM | 310 | CA | ILE | A | 37 | 17.383 | 10.303 | 32.884 | 1.00 11.18 | A |
| ATOM | 311 | CB | ILE | A | 37 | 17.262 | 11.439 | 31.882 | 1.00 11.22 | A |
| ATOM | 312 | CG2 | ILE | A | 37 | 16.680 | 12.660 | 32.600 | 1.00 13.25 | A |
| ATOM | 313 | CG1 | ILE | A | 37 | 18.636 | 11.739 | 31.281 | 1.00 12.70 | A |
| ATOM | 314 | CD1 | ILE | A | 37 | 18.571 | 12.560 | 29.955 | 1.00 13.00 | A |
| ATOM | 315 | C | ILE | A | 37 | 16.082 | 10.105 | 33.703 | 1.00 11.99 | A |
| ATOM | 316 | O | ILE | A | 37 | 16.026 | 10.526 | 34.860 | 1.00 12.24 | A |
| ATOM | 317 | N | LYS | A | 38 | 15.069 | 9.465 | 33.094 | 1.00 11.84 | A |
| ATOM | 318 | CA | LYS | A | 38 | 13.825 | 9.215 | 33.809 | 1.00 13.62 | A |
| ATOM | 319 | CB | LYS | A | 38 | 12.840 | 8.512 | 32.861 | 1.00 15.00 | A |
| ATOM | 320 | CG | LYS | A | 38 | 11.429 | 8.437 | 33.369 | 1.00 17.76 | A |
| ATOM | 321 | CD | LYS | A | 38 | 10.545 | 7.835 | 32.247 | 1.00 20.78 | A |
| ATOM | 322 | CE | LYS | A | 38 | 9.046 | 7.955 | 32.600 | 1.00 25.34 | A |
| ATOM | 323 | NZ | LYS | A | 38 | 8.721 | 7.069 | 33.722 | 1.00 29.03 | A |
| ATOM | 324 | C | LYS | A | 38 | 14.060 | 8.399 | 35.083 | 1.00 12.64 | A |
| ATOM | 325 | O | LYS | A | 38 | 13.490 | 8.724 | 36.163 | 1.00 12.58 | A |
| ATOM | 326 | N | GLN | A | 39 | 14.916 | 7.371 | 35.001 | 1.00 11.99 | A |
| ATOM | 327 | CA | GLN | A | 39 | 15.176 | 6.573 | 36.189 | 1.00 11.84 | A |
| ATOM | 328 | CB | GLN | A | 39 | 16.049 | 5.339 | 35.900 | 1.00 12.90 | A |
| ATOM | 329 | CG | GLN | A | 39 | 15.580 | 4.440 | 34.757 | 1.00 14.71 | A |
| ATOM | 330 | CD | GLN | A | 39 | 14.118 | 4.213 | 34.747 | 1.00 17.73 | A |
| ATOM | 331 | OE1 | GLN | A | 39 | 13.596 | 3.581 | 35.669 | 1.00 22.45 | A |
| ATOM | 332 | NE2 | GLN | A | 39 | 13.420 | 4.701 | 33.701 | 1.00 20.02 | A |
| ATOM | 333 | C | GLN | A | 39 | 15.907 | 7.372 | 37.259 | 1.00 12.24 | A |
| ATOM | 334 | O | GLN | A | 39 | 15.601 | 7.271 | 38.453 | 1.00 12.42 | A |
| ATOM | 335 | N | LEU | A | 40 | 16.883 | 8.195 | 36.854 | 1.00 10.89 | A |
| ATOM | 336 | CA | LEU | A | 40 | 17.632 | 8.980 | 37.853 | 1.00 11.44 | A |
| ATOM | 337 | CB | LEU | A | 40 | 18.860 | 9.648 | 37.198 | 1.00 12.26 | A |
| ATOM | 338 | CG | LEU | A | 40 | 19.827 | 8.591 | 36.625 | 1.00 12.85 | A |
| ATOM | 339 | CD1 | LEU | A | 40 | 21.007 | 9.367 | 36.066 | 1.00 16.06 | A |
| ATOM | 340 | CD2 | LEU | A | 40 | 20.293 | 7.526 | 37.650 | 1.00 17.91 | A |
| ATOM | 341 | C | LEU | A | 40 | 16.763 | 10.046 | 38.497 | 1.00 10.71 | A |
| ATOM | 342 | O | LEU | A | 40 | 16.848 | 10.258 | 39.701 | 1.00 11.30 | A |
| ATOM | 343 | N | GLN | A | 41 | 15.911 | 10.692 | 37.704 | 1.00 11.62 | A |

Figure 7H

| | | | | | | | | | | |
|---|---|---|---|---|---|---|---|---|---|---|
| ATOM | 344 | CA | GLN | A | 41 | 15.038 | 11.695 | 38.322 | 1.00 11.12 | A |
| ATOM | 345 | CB | GLN | A | 41 | 14.241 | 12.447 | 37.257 | 1.00 11.92 | A |
| ATOM | 346 | CG | GLN | A | 41 | 13.250 | 13.381 | 37.845 | 1.00 11.53 | A |
| ATOM | 347 | CD | GLN | A | 41 | 12.230 | 13.933 | 36.838 | 1.00 12.64 | A |
| ATOM | 348 | OE1 | GLN | A | 41 | 11.814 | 13.226 | 35.962 | 1.00 13.16 | A |
| ATOM | 349 | NE2 | GLN | A | 41 | 11.972 | 15.220 | 36.973 | 1.00 13.67 | A |
| ATOM | 350 | C | GLN | A | 41 | 14.081 | 11.031 | 39.332 | 1.00 10.98 | A |
| ATOM | 351 | O | GLN | A | 41 | 13.883 | 11.585 | 40.404 | 1.00 12.39 | A |
| ATOM | 352 | N | ALA | A | 42 | 13.571 | 9.845 | 38.994 | 1.00 12.53 | A |
| ATOM | 353 | CA | ALA | A | 42 | 12.642 | 9.185 | 39.928 | 1.00 12.08 | A |
| ATOM | 354 | CB | ALA | A | 42 | 12.035 | 7.954 | 39.295 | 1.00 13.83 | A |
| ATOM | 355 | C | ALA | A | 42 | 13.383 | 8.856 | 41.218 | 1.00 14.57 | A |
| ATOM | 356 | O | ALA | A | 42 | 12.820 | 8.975 | 42.296 | 1.00 15.73 | A |
| ATOM | 357 | N | ARG | A | 43 | 14.647 | 8.446 | 41.147 | 1.00 13.64 | A |
| ATOM | 358 | CA | ARG | A | 43 | 15.412 | 8.150 | 42.327 | 1.00 16.22 | A |
| ATOM | 359 | CB | ARG | A | 43 | 16.772 | 7.626 | 41.852 | 1.00 18.06 | A |
| ATOM | 360 | CG | ARG | A | 43 | 17.706 | 7.309 | 42.895 | 1.00 22.64 | A |
| ATOM | 361 | CD | ARG | A | 43 | 17.232 | 6.108 | 43.679 | 1.00 25.20 | A |
| ATOM | 362 | NE | ARG | A | 43 | 18.302 | 5.922 | 44.577 | 1.00 27.65 | A |
| ATOM | 363 | CZ | ARG | A | 43 | 18.943 | 4.798 | 44.758 | 1.00 20.75 | A |
| ATOM | 364 | NH1 | ARG | A | 43 | 18.607 | 3.666 | 44.107 | 1.00 24.75 | A |
| ATOM | 365 | NH2 | ARG | A | 43 | 19.983 | 4.899 | 45.516 | 1.00 23.93 | A |
| ATOM | 366 | C | ARG | A | 43 | 15.606 | 9.411 | 43.196 | 1.00 15.07 | A |
| ATOM | 367 | O | ARG | A | 43 | 15.441 | 9.372 | 44.435 | 1.00 17.46 | A |
| ATOM | 368 | N | ILE | A | 44 | 15.930 | 10.529 | 42.553 | 1.00 14.44 | A |
| ATOM | 369 | CA | ILE | A | 44 | 16.181 | 11.794 | 43.242 | 1.00 14.63 | A |
| ATOM | 370 | CB | ILE | A | 44 | 16.801 | 12.854 | 42.280 | 1.00 15.70 | A |
| ATOM | 371 | CG2 | ILE | A | 44 | 16.817 | 14.226 | 42.941 | 1.00 16.89 | A |
| ATOM | 372 | CG1 | ILE | A | 44 | 18.236 | 12.422 | 41.940 | 1.00 16.08 | A |
| ATOM | 373 | CD1 | ILE | A | 44 | 18.765 | 13.127 | 40.739 | 1.00 19.48 | A |
| ATOM | 374 | C | ILE | A | 44 | 14.906 | 12.326 | 43.887 | 1.00 16.35 | A |
| ATOM | 375 | O | ILE | A | 44 | 14.984 | 12.862 | 44.991 | 1.00 19.28 | A |
| ATOM | 376 | N | LEU | A | 45 | 13.747 | 12.150 | 43.258 | 1.00 15.73 | A |
| ATOM | 377 | CA | LEU | A | 45 | 12.515 | 12.682 | 43.883 | 1.00 15.80 | A |
| ATOM | 378 | CB | LEU | A | 45 | 11.505 | 13.032 | 42.801 | 1.00 15.66 | A |
| ATOM | 379 | CG | LEU | A | 45 | 11.867 | 14.181 | 41.878 | 1.00 15.35 | A |
| ATOM | 380 | CD1 | LEU | A | 45 | 10.793 | 14.298 | 40.823 | 1.00 17.27 | A |
| ATOM | 381 | CD2 | LEU | A | 45 | 11.954 | 15.485 | 42.701 | 1.00 18.49 | A |
| ATOM | 382 | C | LEU | A | 45 | 11.903 | 11.710 | 44.867 | 1.00 18.22 | A |
| ATOM | 383 | O | LEU | A | 45 | 11.053 | 12.187 | 45.658 | 1.00 19.14 | A |
| ATOM | 384 | NT | LEU | A | 45 | 12.258 | 10.488 | 44.884 | 1.00 20.39 | A |
| ATOM | 385 | CA | ACE | D | 0 | 10.275 | -0.794 | 28.942 | 1.00 41.14 | B |
| ATOM | 386 | C | ACE | D | 0 | 11.674 | -0.285 | 28.785 | 1.00 40.52 | B |
| ATOM | 387 | O | ACE | D | 0 | 11.905 | 0.677 | 28.016 | 1.00 41.12 | B |
| ATOM | 388 | N | DLY | D | 1 | 12.631 | -0.899 | 29.487 | 1.00 39.74 | B |
| ATOM | 389 | CA | DLY | D | 1 | 13.997 | -0.423 | 29.356 | 1.00 37.31 | B |
| ATOM | 390 | C | DLY | D | 1 | 15.200 | -1.051 | 30.044 | 1.00 35.38 | B |
| ATOM | 391 | O | DLY | D | 1 | 15.133 | -2.044 | 30.785 | 1.00 35.49 | B |
| ATOM | 392 | N | DLA | D | 2 | 16.332 | -0.424 | 29.752 | 1.00 33.19 | B |
| ATOM | 393 | CA | DLA | D | 2 | 17.639 | -0.797 | 30.279 | 1.00 31.99 | B |
| ATOM | 394 | CB | DLA | D | 2 | 18.688 | 0.196 | 29.762 | 1.00 31.34 | B |
| ATOM | 395 | C | DLA | D | 2 | 18.026 | -2.217 | 29.871 | 1.00 31.71 | B |
| ATOM | 396 | O | DLA | D | 2 | 18.511 | -2.982 | 30.647 | 1.00 31.67 | B |
| ATOM | 397 | N | DCS | D | 3 | 17.699 | -2.577 | 28.640 | 1.00 30.76 | B |
| ATOM | 398 | CA | DCS | D | 3 | 18.061 | -3.892 | 28.159 | 1.00 31.11 | B |
| ATOM | 399 | C | DCS | D | 3 | 17.104 | -4.987 | 28.618 | 1.00 31.69 | B |
| ATOM | 400 | O | DCS | D | 3 | 17.531 | -6.020 | 29.111 | 1.00 31.85 | B |
| ATOM | 401 | CB | DCS | D | 3 | 18.128 | -3.876 | 26.638 | 1.00 30.00 | B |

Figure 7I

| ATOM | 402 | SG | DCS | D | 3 | 19.502 | -2.991 | 35.840 | 1.00 | 30.98 | B |
|---|---|---|---|---|---|---|---|---|---|---|---|
| ATOM | 403 | N | DLU | D | 4 | 15.813 | -4.736 | 28.474 | 1.00 | 31.68 | B |
| ATOM | 404 | CA | DLU | D | 4 | 14.782 | -5.702 | 28.834 | 1.00 | 32.07 | B |
| ATOM | 405 | CB | DLU | D | 4 | 13.397 | -5.090 | 28.574 | 1.00 | 33.43 | B |
| ATOM | 406 | CG | DLU | D | 4 | 13.060 | -4.844 | 27.093 | 1.00 | 25.53 | B |
| ATOM | 407 | CD | DLU | D | 4 | 13.663 | -3.568 | 26.500 | 1.00 | 36.29 | B |
| ATOM | 408 | OE1 | DLU | D | 4 | 14.422 | -2.859 | 27.182 | 1.00 | 37.11 | B |
| ATOM | 409 | OE2 | DLU | D | 4 | 13.367 | -3.264 | 25.323 | 1.00 | 37.45 | B |
| ATOM | 410 | C | DLU | D | 4 | 14.875 | -6.180 | 30.276 | 1.00 | 31.86 | B |
| ATOM | 411 | O | DLU | D | 4 | 14.832 | -7.381 | 30.553 | 1.00 | 32.10 | B |
| ATOM | 412 | N | DLA | D | 5 | 15.022 | -5.237 | 31.196 | 1.00 | 30.98 | B |
| ATOM | 413 | CA | DLA | D | 5 | 15.098 | -5.566 | 32.611 | 1.00 | 30.61 | B |
| ATOM | 414 | CB | DLA | D | 5 | 14.984 | -4.296 | 33.406 | 1.00 | 30.83 | B |
| ATOM | 415 | C | DLA | D | 5 | 16.362 | -6.340 | 33.008 | 1.00 | 30.19 | B |
| ATOM | 416 | O | DLA | D | 5 | 16.387 | -7.044 | 34.027 | 1.00 | 30.60 | B |
| ATOM | 417 | N | DRG | D | 6 | 17.418 | -6.202 | 32.216 | 1.00 | 29.09 | B |
| ATOM | 418 | CA | DRG | D | 6 | 18.673 | -6.893 | 32.489 | 1.00 | 28.71 | B |
| ATOM | 419 | CB | DRG | D | 6 | 18.480 | -8.408 | 32.369 | 1.00 | 31.46 | B |
| ATOM | 420 | CG | DRG | D | 6 | 18.169 | -8.847 | 30.969 | 1.00 | 34.88 | B |
| ATOM | 421 | CD | DRG | D | 6 | 19.397 | -8.762 | 30.070 | 1.00 | 37.42 | B |
| ATOM | 422 | NE | DRG | D | 6 | 19.715 | -7.408 | 29.607 | 1.00 | 40.28 | B |
| ATOM | 423 | CZ | DRG | D | 6 | 20.121 | -7.134 | 28.370 | 1.00 | 40.89 | B |
| ATOM | 424 | NH1 | DRG | D | 6 | 20.248 | -8.118 | 27.481 | 1.00 | 42.76 | B |
| ATOM | 425 | NH2 | DRG | D | 6 | 20.409 | -5.891 | 28.015 | 1.00 | 42.55 | B |
| ATOM | 426 | C | DRG | D | 6 | 19.313 | -6.582 | 33.833 | 1.00 | 27.29 | B |
| ATOM | 427 | O | DRG | D | 6 | 19.994 | -7.423 | 34.421 | 1.00 | 27.43 | B |
| ATOM | 428 | N | DIS | D | 7 | 19.100 | -5.379 | 34.342 | 1.00 | 24.49 | B |
| ATOM | 429 | CA | DIS | D | 7 | 19.731 | -5.018 | 35.624 | 1.00 | 22.04 | B |
| ATOM | 430 | CB | DIS | D | 7 | 18.970 | -3.888 | 36.284 | 1.00 | 22.68 | B |
| ATOM | 431 | CG | DIS | D | 7 | 17.655 | -4.321 | 36.854 | 1.00 | 22.88 | B |
| ATOM | 432 | CD2 | DIS | D | 7 | 17.178 | -5.567 | 37.104 | 1.00 | 24.08 | B |
| ATOM | 433 | ND1 | DIS | D | 7 | 16.650 | -3.445 | 37.187 | 1.00 | 25.78 | B |
| ATOM | 434 | CE1 | DIS | D | 7 | 15.595 | -4.134 | 37.608 | 1.00 | 26.45 | B |
| ATOM | 435 | NE2 | DIS | D | 7 | 15.894 | -5.419 | 37.562 | 1.00 | 25.11 | B |
| ATOM | 436 | C | DIS | D | 7 | 21.156 | -4.636 | 35.329 | 1.00 | 21.84 | B |
| ATOM | 437 | O | DIS | D | 7 | 21.412 | -3.743 | 34.536 | 1.00 | 20.32 | B |
| ATOM | 438 | N | DRG | D | 8 | 22.091 | -5.298 | 36.003 | 1.00 | 20.33 | B |
| ATOM | 439 | CA | DRG | D | 8 | 23.494 | -5.122 | 35.778 | 1.00 | 19.80 | B |
| ATOM | 440 | CB | DRG | D | 8 | 24.284 | -5.994 | 36.755 | 1.00 | 20.87 | B |
| ATOM | 441 | CG | DRG | D | 8 | 24.175 | -7.428 | 36.459 | 1.00 | 26.97 | B |
| ATOM | 442 | CD | DRG | D | 8 | 24.743 | -8.207 | 37.631 | 1.00 | 29.07 | B |
| ATOM | 443 | NE | DRG | D | 8 | 24.581 | -9.603 | 37.325 | 1.00 | 31.54 | B |
| ATOM | 444 | CZ | DRG | D | 8 | 25.258 | -10.189 | 36.352 | 1.00 | 31.94 | B |
| ATOM | 445 | NH1 | DRG | D | 8 | 26.139 | -9.485 | 35.658 | 1.00 | 33.88 | B |
| ATOM | 446 | NH2 | DRG | D | 8 | 24.987 | -11.432 | 36.027 | 1.00 | 33.88 | B |
| ATOM | 447 | C | DRG | D | 8 | 23.985 | -3.711 | 35.873 | 1.00 | 17.95 | B |
| ATOM | 448 | O | DRG | D | 8 | 24.856 | -3.361 | 35.124 | 1.00 | 17.42 | B |
| ATOM | 449 | N | DLU | D | 9 | 23.407 | -2.934 | 36.783 | 1.00 | 16.93 | B |
| ATOM | 450 | CA | DLU | D | 9 | 23.900 | -1.578 | 36.951 | 1.00 | 15.49 | B |
| ATOM | 451 | CB | DLU | D | 9 | 23.358 | -0.954 | 38.261 | 1.00 | 16.03 | B |
| ATOM | 452 | CG | DLU | D | 9 | 21.876 | -0.652 | 38.323 | 1.00 | 16.75 | B |
| ATOM | 453 | CD | DLU | D | 9 | 20.996 | -1.816 | 38.786 | 1.00 | 16.82 | B |
| ATOM | 454 | OE1 | DLU | D | 9 | 21.407 | -2.982 | 38.584 | 1.00 | 19.63 | B |
| ATOM | 455 | OE2 | DLU | D | 9 | 19.933 | -1.498 | 39.310 | 1.00 | 20.12 | B |
| ATOM | 456 | C | DLU | D | 9 | 23.601 | -0.717 | 35.747 | 1.00 | 15.97 | B |
| ATOM | 457 | O | DLU | D | 9 | 24.143 | 0.383 | 35.655 | 1.00 | 15.24 | B |
| ATOM | 458 | N | DRP | D | 10 | 22.747 | -1.186 | 34.844 | 1.00 | 15.66 | B |
| ATOM | 459 | CA | DRP | D | 10 | 22.462 | -0.435 | 33.611 | 1.00 | 15.31 | B |

Figure 7J

```
ATOM    460  CE   DRP D  10      20.960   -0.187   33.420  1.00 16.05           B
ATOM    461  CG   DRP D  10      20.354    0.791   34.410  1.00 15.28           B
ATOM    462  CD2  DRP D  10      20.504    2.200   34.384  1.00 15.28           B
ATOM    463  CE2  DRP D  10      19.734    2.730   35.424  1.00 15.74           B
ATOM    464  CE3  DRP D  10      21.237    3.075   33.563  1.00 15.47           B
ATOM    465  CD1  DRP D  10      19.504    0.512   35.449  1.00 16.40           B
ATOM    466  NE1  DRP D  10      19.122    1.676   36.073  1.00 17.22           B
ATOM    467  CZ2  DRP D  10      19.650    4.107   35.666  1.00 15.81           B
ATOM    468  CZ3  DRP D  10      21.174    4.444   33.805  1.00 14.93           B
ATOM    469  CH2  DRP D  10      20.382    4.935   34.850  1.00 15.26           B
ATOM    470  C    DRP D  10      22.000   -1.140   32.376  1.00 17.32           B
ATOM    471  O    DRP D  10      22.790   -0.682   31.244  1.00 16.59           B
ATOM    472  N    DLA D  11      23.744   -2.227   32.572  1.00 17.72           B
ATOM    473  CA   DLA D  11      24.253   -2.940   31.407  1.00 18.88           B
ATOM    474  CB   DLA D  11      25.034   -4.168   31.867  1.00 20.11           B
ATOM    475  C    DLA D  11      25.126   -2.074   30.501  1.00 18.95           B
ATOM    476  O    DLA D  11      25.078   -2.221   29.267  1.00 21.13           B
ATOM    477  N    DRP D  12      25.884   -1.142   31.084  1.00 17.86           B
ATOM    478  CA   DRP D  12      26.759   -0.275   30.317  1.00 17.72           B
ATOM    479  CB   DRP D  12      27.586    0.645   31.239  1.00 18.43           B
ATOM    480  CG   DRP D  12      26.725    1.588   32.059  1.00 16.68           B
ATOM    481  CD2  DRP D  12      26.285    2.900   31.676  1.00 16.49           B
ATOM    482  CE2  DRP D  12      25.459    3.371   32.706  1.00 15.68           B
ATOM    483  CE3  DRP D  12      26.519    3.714   30.561  1.00 17.14           B
ATOM    484  CD1  DRP D  12      26.177    1.335   33.256  1.00 15.60           B
ATOM    485  NE1  DRP D  12      25.402    2.400   33.668  1.00 15.74           B
ATOM    486  CZ2  DRP D  12      24.842    4.628   32.664  1.00 15.78           B
ATOM    487  CZ3  DRP D  12      25.904    4.977   30.525  1.00 17.42           B
ATOM    488  CH2  DRP D  12      25.090    5.406   31.550  1.00 16.81           B
ATOM    489  C    DRP D  12      25.913    0.577   29.346  1.00 18.81           B
ATOM    490  O    DRP D  12      26.347    0.870   28.231  1.00 20.05           B
ATOM    491  N    DEU D  13      24.740    1.020   29.790  1.00 17.43           B
ATOM    492  CA   DEU D  13      23.915    1.866   28.926  1.00 17.59           B
ATOM    493  CB   DEU D  13      22.883    2.647   29.756  1.00 15.97           B
ATOM    494  CG   DEU D  13      21.857    3.489   28.971  1.00 15.31           B
ATOM    495  CD1  DEU D  13      22.559    4.585   28.204  1.00 16.99           B
ATOM    496  CD2  DEU D  13      20.386    4.105   29.936  1.00 16.07           B
ATOM    497  C    DEU D  13      23.265    1.011   27.847  1.00 19.32           B
ATOM    498  O    DEU D  13      23.224    1.429   26.702  1.00 20.12           B
ATOM    499  N    DCS D  14      22.775   -0.180   28.199  1.00 20.93           B
ATOM    500  CA   DCS D  14      22.190   -1.046   27.196  1.00 22.79           B
ATOM    501  C    DCS D  14      23.272   -1.329   26.124  1.00 22.54           B
ATOM    502  O    DCS D  14      22.963   -1.318   24.916  1.00 23.67           B
ATOM    503  CB   DCS D  14      21.675   -2.319   27.874  1.00 23.47           B
ATOM    504  SG   DCS D  14      21.216   -3.669   26.732  1.00 27.91           B
ATOM    505  N    DLA D  15      24.514   -1.568   26.553  1.00 22.47           B
ATOM    506  CA   DLA D  15      25.627   -1.857   25.614  1.00 23.31           B
ATOM    507  CB   DLA D  15      26.868   -2.302   26.401  1.00 24.09           B
ATOM    508  C    DLA D  15      25.987   -0.672   24.717  1.00 24.16           B
ATOM    509  O    DLA D  15      26.511   -0.844   23.614  1.00 25.93           B
ATOM    510  N    DLA D  16      25.723    0.544   25.192  1.00 22.60           B
ATOM    511  CA   DLA D  16      26.017    1.743   24.400  1.00 22.10           B
ATOM    512  CB   DLA D  16      26.006    2.985   25.314  1.00 22.02           B
ATOM    513  C    DLA D  16      24.995    1.932   23.278  1.00 21.95           B
ATOM    514  O    DLA D  16      25.355    2.570   22.256  1.00 22.36           B
ATOM    515  NT   DLA D  16      23.843    1.460   23.410  1.00 23.47           B
ATOM    516  CL-1 CL  I   1      20.914   13.075    1.999  1.00 45.04           I
ATOM    517  OH2  WAT W   1      23.911    6.454  -21.684  1.00 53.50           W
```

Figure 7K

```
ATOM   518  OH2 WAT W    2     30.822   2.444  -19.357  1.00 52.17      W
ATOM   519  OH2 WAT W    3     30.369  13.971  -17.693  1.00 37.33      W
ATOM   520  OH2 WAT W    4     27.699  12.875  -16.588  1.00 46.63      W
ATOM   521  OH2 WAT W    5     23.417   1.727  -13.168  1.00 48.41      W
ATOM   522  OH2 WAT W    6     24.012   1.401  -16.007  1.00 58.65      W
ATOM   523  OH2 WAT W    7     16.572   3.069   -7.418  1.00 36.12      W
ATOM   524  OH2 WAT W    8     32.381  11.029   -8.334  1.00 55.01      W
ATOM   525  OH2 WAT W    9     33.793   7.275  -10.261  1.00 53.14      W
ATOM   526  OH2 WAT W   10     20.318  -0.862  -12.067  1.00 28.89      W
ATOM   527  OH2 WAT W   11     26.434   1.459  -10.129  1.00 43.04      W
ATOM   528  OH2 WAT W   12     27.878   0.323  -12.146  1.00 55.95      W
ATOM   529  OH2 WAT W   13     31.427   0.259  -10.741  1.00 52.47      W
ATOM   530  OH2 WAT W   14     29.889   8.411   -6.889  1.00 56.49      W
ATOM   531  OH2 WAT W   15     22.532   1.843   -4.021  1.00 32.19      W
ATOM   532  OH2 WAT W   16     23.814  -0.534   -4.336  1.00 39.56      W
ATOM   533  OH2 WAT W   17     19.996   1.598   -5.292  1.00 33.28      W
ATOM   534  OH2 WAT W   18     25.262  -3.040   -8.386  1.00 28.37      W
ATOM   535  OH2 WAT W   19     22.556   0.000    0.001  1.00 30.95      W
ATOM   536  OH2 WAT W   20     24.369  -1.421   -1.823  1.00 29.32      W
ATOM   537  OH2 WAT W   21     29.134  -0.583   -6.291  1.00 46.18      W
ATOM   538  OH2 WAT W   22     27.394   2.286   -5.533  1.00 43.67      W
ATOM   539  OH2 WAT W   23     26.774   0.049   -4.387  1.00 45.47      W
ATOM   540  OH2 WAT W   24     30.008   5.236    1.507  1.00 52.80      W
ATOM   541  OH2 WAT W   25     27.776   4.560    0.356  1.00 42.94      W
ATOM   542  OH2 WAT W   26     32.018   6.237    0.261  1.00 53.15      W
ATOM   543  OH2 WAT W   28     18.650   4.426   -0.423  1.00 34.71      W
ATOM   544  OH2 WAT W   29     18.919   1.842   -1.284  1.00 42.23      W
ATOM   545  OH2 WAT W   30     11.826   6.239    7.700  1.00 59.49      W
ATOM   546  OH2 WAT W   31     13.683   5.469    2.919  1.00 52.76      W
ATOM   547  OH2 WAT W   32     16.956   4.594    1.380  1.00 47.84      W
ATOM   548  OH2 WAT W   33     17.260   2.099    7.679  1.00 46.32      W
ATOM   549  OH2 WAT W   34     17.636   1.737   -4.073  1.00 51.94      W
ATOM   550  OH2 WAT W   35     16.221   5.835    9.764  1.00 30.19      W
ATOM   551  OH2 WAT W   36     26.030   8.926    8.979  1.00 51.32      W
ATOM   552  OH2 WAT W   37     13.758   2.898    9.624  1.00 52.05      W
ATOM   553  OH2 WAT W   38     14.899   5.914   11.925  1.00 35.86      W
ATOM   554  OH2 WAT W   39     19.841   0.030   14.724  1.00 45.90      W
ATOM   555  OH2 WAT W   40     13.772   2.335   12.179  1.00 50.60      W
ATOM   556  OH2 WAT W   41     13.367   0.805    6.229  1.00 51.80      W
ATOM   557  OH2 WAT W   42     15.587   3.501   15.845  1.00 30.05      W
ATOM   558  OH2 WAT W   43     14.280   4.098   13.819  1.00 48.74      W
ATOM   559  OH2 WAT W   44     14.273   3.983   18.042  1.00 32.62      W
ATOM   560  OH2 WAT W   45     14.275   2.720   20.720  1.00 40.19      W
ATOM   561  OH2 WAT W   46     21.969   2.228   18.885  1.00 22.32      W
ATOM   562  OH2 WAT W   47     21.588   1.778   21.594  1.00 28.43      W
ATOM   563  OH2 WAT W   48     11.908   3.300   22.023  1.00 50.50      W
ATOM   564  OH2 WAT W   49     13.679   0.626   18.643  1.00 46.64      W
ATOM   565  OH2 WAT W   50     16.369   2.196   22.597  1.00 30.08      W
ATOM   566  OH2 WAT W   51     12.828   6.527   18.634  1.00 37.29      W
ATOM   567  OH2 WAT W   52     24.603   2.631   19.581  1.00 25.55      W
ATOM   568  OH2 WAT W   53     11.867   0.791   23.131  1.00 58.27      W
ATOM   569  OH2 WAT W   54     24.646   5.366   17.812  1.00 50.34      W
ATOM   570  OH2 WAT W   55     20.954   0.091   17.131  1.00 49.14      W
ATOM   571  OH2 WAT W   56     19.747  -0.562   21.394  1.00 36.92      W
ATOM   572  OH2 WAT W   57     14.819   8.442   19.922  1.00 33.61      W
ATOM   573  OH2 WAT W   58     10.854   5.349   19.724  1.00 45.89      W
ATOM   574  OH2 WAT W   59     10.710   9.378   19.376  1.00 37.52      W
ATOM   575  OH2 WAT W   60     10.497  10.303   21.845  1.00 34.96      W
```

Figure 7L

```
ATOM    576  OH2 WAT W   61      12.866    5.691   26.354  1.00  28.86      W
ATOM    577  OH2 WAT W   62      10.758    7.878   25.495  1.00  42.32      W
ATOM    578  OH2 WAT W   63      11.782    6.555   28.773  1.00  29.65      W
ATOM    579  OH2 WAT W   64      10.296    8.472   27.988  1.00  37.31      W
ATOM    580  OH2 WAT W   65      13.316    2.342   26.849  1.00  43.22      W
ATOM    581  OH2 WAT W   66      29.863   -1.693   28.654  1.00  38.41      W
ATOM    582  OH2 WAT W   67      16.468   -1.186   26.444  1.00  32.71      W
ATOM    583  OH2 WAT W   68      20.934   12.065   25.212  1.00  18.68      W
ATOM    584  OH2 WAT W   69       7.101    5.989   26.485  1.00  48.02      W
ATOM    585  OH2 WAT W   70       7.226   10.744   27.574  1.00  33.30      W
ATOM    586  OH2 WAT W   71      16.382   -1.374   34.997  1.00  34.36      W
ATOM    587  OH2 WAT W   72      17.474   -0.717   38.167  1.00  28.82      W
ATOM    588  OH2 WAT W   73      17.984   -2.951   33.186  1.00  27.39      W
ATOM    589  OH2 WAT W   74      16.999    1.929   37.830  1.00  37.09      W
ATOM    590  OH2 WAT W   75      20.595    3.071   39.121  1.00  19.51      W
ATOM    591  OH2 WAT W   76      14.326    5.004   39.584  1.00  20.31      W
ATOM    592  OH2 WAT W   77      11.973    4.544   38.034  1.00  32.93      W
ATOM    593  OH2 WAT W   78      18.317    4.417   39.397  1.00  44.00      W
ATOM    594  OH2 WAT W   79      10.983   -2.804   30.948  1.00  52.39      W
ATOM    595  OH2 WAT W   80      11.064    0.945   32.640  1.00  30.78      W
ATOM    596  OH2 WAT W   81      12.861    0.902   39.566  1.00  51.74      W
ATOM    597  OH2 WAT W   82      14.353   -1.379   39.210  1.00  48.06      W
ATOM    598  OH2 WAT W   83      13.014   -3.417   36.263  1.00  46.54      W
ATOM    599  OH2 WAT W   84      11.101   -2.319   39.669  1.00  61.24      W
ATOM    600  OH2 WAT W   85      20.879   -3.825   31.838  1.00  26.25      W
ATOM    601  OH2 WAT W   86      24.470   -4.753   28.192  1.00  36.86      W
ATOM    602  OH2 WAT W   87      22.117   -5.700   29.831  1.00  38.03      W
ATOM    603  OH2 WAT W   88      19.685    0.721   41.041  1.00  28.21      W
ATOM    604  OH2 WAT W   89      20.274    5.127   40.337  1.00  32.29      W
ATOM    605  OH2 WAT W   90      10.072    4.538   29.943  1.00  33.10      W
ATOM    606  OH2 WAT W   91      10.573    4.216   33.496  1.00  33.22      W
ATOM    607  OH2 WAT W   92      10.336    5.922   36.364  1.00  48.48      W
ATOM    608  OH2 WAT W   93       9.113    5.209   40.333  1.00  51.71      W
ATOM    609  OH2 WAT W   94       9.980    8.713   42.573  1.00  24.98      W
ATOM    610  OH2 WAT W   95      17.708    6.542   -1.798  1.00  36.93      W
ATOM    611  OH2 WAT W   96      10.278   11.397   38.730  1.00  17.13      W
ATOM    612  OH2 WAT W   97      11.290   10.478   36.184  1.00  15.62      W
ATOM    613  OH2 WAT W   98       8.444   12.988   37.395  1.00  17.25      W
ATOM    614  OH2 WAT W   99       8.735    9.911   40.361  1.00  25.18      W
ATOM    615  OH2 WAT W  100       6.665   11.917   35.665  1.00  28.95      W
ATOM    616  OH2 WAT W  101       8.907    9.736   35.113  1.00  28.77      W
ATOM    617  OH2 WAT W  102      10.416    5.919   42.300  1.00  32.80      W
ATOM    618  OH2 WAT W  103       8.278    3.600   38.536  1.00  54.85      W
ATOM    619  OH2 WAT W  104      14.183    7.249   45.734  1.00  23.53      W
ATOM    620  OH2 WAT W  105      11.426    7.965   46.547  1.00  34.68      W
ATOM    621  OH2 WAT W  106      16.907    2.218   41.970  1.00  39.50      W
ATOM    622  OH2 WAT W  107      16.479   14.336   46.761  1.00  23.72      W
ATOM    623  OH2 WAT W  108       8.319   12.931   45.022  1.00  22.11      W
ATOM    624  OH2 WAT W  109       7.189   12.423   42.385  1.00  39.34      W
ATOM    625  OH2 WAT W  110       8.599    9.769   44.603  1.00  40.15      W
ATOM    626  OH2 WAT W  111      26.891   -1.858   33.829  1.00  23.69      W
ATOM    627  OH2 WAT W  112      28.775   -3.310   32.521  1.00  38.13      W
ATOM    628  OH2 WAT W  113      31.335    0.587   33.068  1.00  34.37      W
ATOM    629  OH2 WAT W  114      30.921   -0.919   36.513  1.00  44.24      W
ATOM    630  OH2 WAT W  115      30.098    2.733   29.619  1.00  39.50      W
ATOM    631  OH2 WAT W  116      33.465    2.665   34.521  1.00  52.27      W
ATOM    632  OH2 WAT W  117      25.612   14.159  -18.301  1.00  56.10      W
ATOM    633  OH2 WAT W  118      33.904    2.165  -15.960  1.00  57.70      W
```

Figure 7M

```
ATOM    634  OH2 WAT W 119      33.766    4.315  -14.106  1.00 57.44      W
ATOM    635  OH2 WAT W 120      26.831    7.497    7.075  1.00 40.38      W
ATOM    636  OH2 WAT W 121      26.562    8.206    4.240  1.00 32.00      W
ATOM    637  OH2 WAT W 122      29.081    7.039    3.251  1.00 46.30      W
ATOM    638  OH2 WAT W 123      22.080   -0.975   10.516  1.00 39.31      W
ATOM    639  OH2 WAT W 124      28.185    3.991   13.044  1.00 45.28      W
ATOM    640  OH2 WAT W 125      29.400    7.324   10.996  1.00 52.21      W
ATOM    641  OH2 WAT W 126      12.966    3.595   24.673  1.00 59.42      W
ATOM    642  OH2 WAT W 127       8.932    7.961   36.476  1.00 45.85      W
ATOM    643  OH2 WAT W 128      12.712    5.206   41.719  1.00 38.55      W
ATOM    644  OH2 WAT W 129       9.431   10.564   47.230  1.00 35.27      W
ATOM    645  OH2 WAT W 130       6.643    9.576   45.596  1.00 44.00      W
ATOM    646  OH2 WAT W 131      21.501   13.657   45.856  1.00 43.49      W
ATOM    647  OH2 WAT W 132      19.368   14.112   46.567  1.00 41.15      W
ATOM    648  OH2 WAT W 133      20.913   12.058   48.230  1.00 36.86      W
ATOM    649  OH2 WAT W 134      13.556    4.967   44.137  1.00 49.55      W
ATOM    650  OH2 WAT W 135      17.568    0.000    0.010  1.00 54.94      W
ATOM    651  OH2 WAT W 136      17.847   -0.139   11.093  1.00 42.03      W
ATOM    652  OH2 WAT W 137      25.734    4.074   15.641  1.00 35.36      W
ATOM    653  OH2 WAT W 138       8.107    7.930   38.831  1.00 37.47      W
ATOM    654  OH2 WAT W 139      10.614    4.603   44.378  1.00 61.10      W
ATOM    655  OH2 WAT W 140      14.180   -9.552   32.610  1.00 37.66      W
ATOM    656  OH2 WAT W 141      26.549   -4.072   22.858  1.00 48.05      W
ATOM    657  OH2 WAT W 142      21.688   -2.141   22.847  1.00 36.75      W
ATOM    658  OH2 WAT W 143      15.457    1.462   27.799  1.00 38.11      W
ATOM    659  OH2 WAT W 144      18.956   16.356   45.521  1.00 36.93      W
ATOM    660  OH2 WAT W 145      15.655    2.938   40.183  1.00 40.77      W
ATOM    661  OH2 WAT W 146      15.688   -1.613   19.777  1.00 47.04      W
ATOM    662  OH2 WAT W 147      26.880   -5.627   29.327  1.00 44.89      W
ATOM    663  OH2 WAT W 148      28.682   -5.605   33.707  1.00 43.34      W
ATOM    664  OH2 WAT W 149      28.220   11.179  -23.836  1.00 53.67      W
ATOM    665  OH2 WAT W 150      27.905    3.222   -7.774  1.00 44.54      W
ATOM    666  OH2 WAT W 151      15.403  -11.541   32.995  1.00 47.59      W
TER
END
```

Figure 7N

Inhibition of HIV-1 Membrane Fusion by a D-Peptide

Syncytia Assay with no D-peptide

Syncytia Assay with [100 µM] peptide

NMR Characterization of Aromatic Residues in IQN17/D-Peptide Complexes

D10pep3
D10pep4
D10pep5a
D10pep6
D10pep7a
D10pep10
D10pep12

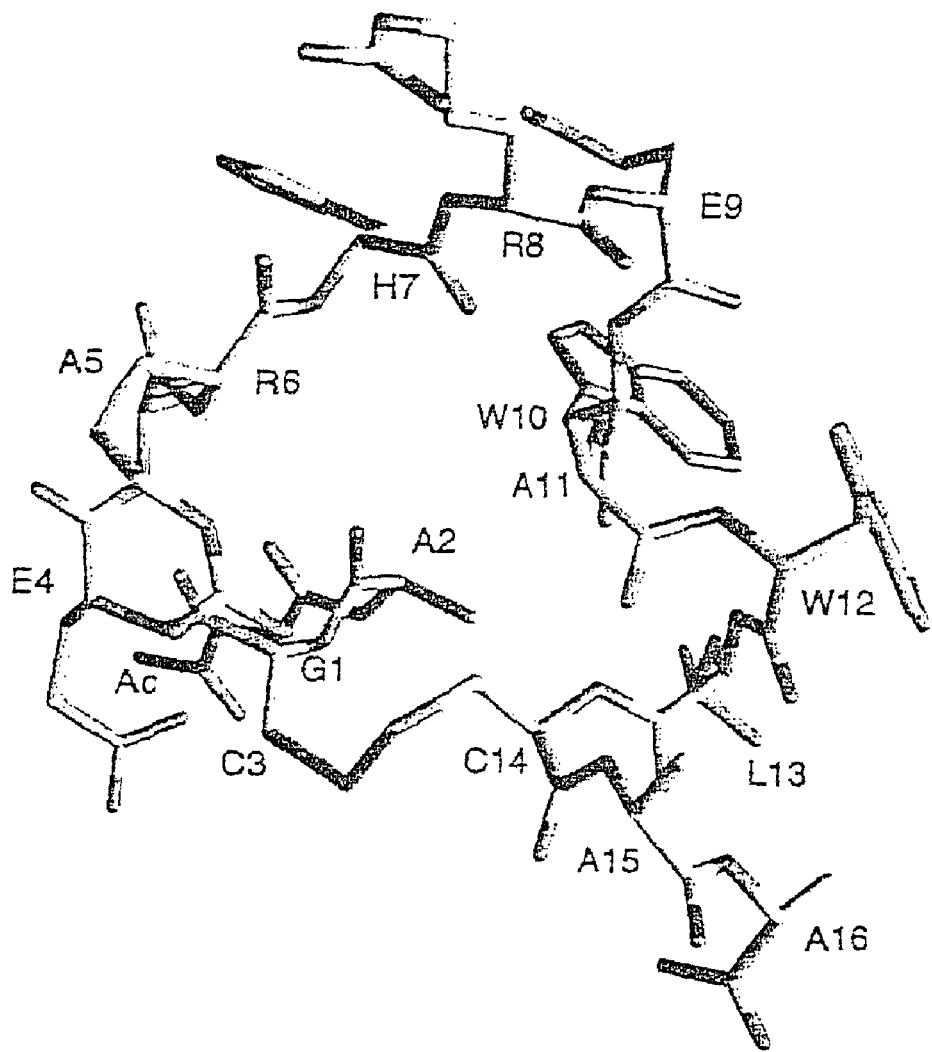
Figure 10: Conformation of D10pep1 in complex with IQN17

```
CRYST1   57.935  121.959   73.669  90.00  90.00  90.00 C2221         1
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.017261  0.000000  0.000000        0.00000
SCALE2      0.000000  0.008199  0.000000        0.00000
SCALE3      0.000000  0.000000  0.013574        0.00000
ATOM      1  CA  ACE A   0      25.795  17.140  37.286  1.00 61.88           A
ATOM      2  C   ACE A   0      25.799  18.376  36.435  1.00 62.00           A
ATOM      3  O   ACE A   0      25.500  19.475  36.921  1.00 62.10           A
ATOM      4  N   ARG A   1      26.134  18.217  35.157  1.00 60.34           A
ATOM      5  CA  ARG A   1      26.203  19.328  34.217  1.00 60.56           A
ATOM      6  CB  ARG A   1      27.212  18.993  33.110  1.00 61.87           A
ATOM      7  CG  ARG A   1      27.630  20.135  32.212  1.00 60.78           A
ATOM      8  CD  ARG A   1      28.500  19.587  31.097  1.00 64.25           A
ATOM      9  NE  ARG A   1      29.018  20.628  30.217  1.00 65.07           A
ATOM     10  CZ  ARG A   1      29.706  20.377  29.109  1.00 63.90           A
ATOM     11  NH1 ARG A   1      29.951  19.124  28.766  1.00 64.20           A
ATOM     12  NH2 ARG A   1      30.157  21.367  28.351  1.00 63.51           A
ATOM     13  C   ARG A   1      24.823  19.573  33.595  1.00 59.45           A
ATOM     14  O   ARG A   1      24.453  20.714  33.294  1.00 57.69           A
ATOM     15  N   MET A   2      24.065  18.494  33.425  1.00 57.60           A
ATOM     16  CA  MET A   2      22.736  18.573  32.836  1.00 59.85           A
ATOM     17  CB  MET A   2      22.273  17.198  32.397  1.00 59.85           A
ATOM     18  CG  MET A   2      21.204  17.251  31.342  1.00 63.56           A
ATOM     19  SD  MET A   2      20.044  15.905  31.454  1.00 67.77           A
ATOM     20  CE  MET A   2      19.089  16.438  32.857  1.00 66.61           A
ATOM     21  C   MET A   2      21.723  19.130  33.834  1.00 61.33           A
ATOM     22  O   MET A   2      20.543  19.276  33.521  1.00 59.97           A
ATOM     23  N   LYS A   3      22.200  19.417  35.041  1.00 62.71           A
ATOM     24  CA  LYS A   3      21.373  19.961  36.107  1.00 63.07           A
ATOM     25  CB  LYS A   3      21.817  19.361  37.449  1.00 64.25           A
ATOM     26  CG  LYS A   3      20.982  19.721  38.687  1.00 64.89           A
ATOM     27  CD  LYS A   3      21.195  21.159  39.160  1.00 64.67           A
ATOM     28  CE  LYS A   3      20.543  21.405  40.525  1.00 64.66           A
ATOM     29  NZ  LYS A   3      19.077  21.123  40.548  1.00 63.04           A
ATOM     30  C   LYS A   3      21.599  21.467  36.062  1.00 64.55           A
ATOM     31  O   LYS A   3      20.639  22.245  36.032  1.00 64.65           A
ATOM     32  N   GLN A   4      22.869  21.873  36.036  1.00 64.34           A
ATOM     33  CA  GLN A   4      23.232  23.289  35.952  1.00 65.46           A
ATOM     34  CB  GLN A   4      24.746  23.447  35.780  1.00 67.71           A
ATOM     35  CG  GLN A   4      25.552  22.954  36.963  1.00 71.16           A
ATOM     36  CD  GLN A   4      25.297  23.771  38.212  1.00 75.19           A
ATOM     37  OE1 GLN A   4      25.618  24.962  38.269  1.00 77.70           A
ATOM     38  NE2 GLN A   4      24.706  23.135  39.225  1.00 76.77           A
ATOM     39  C   GLN A   4      22.508  23.928  34.758  1.00 64.11           A
ATOM     40  O   GLN A   4      22.191  25.128  34.776  1.00 62.08           A
ATOM     41  N   ILE A   5      22.260  23.120  33.726  1.00 59.80           A
ATOM     42  CA  ILE A   5      21.540  23.587  32.552  1.00 58.22           A
ATOM     43  CB  ILE A   5      21.567  22.558  31.398  1.00 56.85           A
ATOM     44  CG2 ILE A   5      20.438  22.851  30.416  1.00 53.92           A
ATOM     45  CG1 ILE A   5      22.942  22.562  30.719  1.00 56.47           A
ATOM     46  CD1 ILE A   5      23.079  21.524  29.614  1.00 59.50           A
ATOM     47  C   ILE A   5      20.083  23.828  32.929  1.00 58.98           A
ATOM     48  O   ILE A   5      19.575  24.928  32.729  1.00 58.48           A
ATOM     49  N   GLU A   6      19.424  22.796  33.472  1.00 59.29           A
ATOM     50  CA  GLU A   6      18.013  22.883  33.877  1.00 56.51           A
ATOM     51  CB  GLU A   6      17.528  21.537  34.448  1.00 55.59           A
```

Figure 11A

```
ATOM     52  CG  GLU A    6      17.636  20.359  33.480  1.00 56.46           A
ATOM     53  CD  GLU A    6      17.293  19.009  34.119  1.00 56.33           A
ATOM     54  OE1 GLU A    6      17.702  18.790  35.278  1.00 53.43           A
ATOM     55  OE2 GLU A    6      16.544  18.157  33.458  1.00 55.03           A
ATOM     56  C   GLU A    6      17.873  23.977  34.926  1.00 54.87           A
ATOM     57  O   GLU A    6      16.793  24.509  35.137  1.00 52.82           A
ATOM     58  N   ASP A    7      18.986  24.300  35.572  1.00 55.62           A
ATOM     59  CA  ASP A    7      19.039  25.336  36.597  1.00 56.65           A
ATOM     60  CB  ASP A    7      20.291  25.162  37.451  1.00 57.46           A
ATOM     61  CG  ASP A    7      20.010  24.471  38.762  1.00 57.37           A
ATOM     62  OD1 ASP A    7      19.180  23.534  38.775  1.00 53.78           A
ATOM     63  OD2 ASP A    7      20.637  24.862  39.771  1.00 57.66           A
ATOM     64  C   ASP A    7      19.034  26.745  36.041  1.00 56.99           A
ATOM     65  O   ASP A    7      18.516  27.662  36.678  1.00 55.43           A
ATOM     66  N   LYS A    8      19.632  26.945  34.873  1.00 58.30           A
ATOM     67  CA  LYS A    8      19.642  28.290  34.312  1.00 59.87           A
ATOM     68  CB  LYS A    8      20.971  28.599  33.612  1.00 62.61           A
ATOM     69  CG  LYS A    8      22.203  28.372  34.487  1.00 66.85           A
ATOM     70  CD  LYS A    8      23.232  29.498  34.357  1.00 70.21           A
ATOM     71  CE  LYS A    8      22.915  30.676  35.293  1.00 72.00           A
ATOM     72  NZ  LYS A    8      21.583  31.323  35.091  1.00 72.05           A
ATOM     73  C   LYS A    8      18.467  28.481  33.354  1.00 58.08           A
ATOM     74  O   LYS A    8      18.145  29.609  32.969  1.00 56.44           A
ATOM     75  N   ILE A    9      17.835  27.376  32.967  1.00 55.29           A
ATOM     76  CA  ILE A    9      16.668  27.436  32.099  1.00 56.69           A
ATOM     77  CB  ILE A    9      16.325  26.052  31.486  1.00 54.89           A
ATOM     78  CG2 ILE A    9      14.892  26.067  30.915  1.00 54.20           A
ATOM     79  CG1 ILE A    9      17.373  25.676  30.423  1.00 55.96           A
ATOM     80  CD1 ILE A    9      17.131  24.339  29.717  1.00 54.22           A
ATOM     81  C   ILE A    9      15.526  27.876  33.018  1.00 57.98           A
ATOM     82  O   ILE A    9      14.603  28.572  32.616  1.00 55.85           A
ATOM     83  N   GLU A   10      15.626  27.458  34.271  1.00 59.96           A
ATOM     84  CA  GLU A   10      14.641  27.788  35.283  1.00 61.12           A
ATOM     85  CB  GLU A   10      14.850  26.901  36.510  1.00 63.01           A
ATOM     86  CG  GLU A   10      13.846  27.117  37.618  1.00 66.89           A
ATOM     87  CD  GLU A   10      14.387  26.672  38.955  1.00 68.37           A
ATOM     88  OE1 GLU A   10      14.844  25.510  39.054  1.00 67.70           A
ATOM     89  OE2 GLU A   10      14.355  27.487  39.903  1.00 68.42           A
ATOM     90  C   GLU A   10      14.872  29.243  35.664  1.00 59.41           A
ATOM     91  O   GLU A   10      13.947  29.958  36.037  1.00 59.95           A
ATOM     92  N   GLU A   11      16.127  29.663  35.565  1.00 57.16           A
ATOM     93  CA  GLU A   11      16.524  31.024  35.893  1.00 55.88           A
ATOM     94  CB  GLU A   11      18.042  31.095  36.019  1.00 58.17           A
ATOM     95  CG  GLU A   11      18.569  32.375  36.627  1.00 62.73           A
ATOM     96  CD  GLU A   11      18.459  32.382  38.139  1.00 67.75           A
ATOM     97  OE1 GLU A   11      19.101  31.512  38.782  1.00 67.91           A
ATOM     98  OE2 GLU A   11      17.736  33.249  38.681  1.00 68.94           A
ATOM     99  C   GLU A   11      16.056  31.976  34.789  1.00 54.76           A
ATOM    100  O   GLU A   11      15.805  33.160  35.030  1.00 54.78           A
ATOM    101  N   ILE A   12      15.945  31.443  33.575  1.00 52.61           A
ATOM    102  CA  ILE A   12      15.510  32.210  32.414  1.00 50.09           A
ATOM    103  CB  ILE A   12      16.002  31.548  31.096  1.00 50.23           A
ATOM    104  CG2 ILE A   12      15.201  32.073  29.905  1.00 48.54           A
ATOM    105  CG1 ILE A   12      17.508  31.773  30.930  1.00 50.30           A
ATOM    106  CD1 ILE A   12      18.114  31.062  29.724  1.00 53.10           A
ATOM    107  C   ILE A   12      13.988  32.324  32.362  1.00 49.83           A
ATOM    108  O   ILE A   12      13.447  33.376  32.017  1.00 47.70           A
ATOM    109  N   GLU A   13      13.306  31.232  32.698  1.00 48.57           A
ATOM    110  CA  GLU A   13      11.849  31.219  32.677  1.00 48.22           A
ATOM    111  CB  GLU A   13      11.320  29.810  32.954  1.00 45.44           A
```

Figure 11B

```
ATOM    112  CG   GLU A   13      11.673  28.794  31.895  1.00 46.65          A
ATOM    113  CD   GLU A   13      11.419  27.372  32.358  1.00 49.90          A
ATOM    114  OE1  GLU A   13      12.051  26.968  33.366  1.00 49.96          A
ATOM    115  OE2  GLU A   13      10.599  26.665  31.720  1.00 50.18          A
ATOM    116  C    GLU A   13      11.357  32.163  33.749  1.00 47.83          A
ATOM    117  O    GLU A   13      10.279  32.731  33.638  1.00 48.72          A
ATOM    118  N    SER A   14      12.168  32.313  34.786  1.00 48.67          A
ATOM    119  CA   SER A   14      11.862  33.187  35.907  1.00 49.89          A
ATOM    120  CB   SER A   14      12.906  32.985  37.014  1.00 49.05          A
ATOM    121  OG   SER A   14      12.634  33.773  38.160  1.00 49.35          A
ATOM    122  C    SER A   14      11.885  34.627  35.415  1.00 50.52          A
ATOM    123  O    SER A   14      10.869  35.313  35.431  1.00 54.15          A
ATOM    124  N    LYS A   15      13.056  35.067  34.971  1.00 49.27          A
ATOM    125  CA   LYS A   15      13.248  36.416  34.474  1.00 51.02          A
ATOM    126  CB   LYS A   15      14.707  36.589  34.042  1.00 54.30          A
ATOM    127  CG   LYS A   15      15.018  37.931  33.417  1.00 58.79          A
ATOM    128  CD   LYS A   15      14.843  39.039  34.437  1.00 63.42          A
ATOM    129  CE   LYS A   15      15.841  38.880  35.576  1.00 65.66          A
ATOM    130  NZ   LYS A   15      15.722  39.983  36.569  1.00 68.14          A
ATOM    131  C    LYS A   15      12.313  36.758  33.305  1.00 50.99          A
ATOM    132  O    LYS A   15      12.022  37.926  33.061  1.00 49.62          A
ATOM    133  N    GLN A   16      11.848  35.740  32.587  1.00 50.06          A
ATOM    134  CA   GLN A   16      10.965  35.937  31.444  1.00 49.96          A
ATOM    135  CB   GLN A   16      10.950  34.684  30.570  1.00 49.89          A
ATOM    136  CG   GLN A   16      10.133  34.810  29.286  1.00 50.59          A
ATOM    137  CD   GLN A   16      10.287  33.603  28.369  1.00 54.27          A
ATOM    138  OE1  GLN A   16       9.799  32.511  28.667  1.00 56.28          A
ATOM    139  NE2  GLN A   16      10.985  33.796  27.250  1.00 54.69          A
ATOM    140  C    GLN A   16       9.551  36.256  31.899  1.00 50.61          A
ATOM    141  O    GLN A   16       8.788  36.931  31.195  1.00 48.56          A
ATOM    142  N    LYS A   17       9.198  35.736  33.067  1.00 49.38          A
ATOM    143  CA   LYS A   17       7.883  35.973  33.623  1.00 49.73          A
ATOM    144  CB   LYS A   17       7.582  34.982  34.750  1.00 52.97          A
ATOM    145  CG   LYS A   17       6.250  35.226  35.448  1.00 56.86          A
ATOM    146  CD   LYS A   17       6.066  34.276  36.618  1.00 59.31          A
ATOM    147  CE   LYS A   17       4.763  34.552  37.354  1.00 59.95          A
ATOM    148  NZ   LYS A   17       4.592  33.621  38.506  1.00 62.05          A
ATOM    149  C    LYS A   17       7.927  37.390  34.163  1.00 48.25          A
ATOM    150  O    LYS A   17       6.977  38.144  34.008  1.00 47.73          A
ATOM    151  N    LYS A   18       9.043  37.750  34.791  1.00 45.58          A
ATOM    152  CA   LYS A   18       9.190  39.101  35.309  1.00 45.26          A
ATOM    153  CB   LYS A   18      10.523  39.270  36.047  1.00 47.34          A
ATOM    154  CG   LYS A   18      10.627  38.493  37.362  1.00 50.10          A
ATOM    155  CD   LYS A   18      11.831  38.976  38.168  1.00 52.93          A
ATOM    156  CE   LYS A   18      11.869  38.358  39.550  1.00 55.07          A
ATOM    157  NZ   LYS A   18      12.933  38.968  40.398  1.00 59.20          A
ATOM    158  C    LYS A   18       9.107  40.110  34.171  1.00 41.59          A
ATOM    159  O    LYS A   18       8.585  41.206  34.349  1.00 42.70          A
ATOM    160  N    ILE A   19       9.633  39.740  33.008  1.00 40.25          A
ATOM    161  CA   ILE A   19       9.605  40.595  31.831  1.00 39.53          A
ATOM    162  CB   ILE A   19      10.494  40.015  30.710  1.00 42.08          A
ATOM    163  CG2  ILE A   19      10.133  40.631  29.369  1.00 41.71          A
ATOM    164  CG1  ILE A   19      11.969  40.214  31.074  1.00 42.52          A
ATOM    165  CD1  ILE A   19      12.939  39.656  30.039  1.00 43.29          A
ATOM    166  C    ILE A   19       8.172  40.725  31.325  1.00 39.27          A
ATOM    167  O    ILE A   19       7.751  41.790  30.899  1.00 37.81          A
ATOM    168  N    GLU A   20       7.421  39.637  31.372  1.00 39.00          A
ATOM    169  CA   GLU A   20       6.036  39.692  30.930  1.00 40.27          A
ATOM    170  CB   GLU A   20       5.437  38.280  30.834  1.00 43.21          A
ATOM    171  CG   GLU A   20       5.898  37.474  29.606  1.00 48.10          A
```

Figure 11C

| | | | | | | | | | | |
|---|---|---|---|---|---|---|---|---|---|---|
| ATOM | 172 | CD | GLU | A | 20 | 5.446 | 36.019 | 29.659 | 1.00 50.57 | A |
| ATOM | 173 | OE1 | GLU | A | 20 | 5.832 | 35.316 | 30.617 | 1.00 52.42 | A |
| ATOM | 174 | OE2 | GLU | A | 20 | 4.708 | 35.575 | 28.752 | 1.00 52.16 | A |
| ATOM | 175 | C | GLU | A | 20 | 5.195 | 40.546 | 31.873 | 1.00 40.09 | A |
| ATOM | 176 | O | GLU | A | 20 | 4.148 | 41.056 | 31.480 | 1.00 40.96 | A |
| ATOM | 177 | N | ASN | A | 21 | 5.637 | 40.694 | 33.119 | 1.00 38.83 | A |
| ATOM | 178 | CA | ASN | A | 21 | 4.880 | 41.498 | 34.071 | 1.00 40.69 | A |
| ATOM | 179 | CB | ASN | A | 21 | 5.216 | 41.107 | 35.507 | 1.00 39.42 | A |
| ATOM | 180 | CG | ASN | A | 21 | 4.616 | 39.766 | 35.892 | 1.00 41.35 | A |
| ATOM | 181 | OD1 | ASN | A | 21 | 3.905 | 39.151 | 35.102 | 1.00 38.98 | A |
| ATOM | 182 | ND2 | ASN | A | 21 | 4.902 | 39.312 | 37.107 | 1.00 40.82 | A |
| ATOM | 183 | C | ASN | A | 21 | 5.163 | 42.958 | 33.846 | 1.00 42.25 | A |
| ATOM | 184 | O | ASN | A | 21 | 4.261 | 43.801 | 33.872 | 1.00 42.61 | A |
| ATOM | 185 | N | GLU | A | 22 | 6.432 | 43.244 | 33.602 | 1.00 41.94 | A |
| ATOM | 186 | CA | GLU | A | 22 | 6.893 | 44.589 | 33.343 | 1.00 41.44 | A |
| ATOM | 187 | CB | GLU | A | 22 | 8.403 | 44.563 | 33.127 | 1.00 43.01 | A |
| ATOM | 188 | CG | GLU | A | 22 | 9.126 | 45.861 | 33.421 | 1.00 49.75 | A |
| ATOM | 189 | CD | GLU | A | 22 | 9.769 | 45.872 | 34.802 | 1.00 52.80 | A |
| ATOM | 190 | OE1 | GLU | A | 22 | 10.611 | 44.988 | 35.077 | 1.00 53.66 | A |
| ATOM | 191 | OE2 | GLU | A | 22 | 9.447 | 46.764 | 35.608 | 1.00 57.41 | A |
| ATOM | 192 | C | GLU | A | 22 | 6.188 | 45.082 | 32.068 | 1.00 41.34 | A |
| ATOM | 193 | O | GLU | A | 22 | 5.851 | 46.263 | 31.954 | 1.00 43.52 | A |
| ATOM | 194 | N | ILE | A | 23 | 5.964 | 44.175 | 31.116 | 1.00 37.55 | A |
| ATOM | 195 | CA | ILE | A | 23 | 5.295 | 44.530 | 29.863 | 1.00 35.10 | A |
| ATOM | 196 | CB | ILE | A | 23 | 5.418 | 43.408 | 28.800 | 1.00 36.19 | A |
| ATOM | 197 | CG2 | ILE | A | 23 | 4.520 | 43.719 | 27.592 | 1.00 35.94 | A |
| ATOM | 198 | CG1 | ILE | A | 23 | 6.876 | 43.288 | 28.340 | 1.00 39.18 | A |
| ATOM | 199 | CD1 | ILE | A | 23 | 7.122 | 42.193 | 27.324 | 1.00 40.80 | A |
| ATOM | 200 | C | ILE | A | 23 | 3.816 | 44.827 | 30.093 | 1.00 33.36 | A |
| ATOM | 201 | O | ILE | A | 23 | 3.284 | 45.796 | 29.568 | 1.00 28.55 | A |
| ATOM | 202 | N | ALA | A | 24 | 3.167 | 43.981 | 30.881 | 1.00 30.41 | A |
| ATOM | 203 | CA | ALA | A | 24 | 1.760 | 44.147 | 31.179 | 1.00 30.11 | A |
| ATOM | 204 | CB | ALA | A | 24 | 1.276 | 42.994 | 32.043 | 1.00 27.29 | A |
| ATOM | 205 | C | ALA | A | 24 | 1.531 | 45.479 | 31.893 | 1.00 31.41 | A |
| ATOM | 206 | O | ALA | A | 24 | 0.562 | 46.183 | 31.608 | 1.00 31.49 | A |
| ATOM | 207 | N | ARG | A | 25 | 2.428 | 45.825 | 32.816 | 1.00 30.94 | A |
| ATOM | 208 | CA | ARG | A | 25 | 2.297 | 47.070 | 33.547 | 1.00 30.44 | A |
| ATOM | 209 | CB | ARG | A | 25 | 3.197 | 47.066 | 34.798 | 1.00 32.01 | A |
| ATOM | 210 | CG | ARG | A | 25 | 2.727 | 46.101 | 35.894 | 1.00 34.49 | A |
| ATOM | 211 | CD | ARG | A | 25 | 3.471 | 46.326 | 37.218 | 1.00 39.65 | A |
| ATOM | 212 | NE | ARG | A | 25 | 4.873 | 45.907 | 37.177 | 1.00 40.74 | A |
| ATOM | 213 | CZ | ARG | A | 25 | 5.308 | 44.687 | 37.496 | 1.00 43.06 | A |
| ATOM | 214 | NH1 | ARG | A | 25 | 4.453 | 43.749 | 37.885 | 1.00 39.85 | A |
| ATOM | 215 | NH2 | ARG | A | 25 | 6.606 | 44.399 | 37.399 | 1.00 40.30 | A |
| ATOM | 216 | C | ARG | A | 25 | 2.590 | 48.270 | 32.651 | 1.00 28.86 | A |
| ATOM | 217 | O | ARG | A | 25 | 1.907 | 49.296 | 32.728 | 1.00 29.35 | A |
| ATOM | 218 | N | ILE | A | 26 | 3.567 | 48.147 | 31.790 | 1.00 26.96 | A |
| ATOM | 219 | CA | ILE | A | 26 | 3.917 | 49.226 | 30.875 | 1.00 29.07 | A |
| ATOM | 220 | CB | ILE | A | 26 | 5.132 | 48.832 | 29.990 | 1.00 28.43 | A |
| ATOM | 221 | CG2 | ILE | A | 26 | 5.239 | 49.760 | 28.799 | 1.00 25.38 | A |
| ATOM | 222 | CG1 | ILE | A | 26 | 6.414 | 48.835 | 30.839 | 1.00 28.70 | A |
| ATOM | 223 | CD1 | ILE | A | 26 | 7.646 | 48.257 | 30.132 | 1.00 27.77 | A |
| ATOM | 224 | C | ILE | A | 26 | 2.719 | 49.571 | 29.968 | 1.00 30.92 | A |
| ATOM | 225 | O | ILE | A | 26 | 2.435 | 50.746 | 29.690 | 1.00 32.33 | A |
| ATOM | 226 | N | LYS | A | 27 | 2.019 | 48.540 | 29.512 | 1.00 30.36 | A |
| ATOM | 227 | CA | LYS | A | 27 | 0.887 | 48.730 | 28.627 | 1.00 30.40 | A |
| ATOM | 228 | CB | LYS | A | 27 | 0.449 | 47.388 | 28.045 | 1.00 33.83 | A |
| ATOM | 229 | CG | LYS | A | 27 | 1.520 | 46.729 | 27.185 | 1.00 39.64 | A |
| ATOM | 230 | CD | LYS | A | 27 | 1.167 | 45.294 | 26.831 | 1.00 44.41 | A |
| ATOM | 231 | CE | LYS | A | 27 | -0.086 | 45.204 | 26.003 | 1.00 46.84 | A |

Figure 11D

| | | | | | | | | | |
|---|---|---|---|---|---|---|---|---|---|
| ATOM | 232 | NZ | LYS A | 27 | -0.384 | 43.774 | 25.698 | 1.00 53.94 | A |
| ATOM | 233 | C | LYS A | 27 | -0.267 | 49.402 | 29.344 | 1.00 28.67 | A |
| ATOM | 234 | O | LYS A | 27 | -0.919 | 50.252 | 28.767 | 1.00 26.05 | A |
| ATOM | 235 | N | LYS A | 28 | -0.511 | 49.020 | 30.593 | 1.00 27.68 | A |
| ATOM | 236 | CA | LYS A | 28 | -1.597 | 49.609 | 31.371 | 1.00 27.30 | A |
| ATOM | 237 | CB | LYS A | 28 | -1.797 | 48.845 | 32.691 | 1.00 24.82 | A |
| ATOM | 238 | CG | LYS A | 28 | -2.961 | 49.384 | 33.573 | 1.00 27.48 | A |
| ATOM | 239 | CD | LYS A | 28 | -4.263 | 49.506 | 32.744 | 1.00 31.59 | A |
| ATOM | 240 | CE | LYS A | 28 | -5.526 | 49.699 | 33.606 | 1.00 30.02 | A |
| ATOM | 241 | NZ | LYS A | 28 | -5.440 | 50.820 | 34.586 | 1.00 31.11 | A |
| ATOM | 242 | C | LYS A | 28 | -1.284 | 51.076 | 31.641 | 1.00 29.57 | A |
| ATOM | 243 | O | LYS A | 28 | -2.164 | 51.951 | 31.566 | 1.00 28.21 | A |
| ATOM | 244 | N | LEU A | 29 | -0.017 | 51.359 | 31.923 | 1.00 29.36 | A |
| ATOM | 245 | CA | LEU A | 29 | 0.385 | 52.723 | 32.179 | 1.00 33.70 | A |
| ATOM | 246 | CB | LEU A | 29 | 1.822 | 52.745 | 32.692 | 1.00 35.26 | A |
| ATOM | 247 | CG | LEU A | 29 | 2.023 | 53.727 | 33.847 | 1.00 38.04 | A |
| ATOM | 248 | CD1 | LEU A | 29 | 3.363 | 53.485 | 34.506 | 1.00 39.85 | A |
| ATOM | 249 | CD2 | LEU A | 29 | 1.891 | 55.149 | 33.332 | 1.00 38.01 | A |
| ATOM | 250 | C | LEU A | 29 | 0.243 | 53.561 | 30.905 | 1.00 34.59 | A |
| ATOM | 251 | O | LEU A | 29 | -0.281 | 54.691 | 30.927 | 1.00 37.16 | A |
| ATOM | 252 | N | LEU A | 30 | 0.721 | 53.020 | 29.792 | 1.00 34.03 | A |
| ATOM | 253 | CA | LEU A | 30 | 0.616 | 53.724 | 28.528 | 1.00 35.56 | A |
| ATOM | 254 | CB | LEU A | 30 | 1.230 | 52.874 | 27.414 | 1.00 38.09 | A |
| ATOM | 255 | CG | LEU A | 30 | 1.470 | 53.508 | 26.050 | 1.00 40.19 | A |
| ATOM | 256 | CD1 | LEU A | 30 | 2.270 | 54.805 | 26.163 | 1.00 39.79 | A |
| ATOM | 257 | CD2 | LEU A | 30 | 2.215 | 52.484 | 25.198 | 1.00 45.44 | A |
| ATOM | 258 | C | LEU A | 30 | -0.882 | 53.980 | 28.263 | 1.00 34.76 | A |
| ATOM | 259 | O | LEU A | 30 | -1.269 | 55.050 | 27.794 | 1.00 33.56 | A |
| ATOM | 260 | N | GLN A | 31 | -1.713 | 52.996 | 28.572 | 1.00 30.55 | A |
| ATOM | 261 | CA | GLN A | 31 | -3.152 | 53.142 | 28.401 | 1.00 31.04 | A |
| ATOM | 262 | CB | GLN A | 31 | -3.865 | 51.839 | 28.782 | 1.00 33.01 | A |
| ATOM | 263 | CG | GLN A | 31 | -5.397 | 51.924 | 28.839 | 1.00 37.09 | A |
| ATOM | 264 | CD | GLN A | 31 | -6.045 | 50.582 | 29.159 | 1.00 45.53 | A |
| ATOM | 265 | OE1 | GLN A | 31 | -5.715 | 49.940 | 30.159 | 1.00 52.72 | A |
| ATOM | 266 | NE2 | GLN A | 31 | -6.973 | 50.151 | 28.310 | 1.00 46.91 | A |
| ATOM | 267 | C | GLN A | 31 | -3.633 | 54.303 | 29.273 | 1.00 31.34 | A |
| ATOM | 268 | O | GLN A | 31 | -4.419 | 55.125 | 28.832 | 1.00 28.45 | A |
| ATOM | 269 | N | LEU A | 32 | -3.141 | 54.376 | 30.509 | 1.00 30.93 | A |
| ATOM | 270 | CA | LEU A | 32 | -3.523 | 55.459 | 31.393 | 1.00 30.83 | A |
| ATOM | 271 | CB | LEU A | 32 | -2.988 | 55.237 | 32.811 | 1.00 29.49 | A |
| ATOM | 272 | CG | LEU A | 32 | -3.572 | 54.156 | 33.732 | 1.00 31.79 | A |
| ATOM | 273 | CD1 | LEU A | 32 | -2.810 | 54.215 | 35.075 | 1.00 33.29 | A |
| ATOM | 274 | CD2 | LEU A | 32 | -5.058 | 54.376 | 33.972 | 1.00 25.39 | A |
| ATOM | 275 | C | LEU A | 32 | -3.031 | 56.797 | 30.860 | 1.00 32.26 | A |
| ATOM | 276 | O | LEU A | 32 | -3.707 | 57.810 | 31.031 | 1.00 35.77 | A |
| ATOM | 277 | N | THR A | 33 | -1.872 | 56.798 | 30.198 | 1.00 31.70 | A |
| ATOM | 278 | CA | THR A | 33 | -1.298 | 58.019 | 29.640 | 1.00 33.33 | A |
| ATOM | 279 | CB | THR A | 33 | 0.158 | 57.787 | 29.156 | 1.00 35.07 | A |
| ATOM | 280 | OG1 | THR A | 33 | 0.949 | 57.272 | 30.238 | 1.00 39.00 | A |
| ATOM | 281 | CG2 | THR A | 33 | 0.776 | 59.087 | 28.687 | 1.00 34.58 | A |
| ATOM | 282 | C | THR A | 33 | -2.120 | 58.560 | 28.471 | 1.00 33.63 | A |
| ATOM | 283 | O | THR A | 33 | -2.237 | 59.767 | 28.298 | 1.00 33.87 | A |
| ATOM | 284 | N | VAL A | 34 | -2.682 | 57.660 | 27.670 | 1.00 35.32 | A |
| ATOM | 285 | CA | VAL A | 34 | -3.507 | 58.046 | 26.531 | 1.00 36.90 | A |
| ATOM | 286 | CB | VAL A | 34 | -3.810 | 56.832 | 25.622 | 1.00 36.47 | A |
| ATOM | 287 | CG1 | VAL A | 34 | -4.825 | 57.200 | 24.550 | 1.00 34.36 | A |
| ATOM | 288 | CG2 | VAL A | 34 | -2.514 | 56.354 | 24.966 | 1.00 38.97 | A |
| ATOM | 289 | C | VAL A | 34 | -4.809 | 58.655 | 27.036 | 1.00 37.01 | A |
| ATOM | 290 | O | VAL A | 34 | -5.250 | 59.695 | 26.540 | 1.00 35.59 | A |
| ATOM | 291 | N | TRP A | 35 | -5.403 | 57.992 | 28.022 | 1.00 36.34 | A |

Figure 11E

| ATOM | 292 | CA | TRP | A | 35 | -6.645 | 58.429 | 28.648 | 1.00 | 38.95 | A |
|------|-----|-----|-----|---|-----|--------|--------|--------|------|-------|---|
| ATOM | 293 | CB | TRP | A | 35 | -7.022 | 57.429 | 29.742 | 1.00 | 44.03 | A |
| ATOM | 294 | CG | TRP | A | 35 | -8.302 | 57.716 | 30.478 | 1.00 | 45.10 | A |
| ATOM | 295 | CD2 | TRP | A | 35 | -8.445 | 58.535 | 31.640 | 1.00 | 46.19 | A |
| ATOM | 296 | CE2 | TRP | A | 35 | -9.820 | 58.545 | 31.973 | 1.00 | 47.39 | A |
| ATOM | 297 | CE3 | TRP | A | 35 | -7.556 | 59.277 | 32.429 | 1.00 | 46.15 | A |
| ATOM | 298 | CD1 | TRP | A | 35 | -9.549 | 57.260 | 30.166 | 1.00 | 45.42 | A |
| ATOM | 299 | NE1 | TRP | A | 35 | -10.466 | 57.752 | 31.063 | 1.00 | 47.75 | A |
| ATOM | 300 | CZ2 | TRP | A | 35 | -10.317 | 59.258 | 33.067 | 1.00 | 48.12 | A |
| ATOM | 301 | CZ3 | TRP | A | 35 | -8.049 | 59.991 | 33.509 | 1.00 | 44.34 | A |
| ATOM | 302 | CH2 | TRP | A | 35 | -9.419 | 59.968 | 33.824 | 1.00 | 47.03 | A |
| ATOM | 303 | C | TRP | A | 35 | -6.408 | 59.814 | 29.259 | 1.00 | 40.04 | A |
| ATOM | 304 | O | TRP | A | 35 | -7.155 | 60.759 | 29.013 | 1.00 | 39.15 | A |
| ATOM | 305 | N | GLY | A | 36 | -5.352 | 59.934 | 30.055 | 1.00 | 38.98 | A |
| ATOM | 306 | CA | GLY | A | 36 | -5.039 | 61.211 | 30.658 | 1.00 | 38.44 | A |
| ATOM | 307 | C | GLY | A | 36 | -5.034 | 62.327 | 29.634 | 1.00 | 38.41 | A |
| ATOM | 308 | O | GLY | A | 36 | -5.626 | 63.390 | 29.845 | 1.00 | 40.58 | A |
| ATOM | 309 | N | ILE | A | 37 | -4.356 | 62.094 | 28.517 | 1.00 | 39.01 | A |
| ATOM | 310 | CA | ILE | A | 37 | -4.279 | 63.079 | 27.451 | 1.00 | 40.60 | A |
| ATOM | 311 | CB | ILE | A | 37 | -3.395 | 62.584 | 26.301 | 1.00 | 40.20 | A |
| ATOM | 312 | CG2 | ILE | A | 37 | -3.509 | 63.517 | 25.136 | 1.00 | 39.97 | A |
| ATOM | 313 | CG1 | ILE | A | 37 | -1.939 | 62.477 | 26.767 | 1.00 | 41.25 | A |
| ATOM | 314 | CD1 | ILE | A | 37 | -1.036 | 61.777 | 25.778 | 1.00 | 38.31 | A |
| ATOM | 315 | C | ILE | A | 37 | -5.662 | 63.366 | 26.886 | 1.00 | 42.00 | A |
| ATOM | 316 | O | ILE | A | 37 | -6.019 | 64.516 | 26.654 | 1.00 | 42.52 | A |
| ATOM | 317 | N | LYS | A | 38 | -6.438 | 62.317 | 26.660 | 1.00 | 42.56 | A |
| ATOM | 318 | CA | LYS | A | 38 | -7.766 | 62.505 | 26.112 | 1.00 | 45.16 | A |
| ATOM | 319 | CB | LYS | A | 38 | -8.459 | 61.156 | 25.925 | 1.00 | 46.50 | A |
| ATOM | 320 | CG | LYS | A | 38 | -9.683 | 61.235 | 25.026 | 1.00 | 53.52 | A |
| ATOM | 321 | CD | LYS | A | 38 | -10.840 | 62.017 | 25.651 | 1.00 | 55.55 | A |
| ATOM | 322 | CE | LYS | A | 38 | -11.812 | 62.480 | 24.581 | 1.00 | 56.01 | A |
| ATOM | 323 | NZ | LYS | A | 38 | -11.165 | 63.504 | 23.714 | 1.00 | 55.27 | A |
| ATOM | 324 | C | LYS | A | 38 | -8.594 | 63.405 | 27.025 | 1.00 | 46.34 | A |
| ATOM | 325 | O | LYS | A | 38 | -9.237 | 64.343 | 26.561 | 1.00 | 48.52 | A |
| ATOM | 326 | N | GLN | A | 39 | -8.554 | 63.120 | 28.332 | 1.00 | 47.82 | A |
| ATOM | 327 | CA | GLN | A | 39 | -9.303 | 63.877 | 29.318 | 1.00 | 49.21 | A |
| ATOM | 328 | CB | GLN | A | 39 | -9.142 | 63.230 | 30.691 | 1.00 | 52.07 | A |
| ATOM | 329 | CG | GLN | A | 39 | -9.431 | 61.742 | 30.727 | 1.00 | 59.01 | A |
| ATOM | 330 | CD | GLN | A | 39 | -10.889 | 61.409 | 30.513 | 1.00 | 61.01 | A |
| ATOM | 331 | OE1 | GLN | A | 39 | -11.742 | 61.800 | 31.310 | 1.00 | 63.56 | A |
| ATOM | 332 | NE2 | GLN | A | 39 | -11.188 | 60.677 | 29.437 | 1.00 | 62.00 | A |
| ATOM | 333 | C | GLN | A | 39 | -8.840 | 65.324 | 29.412 | 1.00 | 48.78 | A |
| ATOM | 334 | O | GLN | A | 39 | -9.649 | 66.243 | 29.431 | 1.00 | 48.03 | A |
| ATOM | 335 | N | LEU | A | 40 | -7.530 | 65.522 | 29.472 | 1.00 | 49.67 | A |
| ATOM | 336 | CA | LEU | A | 40 | -6.980 | 66.861 | 29.590 | 1.00 | 50.78 | A |
| ATOM | 337 | CB | LEU | A | 40 | -5.479 | 66.785 | 29.868 | 1.00 | 49.62 | A |
| ATOM | 338 | CG | LEU | A | 40 | -4.736 | 68.118 | 29.982 | 1.00 | 47.99 | A |
| ATOM | 339 | CD1 | LEU | A | 40 | -5.416 | 69.030 | 31.011 | 1.00 | 51.32 | A |
| ATOM | 340 | CD2 | LEU | A | 40 | -3.300 | 67.852 | 30.376 | 1.00 | 48.82 | A |
| ATOM | 341 | C | LEU | A | 40 | -7.227 | 67.736 | 28.363 | 1.00 | 53.20 | A |
| ATOM | 342 | O | LEU | A | 40 | -7.230 | 68.964 | 28.457 | 1.00 | 53.67 | A |
| ATOM | 343 | N | GLN | A | 41 | -7.433 | 67.104 | 27.215 | 1.00 | 56.61 | A |
| ATOM | 344 | CA | GLN | A | 41 | -7.649 | 67.850 | 25.994 | 1.00 | 60.81 | A |
| ATOM | 345 | CB | GLN | A | 41 | -7.295 | 66.994 | 24.781 | 1.00 | 60.00 | A |
| ATOM | 346 | CG | GLN | A | 41 | -7.257 | 67.753 | 23.467 | 1.00 | 61.60 | A |
| ATOM | 347 | CD | GLN | A | 41 | -6.756 | 66.885 | 22.330 | 1.00 | 61.14 | A |
| ATOM | 348 | OE1 | GLN | A | 41 | -5.630 | 66.377 | 22.367 | 1.00 | 56.12 | A |
| ATOM | 349 | NE2 | GLN | A | 41 | -7.598 | 66.697 | 21.316 | 1.00 | 60.61 | A |
| ATOM | 350 | C | GLN | A | 41 | -9.084 | 68.344 | 25.915 | 1.00 | 63.54 | A |
| ATOM | 351 | O | GLN | A | 41 | -9.388 | 69.277 | 25.179 | 1.00 | 65.13 | A |

Figure 11F

| ATOM | 352 | N | ALA | A | 42 | -9.971 | 67.722 | 26.679 | 1.00 | 67.16 | A |
|------|-----|-----|-----|---|----|--------|--------|--------|------|-------|---|
| ATOM | 353 | CA | ALA | A | 42 | -11.362 | 68.150 | 26.693 | 1.00 | 70.08 | A |
| ATOM | 354 | CB | ALA | A | 42 | -12.252 | 67.043 | 27.249 | 1.00 | 68.59 | A |
| ATOM | 355 | C | ALA | A | 42 | -11.461 | 69.423 | 27.556 | 1.00 | 72.76 | A |
| ATOM | 356 | O | ALA | A | 42 | -12.506 | 69.748 | 28.123 | 1.00 | 73.45 | A |
| ATOM | 357 | N | ARG | A | 43 | -10.338 | 70.137 | 27.642 | 1.00 | 75.35 | A |
| ATOM | 358 | CA | ARG | A | 43 | -10.202 | 71.377 | 28.413 | 1.00 | 76.97 | A |
| ATOM | 359 | CB | ARG | A | 43 | -9.391 | 71.131 | 29.705 | 1.00 | 77.23 | A |
| ATOM | 360 | CG | ARG | A | 43 | -10.130 | 70.250 | 30.753 | 1.00 | 77.83 | A |
| ATOM | 361 | CD | ARG | A | 43 | -9.265 | 69.690 | 31.889 | 1.00 | 76.18 | A |
| ATOM | 362 | NE | ARG | A | 43 | -10.053 | 68.919 | 32.864 | 1.00 | 76.19 | A |
| ATOM | 363 | CZ | ARG | A | 43 | -10.933 | 67.967 | 32.551 | 1.00 | 76.17 | A |
| ATOM | 364 | NH1 | ARG | A | 43 | -11.153 | 67.657 | 31.284 | 1.00 | 76.24 | A |
| ATOM | 365 | NH2 | ARG | A | 43 | -11.605 | 67.326 | 33.507 | 1.00 | 77.89 | A |
| ATOM | 366 | C | ARG | A | 43 | -9.560 | 72.481 | 27.570 | 1.00 | 79.19 | A |
| ATOM | 367 | O | ARG | A | 43 | -10.131 | 72.882 | 26.548 | 1.00 | 79.42 | A |
| ATOM | 368 | N | ILE | A | 44 | -8.381 | 72.970 | 27.993 | 1.00 | 81.42 | A |
| ATOM | 369 | CA | ILE | A | 44 | -7.646 | 74.059 | 27.276 | 1.00 | 84.32 | A |
| ATOM | 370 | CB | ILE | A | 44 | -6.073 | 73.998 | 27.495 | 1.00 | 84.97 | A |
| ATOM | 371 | CG2 | ILE | A | 44 | -5.292 | 74.824 | 26.419 | 1.00 | 85.80 | A |
| ATOM | 372 | CG1 | ILE | A | 44 | -5.728 | 74.612 | 28.829 | 1.00 | 85.52 | A |
| ATOM | 373 | CD1 | ILE | A | 44 | -6.344 | 76.011 | 29.055 | 1.00 | 87.04 | A |
| ATOM | 374 | C | ILE | A | 44 | -7.908 | 73.987 | 25.790 | 1.00 | 86.80 | A |
| ATOM | 375 | O | ILE | A | 44 | -8.577 | 74.829 | 25.234 | 1.00 | 87.60 | A |
| ATOM | 376 | N | LEU | A | 45 | -7.318 | 73.007 | 25.145 | 1.00 | 87.99 | A |
| ATOM | 377 | CA | LEU | A | 45 | -7.541 | 72.910 | 23.737 | 1.00 | 88.13 | A |
| ATOM | 378 | CB | LEU | A | 45 | -6.257 | 72.509 | 23.009 | 1.00 | 88.79 | A |
| ATOM | 379 | CG | LEU | A | 45 | -5.940 | 73.339 | 21.770 | 1.00 | 90.46 | A |
| ATOM | 380 | CD1 | LEU | A | 45 | -7.147 | 73.370 | 20.837 | 1.00 | 91.58 | A |
| ATOM | 381 | CD2 | LEU | A | 45 | -5.596 | 74.779 | 22.173 | 1.00 | 90.84 | A |
| ATOM | 382 | C | LEU | A | 45 | -8.656 | 71.944 | 23.376 | 1.00 | 88.30 | A |
| ATOM | 383 | O | LEU | A | 45 | -9.507 | 71.665 | 24.291 | 1.00 | 87.82 | A |
| ATOM | 384 | NT | LEU | A | 45 | -8.614 | 71.561 | 22.151 | 1.00 | 88.77 | A |
| ATOM | 385 | CA | ACE | B | 0 | 29.175 | 18.175 | 21.874 | 1.00 | 35.90 | B |
| ATOM | 386 | C | ACE | B | 0 | 27.867 | 18.849 | 22.146 | 1.00 | 36.69 | B |
| ATOM | 387 | O | ACE | B | 0 | 27.836 | 20.078 | 22.299 | 1.00 | 33.24 | B |
| ATOM | 388 | N | ARG | B | 1 | 26.771 | 18.065 | 22.218 | 1.00 | 32.69 | B |
| ATOM | 389 | CA | ARG | B | 1 | 25.440 | 18.590 | 22.450 | 1.00 | 34.24 | B |
| ATOM | 390 | CB | ARG | B | 1 | 24.436 | 17.446 | 22.644 | 1.00 | 33.49 | B |
| ATOM | 391 | CG | ARG | B | 1 | 22.976 | 17.873 | 22.651 | 1.00 | 32.92 | B |
| ATOM | 392 | CD | ARG | B | 1 | 22.435 | 18.177 | 21.260 | 1.00 | 34.95 | B |
| ATOM | 393 | NE | ARG | B | 1 | 22.366 | 16.972 | 20.443 | 1.00 | 38.88 | B |
| ATOM | 394 | CZ | ARG | B | 1 | 21.548 | 15.952 | 20.706 | 1.00 | 42.79 | B |
| ATOM | 395 | NH1 | ARG | B | 1 | 20.740 | 16.012 | 21.765 | 1.00 | 44.66 | B |
| ATOM | 396 | NH2 | ARG | B | 1 | 21.550 | 14.868 | 19.943 | 1.00 | 39.72 | B |
| ATOM | 397 | C | ARG | B | 1 | 25.424 | 19.498 | 23.685 | 1.00 | 35.96 | B |
| ATOM | 398 | O | ARG | B | 1 | 24.920 | 20.617 | 23.628 | 1.00 | 36.55 | B |
| ATOM | 399 | N | MET | B | 2 | 26.008 | 19.009 | 24.779 | 1.00 | 39.89 | B |
| ATOM | 400 | CA | MET | B | 2 | 26.077 | 19.769 | 26.022 | 1.00 | 43.08 | B |
| ATOM | 401 | CB | MET | B | 2 | 27.113 | 19.163 | 26.972 | 1.00 | 43.87 | B |
| ATOM | 402 | CG | MET | B | 2 | 26.728 | 17.847 | 27.623 | 1.00 | 46.86 | B |
| ATOM | 403 | SD | MET | B | 2 | 25.304 | 18.010 | 28.700 | 1.00 | 52.01 | B |
| ATOM | 404 | CE | MET | B | 2 | 24.024 | 18.375 | 27.524 | 1.00 | 52.70 | B |
| ATOM | 405 | C | MET | B | 2 | 26.440 | 21.219 | 25.789 | 1.00 | 45.76 | B |
| ATOM | 406 | O | MET | B | 2 | 25.723 | 22.131 | 26.212 | 1.00 | 44.09 | B |
| ATOM | 407 | N | LYS | B | 3 | 27.570 | 21.414 | 25.125 | 1.00 | 47.94 | B |
| ATOM | 408 | CA | LYS | B | 3 | 28.082 | 22.736 | 24.820 | 1.00 | 52.42 | B |
| ATOM | 409 | CB | LYS | B | 3 | 29.455 | 22.565 | 24.151 | 1.00 | 54.64 | B |
| ATOM | 410 | CG | LYS | B | 3 | 30.552 | 23.540 | 24.595 | 1.00 | 58.36 | B |
| ATOM | 411 | CD | LYS | B | 3 | 30.382 | 24.937 | 24.030 | 1.00 | 60.17 | B |

Figure 11G

| ATOM | 412 | CE  | LYS | B | 3  | 31.618 | 25.777 | 24.321 | 1.00 | 62.06 | B |
| ATOM | 413 | NZ  | LYS | B | 3  | 31.561 | 27.140 | 23.704 | 1.00 | 63.71 | B |
| ATOM | 414 | C   | LYS | B | 3  | 27.095 | 23.479 | 23.907 | 1.00 | 52.65 | B |
| ATOM | 415 | O   | LYS | B | 3  | 26.858 | 24.671 | 24.092 | 1.00 | 52.44 | B |
| ATOM | 416 | N   | GLN | B | 4  | 26.517 | 22.774 | 22.934 | 1.00 | 52.13 | B |
| ATOM | 417 | CA  | GLN | B | 4  | 25.549 | 23.387 | 22.032 | 1.00 | 54.04 | B |
| ATOM | 418 | CB  | GLN | B | 4  | 24.930 | 22.330 | 21.105 | 1.00 | 57.72 | B |
| ATOM | 419 | CG  | GLN | B | 4  | 25.792 | 21.880 | 19.925 | 1.00 | 60.44 | B |
| ATOM | 420 | CD  | GLN | B | 4  | 25.855 | 22.923 | 18.816 | 1.00 | 62.71 | B |
| ATOM | 421 | OE1 | GLN | B | 4  | 26.404 | 24.017 | 18.997 | 1.00 | 64.51 | B |
| ATOM | 422 | NE2 | GLN | B | 4  | 25.276 | 22.592 | 17.661 | 1.00 | 62.62 | B |
| ATOM | 423 | C   | GLN | B | 4  | 24.441 | 24.062 | 22.836 | 1.00 | 52.63 | B |
| ATOM | 424 | O   | GLN | B | 4  | 24.013 | 25.162 | 22.518 | 1.00 | 53.56 | B |
| ATOM | 425 | N   | ILE | B | 5  | 23.982 | 23.379 | 23.878 | 1.00 | 52.62 | B |
| ATOM | 426 | CA  | ILE | B | 5  | 22.929 | 23.880 | 24.758 | 1.00 | 52.43 | B |
| ATOM | 427 | CB  | ILE | B | 5  | 22.443 | 22.766 | 25.721 | 1.00 | 51.17 | B |
| ATOM | 428 | CG2 | ILE | B | 5  | 21.412 | 23.329 | 26.691 | 1.00 | 52.10 | B |
| ATOM | 429 | CG1 | ILE | B | 5  | 21.871 | 21.592 | 24.917 | 1.00 | 52.55 | B |
| ATOM | 430 | CD1 | ILE | B | 5  | 21.496 | 20.363 | 25.754 | 1.00 | 53.47 | B |
| ATOM | 431 | C   | ILE | B | 5  | 23.452 | 25.043 | 25.600 | 1.00 | 53.54 | B |
| ATOM | 432 | O   | ILE | B | 5  | 22.743 | 26.013 | 25.849 | 1.00 | 52.58 | B |
| ATOM | 433 | N   | GLU | B | 6  | 24.701 | 24.932 | 26.036 | 1.00 | 55.54 | B |
| ATOM | 434 | CA  | GLU | B | 6  | 25.309 | 25.970 | 26.850 | 1.00 | 56.11 | B |
| ATOM | 435 | CB  | GLU | B | 6  | 26.637 | 25.477 | 27.437 | 1.00 | 53.75 | B |
| ATOM | 436 | CG  | GLU | B | 6  | 26.487 | 24.157 | 28.171 | 1.00 | 53.07 | B |
| ATOM | 437 | CD  | GLU | B | 6  | 27.729 | 23.735 | 28.939 | 1.00 | 50.56 | B |
| ATOM | 438 | OE1 | GLU | B | 6  | 28.816 | 23.611 | 28.329 | 1.00 | 49.24 | B |
| ATOM | 439 | OE2 | GLU | B | 6  | 27.604 | 23.516 | 30.159 | 1.00 | 47.31 | B |
| ATOM | 440 | C   | GLU | B | 6  | 25.522 | 27.217 | 26.009 | 1.00 | 57.04 | B |
| ATOM | 441 | O   | GLU | B | 6  | 25.418 | 28.335 | 26.515 | 1.00 | 58.94 | B |
| ATOM | 442 | N   | ASP | B | 7  | 25.811 | 27.031 | 24.725 | 1.00 | 57.18 | B |
| ATOM | 443 | CA  | ASP | B | 7  | 26.003 | 28.179 | 23.848 | 1.00 | 58.51 | B |
| ATOM | 444 | CB  | ASP | B | 7  | 26.681 | 27.772 | 22.536 | 1.00 | 59.88 | B |
| ATOM | 445 | CG  | ASP | B | 7  | 28.121 | 27.339 | 22.732 | 1.00 | 62.42 | B |
| ATOM | 446 | OD1 | ASP | B | 7  | 28.827 | 27.979 | 23.542 | 1.00 | 62.53 | B |
| ATOM | 447 | OD2 | ASP | B | 7  | 28.559 | 26.382 | 22.056 | 1.00 | 66.19 | B |
| ATOM | 448 | C   | ASP | B | 7  | 24.668 | 28.858 | 23.543 | 1.00 | 58.25 | B |
| ATOM | 449 | O   | ASP | B | 7  | 24.624 | 30.070 | 23.314 | 1.00 | 56.00 | B |
| ATOM | 450 | N   | LYS | B | 8  | 23.591 | 28.069 | 23.547 | 1.00 | 57.96 | B |
| ATOM | 451 | CA  | LYS | B | 8  | 22.240 | 28.563 | 23.276 | 1.00 | 57.58 | B |
| ATOM | 452 | CB  | LYS | B | 8  | 21.331 | 27.405 | 22.838 | 1.00 | 57.99 | B |
| ATOM | 453 | CG  | LYS | B | 8  | 19.911 | 27.844 | 22.484 | 1.00 | 60.08 | B |
| ATOM | 454 | CD  | LYS | B | 8  | 19.915 | 28.785 | 21.280 | 1.00 | 60.12 | B |
| ATOM | 455 | CE  | LYS | B | 8  | 18.697 | 29.725 | 21.268 | 1.00 | 60.76 | B |
| ATOM | 456 | NZ  | LYS | B | 8  | 17.371 | 29.062 | 21.146 | 1.00 | 58.46 | B |
| ATOM | 457 | C   | LYS | B | 8  | 21.653 | 29.248 | 24.517 | 1.00 | 56.86 | B |
| ATOM | 458 | O   | LYS | B | 8  | 20.832 | 30.166 | 24.411 | 1.00 | 53.70 | B |
| ATOM | 459 | N   | ILE | B | 9  | 22.077 | 28.790 | 25.689 | 1.00 | 57.87 | B |
| ATOM | 460 | CA  | ILE | B | 9  | 21.621 | 29.368 | 26.947 | 1.00 | 59.31 | B |
| ATOM | 461 | CB  | ILE | B | 9  | 22.073 | 28.517 | 28.161 | 1.00 | 57.40 | B |
| ATOM | 462 | CG2 | ILE | B | 9  | 21.788 | 29.270 | 29.459 | 1.00 | 57.21 | B |
| ATOM | 463 | CG1 | ILE | B | 9  | 21.361 | 27.165 | 28.154 | 1.00 | 56.21 | B |
| ATOM | 464 | CD1 | ILE | B | 9  | 21.885 | 26.199 | 29.212 | 1.00 | 54.49 | B |
| ATOM | 465 | C   | ILE | B | 9  | 22.216 | 30.770 | 27.093 | 1.00 | 60.74 | B |
| ATOM | 466 | O   | ILE | B | 9  | 21.565 | 31.682 | 27.608 | 1.00 | 61.51 | B |
| ATOM | 467 | N   | GLU | B | 10 | 23.456 | 30.923 | 26.633 | 1.00 | 61.69 | B |
| ATOM | 468 | CA  | GLU | B | 10 | 24.170 | 32.198 | 26.691 | 1.00 | 63.76 | B |
| ATOM | 469 | CB  | GLU | B | 10 | 25.629 | 32.000 | 26.279 | 1.00 | 63.63 | B |
| ATOM | 470 | CG  | GLU | B | 10 | 26.456 | 33.275 | 26.254 | 1.00 | 65.58 | B |
| ATOM | 471 | CD  | GLU | B | 10 | 27.854 | 33.054 | 25.707 | 1.00 | 66.48 | B |

Figure 11H

```
ATOM    472  OE1 GLU B   10      27.979  32.751  24.499  1.00 67.38           B
ATOM    473  OE2 GLU B   10      29.824  33.173  26.485  1.00 66.28           B
ATOM    474  C   GLU B   10      23.515  33.211  25.757  1.00 65.16           B
ATOM    475  O   GLU B   10      23.261  34.251  26.141  1.00 65.81           B
ATOM    476  N   GLU B   11      23.255  32.785  24.524  1.00 66.64           B
ATOM    477  CA  GLU B   11      22.617  33.637  23.529  1.00 67.59           B
ATOM    478  CB  GLU B   11      22.348  32.832  22.252  1.00 68.72           B
ATOM    479  CG  GLU B   11      21.735  33.636  21.117  1.00 72.88           B
ATOM    480  CD  GLU B   11      22.556  34.864  20.767  1.00 74.80           B
ATOM    481  OE1 GLU B   11      23.775  34.717  20.526  1.00 75.81           B
ATOM    482  OE2 GLU B   11      21.978  35.975  20.731  1.00 74.99           B
ATOM    483  C   GLU B   11      21.307  34.197  24.098  1.00 67.17           B
ATOM    484  O   GLU B   11      20.998  35.381  23.918  1.00 68.06           B
ATOM    485  N   ILE B   12      20.541  33.348  24.784  1.00 64.61           B
ATOM    486  CA  ILE B   12      19.288  33.790  25.389  1.00 61.65           B
ATOM    487  CB  ILE B   12      18.458  32.600  25.926  1.00 62.84           B
ATOM    488  CG2 ILE B   12      17.416  33.094  26.940  1.00 62.63           B
ATOM    489  CG1 ILE B   12      17.799  31.864  24.750  1.00 62.13           B
ATOM    490  CD1 ILE B   12      16.910  30.698  25.156  1.00 61.39           B
ATOM    491  C   ILE B   12      19.553  34.776  26.522  1.00 58.17           B
ATOM    492  O   ILE B   12      19.010  35.881  26.523  1.00 55.05           B
ATOM    493  N   GLU B   13      20.388  34.384  27.479  1.00 55.87           B
ATOM    494  CA  GLU B   13      20.710  35.268  28.600  1.00 54.71           B
ATOM    495  CB  GLU B   13      21.817  34.669  29.477  1.00 50.19           B
ATOM    496  CG  GLU B   13      21.447  33.331  30.109  1.00 49.30           B
ATOM    497  CD  GLU B   13      22.577  32.729  30.933  1.00 49.10           B
ATOM    498  OE1 GLU B   13      23.741  32.765  30.472  1.00 50.79           B
ATOM    499  OE2 GLU B   13      22.304  32.194  32.027  1.00 47.00           B
ATOM    500  C   GLU B   13      21.166  36.612  28.047  1.00 55.57           B
ATOM    501  O   GLU B   13      20.790  37.667  28.557  1.00 56.33           B
ATOM    502  N   SER B   14      21.950  36.559  26.977  1.00 56.02           B
ATOM    503  CA  SER B   14      22.468  37.763  26.350  1.00 55.71           B
ATOM    504  CB  SER B   14      23.488  37.389  25.278  1.00 54.62           B
ATOM    505  OG  SER B   14      23.968  38.550  24.629  1.00 56.74           B
ATOM    506  C   SER B   14      21.366  38.624  25.736  1.00 55.96           B
ATOM    507  O   SER B   14      21.469  39.854  25.696  1.00 54.91           B
ATOM    508  N   LYS B   15      20.310  37.979  25.263  1.00 55.94           B
ATOM    509  CA  LYS B   15      19.208  38.704  24.650  1.00 56.72           B
ATOM    510  CB  LYS B   15      18.454  37.779  23.693  1.00 55.67           B
ATOM    511  CG  LYS B   15      17.494  38.484  22.772  1.00 58.33           B
ATOM    512  CD  LYS B   15      17.000  37.527  21.705  1.00 59.89           B
ATOM    513  CE  LYS B   15      16.440  38.282  20.518  1.00 60.44           B
ATOM    514  NZ  LYS B   15      16.020  37.375  19.412  1.00 63.67           B
ATOM    515  C   LYS B   15      18.282  39.207  25.748  1.00 56.31           B
ATOM    516  O   LYS B   15      17.716  40.296  25.661  1.00 56.65           B
ATOM    517  N   GLN B   16      18.146  38.403  26.791  1.00 56.76           B
ATOM    518  CA  GLN B   16      17.293  38.748  27.911  1.00 57.28           B
ATOM    519  CB  GLN B   16      17.306  37.604  28.923  1.00 56.94           B
ATOM    520  CG  GLN B   16      16.000  37.394  29.652  1.00 55.90           B
ATOM    521  CD  GLN B   16      15.908  36.017  30.300  1.00 56.24           B
ATOM    522  OE1 GLN B   16      16.613  35.722  31.263  1.00 57.78           B
ATOM    523  NE2 GLN B   16      15.044  35.160  29.760  1.00 55.69           B
ATOM    524  C   GLN B   16      17.825  40.040  28.528  1.00 58.82           B
ATOM    525  O   GLN B   16      17.049  40.929  28.905  1.00 59.68           B
ATOM    526  N   LYS B   17      19.148  40.163  28.521  1.00 59.44           B
ATOM    527  CA  LYS B   17      19.711  41.379  29.189  1.00 59.84           B
ATOM    528  CB  LYS B   17      21.228  41.275  29.386  1.00 60.80           B
ATOM    529  CG  LYS B   17      21.740  42.343  30.356  1.00 64.52           B
ATOM    530  CD  LYS B   17      23.250  42.325  30.576  1.00 65.30           B
ATOM    531  CE  LYS B   17      24.008  42.784  29.344  1.00 67.22           B
```

Figure 1II

| | | | | | | | | | | |
|---|---|---|---|---|---|---|---|---|---|---|
| ATOM | 532 | NZ | LYS | B | 17 | 25.465 | 42.963 | 29.625 | 1.00 67.09 | B |
| ATOM | 533 | C | LYS | B | 17 | 19.389 | 42.522 | 28.230 | 1.00 59.16 | B |
| ATOM | 534 | O | LYS | B | 17 | 19.088 | 43.634 | 28.656 | 1.00 55.77 | B |
| ATOM | 535 | N | LYS | B | 18 | 19.433 | 42.233 | 26.931 | 1.00 58.38 | B |
| ATOM | 536 | CA | LYS | B | 18 | 19.128 | 43.248 | 25.931 | 1.00 56.35 | B |
| ATOM | 537 | CB | LYS | B | 18 | 19.247 | 42.675 | 24.511 | 1.00 59.38 | B |
| ATOM | 538 | CG | LYS | B | 18 | 20.617 | 42.083 | 24.130 | 1.00 61.47 | B |
| ATOM | 539 | CD | LYS | B | 18 | 21.768 | 43.111 | 24.099 | 1.00 61.91 | B |
| ATOM | 540 | CE | LYS | B | 18 | 22.034 | 43.761 | 25.461 | 1.00 63.50 | B |
| ATOM | 541 | NZ | LYS | B | 18 | 23.248 | 44.620 | 25.423 | 1.00 63.66 | B |
| ATOM | 542 | C | LYS | B | 18 | 17.706 | 43.761 | 26.163 | 1.00 58.27 | B |
| ATOM | 543 | O | LYS | B | 18 | 17.475 | 44.969 | 26.254 | 1.00 58.82 | B |
| ATOM | 544 | N | ILE | B | 19 | 16.757 | 42.835 | 26.268 | 1.00 56.89 | B |
| ATOM | 545 | CA | ILE | B | 19 | 15.356 | 43.189 | 26.488 | 1.00 53.76 | B |
| ATOM | 546 | CB | ILE | B | 19 | 14.455 | 41.931 | 26.488 | 1.00 53.33 | B |
| ATOM | 547 | CG2 | ILE | B | 19 | 13.057 | 42.286 | 26.976 | 1.00 52.66 | B |
| ATOM | 548 | CG1 | ILE | B | 19 | 14.416 | 41.322 | 25.081 | 1.00 52.79 | B |
| ATOM | 549 | CD1 | ILE | B | 19 | 13.543 | 40.069 | 24.970 | 1.00 54.45 | B |
| ATOM | 550 | C | ILE | B | 19 | 15.117 | 43.961 | 27.786 | 1.00 52.88 | B |
| ATOM | 551 | O | ILE | B | 19 | 14.327 | 44.897 | 27.809 | 1.00 51.74 | B |
| ATOM | 552 | N | GLU | B | 20 | 15.781 | 43.565 | 28.869 | 1.00 51.04 | B |
| ATOM | 553 | CA | GLU | B | 20 | 15.601 | 44.267 | 30.128 | 1.00 50.08 | B |
| ATOM | 554 | CB | GLU | B | 20 | 16.403 | 43.613 | 31.253 | 1.00 49.90 | B |
| ATOM | 555 | CG | GLU | B | 20 | 15.969 | 42.207 | 31.584 | 1.00 54.19 | B |
| ATOM | 556 | CD | GLU | B | 20 | 16.761 | 41.620 | 32.736 | 1.00 55.98 | B |
| ATOM | 557 | OE1 | GLU | B | 20 | 18.010 | 41.568 | 32.641 | 1.00 53.23 | B |
| ATOM | 558 | OE2 | GLU | B | 20 | 16.127 | 41.215 | 33.735 | 1.00 56.20 | B |
| ATOM | 559 | C | GLU | B | 20 | 16.053 | 45.706 | 29.965 | 1.00 49.26 | B |
| ATOM | 560 | O | GLU | B | 20 | 15.479 | 46.611 | 30.561 | 1.00 48.88 | B |
| ATOM | 561 | N | ASN | B | 21 | 17.093 | 45.912 | 29.163 | 1.00 49.15 | B |
| ATOM | 562 | CA | ASN | B | 21 | 17.596 | 47.256 | 28.930 | 1.00 49.99 | B |
| ATOM | 563 | CB | ASN | B | 21 | 18.885 | 47.229 | 28.098 | 1.00 51.35 | B |
| ATOM | 564 | CG | ASN | B | 21 | 20.054 | 46.576 | 28.834 | 1.00 54.79 | B |
| ATOM | 565 | OD1 | ASN | B | 21 | 20.421 | 46.978 | 29.943 | 1.00 55.96 | B |
| ATOM | 566 | ND2 | ASN | B | 21 | 20.656 | 45.572 | 28.205 | 1.00 57.15 | B |
| ATOM | 567 | C | ASN | B | 21 | 16.537 | 48.078 | 28.202 | 1.00 49.83 | B |
| ATOM | 568 | O | ASN | B | 21 | 16.249 | 49.209 | 28.591 | 1.00 50.14 | B |
| ATOM | 569 | N | GLU | B | 22 | 15.957 | 47.497 | 27.153 | 1.00 47.34 | B |
| ATOM | 570 | CA | GLU | B | 22 | 14.942 | 48.160 | 26.354 | 1.00 44.99 | B |
| ATOM | 571 | CB | GLU | B | 22 | 14.534 | 47.272 | 25.174 | 1.00 44.99 | B |
| ATOM | 572 | CG | GLU | B | 22 | 13.703 | 47.990 | 24.116 | 1.00 51.85 | B |
| ATOM | 573 | CD | GLU | B | 22 | 14.377 | 49.268 | 23.621 | 1.00 54.71 | B |
| ATOM | 574 | OE1 | GLU | B | 22 | 15.543 | 49.191 | 23.182 | 1.00 55.60 | B |
| ATOM | 575 | OE2 | GLU | B | 22 | 13.743 | 50.350 | 23.673 | 1.00 57.01 | B |
| ATOM | 576 | C | GLU | B | 22 | 13.710 | 48.521 | 27.183 | 1.00 44.17 | B |
| ATOM | 577 | O | GLU | B | 22 | 13.044 | 49.527 | 26.916 | 1.00 45.50 | B |
| ATOM | 578 | N | ILE | B | 23 | 13.386 | 47.693 | 28.169 | 1.00 42.28 | B |
| ATOM | 579 | CA | ILE | B | 23 | 12.241 | 47.977 | 29.024 | 1.00 40.61 | B |
| ATOM | 580 | CB | ILE | B | 23 | 11.801 | 46.724 | 29.809 | 1.00 38.57 | B |
| ATOM | 581 | CG2 | ILE | B | 23 | 10.836 | 47.096 | 30.925 | 1.00 37.31 | B |
| ATOM | 582 | CG1 | ILE | B | 23 | 11.138 | 45.733 | 28.850 | 1.00 38.28 | B |
| ATOM | 583 | CD1 | ILE | B | 23 | 10.634 | 44.436 | 29.530 | 1.00 38.32 | B |
| ATOM | 584 | C | ILE | B | 23 | 12.626 | 49.108 | 29.974 | 1.00 41.50 | B |
| ATOM | 585 | O | ILE | B | 23 | 11.793 | 49.926 | 30.349 | 1.00 41.54 | B |
| ATOM | 586 | N | ALA | B | 24 | 13.898 | 49.170 | 30.348 | 1.00 40.42 | B |
| ATOM | 587 | CA | ALA | B | 24 | 14.349 | 50.240 | 31.224 | 1.00 38.49 | B |
| ATOM | 588 | CB | ALA | B | 24 | 15.811 | 50.059 | 31.578 | 1.00 34.26 | B |
| ATOM | 589 | C | ALA | B | 24 | 14.147 | 51.562 | 30.490 | 1.00 37.76 | B |
| ATOM | 590 | O | ALA | B | 24 | 13.674 | 52.528 | 31.078 | 1.00 38.39 | B |
| ATOM | 591 | N | ARG | B | 25 | 14.498 | 51.591 | 29.204 | 1.00 36.47 | B |

Figure 11J

| ATOM | 592 | CA | ARG | B | 25 | 14.354 | 52.796 | 28.394 | 1.00 | 38.10 | B |
|------|-----|-----|-----|---|----|--------|--------|--------|------|-------|---|
| ATOM | 593 | CB | ARG | B | 25 | 15.086 | 52.644 | 27.051 | 1.00 | 40.70 | B |
| ATOM | 594 | CG | ARG | B | 25 | 16.609 | 52.668 | 27.195 | 1.00 | 46.74 | B |
| ATOM | 595 | CD | ARG | B | 25 | 17.315 | 52.949 | 25.879 | 1.00 | 51.86 | B |
| ATOM | 596 | NE | ARG | B | 25 | 17.268 | 51.823 | 24.954 | 1.00 | 56.83 | B |
| ATOM | 597 | CZ | ARG | B | 25 | 17.894 | 50.666 | 25.152 | 1.00 | 59.56 | B |
| ATOM | 598 | NH1 | ARG | B | 25 | 18.615 | 50.477 | 26.253 | 1.00 | 60.08 | B |
| ATOM | 599 | NH2 | ARG | B | 25 | 17.792 | 49.696 | 24.257 | 1.00 | 59.81 | B |
| ATOM | 600 | C | ARG | B | 25 | 12.901 | 53.185 | 28.158 | 1.00 | 36.71 | B |
| ATOM | 601 | O | ARG | B | 25 | 12.555 | 54.361 | 28.165 | 1.00 | 36.54 | B |
| ATOM | 602 | N | ILE | B | 26 | 12.051 | 52.197 | 27.942 | 1.00 | 36.23 | B |
| ATOM | 603 | CA | ILE | B | 26 | 10.642 | 52.454 | 27.733 | 1.00 | 34.33 | B |
| ATOM | 604 | CB | ILE | B | 26 | 9.944 | 51.152 | 27.370 | 1.00 | 34.16 | B |
| ATOM | 605 | CG2 | ILE | B | 26 | 8.432 | 51.293 | 27.496 | 1.00 | 31.45 | B |
| ATOM | 606 | CG1 | ILE | B | 26 | 10.423 | 50.722 | 25.985 | 1.00 | 34.01 | B |
| ATOM | 607 | CD1 | ILE | B | 26 | 9.879 | 49.403 | 25.540 | 1.00 | 34.37 | B |
| ATOM | 608 | C | ILE | B | 26 | 10.046 | 53.059 | 29.005 | 1.00 | 34.32 | B |
| ATOM | 609 | O | ILE | B | 26 | 9.317 | 54.053 | 28.956 | 1.00 | 33.13 | B |
| ATOM | 610 | N | LYS | B | 27 | 10.371 | 52.457 | 30.141 | 1.00 | 34.59 | B |
| ATOM | 611 | CA | LYS | B | 27 | 9.898 | 52.941 | 31.433 | 1.00 | 35.31 | B |
| ATOM | 612 | CB | LYS | B | 27 | 10.366 | 52.005 | 32.544 | 1.00 | 36.43 | B |
| ATOM | 613 | CG | LYS | B | 27 | 9.398 | 50.872 | 32.885 | 1.00 | 40.24 | B |
| ATOM | 614 | CD | LYS | B | 27 | 10.162 | 49.643 | 33.347 | 1.00 | 44.60 | B |
| ATOM | 615 | CE | LYS | B | 27 | 11.278 | 49.991 | 34.334 | 1.00 | 50.65 | B |
| ATOM | 616 | NZ | LYS | B | 27 | 12.209 | 48.831 | 34.560 | 1.00 | 54.97 | B |
| ATOM | 617 | C | LYS | B | 27 | 10.382 | 54.355 | 31.712 | 1.00 | 35.58 | B |
| ATOM | 618 | O | LYS | B | 27 | 9.666 | 55.140 | 32.318 | 1.00 | 36.82 | B |
| ATOM | 619 | N | LYS | B | 28 | 11.599 | 54.670 | 31.268 | 1.00 | 36.91 | B |
| ATOM | 620 | CA | LYS | B | 28 | 12.189 | 55.993 | 31.463 | 1.00 | 37.71 | B |
| ATOM | 621 | CB | LYS | B | 28 | 13.627 | 56.017 | 30.958 | 1.00 | 42.60 | B |
| ATOM | 622 | CG | LYS | B | 28 | 14.604 | 56.755 | 31.851 | 1.00 | 49.26 | B |
| ATOM | 623 | CD | LYS | B | 28 | 15.299 | 55.778 | 32.818 | 1.00 | 55.52 | B |
| ATOM | 624 | CE | LYS | B | 28 | 14.318 | 54.979 | 33.680 | 1.00 | 58.79 | B |
| ATOM | 625 | NZ | LYS | B | 28 | 15.015 | 53.887 | 34.421 | 1.00 | 59.10 | B |
| ATOM | 626 | C | LYS | B | 28 | 11.397 | 57.044 | 30.677 | 1.00 | 37.60 | B |
| ATOM | 627 | O | LYS | B | 28 | 10.956 | 58.045 | 31.240 | 1.00 | 40.12 | B |
| ATOM | 628 | N | LEU | B | 29 | 11.250 | 56.826 | 29.368 | 1.00 | 35.33 | B |
| ATOM | 629 | CA | LEU | B | 29 | 10.515 | 57.754 | 28.524 | 1.00 | 35.90 | B |
| ATOM | 630 | CB | LEU | B | 29 | 10.440 | 57.267 | 27.071 | 1.00 | 36.49 | B |
| ATOM | 631 | CG | LEU | B | 29 | 9.495 | 58.127 | 26.202 | 1.00 | 37.58 | B |
| ATOM | 632 | CD1 | LEU | B | 29 | 9.958 | 59.581 | 26.260 | 1.00 | 36.39 | B |
| ATOM | 633 | CD2 | LEU | B | 29 | 9.441 | 57.641 | 24.744 | 1.00 | 35.00 | B |
| ATOM | 634 | C | LEU | B | 29 | 9.103 | 57.912 | 29.047 | 1.00 | 35.09 | B |
| ATOM | 635 | O | LEU | B | 29 | 8.568 | 59.015 | 29.095 | 1.00 | 34.76 | B |
| ATOM | 636 | N | LEU | B | 30 | 8.512 | 56.787 | 29.426 | 1.00 | 33.74 | B |
| ATOM | 637 | CA | LEU | B | 30 | 7.161 | 56.746 | 29.946 | 1.00 | 30.65 | B |
| ATOM | 638 | CB | LEU | B | 30 | 6.789 | 55.294 | 30.181 | 1.00 | 32.72 | B |
| ATOM | 639 | CG | LEU | B | 30 | 5.385 | 54.822 | 30.558 | 1.00 | 31.65 | B |
| ATOM | 640 | CD1 | LEU | B | 30 | 4.353 | 55.404 | 29.599 | 1.00 | 34.37 | B |
| ATOM | 641 | CD2 | LEU | B | 30 | 5.377 | 53.282 | 30.511 | 1.00 | 31.69 | B |
| ATOM | 642 | C | LEU | B | 30 | 6.985 | 57.588 | 31.213 | 1.00 | 31.56 | B |
| ATOM | 643 | O | LEU | B | 30 | 6.051 | 58.398 | 31.301 | 1.00 | 26.54 | B |
| ATOM | 644 | N | GLN | B | 31 | 7.860 | 57.442 | 32.206 | 1.00 | 31.24 | B |
| ATOM | 645 | CA | GLN | B | 31 | 7.668 | 58.265 | 33.398 | 1.00 | 33.01 | B |
| ATOM | 646 | CB | GLN | B | 31 | 8.551 | 57.801 | 34.564 | 1.00 | 33.79 | B |
| ATOM | 647 | CG | GLN | B | 31 | 10.013 | 57.729 | 34.321 | 1.00 | 40.91 | B |
| ATOM | 648 | CD | GLN | B | 31 | 10.737 | 57.086 | 35.491 | 1.00 | 44.04 | B |
| ATOM | 649 | OE1 | GLN | B | 31 | 10.804 | 57.648 | 36.598 | 1.00 | 43.99 | B |
| ATOM | 650 | NE2 | GLN | B | 31 | 11.270 | 55.889 | 35.258 | 1.00 | 41.97 | B |
| ATOM | 651 | C | GLN | B | 31 | 7.906 | 59.734 | 33.072 | 1.00 | 34.12 | B |

Figure 11K

| | | | | | | | | | | |
|---|---|---|---|---|---|---|---|---|---|---|
| ATOM | 652 | O | GLN | B | 31 | 7.420 | 60.636 | 33.766 | 1.00 30.63 | B |
| ATOM | 653 | N | LEU | B | 32 | 8.629 | 59.961 | 31.984 | 1.00 34.46 | B |
| ATOM | 654 | CA | LEU | B | 32 | 8.935 | 61.292 | 31.523 | 1.00 36.10 | B |
| ATOM | 655 | CB | LEU | B | 32 | 10.070 | 61.231 | 30.504 | 1.00 40.01 | B |
| ATOM | 656 | CG | LEU | B | 32 | 10.340 | 62.546 | 29.775 | 1.00 40.15 | B |
| ATOM | 657 | CD1 | LEU | B | 32 | 10.853 | 63.586 | 30.765 | 1.00 43.23 | B |
| ATOM | 658 | CD2 | LEU | B | 32 | 11.354 | 62.310 | 28.668 | 1.00 43.00 | B |
| ATOM | 659 | C | LEU | B | 32 | 7.711 | 61.949 | 30.890 | 1.00 36.08 | B |
| ATOM | 660 | O | LEU | B | 32 | 7.552 | 63.162 | 30.964 | 1.00 37.71 | B |
| ATOM | 661 | N | THR | B | 33 | 6.859 | 61.149 | 30.255 | 1.00 32.40 | B |
| ATOM | 662 | CA | THR | B | 33 | 5.659 | 61.679 | 29.617 | 1.00 31.31 | B |
| ATOM | 663 | CB | THR | B | 33 | 5.179 | 60.753 | 28.480 | 1.00 30.70 | B |
| ATOM | 664 | OG1 | THR | B | 33 | 4.536 | 59.603 | 29.030 | 1.00 40.03 | B |
| ATOM | 665 | CG2 | THR | B | 33 | 6.371 | 60.282 | 27.654 | 1.00 31.28 | B |
| ATOM | 666 | C | THR | B | 33 | 4.550 | 61.845 | 30.668 | 1.00 30.03 | B |
| ATOM | 667 | O | THR | B | 33 | 3.739 | 62.772 | 30.585 | 1.00 30.10 | B |
| ATOM | 668 | N | VAL | B | 34 | 4.507 | 60.933 | 31.636 | 1.00 27.29 | B |
| ATOM | 669 | CA | VAL | B | 34 | 3.546 | 61.010 | 32.735 | 1.00 25.28 | B |
| ATOM | 670 | CB | VAL | B | 34 | 3.695 | 59.806 | 33.690 | 1.00 26.71 | B |
| ATOM | 671 | CG1 | VAL | B | 34 | 2.920 | 60.036 | 34.985 | 1.00 27.25 | B |
| ATOM | 672 | CG2 | VAL | B | 34 | 3.176 | 58.565 | 32.997 | 1.00 23.84 | B |
| ATOM | 673 | C | VAL | B | 34 | 3.822 | 62.310 | 33.476 | 1.00 22.65 | B |
| ATOM | 674 | O | VAL | B | 34 | 2.899 | 63.064 | 33.763 | 1.00 21.36 | B |
| ATOM | 675 | N | TRP | B | 35 | 5.100 | 62.580 | 33.757 | 1.00 22.24 | B |
| ATOM | 676 | CA | TRP | B | 35 | 5.502 | 63.828 | 34.414 | 1.00 20.87 | B |
| ATOM | 677 | CB | TRP | B | 35 | 7.016 | 63.843 | 34.653 | 1.00 23.71 | B |
| ATOM | 678 | CG | TRP | B | 35 | 7.523 | 65.040 | 35.434 | 1.00 26.08 | B |
| ATOM | 679 | CD2 | TRP | B | 35 | 7.013 | 65.551 | 36.681 | 1.00 25.13 | B |
| ATOM | 680 | CE2 | TRP | B | 35 | 7.767 | 66.698 | 37.003 | 1.00 28.35 | B |
| ATOM | 681 | CE3 | TRP | B | 35 | 5.985 | 65.143 | 37.547 | 1.00 24.83 | B |
| ATOM | 682 | CD1 | TRP | B | 35 | 8.540 | 65.880 | 35.074 | 1.00 25.67 | B |
| ATOM | 683 | NE1 | TRP | B | 35 | 8.692 | 66.877 | 36.006 | 1.00 27.74 | B |
| ATOM | 684 | CZ2 | TRP | B | 35 | 7.532 | 67.455 | 38.165 | 1.00 28.38 | B |
| ATOM | 685 | CZ3 | TRP | B | 35 | 5.749 | 65.889 | 38.699 | 1.00 23.47 | B |
| ATOM | 686 | CH2 | TRP | B | 35 | 6.516 | 67.034 | 38.999 | 1.00 28.31 | B |
| ATOM | 687 | C | TRP | B | 35 | 5.121 | 65.039 | 33.564 | 1.00 24.26 | B |
| ATOM | 688 | O | TRP | B | 35 | 4.695 | 66.063 | 34.088 | 1.00 23.94 | B |
| ATOM | 689 | N | GLY | B | 36 | 5.308 | 64.927 | 32.247 | 1.00 25.59 | B |
| ATOM | 690 | CA | GLY | B | 36 | 4.961 | 66.013 | 31.348 | 1.00 23.22 | B |
| ATOM | 691 | C | GLY | B | 36 | 3.479 | 66.364 | 31.343 | 1.00 25.72 | B |
| ATOM | 692 | O | GLY | B | 36 | 3.138 | 67.539 | 31.352 | 1.00 28.94 | B |
| ATOM | 693 | N | ILE | B | 37 | 2.610 | 65.356 | 31.311 | 1.00 27.20 | B |
| ATOM | 694 | CA | ILE | B | 37 | 1.160 | 65.560 | 31.315 | 1.00 24.67 | B |
| ATOM | 695 | CB | ILE | B | 37 | 0.429 | 64.223 | 31.230 | 1.00 24.72 | B |
| ATOM | 696 | CG2 | ILE | B | 37 | -1.085 | 64.410 | 31.416 | 1.00 29.15 | B |
| ATOM | 697 | CG1 | ILE | B | 37 | 0.700 | 63.581 | 29.879 | 1.00 22.40 | B |
| ATOM | 698 | CD1 | ILE | B | 37 | 0.023 | 62.237 | 29.714 | 1.00 24.46 | B |
| ATOM | 699 | C | ILE | B | 37 | 0.734 | 66.295 | 32.579 | 1.00 25.86 | B |
| ATOM | 700 | O | ILE | B | 37 | -0.019 | 67.255 | 32.517 | 1.00 25.23 | B |
| ATOM | 701 | N | LYS | B | 38 | 1.242 | 65.840 | 33.722 | 1.00 26.17 | B |
| ATOM | 702 | CA | LYS | B | 38 | 0.967 | 66.449 | 35.020 | 1.00 22.96 | B |
| ATOM | 703 | CB | LYS | B | 38 | 1.656 | 65.652 | 36.130 | 1.00 22.07 | B |
| ATOM | 704 | CG | LYS | B | 38 | 0.953 | 64.410 | 36.522 | 1.00 25.14 | B |
| ATOM | 705 | CD | LYS | B | 38 | -0.225 | 64.727 | 37.423 | 1.00 28.48 | B |
| ATOM | 706 | CE | LYS | B | 38 | -1.014 | 63.468 | 37.617 | 1.00 28.77 | B |
| ATOM | 707 | NZ | LYS | B | 38 | -1.331 | 62.953 | 36.269 | 1.00 34.06 | B |
| ATOM | 708 | C | LYS | B | 38 | 1.458 | 67.877 | 35.102 | 1.00 23.87 | B |
| ATOM | 709 | O | LYS | B | 38 | 0.770 | 68.736 | 35.640 | 1.00 20.93 | B |
| ATOM | 710 | N | GLN | B | 39 | 2.662 | 68.140 | 34.593 | 1.00 26.53 | B |
| ATOM | 711 | CA | GLN | B | 39 | 3.189 | 69.493 | 34.682 | 1.00 30.76 | B |

Figure 11L

| ATOM | 712 | CB  | GLN | B | 39 | 4.629  | 69.583 | 34.297 | 1.00 | 35.05 | B |
| ATOM | 713 | CG  | GLN | B | 39 | 5.436  | 70.614 | 34.985 | 1.00 | 43.49 | B |
| ATOM | 714 | CD  | GLN | B | 39 | 4.822  | 72.026 | 35.008 | 1.00 | 48.65 | B |
| ATOM | 715 | OE1 | GLN | B | 39 | 4.889  | 72.774 | 34.021 | 1.00 | 51.46 | B |
| ATOM | 716 | NE2 | GLN | B | 39 | 4.220  | 72.389 | 36.143 | 1.00 | 47.35 | B |
| ATOM | 717 | C   | GLN | B | 39 | 2.343  | 70.417 | 33.843 | 1.00 | 31.81 | B |
| ATOM | 718 | O   | GLN | B | 39 | 2.125  | 71.574 | 34.206 | 1.00 | 31.08 | B |
| ATOM | 719 | N   | LEU | B | 40 | 1.897  | 69.904 | 32.703 | 1.00 | 31.01 | B |
| ATOM | 720 | CA  | LEU | B | 40 | 1.065  | 70.671 | 31.807 | 1.00 | 33.41 | B |
| ATOM | 721 | CB  | LEU | B | 40 | 0.872  | 69.886 | 30.517 | 1.00 | 32.63 | B |
| ATOM | 722 | CG  | LEU | B | 40 | -0.126 | 70.405 | 29.482 | 1.00 | 34.65 | B |
| ATOM | 723 | CD1 | LEU | B | 40 | 0.171  | 71.843 | 29.092 | 1.00 | 35.24 | B |
| ATOM | 724 | CD2 | LEU | B | 40 | -0.058 | 69.495 | 28.281 | 1.00 | 35.90 | B |
| ATOM | 725 | C   | LEU | B | 40 | -0.289 | 70.943 | 32.469 | 1.00 | 36.85 | B |
| ATOM | 726 | O   | LEU | B | 40 | -0.874 | 72.010 | 32.314 | 1.00 | 37.81 | B |
| ATOM | 727 | N   | GLN | B | 41 | -0.768 | 69.964 | 33.215 | 1.00 | 36.13 | B |
| ATOM | 728 | CA  | GLN | B | 41 | -2.046 | 70.063 | 33.894 | 1.00 | 37.74 | B |
| ATOM | 729 | CB  | GLN | B | 41 | -2.369 | 68.718 | 34.517 | 1.00 | 41.31 | B |
| ATOM | 730 | CG  | GLN | B | 41 | -3.833 | 68.459 | 34.735 | 1.00 | 47.08 | B |
| ATOM | 731 | CD  | GLN | B | 41 | -4.070 | 67.139 | 35.420 | 1.00 | 54.09 | B |
| ATOM | 732 | OE1 | GLN | B | 41 | -3.517 | 66.102 | 35.013 | 1.00 | 55.42 | B |
| ATOM | 733 | NE2 | GLN | B | 41 | -4.908 | 67.154 | 36.461 | 1.00 | 54.90 | B |
| ATOM | 734 | C   | GLN | B | 41 | -2.039 | 71.148 | 34.974 | 1.00 | 39.95 | B |
| ATOM | 735 | O   | GLN | B | 41 | -2.988 | 71.925 | 35.089 | 1.00 | 29.23 | B |
| ATOM | 736 | N   | ALA | B | 42 | -0.972 | 71.194 | 35.767 | 1.00 | 39.05 | B |
| ATOM | 737 | CA  | ALA | B | 42 | -0.845 | 72.188 | 36.824 | 1.00 | 38.56 | B |
| ATOM | 738 | CB  | ALA | B | 42 | 0.345  | 71.852 | 37.757 | 1.00 | 34.14 | B |
| ATOM | 739 | C   | ALA | B | 42 | -0.647 | 73.566 | 36.228 | 1.00 | 40.18 | B |
| ATOM | 740 | O   | ALA | B | 42 | -1.139 | 74.560 | 36.765 | 1.00 | 41.44 | B |
| ATOM | 741 | N   | ARG | B | 43 | 0.078  | 73.634 | 35.118 | 1.00 | 41.82 | B |
| ATOM | 742 | CA  | ARG | B | 43 | 0.340  | 74.910 | 34.476 | 1.00 | 43.71 | B |
| ATOM | 743 | CB  | ARG | B | 43 | 1.242  | 74.713 | 33.260 | 1.00 | 47.26 | B |
| ATOM | 744 | CG  | ARG | B | 43 | 1.703  | 75.997 | 32.592 | 1.00 | 51.08 | B |
| ATOM | 745 | CD  | ARG | B | 43 | 2.582  | 75.677 | 31.401 | 1.00 | 54.95 | B |
| ATOM | 746 | NE  | ARG | B | 43 | 3.778  | 74.947 | 31.813 | 1.00 | 57.04 | B |
| ATOM | 747 | CZ  | ARG | B | 43 | 4.819  | 75.499 | 32.428 | 1.00 | 56.95 | B |
| ATOM | 748 | NH1 | ARG | B | 43 | 4.816  | 76.794 | 32.703 | 1.00 | 55.89 | B |
| ATOM | 749 | NH2 | ARG | B | 43 | 5.858  | 74.753 | 32.781 | 1.00 | 57.00 | B |
| ATOM | 750 | C   | ARG | B | 43 | -0.987 | 75.521 | 34.048 | 1.00 | 42.38 | B |
| ATOM | 751 | O   | ARG | B | 43 | -1.308 | 76.657 | 34.398 | 1.00 | 41.41 | B |
| ATOM | 752 | N   | ILE | B | 44 | -1.756 | 74.736 | 33.310 | 1.00 | 41.63 | B |
| ATOM | 753 | CA  | ILE | B | 44 | -3.059 | 75.143 | 32.810 | 1.00 | 43.24 | B |
| ATOM | 754 | CB  | ILE | B | 44 | -3.634 | 74.085 | 31.866 | 1.00 | 44.23 | B |
| ATOM | 755 | CG2 | ILE | B | 44 | -5.083 | 74.403 | 31.592 | 1.00 | 45.04 | B |
| ATOM | 756 | CG1 | ILE | B | 44 | -2.778 | 73.964 | 30.600 | 1.00 | 47.45 | B |
| ATOM | 757 | CD1 | ILE | B | 44 | -3.156 | 72.745 | 29.719 | 1.00 | 49.42 | B |
| ATOM | 758 | C   | ILE | B | 44 | -4.081 | 75.306 | 33.935 | 1.00 | 42.37 | B |
| ATOM | 759 | O   | ILE | B | 44 | -4.422 | 76.416 | 34.332 | 1.00 | 42.08 | B |
| ATOM | 760 | N   | LEU | B | 45 | -4.573 | 74.162 | 34.398 | 1.00 | 42.20 | B |
| ATOM | 761 | CA  | LEU | B | 45 | -5.564 | 74.042 | 35.450 | 1.00 | 43.16 | B |
| ATOM | 762 | CB  | LEU | B | 45 | -6.041 | 72.592 | 35.513 | 1.00 | 46.08 | B |
| ATOM | 763 | CG  | LEU | B | 45 | -6.459 | 72.001 | 34.162 | 1.00 | 47.45 | B |
| ATOM | 764 | CD1 | LEU | B | 45 | -7.011 | 70.594 | 34.257 | 1.00 | 47.51 | B |
| ATOM | 765 | CD2 | LEU | B | 45 | -7.504 | 72.899 | 33.521 | 1.00 | 48.61 | B |
| ATOM | 766 | C   | LEU | B | 45 | -5.016 | 74.467 | 36.810 | 1.00 | 43.48 | B |
| ATOM | 767 | O   | LEU | B | 45 | -5.674 | 75.260 | 37.483 | 1.00 | 45.15 | B |
| ATOM | 768 | NT  | LEU | B | 45 | -3.945 | 73.987 | 37.206 | 1.00 | 45.66 | B |
| ATOM | 769 | CA  | ACE | C | 0  | 15.143 | 11.286 | 26.819 | 1.00 | 82.49 | C |
| ATOM | 770 | C   | ACE | C | 0  | 14.856 | 12.476 | 27.674 | 1.00 | 82.44 | C |
| ATOM | 771 | O   | ACE | C | 0  | 13.700 | 12.858 | 27.851 | 1.00 | 84.06 | C |

Figure 11M

| ATOM | 772 | N   | ARG | C | 1 | 15.890 | 13.103 | 28.220 | 1.00 | 82.91 | C |
|------|-----|-----|-----|---|---|--------|--------|--------|------|-------|---|
| ATOM | 773 | CA  | ARG | C | 1 | 15.663 | 14.253 | 29.073 | 1.00 | 83.87 | C |
| ATOM | 774 | CB  | ARG | C | 1 | 16.156 | 13.970 | 30.491 | 1.00 | 83.74 | C |
| ATOM | 775 | CG  | ARG | C | 1 | 15.769 | 15.065 | 31.456 | 1.00 | 83.47 | C |
| ATOM | 776 | CD  | ARG | C | 1 | 14.340 | 15.542 | 31.156 | 1.00 | 81.66 | C |
| ATOM | 777 | NE  | ARG | C | 1 | 13.249 | 14.748 | 31.726 | 1.00 | 81.00 | C |
| ATOM | 778 | CZ  | ARG | C | 1 | 13.069 | 13.434 | 31.597 | 1.00 | 79.16 | C |
| ATOM | 779 | NH1 | ARG | C | 1 | 13.901 | 12.678 | 30.889 | 1.00 | 79.80 | C |
| ATOM | 780 | NH2 | ARG | C | 1 | 12.010 | 12.875 | 32.168 | 1.00 | 79.18 | C |
| ATOM | 781 | C   | ARG | C | 1 | 16.282 | 15.541 | 28.550 | 1.00 | 85.03 | C |
| ATOM | 782 | O   | ARG | C | 1 | 15.975 | 16.644 | 29.016 | 1.00 | 85.10 | C |
| ATOM | 783 | N   | MET | C | 2 | 17.169 | 15.394 | 27.581 | 1.00 | 85.40 | C |
| ATOM | 784 | CA  | MET | C | 2 | 17.778 | 16.568 | 27.012 | 1.00 | 86.91 | C |
| ATOM | 785 | CB  | MET | C | 2 | 19.063 | 16.215 | 26.290 | 1.00 | 88.20 | C |
| ATOM | 786 | CG  | MET | C | 2 | 19.711 | 17.410 | 25.653 | 1.00 | 89.72 | C |
| ATOM | 787 | SD  | MET | C | 2 | 21.192 | 16.917 | 24.823 | 1.00 | 94.98 | C |
| ATOM | 788 | CE  | MET | C | 2 | 22.111 | 16.349 | 26.176 | 1.00 | 91.53 | C |
| ATOM | 789 | C   | MET | C | 2 | 16.771 | 17.154 | 26.036 | 1.00 | 87.44 | C |
| ATOM | 790 | O   | MET | C | 2 | 16.699 | 18.368 | 25.872 | 1.00 | 89.05 | C |
| ATOM | 791 | N   | LYS | C | 3 | 16.001 | 16.278 | 25.391 | 1.00 | 85.66 | C |
| ATOM | 792 | CA  | LYS | C | 3 | 14.973 | 16.712 | 24.444 | 1.00 | 83.09 | C |
| ATOM | 793 | CB  | LYS | C | 3 | 14.033 | 15.551 | 24.107 | 1.00 | 82.50 | C |
| ATOM | 794 | CG  | LYS | C | 3 | 12.921 | 15.895 | 23.122 | 1.00 | 81.54 | C |
| ATOM | 795 | CD  | LYS | C | 3 | 11.926 | 14.746 | 23.005 | 1.00 | 81.93 | C |
| ATOM | 796 | CE  | LYS | C | 3 | 10.866 | 15.022 | 21.952 | 1.00 | 80.79 | C |
| ATOM | 797 | NZ  | LYS | C | 3 | 10.154 | 16.300 | 22.214 | 1.00 | 82.56 | C |
| ATOM | 798 | C   | LYS | C | 3 | 14.177 | 17.809 | 25.128 | 1.00 | 82.12 | C |
| ATOM | 799 | O   | LYS | C | 3 | 14.053 | 18.925 | 24.617 | 1.00 | 81.76 | C |
| ATOM | 800 | N   | GLN | C | 4 | 13.651 | 17.474 | 26.303 | 1.00 | 80.32 | C |
| ATOM | 801 | CA  | GLN | C | 4 | 12.856 | 18.401 | 27.094 | 1.00 | 78.67 | C |
| ATOM | 802 | CB  | GLN | C | 4 | 12.504 | 17.759 | 28.440 | 1.00 | 79.91 | C |
| ATOM | 803 | CG  | GLN | C | 4 | 12.122 | 16.275 | 28.356 | 1.00 | 80.66 | C |
| ATOM | 804 | CD  | GLN | C | 4 | 11.087 | 15.971 | 27.280 | 1.00 | 81.02 | C |
| ATOM | 805 | OE1 | GLN | C | 4 | 11.348 | 16.140 | 26.082 | 1.00 | 79.52 | C |
| ATOM | 806 | NE2 | GLN | C | 4 |  9.907 | 15.516 | 27.701 | 1.00 | 81.57 | C |
| ATOM | 807 | C   | GLN | C | 4 | 13.667 | 19.680 | 27.299 | 1.00 | 77.97 | C |
| ATOM | 808 | O   | GLN | C | 4 | 13.186 | 20.781 | 27.032 | 1.00 | 78.45 | C |
| ATOM | 809 | N   | ILE | C | 5 | 14.902 | 19.530 | 27.772 | 1.00 | 76.07 | C |
| ATOM | 810 | CA  | ILE | C | 5 | 15.785 | 20.670 | 27.974 | 1.00 | 73.89 | C |
| ATOM | 811 | CB  | ILE | C | 5 | 17.206 | 20.220 | 28.381 | 1.00 | 73.07 | C |
| ATOM | 812 | CG2 | ILE | C | 5 | 18.175 | 21.388 | 28.264 | 1.00 | 71.17 | C |
| ATOM | 813 | CG1 | ILE | C | 5 | 17.174 | 19.623 | 29.795 | 1.00 | 72.84 | C |
| ATOM | 814 | CD1 | ILE | C | 5 | 18.518 | 19.113 | 30.285 | 1.00 | 71.39 | C |
| ATOM | 815 | C   | ILE | C | 5 | 15.880 | 21.423 | 26.656 | 1.00 | 74.14 | C |
| ATOM | 816 | O   | ILE | C | 5 | 15.939 | 22.651 | 26.628 | 1.00 | 73.70 | C |
| ATOM | 817 | N   | GLU | C | 6 | 15.895 | 20.664 | 25.567 | 1.00 | 73.88 | C |
| ATOM | 818 | CA  | GLU | C | 6 | 15.972 | 21.222 | 24.225 | 1.00 | 73.70 | C |
| ATOM | 819 | CB  | GLU | C | 6 | 16.395 | 20.135 | 23.229 | 1.00 | 72.24 | C |
| ATOM | 820 | CG  | GLU | C | 6 | 17.787 | 19.535 | 23.464 | 1.00 | 69.96 | C |
| ATOM | 821 | CD  | GLU | C | 6 | 18.922 | 20.428 | 22.985 | 1.00 | 68.01 | C |
| ATOM | 822 | OE1 | GLU | C | 6 | 19.044 | 21.575 | 23.461 | 1.00 | 65.93 | C |
| ATOM | 823 | OE2 | GLU | C | 6 | 19.702 | 19.963 | 22.125 | 1.00 | 68.18 | C |
| ATOM | 824 | C   | GLU | C | 6 | 14.602 | 21.773 | 23.842 | 1.00 | 74.50 | C |
| ATOM | 825 | O   | GLU | C | 6 | 14.476 | 22.546 | 22.890 | 1.00 | 75.27 | C |
| ATOM | 826 | N   | ASP | C | 7 | 13.577 | 21.372 | 24.587 | 1.00 | 74.82 | C |
| ATOM | 827 | CA  | ASP | C | 7 | 12.218 | 21.838 | 24.327 | 1.00 | 76.17 | C |
| ATOM | 828 | CB  | ASP | C | 7 | 11.195 | 20.742 | 24.644 | 1.00 | 77.40 | C |
| ATOM | 829 | CG  | ASP | C | 7 | 11.408 | 19.488 | 23.818 | 1.00 | 78.45 | C |
| ATOM | 830 | OD1 | ASP | C | 7 | 11.518 | 19.609 | 22.580 | 1.00 | 79.26 | C |
| ATOM | 831 | OD2 | ASP | C | 7 | 11.452 | 18.380 | 24.404 | 1.00 | 79.10 | C |

Figure 11N

| ATOM | 832 | C | ASP | C | 7 | 11.906 | 23.079 | 25.160 | 1.00 | 75.92 | C |
|---|---|---|---|---|---|---|---|---|---|---|---|
| ATOM | 833 | O | ASP | C | 7 | 11.379 | 24.063 | 24.643 | 1.00 | 77.15 | C |
| ATOM | 834 | N | LYS | C | 8 | 12.223 | 23.024 | 26.452 | 1.00 | 74.05 | C |
| ATOM | 835 | CA | LYS | C | 8 | 11.987 | 24.157 | 27.336 | 1.00 | 71.19 | C |
| ATOM | 836 | CB | LYS | C | 8 | 12.565 | 23.886 | 28.727 | 1.00 | 72.69 | C |
| ATOM | 837 | CG | LYS | C | 8 | 11.647 | 24.225 | 29.901 | 1.00 | 72.96 | C |
| ATOM | 838 | CD | LYS | C | 8 | 10.428 | 23.312 | 29.921 | 1.00 | 75.00 | C |
| ATOM | 839 | CE | LYS | C | 8 | 9.587 | 23.471 | 31.197 | 1.00 | 76.69 | C |
| ATOM | 840 | NZ | LYS | C | 8 | 8.998 | 24.829 | 31.389 | 1.00 | 73.68 | C |
| ATOM | 841 | C | LYS | C | 8 | 12.727 | 25.319 | 26.679 | 1.00 | 69.24 | C |
| ATOM | 842 | O | LYS | C | 8 | 12.295 | 26.469 | 26.745 | 1.00 | 69.77 | C |
| ATOM | 843 | N | ILE | C | 9 | 13.855 | 25.013 | 26.046 | 1.00 | 65.63 | C |
| ATOM | 844 | CA | ILE | C | 9 | 14.609 | 26.053 | 25.362 | 1.00 | 64.27 | C |
| ATOM | 845 | CB | ILE | C | 9 | 15.950 | 25.511 | 24.812 | 1.00 | 62.88 | C |
| ATOM | 846 | CG2 | ILE | C | 9 | 16.585 | 26.515 | 23.871 | 1.00 | 62.42 | C |
| ATOM | 847 | CG1 | ILE | C | 9 | 16.900 | 25.231 | 25.976 | 1.00 | 64.19 | C |
| ATOM | 848 | CD1 | ILE | C | 9 | 18.244 | 24.656 | 25.557 | 1.00 | 64.32 | C |
| ATOM | 849 | C | ILE | C | 9 | 13.756 | 26.605 | 24.223 | 1.00 | 63.69 | C |
| ATOM | 850 | O | ILE | C | 9 | 13.735 | 27.816 | 23.985 | 1.00 | 63.21 | C |
| ATOM | 851 | N | GLU | C | 10 | 13.036 | 25.712 | 23.543 | 1.00 | 62.89 | C |
| ATOM | 852 | CA | GLU | C | 10 | 12.163 | 26.092 | 22.429 | 1.00 | 62.21 | C |
| ATOM | 853 | CB | GLU | C | 10 | 11.419 | 24.865 | 21.886 | 1.00 | 63.68 | C |
| ATOM | 854 | CG | GLU | C | 10 | 10.451 | 25.180 | 20.751 | 1.00 | 66.12 | C |
| ATOM | 855 | CD | GLU | C | 10 | 9.688 | 23.961 | 20.251 | 1.00 | 67.29 | C |
| ATOM | 856 | OE1 | GLU | C | 10 | 8.874 | 24.125 | 19.318 | 1.00 | 69.26 | C |
| ATOM | 857 | OE2 | GLU | C | 10 | 9.894 | 22.845 | 20.780 | 1.00 | 68.71 | C |
| ATOM | 858 | C | GLU | C | 10 | 11.142 | 27.147 | 22.831 | 1.00 | 60.65 | C |
| ATOM | 859 | O | GLU | C | 10 | 10.991 | 28.157 | 22.147 | 1.00 | 60.16 | C |
| ATOM | 860 | N | GLU | C | 11 | 10.429 | 26.898 | 23.927 | 1.00 | 60.41 | C |
| ATOM | 861 | CA | GLU | C | 11 | 9.415 | 27.826 | 24.435 | 1.00 | 58.98 | C |
| ATOM | 862 | CB | GLU | C | 11 | 8.736 | 27.243 | 25.683 | 1.00 | 59.35 | C |
| ATOM | 863 | CG | GLU | C | 11 | 9.709 | 26.588 | 26.652 | 1.00 | 61.78 | C |
| ATOM | 864 | CD | GLU | C | 11 | 9.376 | 26.801 | 28.127 | 1.00 | 63.00 | C |
| ATOM | 865 | OE1 | GLU | C | 11 | 9.329 | 27.972 | 28.563 | 1.00 | 64.82 | C |
| ATOM | 866 | OE2 | GLU | C | 11 | 9.184 | 25.804 | 28.855 | 1.00 | 60.50 | C |
| ATOM | 867 | C | GLU | C | 11 | 10.021 | 29.186 | 24.772 | 1.00 | 58.03 | C |
| ATOM | 868 | O | GLU | C | 11 | 9.519 | 30.229 | 24.351 | 1.00 | 59.21 | C |
| ATOM | 869 | N | ILE | C | 12 | 11.103 | 29.178 | 25.532 | 1.00 | 56.15 | C |
| ATOM | 870 | CA | ILE | C | 12 | 11.765 | 30.415 | 25.902 | 1.00 | 56.41 | C |
| ATOM | 871 | CB | ILE | C | 12 | 13.043 | 30.139 | 26.710 | 1.00 | 55.29 | C |
| ATOM | 872 | CG2 | ILE | C | 12 | 13.791 | 31.448 | 26.950 | 1.00 | 52.26 | C |
| ATOM | 873 | CG1 | ILE | C | 12 | 12.680 | 29.404 | 28.008 | 1.00 | 55.06 | C |
| ATOM | 874 | CD1 | ILE | C | 12 | 13.858 | 29.085 | 28.914 | 1.00 | 55.11 | C |
| ATOM | 875 | C | ILE | C | 12 | 12.132 | 31.239 | 24.671 | 1.00 | 57.76 | C |
| ATOM | 876 | O | ILE | C | 12 | 11.944 | 32.454 | 24.659 | 1.00 | 59.18 | C |
| ATOM | 877 | N | GLU | C | 13 | 12.668 | 30.589 | 23.642 | 1.00 | 60.62 | C |
| ATOM | 878 | CA | GLU | C | 13 | 13.039 | 31.312 | 22.423 | 1.00 | 62.64 | C |
| ATOM | 879 | CB | GLU | C | 13 | 13.916 | 30.449 | 21.497 | 1.00 | 66.02 | C |
| ATOM | 880 | CG | GLU | C | 13 | 13.319 | 29.091 | 21.138 | 1.00 | 70.85 | C |
| ATOM | 881 | CD | GLU | C | 13 | 14.091 | 28.355 | 20.041 | 1.00 | 73.58 | C |
| ATOM | 882 | OE1 | GLU | C | 13 | 15.330 | 28.233 | 20.163 | 1.00 | 72.99 | C |
| ATOM | 883 | OE2 | GLU | C | 13 | 13.456 | 27.887 | 19.064 | 1.00 | 73.78 | C |
| ATOM | 884 | C | GLU | C | 13 | 11.785 | 31.748 | 21.679 | 1.00 | 60.74 | C |
| ATOM | 885 | O | GLU | C | 13 | 11.808 | 32.733 | 20.946 | 1.00 | 61.13 | C |
| ATOM | 886 | N | SER | C | 14 | 10.695 | 31.010 | 21.864 | 1.00 | 59.71 | C |
| ATOM | 887 | CA | SER | C | 14 | 9.432 | 31.350 | 21.213 | 1.00 | 60.53 | C |
| ATOM | 888 | CB | SER | C | 14 | 8.392 | 30.248 | 21.439 | 1.00 | 59.88 | C |
| ATOM | 889 | OG | SER | C | 14 | 7.157 | 30.571 | 20.820 | 1.00 | 56.34 | C |
| ATOM | 890 | C | SER | C | 14 | 8.921 | 32.668 | 21.790 | 1.00 | 61.04 | C |
| ATOM | 891 | O | SER | C | 14 | 8.793 | 33.655 | 21.073 | 1.00 | 59.08 | C |

Figure 11O

```
ATOM    892  N   LYS C  15       8.632  32.671  23.091  1.00 62.79           C
ATOM    893  CA  LYS C  15       8.153  33.873  23.771  1.00 64.30           C
ATOM    894  CB  LYS C  15       7.949  33.612  25.273  1.00 65.74           C
ATOM    895  CG  LYS C  15       6.637  32.903  25.642  1.00 68.25           C
ATOM    896  CD  LYS C  15       6.534  32.695  27.154  1.00 69.92           C
ATOM    897  CE  LYS C  15       5.186  32.131  27.564  1.00 70.69           C
ATOM    898  NZ  LYS C  15       4.078  33.079  27.241  1.00 73.69           C
ATOM    899  C   LYS C  15       9.130  35.029  23.601  1.00 64.03           C
ATOM    900  O   LYS C  15       8.723  36.175  23.408  1.00 64.04           C
ATOM    901  N   GLN C  16      10.418  34.721  23.678  1.00 63.47           C
ATOM    902  CA  GLN C  16      11.451  35.733  23.537  1.00 65.82           C
ATOM    903  CB  GLN C  16      12.813  35.064  23.393  1.00 65.17           C
ATOM    904  CG  GLN C  16      13.970  36.027  23.413  1.00 65.29           C
ATOM    905  CD  GLN C  16      14.944  35.695  24.516  1.00 66.93           C
ATOM    906  OE1 GLN C  16      15.940  36.389  24.719  1.00 68.97           C
ATOM    907  NE2 GLN C  16      14.657  34.621  25.244  1.00 66.55           C
ATOM    908  C   GLN C  16      11.157  36.605  22.317  1.00 67.53           C
ATOM    909  O   GLN C  16      11.172  37.836  22.397  1.00 68.90           C
ATOM    910  N   LYS C  17      10.886  35.952  21.193  1.00 67.63           C
ATOM    911  CA  LYS C  17      10.566  36.648  19.954  1.00 67.83           C
ATOM    912  CB  LYS C  17      10.355  35.627  18.833  1.00 69.39           C
ATOM    913  CG  LYS C  17       9.747  36.199  17.556  1.00 72.05           C
ATOM    914  CD  LYS C  17      10.657  37.203  16.835  1.00 73.47           C
ATOM    915  CE  LYS C  17       9.946  37.784  15.613  1.00 74.71           C
ATOM    916  NZ  LYS C  17      10.885  38.603  14.795  1.00 76.15           C
ATOM    917  C   LYS C  17       9.306  37.492  20.123  1.00 66.64           C
ATOM    918  O   LYS C  17       9.244  38.632  19.652  1.00 67.45           C
ATOM    919  N   LYS C  18       8.300  36.924  20.784  1.00 64.29           C
ATOM    920  CA  LYS C  18       7.049  37.641  21.019  1.00 63.62           C
ATOM    921  CB  LYS C  18       5.979  36.719  21.627  1.00 64.15           C
ATOM    922  CG  LYS C  18       5.088  36.062  20.586  1.00 66.52           C
ATOM    923  CD  LYS C  18       3.935  35.297  21.220  1.00 68.98           C
ATOM    924  CE  LYS C  18       4.427  34.076  21.970  1.00 70.96           C
ATOM    925  NZ  LYS C  18       5.098  33.116  21.040  1.00 72.62           C
ATOM    926  C   LYS C  18       7.265  38.852  21.922  1.00 61.00           C
ATOM    927  O   LYS C  18       6.854  39.958  21.585  1.00 61.84           C
ATOM    928  N   ILE C  19       7.904  38.653  23.067  1.00 56.58           C
ATOM    929  CA  ILE C  19       8.179  39.765  23.961  1.00 53.92           C
ATOM    930  CB  ILE C  19       9.101  39.329  25.119  1.00 52.10           C
ATOM    931  CG2 ILE C  19       9.719  40.545  25.799  1.00 51.95           C
ATOM    932  CG1 ILE C  19       8.304  38.463  26.095  1.00 51.65           C
ATOM    933  CD1 ILE C  19       9.103  37.908  27.247  1.00 50.93           C
ATOM    934  C   ILE C  19       8.833  40.893  23.165  1.00 53.24           C
ATOM    935  O   ILE C  19       8.604  42.069  23.438  1.00 52.35           C
ATOM    936  N   GLU C  20       9.642  40.534  22.173  1.00 53.82           C
ATOM    937  CA  GLU C  20      10.294  41.536  21.338  1.00 54.86           C
ATOM    938  CB  GLU C  20      11.393  40.910  20.472  1.00 55.74           C
ATOM    939  CG  GLU C  20      12.554  40.318  21.251  1.00 56.50           C
ATOM    940  CD  GLU C  20      13.683  39.851  20.352  1.00 56.98           C
ATOM    941  OE1 GLU C  20      13.473  38.918  19.543  1.00 56.87           C
ATOM    942  OE2 GLU C  20      14.786  40.427  20.453  1.00 58.79           C
ATOM    943  C   GLU C  20       9.245  42.168  20.437  1.00 55.80           C
ATOM    944  O   GLU C  20       9.311  43.382  20.166  1.00 55.44           C
ATOM    945  N   ASN C  21       8.289  41.389  19.972  1.00 55.46           C
ATOM    946  CA  ASN C  21       7.223  41.899  19.118  1.00 57.62           C
ATOM    947  CB  ASN C  21       6.392  40.754  18.530  1.00 59.92           C
ATOM    948  CG  ASN C  21       7.060  40.101  17.325  1.00 63.29           C
ATOM    949  OD1 ASN C  21       6.574  39.092  16.806  1.00 62.67           C
ATOM    950  ND2 ASN C  21       8.169  40.684  16.866  1.00 61.87           C
ATOM    951  C   ASN C  21       6.307  42.829  19.891  1.00 58.25           C
```

Figure 11P

| | | | | | | | | | | |
|---|---|---|---|---|---|---|---|---|---|---|
| ATOM | 952 | O | ASN | C | 21 | 5.649 | 43.697 | 19.309 | 1.00 59.75 | C |
| ATOM | 953 | N | GLU | C | 22 | 6.255 | 42.645 | 21.206 | 1.00 56.32 | C |
| ATOM | 954 | CA | GLU | C | 22 | 5.411 | 43.489 | 22.030 | 1.00 53.64 | C |
| ATOM | 955 | CB | GLU | C | 22 | 5.014 | 42.756 | 23.313 | 1.00 55.42 | C |
| ATOM | 956 | CG | GLU | C | 22 | 3.786 | 43.357 | 23.967 | 1.00 60.13 | C |
| ATOM | 957 | CD | GLU | C | 22 | 2.506 | 43.082 | 23.188 | 1.00 61.82 | C |
| ATOM | 958 | OE1 | GLU | C | 22 | 2.559 | 43.024 | 21.942 | 1.00 62.49 | C |
| ATOM | 959 | OE2 | GLU | C | 22 | 1.435 | 42.954 | 23.825 | 1.00 63.39 | C |
| ATOM | 960 | C | GLU | C | 22 | 6.158 | 44.791 | 22.344 | 1.00 50.89 | C |
| ATOM | 961 | O | GLU | C | 22 | 5.573 | 45.873 | 22.282 | 1.00 49.72 | C |
| ATOM | 962 | N | ILE | C | 23 | 7.448 | 44.691 | 22.665 | 1.00 47.08 | C |
| ATOM | 963 | CA | ILE | C | 23 | 8.259 | 45.876 | 22.948 | 1.00 46.40 | C |
| ATOM | 964 | CB | ILE | C | 23 | 9.752 | 45.504 | 23.290 | 1.00 47.53 | C |
| ATOM | 965 | CG2 | ILE | C | 23 | 10.707 | 46.653 | 22.910 | 1.00 44.86 | C |
| ATOM | 966 | CG1 | ILE | C | 23 | 9.898 | 45.178 | 24.783 | 1.00 45.28 | C |
| ATOM | 967 | CD1 | ILE | C | 23 | 9.101 | 44.004 | 25.256 | 1.00 45.91 | C |
| ATOM | 968 | C | ILE | C | 23 | 8.222 | 46.771 | 21.717 | 1.00 46.76 | C |
| ATOM | 969 | O | ILE | C | 23 | 8.317 | 47.999 | 21.822 | 1.00 46.87 | C |
| ATOM | 970 | N | ALA | C | 24 | 8.071 | 46.137 | 20.556 | 1.00 47.50 | C |
| ATOM | 971 | CA | ALA | C | 24 | 8.002 | 46.828 | 19.271 | 1.00 46.10 | C |
| ATOM | 972 | CB | ALA | C | 24 | 8.112 | 45.809 | 18.126 | 1.00 44.51 | C |
| ATOM | 973 | C | ALA | C | 24 | 6.706 | 47.644 | 19.137 | 1.00 45.09 | C |
| ATOM | 974 | O | ALA | C | 24 | 6.741 | 48.810 | 18.752 | 1.00 43.05 | C |
| ATOM | 975 | N | ARG | C | 25 | 5.566 | 47.034 | 19.445 | 1.00 43.64 | C |
| ATOM | 976 | CA | ARG | C | 25 | 4.301 | 47.753 | 19.346 | 1.00 45.79 | C |
| ATOM | 977 | CB | ARG | C | 25 | 3.115 | 46.807 | 19.581 | 1.00 44.07 | C |
| ATOM | 978 | CG | ARG | C | 25 | 3.045 | 45.680 | 18.564 | 1.00 48.16 | C |
| ATOM | 979 | CD | ARG | C | 25 | 1.677 | 44.986 | 18.458 | 1.00 50.13 | C |
| ATOM | 980 | NE | ARG | C | 25 | 1.216 | 44.299 | 19.664 | 1.00 54.12 | C |
| ATOM | 981 | CZ | ARG | C | 25 | 0.665 | 44.888 | 20.725 | 1.00 58.36 | C |
| ATOM | 982 | NH1 | ARG | C | 25 | 0.475 | 46.206 | 20.756 | 1.00 59.26 | C |
| ATOM | 983 | NH2 | ARG | C | 25 | 0.268 | 44.148 | 21.755 | 1.00 59.83 | C |
| ATOM | 984 | C | ARG | C | 25 | 4.257 | 48.908 | 20.345 | 1.00 47.24 | C |
| ATOM | 985 | O | ARG | C | 25 | 3.941 | 50.038 | 19.978 | 1.00 50.68 | C |
| ATOM | 986 | N | ILE | C | 26 | 4.584 | 48.617 | 21.601 | 1.00 47.54 | C |
| ATOM | 987 | CA | ILE | C | 26 | 4.591 | 49.608 | 22.673 | 1.00 44.40 | C |
| ATOM | 988 | CB | ILE | C | 26 | 5.042 | 48.959 | 24.001 | 1.00 43.91 | C |
| ATOM | 989 | CG2 | ILE | C | 26 | 5.259 | 50.026 | 25.071 | 1.00 45.47 | C |
| ATOM | 990 | CG1 | ILE | C | 26 | 4.010 | 47.930 | 24.450 | 1.00 42.59 | C |
| ATOM | 991 | CD1 | ILE | C | 26 | 4.445 | 47.138 | 25.663 | 1.00 40.19 | C |
| ATOM | 992 | C | ILE | C | 26 | 5.532 | 50.766 | 22.379 | 1.00 44.58 | C |
| ATOM | 993 | O | ILE | C | 26 | 5.193 | 51.935 | 22.564 | 1.00 42.04 | C |
| ATOM | 994 | N | LYS | C | 27 | 6.721 | 50.422 | 21.919 | 1.00 46.75 | C |
| ATOM | 995 | CA | LYS | C | 27 | 7.754 | 51.394 | 21.619 | 1.00 51.78 | C |
| ATOM | 996 | CB | LYS | C | 27 | 8.915 | 50.674 | 20.951 | 1.00 54.23 | C |
| ATOM | 997 | CG | LYS | C | 27 | 10.184 | 51.465 | 20.863 | 1.00 57.21 | C |
| ATOM | 998 | CD | LYS | C | 27 | 11.313 | 50.479 | 20.644 | 1.00 60.99 | C |
| ATOM | 999 | CE | LYS | C | 27 | 12.660 | 51.064 | 21.014 | 1.00 62.83 | C |
| ATOM | 1000 | NZ | LYS | C | 27 | 13.750 | 50.060 | 20.828 | 1.00 64.49 | C |
| ATOM | 1001 | C | LYS | C | 27 | 7.299 | 52.556 | 20.750 | 1.00 52.44 | C |
| ATOM | 1002 | O | LYS | C | 27 | 7.334 | 53.710 | 21.165 | 1.00 54.11 | C |
| ATOM | 1003 | N | LYS | C | 28 | 6.877 | 52.239 | 19.538 | 1.00 53.88 | C |
| ATOM | 1004 | CA | LYS | C | 28 | 6.435 | 53.250 | 18.599 | 1.00 55.29 | C |
| ATOM | 1005 | CB | LYS | C | 28 | 6.169 | 52.582 | 17.249 | 1.00 57.59 | C |
| ATOM | 1006 | CG | LYS | C | 28 | 7.390 | 51.841 | 16.717 | 1.00 59.15 | C |
| ATOM | 1007 | CD | LYS | C | 28 | 7.041 | 50.830 | 15.635 | 1.00 62.19 | C |
| ATOM | 1008 | CE | LYS | C | 28 | 8.292 | 50.088 | 15.158 | 1.00 63.12 | C |
| ATOM | 1009 | NZ | LYS | C | 28 | 9.029 | 49.411 | 16.282 | 1.00 65.69 | C |
| ATOM | 1010 | C | LYS | C | 28 | 5.187 | 53.931 | 19.122 | 1.00 55.14 | C |
| ATOM | 1011 | O | LYS | C | 28 | 5.052 | 55.147 | 19.030 | 1.00 57.43 | C |

Figure 11Q

| | | | | | | | | | |
|---|---|---|---|---|---|---|---|---|---|
| ATOM | 1012 | N | LEU | C | 29 | 4.275 | 53.138 | 19.671 | 1.00 52.27 | C |
| ATOM | 1013 | CA | LEU | C | 29 | 3.025 | 53.649 | 20.214 | 1.00 51.04 | C |
| ATOM | 1014 | CB | LEU | C | 29 | 2.281 | 52.485 | 20.855 | 1.00 51.13 | C |
| ATOM | 1015 | CG | LEU | C | 29 | 0.776 | 52.493 | 21.051 | 1.00 50.66 | C |
| ATOM | 1016 | CD1 | LEU | C | 29 | 0.051 | 53.868 | 19.755 | 1.00 51.59 | C |
| ATOM | 1017 | CD2 | LEU | C | 29 | 0.389 | 51.100 | 21.491 | 1.00 50.29 | C |
| ATOM | 1018 | C | LEU | C | 29 | 3.347 | 54.739 | 21.245 | 1.00 50.83 | C |
| ATOM | 1019 | O | LEU | C | 29 | 2.739 | 55.805 | 21.269 | 1.00 53.58 | C |
| ATOM | 1020 | N | LEU | C | 30 | 4.327 | 54.457 | 22.089 | 1.00 50.52 | C |
| ATOM | 1021 | CA | LEU | C | 30 | 4.767 | 55.397 | 23.100 | 1.00 48.88 | C |
| ATOM | 1022 | CB | LEU | C | 30 | 5.813 | 54.730 | 23.997 | 1.00 48.03 | C |
| ATOM | 1023 | CG | LEU | C | 30 | 6.485 | 55.530 | 25.113 | 1.00 47.31 | C |
| ATOM | 1024 | CD1 | LEU | C | 30 | 5.447 | 56.172 | 26.033 | 1.00 45.24 | C |
| ATOM | 1025 | CD2 | LEU | C | 30 | 7.398 | 54.575 | 25.889 | 1.00 48.28 | C |
| ATOM | 1026 | C | LEU | C | 30 | 5.374 | 56.587 | 22.379 | 1.00 48.83 | C |
| ATOM | 1027 | O | LEU | C | 30 | 5.020 | 57.736 | 22.642 | 1.00 48.40 | C |
| ATOM | 1028 | N | GLN | C | 31 | 6.298 | 56.289 | 21.470 | 1.00 49.93 | C |
| ATOM | 1029 | CA | GLN | C | 31 | 6.983 | 57.304 | 20.670 | 1.00 52.00 | C |
| ATOM | 1030 | CB | GLN | C | 31 | 7.822 | 56.609 | 19.590 | 1.00 55.56 | C |
| ATOM | 1031 | CG | GLN | C | 31 | 8.628 | 57.513 | 18.645 | 1.00 61.26 | C |
| ATOM | 1032 | CD | GLN | C | 31 | 9.768 | 58.241 | 19.333 | 1.00 64.58 | C |
| ATOM | 1033 | OE1 | GLN | C | 31 | 10.233 | 57.818 | 20.391 | 1.00 68.00 | C |
| ATOM | 1034 | NE2 | GLN | C | 31 | 10.249 | 59.318 | 18.715 | 1.00 64.37 | C |
| ATOM | 1035 | C | GLN | C | 31 | 5.947 | 58.235 | 20.009 | 1.00 49.56 | C |
| ATOM | 1036 | O | GLN | C | 31 | 6.192 | 59.415 | 19.814 | 1.00 45.68 | C |
| ATOM | 1037 | N | LEU | C | 32 | 4.793 | 57.657 | 19.675 | 1.00 47.64 | C |
| ATOM | 1038 | CA | LEU | C | 32 | 3.723 | 58.401 | 19.034 | 1.00 48.95 | C |
| ATOM | 1039 | CB | LEU | C | 32 | 2.689 | 57.433 | 18.461 | 1.00 50.72 | C |
| ATOM | 1040 | CG | LEU | C | 32 | 1.602 | 57.925 | 17.502 | 1.00 51.93 | C |
| ATOM | 1041 | CD1 | LEU | C | 32 | 2.209 | 58.293 | 16.154 | 1.00 50.26 | C |
| ATOM | 1042 | CD2 | LEU | C | 32 | 0.554 | 56.840 | 17.313 | 1.00 51.55 | C |
| ATOM | 1043 | C | LEU | C | 32 | 3.070 | 59.295 | 20.077 | 1.00 49.32 | C |
| ATOM | 1044 | O | LEU | C | 32 | 3.040 | 60.519 | 19.929 | 1.00 50.01 | C |
| ATOM | 1045 | N | THR | C | 33 | 2.545 | 58.659 | 21.125 | 1.00 48.74 | C |
| ATOM | 1046 | CA | THR | C | 33 | 1.878 | 59.324 | 22.246 | 1.00 43.86 | C |
| ATOM | 1047 | CB | THR | C | 33 | 1.643 | 58.329 | 23.400 | 1.00 46.04 | C |
| ATOM | 1048 | OG1 | THR | C | 33 | 0.707 | 57.332 | 22.977 | 1.00 47.18 | C |
| ATOM | 1049 | CG2 | THR | C | 33 | 1.121 | 59.039 | 24.639 | 1.00 42.89 | C |
| ATOM | 1050 | C | THR | C | 33 | 2.683 | 60.494 | 22.771 | 1.00 41.04 | C |
| ATOM | 1051 | O | THR | C | 33 | 2.132 | 61.537 | 23.122 | 1.00 39.26 | C |
| ATOM | 1052 | N | VAL | C | 34 | 3.992 | 60.303 | 22.843 | 1.00 38.83 | C |
| ATOM | 1053 | CA | VAL | C | 34 | 4.886 | 61.346 | 23.301 | 1.00 36.90 | C |
| ATOM | 1054 | CB | VAL | C | 34 | 6.329 | 60.825 | 23.377 | 1.00 33.71 | C |
| ATOM | 1055 | CG1 | VAL | C | 34 | 7.270 | 61.907 | 23.904 | 1.00 29.40 | C |
| ATOM | 1056 | CG2 | VAL | C | 34 | 6.366 | 59.590 | 24.251 | 1.00 31.78 | C |
| ATOM | 1057 | C | VAL | C | 34 | 4.795 | 62.437 | 22.254 | 1.00 38.65 | C |
| ATOM | 1058 | O | VAL | C | 34 | 4.489 | 63.595 | 22.556 | 1.00 39.38 | C |
| ATOM | 1059 | N | TRP | C | 35 | 5.049 | 62.038 | 21.010 | 1.00 42.18 | C |
| ATOM | 1060 | CA | TRP | C | 35 | 5.002 | 62.937 | 19.868 | 1.00 40.00 | C |
| ATOM | 1061 | CB | TRP | C | 35 | 4.991 | 62.134 | 18.563 | 1.00 40.06 | C |
| ATOM | 1062 | CG | TRP | C | 35 | 4.848 | 63.020 | 17.399 | 1.00 36.56 | C |
| ATOM | 1063 | CD2 | TRP | C | 35 | 3.696 | 63.161 | 16.561 | 1.00 36.91 | C |
| ATOM | 1064 | CE2 | TRP | C | 35 | 3.968 | 64.212 | 15.673 | 1.00 41.20 | C |
| ATOM | 1065 | CE3 | TRP | C | 35 | 2.457 | 62.505 | 16.503 | 1.00 40.31 | C |
| ATOM | 1066 | CD1 | TRP | C | 35 | 5.748 | 63.944 | 16.974 | 1.00 35.30 | C |
| ATOM | 1067 | NE1 | TRP | C | 35 | 5.228 | 64.673 | 15.945 | 1.00 39.45 | C |
| ATOM | 1068 | CZ2 | TRP | C | 35 | 3.037 | 64.643 | 14.704 | 1.00 38.75 | C |
| ATOM | 1069 | CZ3 | TRP | C | 35 | 1.528 | 62.934 | 15.541 | 1.00 39.54 | C |
| ATOM | 1070 | CH2 | TRP | C | 35 | 1.827 | 63.984 | 14.651 | 1.00 41.30 | C |
| ATOM | 1071 | C | TRP | C | 35 | 3.764 | 63.833 | 19.901 | 1.00 39.80 | C |

Figure 11R

```
ATOM   1072  O    TRP C  35       3.868  65.052  19.769  1.00 38.39           C
ATOM   1073  N    GLY C  36       2.601  63.210  20.059  1.00 36.88           C
ATOM   1074  CA   GLY C  36       1.356  63.957  20.103  1.00 38.94           C
ATOM   1075  C    GLY C  36       1.315  64.973  21.226  1.00 38.45           C
ATOM   1076  O    GLY C  36       0.931  66.114  21.001  1.00 37.76           C
ATOM   1077  N    ILE C  37       1.700  64.557  22.435  1.00 40.86           C
ATOM   1078  CA   ILE C  37       1.724  65.442  23.604  1.00 36.66           C
ATOM   1079  CB   ILE C  37       2.352  64.755  24.857  1.00 36.83           C
ATOM   1080  CG2  ILE C  37       2.489  65.766  26.005  1.00 27.22           C
ATOM   1081  CG1  ILE C  37       1.512  63.548  25.275  1.00 37.14           C
ATOM   1082  CD1  ILE C  37       2.066  62.794  26.501  1.00 35.85           C
ATOM   1083  C    ILE C  37       2.587  66.655  23.284  1.00 38.37           C
ATOM   1084  O    ILE C  37       2.187  67.788  23.529  1.00 37.68           C
ATOM   1085  N    LYS C  38       3.775  66.399  22.740  1.00 40.28           C
ATOM   1086  CA   LYS C  38       4.717  67.456  22.381  1.00 42.51           C
ATOM   1087  CB   LYS C  38       5.927  66.868  21.639  1.00 46.36           C
ATOM   1088  CG   LYS C  38       7.109  67.829  21.391  1.00 52.00           C
ATOM   1089  CD   LYS C  38       8.125  67.162  20.433  1.00 56.10           C
ATOM   1090  CE   LYS C  38       9.365  68.008  20.096  1.00 56.61           C
ATOM   1091  NZ   LYS C  38      10.340  68.155  21.222  1.00 59.57           C
ATOM   1092  C    LYS C  38       3.995  68.445  21.483  1.00 42.06           C
ATOM   1093  O    LYS C  38       4.351  69.628  21.428  1.00 41.76           C
ATOM   1094  N    GLN C  39       2.977  67.966  20.774  1.00 39.73           C
ATOM   1095  CA   GLN C  39       2.232  68.862  19.908  1.00 40.05           C
ATOM   1096  CB   GLN C  39       1.499  68.100  18.778  1.00 41.27           C
ATOM   1097  CG   GLN C  39       2.385  67.148  17.928  1.00 42.44           C
ATOM   1098  CD   GLN C  39       3.681  67.786  17.465  1.00 42.00           C
ATOM   1099  OE1  GLN C  39       3.678  68.822  16.813  1.00 44.81           C
ATOM   1100  NE2  GLN C  39       4.802  67.163  17.802  1.00 46.04           C
ATOM   1101  C    GLN C  39       1.241  69.638  20.781  1.00 36.22           C
ATOM   1102  O    GLN C  39       1.344  70.845  20.885  1.00 34.78           C
ATOM   1103  N    LEU C  40       0.285  68.950  21.398  1.00 34.58           C
ATOM   1104  CA   LEU C  40      -0.696  69.625  22.268  1.00 36.22           C
ATOM   1105  CB   LEU C  40      -1.465  68.595  23.096  1.00 34.67           C
ATOM   1106  CG   LEU C  40      -2.365  69.192  24.186  1.00 34.61           C
ATOM   1107  CD1  LEU C  40      -3.392  70.142  23.510  1.00 34.28           C
ATOM   1108  CD2  LEU C  40      -3.057  68.084  24.972  1.00 30.45           C
ATOM   1109  C    LEU C  40      -0.029  70.630  23.226  1.00 36.51           C
ATOM   1110  O    LEU C  40      -0.494  71.755  23.419  1.00 36.17           C
ATOM   1111  N    GLN C  41       1.068  70.220  23.832  1.00 36.56           C
ATOM   1112  CA   GLN C  41       1.764  71.106  24.751  1.00 38.77           C
ATOM   1113  CB   GLN C  41       2.883  70.310  25.433  1.00 38.66           C
ATOM   1114  CG   GLN C  41       3.606  70.994  26.582  1.00 46.41           C
ATOM   1115  CD   GLN C  41       4.245  69.979  27.529  1.00 50.25           C
ATOM   1116  OE1  GLN C  41       4.898  69.028  27.091  1.00 53.94           C
ATOM   1117  NE2  GLN C  41       4.063  70.180  28.831  1.00 52.04           C
ATOM   1118  C    GLN C  41       2.291  72.336  23.998  1.00 37.58           C
ATOM   1119  O    GLN C  41       2.190  73.466  24.486  1.00 38.73           C
ATOM   1120  N    ALA C  42       2.827  72.128  22.795  1.00 36.75           C
ATOM   1121  CA   ALA C  42       3.365  73.249  22.014  1.00 36.93           C
ATOM   1122  CB   ALA C  42       4.084  72.717  20.779  1.00 32.48           C
ATOM   1123  C    ALA C  42       2.241  74.209  21.600  1.00 35.85           C
ATOM   1124  O    ALA C  42       2.407  75.427  21.602  1.00 34.18           C
ATOM   1125  N    ARG C  43       1.101  73.629  21.249  1.00 32.51           C
ATOM   1126  CA   ARG C  43      -0.072  74.365  20.829  1.00 34.59           C
ATOM   1127  CB   ARG C  43      -1.152  73.357  20.524  1.00 34.80           C
ATOM   1128  CG   ARG C  43      -2.467  73.891  20.060  1.00 36.54           C
ATOM   1129  CD   ARG C  43      -3.310  72.667  19.769  1.00 37.93           C
ATOM   1130  NE   ARG C  43      -4.631  72.945  19.236  1.00 40.51           C
ATOM   1131  CZ   ARG C  43      -5.481  71.985  18.901  1.00 42.74           C
```

Figure 11S

| | | | | | | | | | | |
|---|---|---|---|---|---|---|---|---|---|---|
| ATOM | 1132 | NH1 | ARG | C | 43 | -5.127 | 70.717 | 19.051 | 1.00 41.40 | C |
| ATOM | 1133 | NH2 | ARG | C | 43 | -6.676 | 72.289 | 18.421 | 1.00 44.00 | C |
| ATOM | 1134 | C | ARG | C | 43 | -0.568 | 75.347 | 21.883 | 1.00 37.96 | C |
| ATOM | 1135 | O | ARG | C | 43 | -1.049 | 76.425 | 21.558 | 1.00 36.78 | C |
| ATOM | 1136 | N | ILE | C | 44 | -0.434 | 74.971 | 23.151 | 1.00 41.66 | C |
| ATOM | 1137 | CA | ILE | C | 44 | -0.901 | 75.799 | 24.250 | 1.00 43.04 | C |
| ATOM | 1138 | CB | ILE | C | 44 | -1.403 | 74.891 | 25.390 | 1.00 45.88 | C |
| ATOM | 1139 | CG2 | ILE | C | 44 | -1.802 | 75.717 | 26.594 | 1.00 46.21 | C |
| ATOM | 1140 | CG1 | ILE | C | 44 | -2.572 | 74.041 | 24.876 | 1.00 46.16 | C |
| ATOM | 1141 | CD1 | ILE | C | 44 | -2.926 | 72.877 | 25.786 | 1.00 50.31 | C |
| ATOM | 1142 | C | ILE | C | 44 | 0.109 | 76.802 | 24.807 | 1.00 41.15 | C |
| ATOM | 1143 | O | ILE | C | 44 | -0.235 | 77.961 | 25.047 | 1.00 40.03 | C |
| ATOM | 1144 | N | LEU | C | 45 | 1.345 | 76.350 | 25.005 | 1.00 40.33 | C |
| ATOM | 1145 | CA | LEU | C | 45 | 2.401 | 77.184 | 25.579 | 1.00 39.81 | C |
| ATOM | 1146 | CB | LEU | C | 45 | 3.357 | 76.322 | 26.422 | 1.00 40.22 | C |
| ATOM | 1147 | CG | LEU | C | 45 | 2.889 | 75.608 | 27.694 | 1.00 40.80 | C |
| ATOM | 1148 | CD1 | LEU | C | 45 | 1.733 | 74.714 | 27.364 | 1.00 42.51 | C |
| ATOM | 1149 | CD2 | LEU | C | 45 | 4.029 | 74.789 | 28.299 | 1.00 39.44 | C |
| ATOM | 1150 | C | LEU | C | 45 | 3.215 | 77.953 | 24.540 | 1.00 38.95 | C |
| ATOM | 1151 | O | LEU | C | 45 | 3.071 | 77.689 | 23.327 | 1.00 39.83 | C |
| ATOM | 1152 | NT | LEU | C | 45 | 4.014 | 78.810 | 24.964 | 1.00 39.47 | C |
| ATOM | 1153 | OH2 | TIP | W | 2 | 8.280 | 62.369 | 27.138 | 1.00 38.82 | W |
| ATOM | 1154 | OH2 | TIP | W | 3 | 28.782 | 24.001 | 17.582 | 1.00 78.47 | W |
| ATOM | 1155 | OH2 | TIP | W | 4 | 0.492 | 62.209 | 33.896 | 1.00 50.43 | W |
| ATOM | 1156 | OH2 | TIP | W | 5 | 6.020 | 70.609 | 23.199 | 1.00 45.29 | W |
| ATOM | 1157 | OH2 | TIP | W | 6 | 1.993 | 78.695 | 31.896 | 1.00 37.25 | W |
| ATOM | 1158 | OH2 | TIP | W | 7 | 20.294 | 18.975 | 19.485 | 1.00 49.56 | W |
| ATOM | 1159 | OH2 | TIP | W | 8 | 18.592 | 15.442 | 35.405 | 1.00 34.86 | W |
| ATOM | 1160 | OH2 | TIP | W | 9 | -5.907 | 64.337 | 32.524 | 1.00 31.24 | W |
| ATOM | 1161 | OH2 | TIP | W | 10 | 11.567 | 18.853 | 30.945 | 1.00 47.94 | W |
| ATOM | 1162 | OH2 | TIP | W | 11 | -9.321 | 65.456 | 23.794 | 1.00 46.60 | W |
| ATOM | 1163 | OH2 | TIP | W | 12 | -2.842 | 65.953 | 28.078 | 1.00 59.15 | W |
| ATOM | 1164 | OH2 | TIP | W | 13 | -1.409 | 77.305 | 18.859 | 1.00 37.51 | W |
| ATOM | 1165 | OH2 | TIP | W | 14 | -5.597 | 64.224 | 37.408 | 1.00 39.02 | W |
| ATOM | 1166 | OH2 | TIP | W | 15 | -5.079 | 75.908 | 18.460 | 1.00 48.65 | W |
| ATOM | 1167 | OH2 | TIP | W | 16 | 12.444 | 58.431 | 21.920 | 1.00 62.97 | W |
| ATOM | 1168 | OH2 | TIP | W | 17 | -12.927 | 70.555 | 24.520 | 1.00 61.81 | W |
| ATOM | 1169 | OH2 | TIP | W | 18 | 14.897 | 23.356 | 34.046 | 1.00 40.13 | W |
| ATOM | 1170 | OH2 | TIP | W | 19 | 3.154 | 40.721 | 28.964 | 1.00 29.89 | W |
| ATOM | 1171 | OH2 | TIP | W | 20 | 4.290 | 81.951 | 24.440 | 1.00 44.83 | W |
| ATOM | 1172 | OH2 | TIP | W | 21 | 26.490 | 23.104 | 32.265 | 1.00 62.67 | W |
| ATOM | 1173 | OH2 | TIP | W | 22 | 13.085 | 59.162 | 33.622 | 1.00 54.53 | W |
| ATOM | 1174 | OH2 | TIP | W | 23 | -0.166 | 45.626 | 35.200 | 1.00 56.34 | W |
| ATOM | 1175 | OH2 | TIP | W | 24 | -10.278 | 62.692 | 33.867 | 1.00 64.05 | W |
| ATOM | 1176 | OH2 | TIP | W | 25 | 22.697 | 10.892 | 29.710 | 1.00100.00 | W |
| ATOM | 1177 | OH2 | TIP | W | 26 | 4.281 | 39.194 | 26.136 | 1.00 62.29 | W |
| ATOM | 1178 | OH2 | TIP | W | 27 | 22.833 | 20.843 | 19.882 | 1.00 59.57 | W |
| ATOM | 1179 | OH2 | TIP | W | 28 | -10.030 | 74.838 | 23.517 | 1.00 53.18 | W |
| ATOM | 1180 | OH2 | TIP | W | 29 | 1.246 | 80.456 | 24.973 | 1.00 36.18 | W |
| ATOM | 1181 | OH2 | TIP | W | 30 | -3.034 | 76.181 | 17.506 | 1.00 50.44 | W |
| ATOM | 1182 | OH2 | TIP | W | 31 | 1.424 | 49.275 | 18.155 | 1.00 44.03 | W |
| ATOM | 1183 | OH2 | TIP | W | 32 | 6.269 | 64.921 | 23.710 | 1.00 31.68 | W |
| ATOM | 1184 | OH2 | TIP | W | 33 | 27.134 | 28.497 | 40.798 | 1.00 60.31 | W |
| ATOM | 1185 | OH2 | TIP | W | 34 | 24.326 | 28.221 | 41.517 | 1.00 85.52 | W |
| ATOM | 1186 | OH2 | TIP | W | 35 | 24.492 | 26.009 | 31.850 | 1.00 68.20 | W |
| ATOM | 1187 | OH2 | TIP | W | 36 | 17.270 | 23.540 | 41.621 | 1.00 45.61 | W |
| ATOM | 1188 | OH2 | TIP | W | 37 | 17.175 | 27.169 | 41.299 | 1.00 57.26 | W |
| ATOM | 1189 | OH2 | TIP | W | 38 | 17.133 | 30.154 | 42.769 | 1.00 94.65 | W |
| ATOM | 1190 | OH2 | TIP | W | 39 | 23.961 | 29.473 | 38.207 | 1.00 73.43 | W |
| ATOM | 1191 | OH2 | TIP | W | 40 | 26.646 | 30.299 | 35.030 | 1.00 86.46 | W |

Figure 11T

```
ATOM   1192  OH2 TIP W   41     21.799  33.921  37.475  1.00 98.23      W
ATOM   1193  OH2 TIP W   42     12.296  24.508  37.800  1.00 73.10      W
ATOM   1194  OH2 TIP W   43     10.910  28.524  40.599  1.00 65.23      W
ATOM   1195  OH2 TIP W   44      8.726  30.065  36.214  1.00 62.46      W
ATOM   1196  OH2 TIP W   45     20.748  34.061  34.804  1.00 62.12      W
ATOM   1197  OH2 TIP W   46      7.462  29.159  29.170  1.00 86.23      W
ATOM   1198  OH2 TIP W   47      7.466  31.280  33.124  1.00 56.10      W
ATOM   1199  OH2 TIP W   48      6.666  26.619  36.241  1.00 52.76      W
ATOM   1200  OH2 TIP W   49      3.823  27.148  35.557  1.00 92.76      W
ATOM   1201  OH2 TIP W   50      7.608  28.183  32.367  1.00 83.54      W
ATOM   1202  OH2 TIP W   51     10.064  35.767  38.975  1.00 68.12      W
ATOM   1203  OH2 TIP W   52     14.649  36.973  38.236  1.00 73.09      W
ATOM   1204  OH2 TIP W   53     16.799  36.406  39.778  1.00 48.69      W
ATOM   1205  OH2 TIP W   54     15.456  39.954  39.598  1.00 48.97      W
ATOM   1206  OH2 TIP W   55      8.442  41.891  37.753  1.00 57.63      W
ATOM   1207  OH2 TIP W   56      9.926  44.040  39.986  1.00 80.20      W
ATOM   1208  OH2 TIP W   57      3.713  35.630  32.034  1.00 65.94      W
ATOM   1209  OH2 TIP W   58      4.004  32.569  30.481  1.00 98.02      W
ATOM   1210  OH2 TIP W   59     13.514  45.594  36.374  1.00 45.92      W
ATOM   1211  OH2 TIP W   60     12.274  44.358  32.693  1.00 69.72      W
ATOM   1212  OH2 TIP W   61     -1.770  41.459  30.288  1.00 86.62      W
ATOM   1213  OH2 TIP W   62     -0.747  39.619  34.003  1.00 85.57      W
ATOM   1214  OH2 TIP W   63      2.370  42.056  36.997  1.00 63.26      W
ATOM   1215  OH2 TIP W   64      7.646  47.813  26.559  1.00 86.77      W
ATOM   1216  OH2 TIP W   65     -1.942  50.096  25.818  1.00 33.47      W
ATOM   1217  OH2 TIP W   66     -0.455  48.262  24.057  1.00 48.49      W
ATOM   1218  OH2 TIP W   67     -1.850  44.976  32.352  1.00 46.88      W
ATOM   1219  OH2 TIP W   68     -4.779  47.469  30.587  1.00 53.38      W
ATOM   1220  OH2 TIP W   69     -8.800  47.417  33.155  1.00 55.34      W
ATOM   1221  OH2 TIP W   70     -7.762  51.374  35.608  1.00 72.46      W
ATOM   1222  OH2 TIP W   71      5.493  50.307  35.418  1.00 63.93      W
ATOM   1223  OH2 TIP W   72     -2.293  60.557  33.176  1.00 58.13      W
ATOM   1224  OH2 TIP W   73     -3.891  59.956  22.859  1.00 42.99      W
ATOM   1225  OH2 TIP W   74     -2.324  52.365  23.808  1.00 68.12      W
ATOM   1226  OH2 TIP W   75     -4.610  53.603  23.534  1.00 99.86      W
ATOM   1227  OH2 TIP W   76     -5.369  51.351  24.806  1.00 66.59      W
ATOM   1228  OH2 TIP W   77     -9.158  53.927  27.711  1.00 59.38      W
ATOM   1229  OH2 TIP W   78     -6.839  60.379  22.155  1.00 48.43      W
ATOM   1230  OH2 TIP W   79     -7.811  55.209  31.835  1.00 63.25      W
ATOM   1231  OH2 TIP W   80     -8.988  55.740  34.680  1.00 48.03      W
ATOM   1232  OH2 TIP W   81    -14.358  62.793  31.478  1.00 77.34      W
ATOM   1233  OH2 TIP W   82    -14.884  67.194  30.264  1.00100.00      W
ATOM   1234  OH2 TIP W   83    -13.964  62.903  27.850  1.00 61.59      W
ATOM   1235  OH2 TIP W   84    -16.467  64.338  27.598  1.00 62.99      W
ATOM   1236  OH2 TIP W   85    -14.165  71.419  31.235  1.00 58.55      W
ATOM   1237  OH2 TIP W   86    -12.150  75.052  20.683  1.00 54.74      W
ATOM   1238  OH2 TIP W   87    -15.348  66.527  23.972  1.00 86.65      W
ATOM   1239  OH2 TIP W   88     23.657  18.784  16.110  1.00 46.11      W
ATOM   1240  OH2 TIP W   89     21.774  13.448  17.383  1.00 55.62      W
ATOM   1241  OH2 TIP W   90     28.955  20.801  18.398  1.00 47.29      W
ATOM   1242  OH2 TIP W   91     19.043  22.428  18.931  1.00 70.31      W
ATOM   1243  OH2 TIP W   92     32.348  21.741  32.055  1.00 80.85      W
ATOM   1244  OH2 TIP W   93     31.544  26.386  31.293  1.00 80.53      W
ATOM   1245  OH2 TIP W   94     30.484  31.504  24.099  1.00 51.19      W
ATOM   1246  OH2 TIP W   95     28.981  30.812  18.458  1.00 98.45      W
ATOM   1247  OH2 TIP W   96     25.233  35.680  28.569  1.00 53.47      W
ATOM   1248  OH2 TIP W   97     25.740  37.432  31.266  1.00 96.40      W
ATOM   1249  OH2 TIP W   98     18.343  27.853  17.008  1.00 87.39      W
ATOM   1250  OH2 TIP W   99     26.162  40.002  24.887  1.00 63.29      W
ATOM   1251  OH2 TIP W  100     18.896  37.649  32.149  1.00 75.85      W
```

Figure 11U

```
ATOM  1252  OH2  TIP  W  101   20.897  31.301  18.264  1.00  88.40   W
ATOM  1253  OH2  TIP  W  102   19.191  42.582  21.453  1.00  55.18   W
ATOM  1254  OH2  TIP  W  103   23.958  41.186  26.907  1.00  78.30   W
ATOM  1255  OH2  TIP  W  104   18.433  46.716  22.932  1.00  54.59   W
ATOM  1256  OH2  TIP  W  105   22.353  48.547  25.042  1.00  59.94   W
ATOM  1257  OH2  TIP  W  106   21.797  41.049  34.496  1.00  78.60   W
ATOM  1258  OH2  TIP  W  107   21.437  46.210  33.535  1.00  75.53   W
ATOM  1259  OH2  TIP  W  108   14.907  43.959  21.380  1.00  54.65   W
ATOM  1260  OH2  TIP  W  109   15.635  42.456  19.119  1.00  58.03   W
ATOM  1261  OH2  TIP  W  110   19.533  44.310  23.666  1.00  80.58   W
ATOM  1262  OH2  TIP  W  111   18.747  50.736  29.399  1.00  60.97   W
ATOM  1263  OH2  TIP  W  112   21.131  52.757  28.680  1.00  55.70   W
ATOM  1264  OH2  TIP  W  113   17.303  55.311  38.133  1.00  72.59   W
ATOM  1265  OH2  TIP  W  114   18.939  58.215  28.845  1.00  79.75   W
ATOM  1266  OH2  TIP  W  115   14.666  59.680  28.964  1.00  50.64   W
ATOM  1267  OH2  TIP  W  116   17.408  62.649  28.523  1.00  74.43   W
ATOM  1268  OH2  TIP  W  117   12.106  61.533  23.810  1.00  89.64   W
ATOM  1269  OH2  TIP  W  118   10.138  60.131  37.626  1.00  89.60   W
ATOM  1270  OH2  TIP  W  119   14.125  60.999  36.831  1.00  78.03   W
ATOM  1271  OH2  TIP  W  120    6.987  65.584  27.400  1.00  63.28   W
ATOM  1272  OH2  TIP  W  121    8.699  65.761  30.950  1.00  64.96   W
ATOM  1273  OH2  TIP  W  122   11.912  66.582  33.458  1.00  45.24   W
ATOM  1274  OH2  TIP  W  123    7.712  69.520  31.053  1.00  89.81   W
ATOM  1275  OH2  TIP  W  124    0.300  66.328  28.053  1.00  83.63   W
ATOM  1276  OH2  TIP  W  125   18.739  12.093  36.575  1.00  68.16   W
ATOM  1277  OH2  TIP  W  126    8.341  17.901  23.874  1.00  69.12   W
ATOM  1278  OH2  TIP  W  127    6.665  20.667  30.766  1.00  79.31   W
ATOM  1279  OH2  TIP  W  128   13.178  21.216  32.239  1.00  55.97   W
ATOM  1280  OH2  TIP  W  129    7.700  21.187  21.255  1.00  66.56   W
ATOM  1281  OH2  TIP  W  130   17.038  26.024  19.828  1.00  40.17   W
ATOM  1282  OH2  TIP  W  131    9.682  31.384  16.376  1.00  77.12   W
ATOM  1283  OH2  TIP  W  132   11.568  29.117  15.187  1.00  59.43   W
ATOM  1284  OH2  TIP  W  133    2.602  30.287  27.387  1.00  64.52   W
ATOM  1285  OH2  TIP  W  134   10.743  41.812  16.813  1.00  84.35   W
ATOM  1286  OH2  TIP  W  135   13.070  38.706  12.664  1.00  61.24   W
ATOM  1287  OH2  TIP  W  136    9.262  44.518  14.939  1.00  51.92   W
ATOM  1288  OH2  TIP  W  137   12.139  53.137  17.554  1.00  56.22   W
ATOM  1289  OH2  TIP  W  138   14.403  57.453  15.838  1.00  66.72   W
ATOM  1290  OH2  TIP  W  139   11.017  71.423  23.035  1.00  71.76   W
ATOM  1291  OH2  TIP  W  140   10.451  75.718  24.795  1.00  58.85   W
ATOM  1292  OH2  TIP  W  141   11.223  65.048  21.172  1.00  84.46   W
ATOM  1293  OH2  TIP  W  142    8.196  70.691  21.387  1.00  66.14   W
ATOM  1294  OH2  TIP  W  143    3.381  51.168  17.717  1.00  51.91   W
ATOM  1295  OH2  TIP  W  144   13.735  48.059  19.325  1.00  73.18   W
ATOM  1296  OH2  TIP  W  145    2.524  42.027  17.393  1.00  80.66   W
ATOM  1297  OH2  TIP  W  146    2.024  39.150  18.549  1.00  74.07   W
ATOM  1298  OH2  TIP  W  147    0.486  41.584  19.991  1.00  97.41   W
ATOM  1299  OH2  TIP  W  148    0.060  40.945  24.577  1.00  78.10   W
ATOM  1300  OH2  TIP  W  149   14.261  36.624  16.034  1.00  71.76   W
ATOM  1301  OH2  TIP  W  150   17.041  33.288  18.134  1.00  55.41   W
ATOM  1302  OH2  TIP  W  151   12.012  53.850  23.650  1.00  34.32   W
ATOM  1303  OH2  TIP  W  152    0.421  41.869  28.444  1.00  53.88   W
ATOM  1304  CL-1 CL   I    1   13.184  36.734  27.569  1.00  62.34   I
END
```

Figure IIV

INHIBITORS OF HIV MEMBRANE FUSION

RELATED APPLICATIONS

This application is a continuation of U.S. application Ser. No. 09/746,742, now U.S. Pat. No. 6,841,657, entitled Inhibitors of HIV Membrane Fusion, by Debra M. Eckert, David C. Chan, Vladimir N. Malashkevich, Peter A. Carr, and Peter S. Kim, filed Dec. 21, 2000, which is a continuation of International Application No. PCT/US99/17351, entitled Inhibitors of HIV Membrane Infusion, by Debra M. Eckert, David C. Chan, Vladimir Malashkevich, Peter A. Carr and Peter S. Kim, filed Jul. 30, 1999, which is related to U.S. Provisional Application 60/043,280, entitled Core Structure of gp41 from the HIV Envelope Glycoprotein, by David C. Chan, Deborah Fass, Min Lu, James M. Berger and Peter S. Kim, filed Apr. 17, 1997 and U.S. application Ser. No. 09/062,241, entitled Core Structure of gp41 from the HIV Envelope Glycoprotein, by David C. Chan, Deborah Fass, Min Lu, James M. Berger and Peter S. Kim, filed Apr. 17, 1998. U.S. application Ser. No. 09/746,742 also claims priority to PCT/US99/17351 under 35 U.S.C. §120, which claims the benefit of U.S. Provisional Application 60/094,676, entitled Inhibitors of HIV Membrane Fusion by David C. Chan, Debra M. Ehrgott and Peter S. Kim, filed Jul. 30, 1998; U.S. Provisional Application 60/100,265, entitled Inhibitors of HIV Membrane Fusion, by David C. Chan, Debra M. Ehrgott and Peter S. Kim, filed Sep. 14, 1998 and U.S. Provisional Application 60/101,058, entitled Inhibitors of HIV Membrane Fusion, by David C. Chan, Debra M. Ehrgott and Peter S. Kim, filed Sep. 18, 1998; and U.S. Provisional Application 60/132,295, entitled Inhibitors of HIV Membrane Fusion, by Debra M. Ehrgott, David C. Chan, Vladimir Malashkevich and Peter S. Kim, filed May 3, 1999. The entire teachings of these referenced applications are incorporated herein by reference.

GOVERNMENT SUPPORT

The invention was supported, in whole or in part, by National Institutes of Health Grant Number P01 GM56552. The United States Government has certain rights in the invention.

BACKGROUND OF THE INVENTION

Structural studies of proteins from human immunodeficiency virus type 1 (HIV-1) have been essential in the development of anti-retroviral drugs. Structure-based drug development has been most intense for reverse transcriptase inhibitors and protease inhibitors, the two classes of HIV-1 drugs in clinical use. It would also be useful to be able to carry out structure-based drug development against HIV entry.

SUMMARY OF THE INVENTION

As described herein, the cavities on the surface of the N-helix coiled-coil of HIV envelope protein gp41 subunit (e.g., HIV-1 envelope protein gp41-subunit) are targets for drugs or other agents which, by binding the coiled-coil surface, particularly the cavities, inhibit HIV entry into cells. This is useful as the basis for identifying and designing drugs or agents which inhibit entry of HIV (e.g., HIV-1, HIV-2) into cells.

Results described herein show that the coiled-coil cavity (also referred to as the hydrophobic pocket) in the gp41 core is an attractive drug target and that molecules which bind the cavity interfere with (inhibit) HIV infectivity (HIV entry into cells). Applicants have shown, for the first time, that conserved residues projecting into the hydrophobic pocket clearly play a major role in the ability of C34 to inhibit HIV-1 infection. The importance of cavity contacts (between the N-helix coiled-coil cavity and residues of the C peptide region of gp41) to gp41 function is clear. Conversely, the importance of preventing such cavity contacts in inhibiting gp41 function and, thus, inhibiting HIV-1 entry into cells, is also clear. In addition, directing drugs against the hydrophobic pocket of the central-coiled coil of gp41 targets one of the most highly conserved regions of the HIV-1 envelope proteins, which means that drugs which target the coiled-coil surface, and particularly its hydrophobic pocket, will have broad activity against diverse HIV isolates and that it will be difficult for drug-escape mutants to emerge.

A variety of methods, such as mirror-image phage display techniques (T. N. Schumacher, et al., *Science,* 271:1854 (1996)), combinatorial chemistry (A. Borchardt, S. D. Liberles, S. R. Biggar, G. R. Crabtree, S. L. Schreiber, *Chem. Biol.,* 4:961 (1997); J. C. Chabala, *Curr. Opin. Biotechnol.,* 6:632 (1995)), rational drug design and other drug screening and medicinal chemistry methods can be used to identify D-peptides, peptidomimetics and small molecules that bind the coiled-coil cavity with sufficient affinity to inhibit HIV-1 infection. The close correlation between N36/C34 stability and C34 potency, described herein, suggests that the effectiveness of such compounds will depend critically on the strength of their cavity-contacts. As described herein, candidate compounds can be tested for their ability to interfere with formation of a stable complex between C34 and N36 or their ability to disrupt binding of the two (disrupt the complex), thereby providing rapid, quantitative screens to identify and evaluate potential inhibitors of HIV-1 entry.

Alternatively, screening can be carried out to identify molecules or compounds which interfere with or disrupt binding of the N-helix coiled-coil cavity and a peptide which binds the cavity, thus providing methods of identifying molecules which are "pocket specific" binding agents or drugs. Molecules and compounds described herein (also referred to as drugs or agents) are useful to inactivate gp41 and, thus, prevent or reduce (inhibit) HIV-1 entry into cells. Without wishing to be bound by theory, it is reasonable to propose that these inhibitors bind to the pre-hairpin intermediate of gp41 and prevent its conversion to the trimeric hairpin structure of the gp41 core which corresponds to the fusion-active state of gp41. (Chan, D. C. and P. S. Kim, *Cell,* 93:681 (1998), See FIG. 1). Thus, the present methods are useful to identify drugs or agents which inhibit (totally or partially) formation of the fusion-active state of HIV-1 gp41 envelope protein. In the method, the ability of a candidate inhibitor (also referred to as a candidate drug), which can be any type of compound or molecule, such as a small molecule (e.g., a small organic molecule), a peptide (a D-peptide or an L-peptide), a peptidomimetic, a protein or an antibody, to bind the N-helix coiled-coil of gp41 and form a stable complex is assessed. Compounds or molecules which bind to the N-helix coiled-coil are further assessed for their ability to inhibit gp41 function (inhibit membrane fusion), such as through HIV-1 infection (viral entry) and syncytium assays, representative models of which are described and referenced herein. Those agents shown to inhibit gp41 function through such assays can be further assessed for their activity in additional in vitro assays and in appropriate animal models (e.g., Letvin, N. L., *Science,* 280, (5371): 1875-1880 (1998), Hirsch, V. M. and P. R. Johnson, *Virus Research,* 32 (2): 183-203 (1994); Reimann, K. A. et al., *J. Vivol.,* 70 (10): 6922-6928 (1996)).

Any suitable approach can be used to assess binding of candidate inhibitors to the N-helix coiled-coil and, as a result of the work described herein, to the N-helix coiled coil cavity. In one embodiment, the ability of a candidate inhibitor to bind the synthetic peptide N36 (described in Lu, M. et al., *J. Biomol. Struct. Dyn.* 15: 465 (1997), Chan, D. C. et al., *Cell,* 89, 263 (1997) and U.S. Provisional Application 60/043,280, entitled Core Structure of gp41 From the HIV Envelope Glycoprotein, by David C. Chan, Deborah Fass, Min Lu, James M. Berger and Peter S. Kim, filed Apr. 17, 1997) is assessed. The stability of the resulting complexes is assessed using methods described herein.

In a particular embodiment of the method of identifying compounds or molecules (drugs or agents) which bind the N-helix coiled-coil cavity, a soluble model that presents the gp41 coiled-coil cavity is used. The six helix bundle of HIV gp41 consists of an internal trimeric coiled-coil, composed of three identical N-peptides, surrounded by three C-peptides which fit into a conserved hydrophobic groove on the outside of the trimeric coiled-coil. The C-terminal end of the trimeric coiled-coil contains a large cavity into which bulky hydrophobic groups from the C-peptide pack. This hydrophobic pocket is used as the target for anti-HIV drug discovery and/or design. Unfortunately, in the absence of the C-peptide, the N-peptide is aggregated and not 100% helical. Thus, simply using an N peptide from HIV-1 gp41, such as N36, N51 (Lu, M. et al., *Nature Struct. Biology,* 1995) or DP-107 (Wild et al., *PNAS* 89:10537-10541 (1992) is unlikely to provide an effective model for the N-helix coiled-coil.

As described herein, Applicants have succeeded in producing a soluble, non-aggregating trimeric peptide model of the hydrophobic pocket of HIV gp41 and, thus, for the first time, have provided a model that properly presents this hydrophobic pocket or cavity (in a manner or configuration which forms a similar structure to the corresponding residues in the HIV gp41 structure). (The terms "pocket" and "cavity" are used interchangeably.) As described, a peptide (also referred to as a fusion protein) which includes a soluble, trimeric coiled coil portion and a portion from the N-peptide region of HIV gp41 that includes the amino acid residues which form the pocket or cavity of the N-helix coiled-coil of HIVgp41 (the pocket-comprising residues of the N-peptide) has been produced and shown to be such a soluble model, useful to identify molecules or compounds which inhibit HIV gp41 function and, thus, HIV entry into cells. The trimeric version of the coiled-coil in the peptide (also referred to as a fusion protein) can be the coiled-coil region of a protein which is not a protein of HIV (a non HIV protein, such as GCN4-pI$_O$I) or a protein of HIV origin (a protein derived from HIV or having the same or a similar amino acid sequence as an HIV protein). In a specific embodiment, the soluble, non-aggregating trimeric peptide model of the large cavity, referred to as IQN17, comprises a trimeric version of the coiled-coil region of GCN4, the yeast transcription activator, and a portion of the C-terminal end of the N peptide of gp41. IQN17 contains 29 residues of GCN4-pI$_O$I (formerly referred to as GCN4-pIQ in U.S. Provisional Application 60/101,058) (Eckert, D. M. et al. *J. Mol. Biol.,* 284:859-865 (1998)), including three mutations for increased solubility, and 17 residues of HIV; there is a one residue overlap between the two proteins, making the total length of the fusion protein 45 residues. The sequence of GCN4-pI$_O$I is: ac-RMKQIEDKIEEI LSKQYHIENEIAR IKKLIGER (SEQ ID NO:1). The HIV Sequence is: LLQLTVWG IKQLQARIL (SEQ ID NO:20). The sequence of IQN17 is: ac-RMKQIEDKIEEIESKQKKIENELARIKK LLQLTVWGIKQLOARIL-am (SEQ ID No:2). The HIV portion is underlined in SEQ ID No: 2; ac- represents an N-terminal acetyl group and -am represents a C-terminal amide. The sequence of the soluble, trimeric version of the coiled-coil region of GCN4 (referred to as a soluble, trimeric coiled coil of GCN4) in IQN17 is: RMKQIEDKIEE-IESKQKKIENEIARIKK (SEQ ID No: 25). The superhelix parameters such as rise and pitch (Harbury, P. B. et al., *Nature* 371:80-83 (1994); Harbury et al., *PNAS* 92:8408-8412 (1995)) of the GCN4-pI$_O$I coiled coil are nearly identical to the HIV gp41 N-helix coiled coil. Therefore, the resulting fusion protein molecule (IQN17) is predicted to form a long trimeric coiled coil, which presents the N-peptide hydrophobic cavity at the C terminus. IQN17 is fully helical, as determined by circular dichroism, with a molar ellipicity at 222 nm of $-36,000$ deg cm$^2$ dmol$^{-1}$. As determined by sedimentation equilibrium, IQN17 is close to a discrete trimeric species with a ratio of observed molecular weight to calculated molecular weight ranging from 3.00 to 3.16 times the monomer molecular weight at a concentration of 20 µM. As determined by X-ray crystallography, IQN17 presents the N-peptide hydrophobic pocket in a manner that is nearly identical to the pocket in the HIV gp41 N-helix coiled coil.

The IQN17 molecule (in the natural L-handedness or enantiomeric D-handedness) can be used in screens, including high-throughput drug screens, to identify molecules that bind to the coiled-coil pocket. The IQN17 molecule, in the D-handedness, has been used as a target in mirror image phage display (Schumacher et al., *Science,* 271: 1854, 1996) to identify small molecules (D-peptides) which bind to the hydrophobic pocket of gp41 (in the natural L-handedness) and inhibit HIV-membrane fusion. The desired target (the N-helix of HIV gp41 which includes the hydrophobic pocket) is the exact mirror image of the naturally-occurring target. It is used to screen a library or collection of compounds or molecules which are to be assessed for their ability to bind the mirror image of the naturally-ocurring coiled-coil pocket. The mirror image of a compound or molecule found to bind the mirror image of the naturally-occurring gp41 pocket, will bind the gp41 pocket in the natural handedness. The library or collection screened can be of any type, such as a phage display library, peptide library, DNA library, RNA library, combinatorial library, collection of chemical agents or drugs, cell lysate, cell culture medium or supernatant containing products produced by cells. In the case of a phage display library, the D-target is used to screen phage coat proteins. Specific phage clones that bind to the target are identified and the mirror images of the expressed proteins are chemically synthesized with D-amino acids. By using IQN17 in mirror-image phage display, D-peptides that bind to the gp41 hydrophobic pocket have been identified. Further assessment has been carried out, as described, to demonstrate the ability of D-peptides to inhibit HIV gp41 function. D-peptides which bind the gp41 hydrophobic pocket and inhibit HIV infectivity have been identified. D-peptides which bind the hydrophobic pocket also will serve as lead molecules for drug development and/or reagents for drug discovery (where the drugs bind to the coiled-coil pocket and inhibit HIV infectivity). The IQN17 molecule, in the natural L-handedness, can be used in screens, including high-throughput screens, to identify molecules that bind to the coiled-coil pocket. IQN17 can be used to screen a collection or library of compounds or molecules which are to be assessed for their ability to bind the hydrophobic pocket. The library or collection screened can be of any type, such as a phage display library, RNA library, DNA library, peptide library, combinatorial library, collection of chemical agents or drugs, cell lysate, cell culture medium or supernatant containing products produced by cells. Compounds or molecules which bind the hydrophobic pocket also will serve as lead molecules for drug development and/or reagents for drug discovery.

Fusion proteins which are variants of IQN17 can be produced and used to screen for drugs which bind the gp41 N-helix coiled-coil pocket. Any of a wide variety of variations can be made in the GCN4-pI$_Q$I component of IQN17 and used in the method, provided that these changes do not alter the trimeric state of the coiled-coil. For example, the amino acid composition of the GCN4 component can be changed by the addition, substitution, modification and/or deletion of one or more amino acid residues, provided that the trimeric state of the coiled-coil is maintained. For example, the Asp residue in IQN17 (at a "f-position" of the coiled coil) can be replaced by any of the naturally-occurring amino acids. (O'Neil and DeGrado, *Science* 250:646 (1990)). Alternatively, this component of the fusion protein can be a trimeric version of the coiled-coil region of another protein, such as that from Moloney Murine Leukemia Virus (Fass, D. et al. *Nature Struct. Biology,* 3:465 (1996)), GCN4-pII (Harbury et al., *Nature,* 317:80, 1994) or the ABC heterotrimer (Nautiyal and Alber, *Protein Science* 8:84 (1999)).

Changes can also be made in the amino acid composition of the fusion protein component which is the C-terminal portion of the HIV gp41 N peptide to produce IQN17 variants. The C-terminal portion can be changed by the addition, substitution, modification and/or deletion of one or more amino acid residues. The amino acid composition of either or both components of the fusion protein can be altered, and there is no limit to the number or types of amino acid residue changes possible, provided that the trimeric state of the coiled-coil and the hydrophobic pocket of the N peptide of HIV gp41 are maintained. IQN17, IQN17 variants or any soluble model of the large cavity can be used to screen for drugs which bind the N-helix coiled-coil, especially the pocket, or for lead drug candidates or candidates for use in vaccine preparations, to be further screened using methods known to those of skill in the art, such as in a high throughput format.

Results described herein are useful to screen for inhibitors of HIV gp41 which are variants of C34 as described below. Once a variant of C34, such as a C34 variant which stably binds N36, has been identified, it can be used and further assessed as obtained or it can be modified (e.g., by altering, adding, deleting or substituting at least one amino acid residue or adding a non-amino acid substituent), if desired or needed (e.g., to enhance stability, solubility, bioavailability). Alternatively, a C34 variant can be assessed to determine if a shorter component (region of fewer amino acid residues) also is active as an inhibitor. As discussed herein, the three C34 residues Trp$^{628}$, Trp$^{631}$ and Ile$^{635}$ that pack into the deep, conserved pocket in the N36 trimer are critical for inhibitory activity. The observation that C34 variants that have a higher affinity for the N36 coiled-coil have more potent inhibitory activity against HIV infection forms the basis for screens to identify and evaluate potential inhibitors. For example, using the "split-synthesis" technique (Chen, C. L., et al. *Methods Enzymol.* 267:211-219 (1996); Lam, K. S. et al., *Nature,* 354: 82-84, (1991)) of combinatorial peptide chemistry, a library of C34 variants is synthesized in which the three critical hydrophobic residues are randomly replaced by chemical substitutions of varying hydrophobic character. This synthesis technique results in the generation of a vast library of beads, each containing many copies of a single variant C34 peptide (i.e., a "one-bead, one-compound" type of library). To identify C34 variants which stably bind the N-helix coiled-coil, a labeled version of N36 (or a modified N-peptide) is mixed with the peptide beads under conditions (e.g., elevated temperature) that restrict binding to only those C34 variants with the highest affinity. Binding is measured by detection of the label on the N-helix peptide, using known methods. Simple modifications of the split-synthesis technique allow ready identification of the selected peptide sequence by mass spectroscopy (Youngquist, R. S. et al., *J. Amer. Chem. Soc.* 117, 3900-3906 (1995)). The C34 variants selected, particularly those with the highest binding affinities for N36, are tested in syncytium and infection assays for gp41 inhibitory activity. Truncated versions of these C34 variants, containing only the cavity-binding region, can also be tested for inhibitory activity. Alternatively, a library of other peptides to be assessed can be synthesized to generate a library of beads, each containing (having bound thereto) a peptide to be assessed. This library is analyzed as described above for the C34 variants and resulting hits (members with appropriate binding affinities for N36) are further analyzed for gp41 inhibitory activity. As a second example, the N36 peptide or the soluble variants described earlier, such as IQN17, GCN4-N-helix peptide can be used as a target for phage display or mirror-image phage display techniques to identify peptides that bind to the cavity.

IQN17 can also be used to raise antibodies (monoclonal and/or polyclonal) that bind to the coiled-coil cavity. IQN17 can further be used, either alone or in combination with other materials, in a vaccine, which will elicit the production of antibodies that bind to the coiled-coil in the individual to whom it is administered (the vaccinee), and thereby offer protection against infection and/or disease.

Peptides, both D-peptides and L-peptides, which fit into a deep hydrophobic pocket in the trimeric N-helix coiled-coil of HIV-1 envelope glycoprotein gp41 are also the subject of this invention. The D-peptides are the first molecules that have been shown to bind exclusively to the gp41 hydrophobic pocket. The observation that these D-peptides inhibit gp41-mediated membrane fusion processes (syncytia formation and viral infection) provides the first direct demonstration that HIV-1 infection can be inhibited by molecules that bind specifically to pocket. The validation of the gp41 hydrophobic pocket as a drug target sets the stage for the development of a new class of orally bioavailable anti-HIV drugs, that work by inhibiting viral entry into cells. Such drugs would be a useful addition to the current regimen used to treat HIV-1 infection with combination therapies. D-peptides, such as the D-peptides described herein, portions, modification and variants thereof and larger molecules (e.g., polypeptides) which comprise all or a portion of a D-peptide described herein, are useful to inhibit HIV membrane fusion and, thus, HIV entry into cells. D-peptides, corresponding to the D-amino acid version of phage sequences identified as described herein, are inhibitors of HIV-1 infection and syncytia formation. The C-terminal residues in these D-peptide inhibitors have the sequence pattern: CXXXXXEWXWLCAA-am (SEQ ID NO: 69). (In the phage-display library, the positions corresponding to the C residues were encoded as either C or S, the positions corresponding to the AA residues were encoded as such and the other 10 positions (indicated by X) were randomly encoded. The -am represents a C-terminal amide, added as part of the peptide synthesis procedure.) The N-terminal residues in the D-peptide inhibitors are, for example, ac-GA, ac-KKGA (SEQ ID NO: 70), or ac-KKKKGA (SEQ ID NO: 71). The ac- represents an N-terminal acetyl group added as part of the peptide synthesis procedure. The C-terminal amide and the N-terminal acetyl group are optional components of D-peptides of this invention. Other N-terminal residues can be included, in place of or in addition to those in the previous sentence, as desired (e.g., to increase solubility). For example, D-peptides of the following sequences are also the subject of this invention:

```
ac-XXCXXXXXEWXWLCXX-am;        (SEQ ID NO: 28)

ac-KKXXCXXXXXEWXWLCXX-am;      (SEQ ID NO: 29)

ac-KKKKXXCXXXXXEWXWLCXX-am;    (SEQ ID NO: 30)

ac-XXCXXXXXEWXWLCXXX-am;       (SEQ ID NO: 31)

ac-KKXXCXXXXXEWXWLCXXX-am;     (SEQ ID NO: 32)
and ac-KKKKXXCXXXXXEWXWLCXXX-am.   (SEQ ID NO: 33)
```

The amino acid residues are represented by the single letter convention and X represents any amino acid residue (naturally occurring or non-naturally occurring) or other moiety, such as a modified amino acid residue.

Further, the ten amino acid residue "core" (the 10-mer which is flanked at each end by a cysteine residue) of the 12 amino acid residue peptide, as well as portions, modifications and variants of the 10-mers are also useful to inhibit membrane fusion and entry of HIV into cells. Variants, portions and modifications of these peptides are also useful as inhibitors. As described further herein, D-peptides which comprise a consensus sequence (e.g., WXWL (SEQ ID NO: 23), EWXWL (SEQ ID NO: 24), CXXXXXEWXWLC (SEQ ID NO: 63) or a portion thereof) have been shown to bind the N-helix coiled-coil and are useful to inhibit membrane fusion and entry of HIV into cells. The enantiomeric peptides (D-peptides) do not serve as efficient substrates for enzymes, such as proteases and, therefore, are more resistant to proteolytic degradation than are L-peptides; they are also less immunogenic than are L-peptides.

Specific embodiments of D-peptides of the present invention are:

```
(a)   CDLKAKEWFWLC;                 (SEQ ID NO: 3)

(b)   CEARHREWAWLC;                 (SEQ ID NO: 4)

(c)   CELLGWEWAWLC;                 (SEQ ID NO: 5)

(d)   CLLRAPEWGWLC;                 (SEQ ID NO: 6)

(e)   CSRSQPEWEWLC;                 (SEQ ID NO: 7)

(f)   CGLGQEEWFWLC;                 (SEQ ID NO: 8)

(g)   CMRGEWEWSWLC;                 (SEQ ID NO: 9)

(h)   CPPLNKEWAWLC;                 (SEQ ID NO: 10)

(i)   CVLKAKEWFWLC;                 (SEQ ID NO: 11)

(j)   KKGACGLGQEEWFWLC;             (SEQ ID NO: 15)

(k)   KKGACELLGWEWAWLC;             (SEQ ID NO: 16)

(l)   KKKKGACELLGWEWAWLC;           (SEQ ID NO: 17)

(m)   KKGACMRGEWEWSWLC;             (SEQ ID NO: 18)

(n)   KKGACPPLNKEWAWLC;             (SEQ ID NO: 19)

(o)   a D-peptide comprising        (SEQ ID NO: 23)
      WXWL;

(p)   a D-peptide comprising        (SEQ ID NO: 24)
      EWXWL;

(q)   a D-peptide comprising        (SEQ ID NO: 12)
      CXXXXXEWXWL;

(r)   ac-GACEARHREWAWLCAA-am;       (SEQ ID NO: 34)

(r)   ac-KKGACEARHREWAWLCAA-am;     (SEQ ID NO: 38)

(t)   ac-KKKKGACEARHREWAWLCAA-am;   (SEQ ID NO: 43)

(u)   ac-GACGLGQEEWFWLCAA-am;       (SEQ ID NO: 44)

(v)   ac-KKGACGLGQEEWFWLCAA-am;     (SEQ ID NO: 64)

(w)   ac-KKKKGACGLGQEEWFWLCAA-am;   (SEQ ID NO: 45)

(x)   ac-GACDLKAKEWFWLCAA-am;       (SEQ ID NO: 35)

(y)   ac-KKGACDLKAKEWFWLCAA-am;     (SEQ ID NO: 39)

(z)   ac-KKKKGACDLKAKEWFWLCAA-am;   (SEQ ID NO: 46)

(a')  ac-GACELLGWEWAWLCC-am;        (SEQ ID NO: 47)

(b')  ac-KKGACELLGWEWAWLCAA-am;     (SEQ ID NO: 65)

(c')  ac-KKKKGACELLGWEWAWLCAA-am;   (SEQ ID NO: 66)

(d')  ac-GACSRSQPEWEWLCAA-am;       (SEQ ID NO: 36)

(e')  ac-KKGACSRSQPEWEWLCAA-am;     (SEQ ID NO: 40)

(f')  ac-KKKKGACSRSQPEWEWLCAA-am;   (SEQ ID NO: 48)

(g')  ac-GACLLRAPEWGWLCAA-am;       (SEQ ID NO: 37)

(h')  ac-KKGACLLRAPEWGWLCAA-am;     (SEQ ID NO: 41)

(i')  ac-KKKKGACLLRAPEWGWLCAA-am;   (SEQ ID NO: 49)

(j')  ac-GACMRGEWEWSWLCAA-am;       (SEQ ID NO: 50)

(k')  ac-KKGACMRGEWEWSWLCAA-am;     (SEQ ID NO: 67)

(l')  ac-KKKKGACMRGEWEWSWLCAA-am;   (SEQ ID NO: 51)

(m')  ac-GACPPLNKEWAWLCAA-am;       (SEQ ID NO: 52)

(n')  ac-KKGACPPLNKEWAWLCAA-am;     (SEQ ID NO: 68)

(o')  ac-KKKKGACPPLNKEWAWLCAA-am;   (SEQ ID NO: 53)

(p')  ac-GACXXXXXEWXWLCAA-am;       (SEQ ID NO: 54)

(q')  ac-KKGACXXXXXEWXWLCAA-am;     (SEQ ID NO: 55)

(r')  ac-KKKKGACXXXXXEWXWLCAA-am;   (SEQ ID NO: 56)

(s')  ac-XXCXXXXXEWXWLCXX-am;       (SEQ ID NO: 57)

(t')  ac-KKXXCXXXXXEWXWLCXX-am;     (SEQ ID NO: 58)

(u')  ac-KKKKXXCXXXXXEWXWLCXX-am;   (SEQ ID NO: 59)

(v')  ac-XXCXXXXXEWXWLCXXX-am;     (SEQ ID NO: 60)

(w')  ac-KKXXCXXXXXEWXWLCXXX-am;   (SEQ ID NO: 61)

(x')  ac-KKKKXXCXXXXXEWXWLCXXX-am; (SEQ ID NO: 62)
and (y')  a variant of a sequence of (a) through (x'),
      wherein the variant binds the N-helix coiled-
      coil cavity of HIV gp41, wherein ac- at the
      C-terminus and -am at the N-terminus are
      optional.
```

D-peptides described herein, which are ligands shown to bind the N-helix pocket, are also useful in drug screens to identify compounds or molecules (e.g., from chemical libraries, recombinantly produced products, naturally-occurring substances, culture media or supernatants) which bind the N-helix pocket and thus, are also inhibitors of HIV. For example, a competitive assay can be carried out by combining a D-peptide which binds the N-helix cavity (e.g., a D-peptide described herein); IQN17 (e.g., in the natural L-handedness), or another fusion protein which is a soluble model that presents the N-helix cavity; and a candidate inhibitor (a compound or molecule to be assessed for its ability to bind the N-helix cavity). For example, D10pep5 or D10pep1, IQN17, and a candidate inhibitor (candidate drug) can be combined using buffer conditions and peptide concentrations appropriate for binding of D10pep5 or D10pep1 to IQN17. The extent to which binding of the D-peptide occurs is determined and compared to the extent to which binding occurs under the same conditions, but in the absence of a compound or molecule (referred to as a candidate drug or candidate inhibitor) to be assessed for its ability to bind the N-helix coiled-coil cavity of HIV gp41 envelope protein (in a control). If binding of D10pep5 or D10pep1 occurs to a lesser extent in the presence of the candidate inhibitor (test sample) than in its absence (control sample), the candidate inhibitor is a ligand which binds the N-helix coiled-coil cavity and, thus, is an inhibitor. Inhibitors identified in this manner can be further assessed for their activity in viral infectivity assays and synctia formation assays, such as those described herein. Those inhibitors which show activity in such assays can be further assessed in an appropriate animal model or in humans.

Any method by which binding of the D-peptide, known to bind the N-helix cavity, can be detected can be used to assess whether the candidate inhibitor interferes with binding. For example, the D-peptide can be detectably labeled and the extent to which the label appears on the N-helix cavity (as a result of binding of the D-peptide) detected, in the presence and in the absence of the candidate inhibitor. If less label appears on the N-helix cavity of IQN17 (or other appropriate fusion protein) in the presence of the candidate inhibitor (in the test sample) than in its absence (in the control sample), then the candidate inhibitor is a ligand which binds the N-helix cavity (and interferes with binding of the D-peptide). Alternatively, the D-peptide (e.g., D10pep5 or D10pep1) and IQN17 can be labeled with a fluorophore (e.g., with EDANS; 5-(2'aminoethyl)aminonaphthalene-1-sulfonic acid) with an appropriate quencher that quenches the fluorescent signal of the fluorophore when it is in close proximity (e.g., DABCYL; 4-(4'-dimethylaminophenylazo)benzoic acid). If the candidate inhibitor binds the N-helix cavity of IQN17, fluorescence is observed, since, as a result of binding of the candidate inhibitor, the D-peptide is not brought into sufficiently close proximity to the quencher to permit it to quench the reporter signal. Alternatively, the fluorescent reporter molecule can be on the IQN17 and an appropriate quencher on the D-peptide. In either case, the position of the reporter or quencher on IQN17 must be such that when the D-peptide binds the N-helix cavity, the reporter and quencher moieties are in sufficiently close proximity to each other that quenching occurs (Tyagi, S., et al., *Nature Biotechnology* 16:49 (1998)).

Also the subject of this invention are drugs (compounds and molecules) which bind the N-helix coiled-coil pocket of HIV gp41 and inhibit (partially or totally) HIV entry into cells. In one embodiment, these drugs can be identified as described herein or by other methods. Drugs which bind the N-helix coiled-coil pocket of HIV gp41 are useful as therapeutic agents (to prevent HIV entry into cells or reduce the extent to which it occurs), as research tools (e.g., to study the mechanism of HIV gp41 function) and to assess the rate of viral clearance by an individual (e.g., in an animal model or an infected human).

Also the subject of this invention are compositions, useful in methods of interfering with entry of HIV into a mucosal cell; these compositions comprise an appropriate carrier or base and at least one component selected from the group consisting of:
(a) C34 peptide;
(b) DP178;
(c) T649;
(d) T1249;
(e) a derivative of (a)-(d);
(f) a D-peptide which binds to the hydrophobic pocket of HIV gp41;
(g) a derivative of (f);
(h) a combination of two or more of (a)-(g); and
(i) a molecule that inhibits HIV infectivity by binding to the N-helix coiled coil.

The compositions can comprise one such component or two or more components.

A further subject of this invention are compositions (e.g., proteins or proteinaceous materials) that can be used to elicit an immune response (e.g., antibody production) that will protect (partially or totally) against HIV infection and/or disease. Such compositions are useful as protective agents (e.g., vaccines) and to obtain antibodies (monoclonal and/or polyclonal) that are useful as research tools, diagnostic tools, drug screening reagents, and to assess viral dynamics (rates of production and clearance of virus) in animal models or infected humans.

Also the subject of this invention is a list of atomic coordinates for the X-ray crystal structure of the complex between IQN17 and D10pep1. Also the subject of this invention is a list of coordinates for the X-ray crystal structure of IQN17. These coordinates can be used (e.g., as an electronic file for computer graphics programs) to create a model of the complex which indicates how D10pep1 binds to the N-helix coiled-coil cavity and models of the N-helix coiled-coil cavity. Such models can be used, in methods known to those of skill in the art such as in computer graphics modeling, to build new models to evaluate the likelihood of binding to the N-helix coiled-coil cavity by other peptides, peptidomimetics, small molecules, drugs or other compounds. Such models can also be used to build new models for the structures of molecules (peptides, peptidomimetics, small organic molecules, drugs or other compounds) that bind the N-helix coiled-coil cavity (e.g., H. Kubinyi, *Curr. Op. Drug Discov. Develop.*, 1:16 (1998); P. L. Wood, ibid, 1:34 (1998); J. R. Morphy, ibid, 1:59 (1998)). These models and the corresponding lists of atomic coordinates can be used to identify, evaluate, discover and design more effective and/or new D-peptides, L-peptides, peptidomimetics, other small molecules or drugs that inhibit HIV infectivity, using methods known to those of skill in the art. A further subject of this invention is a method of producing or identifying a drug which fits (packs into, binds) the N-helix coiled-coil pocket of HIV gp41 through the use of atomic coordinates of a crystal, such as a crystal of a soluble, trimeric peptide model of the HIV gp41 hydrophobic pocket described herein (e.g., IQN17 or a variant thereof), a crystal of such a model in complex with a D-peptide (e.g., IQN17 or a variant thereof in complex with a D-peptide described herein, such as D10pep1) or a crystal of the N-peptide region of HIV gp41 comprising the amino acid residues which comprise the pocket of the N-helix coiled-coil of HIV gp41. The method comprises obtaining a crystal of the soluble model, such as the empty soluble model (not in complex with a D-peptide), obtaining the atomic coordinates of the crystal (e.g., of the crystal of the empty soluble model, such as IQN17); using the atomic coordinates obtained to define the N-helix coiled-coil pocket of HIV gp41; identifying a molecule or compound which fits the N-helix coiled-coil pocket and obtaining the molecule or compound; contacting the molecule or compound with the N-helix coiled-coil pocket (e.g., by contacting it with a polypeptide which comprises the pocket (e.g., IQN17 or a variant thereof or the N-peptide) to assess (determine) the ability of the molecule or compound to fit the pocket of HIV gp41, wherein in the molecule or compound fits the pocket, it is a drug which fits the N-helix coiled-coil pocket, whereby a drug which fits the pocket is produced. The atomic coordinates of the crystal can be obtained by X-ray diffraction studies or form a computer file or Protein Data Base (PDB), such as the PDB presented herein for IQN17 (FIGS. 11A-11V).

Similarly, the method can be carried out using a crystal of a soluble trimeric model in complex with a D-peptide (e.g., a D-peptide described herein, such as D10pep1) or a crystal of the N-peptide region of HIV gp41 which comprises the pocket of the N-helix coiled coil.

Drugs produces in this manner can be further assessed to conform their ability to fit into the pocket (e.g., by NMR) and can be assessed for their ability to inhibit HIV entry into cells (e.g., by a syncytia assay or infectivity assay).

The teachings and entire contents of all documents cited herein are expressly incorporated by reference into this application.

BRIEF DESCRIPTION OF THE DRAWINGS

FIG. 1 is a schematic of HIV-1 gp41 showing the N36 (SGIVQQQNNLLRAIEAQQHLLQLTVWGIKQLQARIL) (SEQ ID NO: 13) and C34 (WMEWDREINNYTSLIHSLIEESQNQQEKNEQELL) (SEQ ID NO: 14) peptides located within two regions containing 4,3 hydrophobic heptad repeats (labeled heptad repeat 1 and heptad repeat 2, also referred to as N-peptide region and C-peptide region, respectively). The underlined residues in C34 were mutated in this study. Three of these residues (W, W and I) project into the N36 cavity, whereas two of these residues (M and R) do not. FP, fusion peptide; S-S, disulfide bond; TM, transmembrane region; INTRA, intraviral region.

FIG. 2 is a graph showing the correlation of C34 inhibitory potency with N36/C34 stability. C34 peptide variants containing substitutions at position $Trp^{631}$ were tested for inhibition of viral entry (filled circles) and cell-cell fusion (open circles). $IC_{50}$ values are plotted on a logarithmic scale against the Tm (melting temperature) of the corresponding N36/C34 complex. The identities and chemical structures of the substitutions are drawn under the corresponding data points. In order of increasing hydrophobic bulk, the substitutions were: glycine (Gly), alanine (Ala), L-α-aminobutyric acid (Abu), valine (Val), leucine (Leu), phenylalanine (Phe), the wildtype residue tryptophan (Trp), and L-β-(1-naphthyl) alanine (Nal). Error bars indicate the standard error from triplicate experiments.

FIG. 3 shows the amino acid sequences of D-peptides (SEQ ID NOS: 34, 38, 15, 35, 16, 17, 36, 40, 41, 18 and 19) and the consensus sequence (SEQ ID NO.: 12). As represented, each peptide is flanked by GA on the N-terminus and AA on the C-terminus, and comprises a blocking group at the N-terminus: (Acetyl-GA-C-10mer-C-AA-$CONH_2$; this can also be represented as ac-GA-C-10mer-C-AA-am). The single letter conventions which are used to represent amino acid residues are as follows: G=glycine; A=alanine; C=cysteine; D=aspartic acid; L=leucine; K=lysine; E=glutamic acid; W=tryptophan; F=phenylalanine; R=arginine; H=histidine; S=serine; and Q=glutamine.

FIG. 4 is a schematic representation of mirror-image phage display with the D-IQN17 target, in which: (1) rounds of phage selection are carried out to identify binders to D-IQN17; (2) individual clones are sequenced; (3) binding specificity is assessed by determining whether the phage bind to the gp41 region of D-IQN17; (4) D-peptides of those phage sequences which bind are produced; and (5) the anti-HIV activity of the D-peptides is assayed.

FIGS. 5A and 5B show the crystal structure of IQN17 bound to D10pep1. IQN17 is shown to be a continuous three-stranded coil, and binding of the conserved amino acid residues of D10pep1 is shown to be to the hydrophobic pocket of IQN17, formed by the 17 residues derived from HIV gp41. FIG. 5A shows IQN17, consisting of GCN4-$pI_QI$ residues fused to HIV-1 gp41 residues and the binding of D10pep1 to the hydrophobic pocket of IQN17 (area within box). The D-peptide which binds to the pocket is represented by the branched extensions (i.e., stick representation). FIG. 5B is an enlargement of the area within the box and shows the conserved residues that pack into the pocket (Trp, Trp Leu) as well as a glutamic acid (Glu).

FIGS. 6A and 6B show results of syncytia assays, using the D-peptides described herein. FIG. 6A is a graphic representation of results of syncytia assays. FIG. 6B represents $IC_{50}$ data for D-peptides, with results from one or more experiments.

FIGS. 7A-7N are the PDB file which lists the atomic coordinates for the crystal structure of D10pep1 bound to IQN17, in which residues 0-28 of the A chain are derived from the GCN4-$pI_QI$ sequence (with three mutations), residues 29-45 of the A chain are derived from the HIVgp41 sequence, residues 0-16 of the D chain represent the D-peptide, ordered water molecules are represented as W, and a bound chloride ion as chain I. Residue 0 represents the acetyl group. The PDB file represents a monomer; the trimer is formed by crystallographic symmetry.

FIGS. 8A and 8B show results of assessment of inhibition of HIV-1 membrane fusion by a D-peptide. FIG. 8A shows results of syncytia assay with no D-peptide. FIG. 8B shows results of syncytia assay with D-peptide.

FIGS. 9A-9C show results of $^1H$ NMR experiments characterizing the aromatic residues of IQN17/D-peptide complexes. FIG. 9A shows 1D-NMR spectra of D10pep1a (top), IQN17 (middle) and a 1:1 complex of D10pep1a and IQN17 (bottom). The x-axis is the same as for (C) below. Upfield peaks assigned to the four scalar-coupled aromatic ring protons of Trp-571 are indicated. The unmarked upfield peak of the bottom trace corresponds to an unassigned Ha resonance. FIG. 9B shows ID spectra of 1:1 complexes between IQN17 and each D-peptide (as labeled). The same four protons are indicated in some spectra. FIG. 9C shows a 2D-NMR TOCSY spectrum of IQN17/D10pep1a complex. Cross-peaks linking these four tryptophan protons are indicated, along with specific assignments. The TOCSY mixing time was 42 ms.

FIG. 10 shows the conformation of the D10pep1 peptide as in the complex with IQN17, as determined by X-ray crystallography.

FIGS. 11A-11V are the PDB file which lists the atomic coordinates for the crystal structure of IQN17, in which residues 0-28 of the A, B and C chains of the IQN17 trimer are derived from GCN4-$pI_QI$ sequence (with three mutations), residues 29-45 of the chains A, B, and C are derived from HIV gp41, ordered water molecules are represented as W, and a bound chloride ion as chain I. The PDB file represents a whole trimer in the crystallographic asymmetric unit.

DETAILED DESCRIPTION OF THE INVENTION

The gp41 subunit of the HIV-1 envelope protein mediates fusion of viral and cellular membranes. The crystal structure of the gp41 ectodomain core is a six-helix bundle composed of three helical hairpins, each consisting of an N-helix paired with an antiparallel C-helix (D. C. Chan, D. Fass, J. M. Berger, P. S. Kim, Cell, 89:263 (1997), W. Weissenhom, A. Dessen, S. C. Harrison, J. J. Skehel, D. C. Wiley, Nature, 387:426 (1997); K. Tan, J. Liu, J. Wang, S. Shen, M. Lu, Proc. Natl. Acad. Sci. USA, 94:12303 (1997). Three N-helices form an interior, trimeric coiled-coil, and three C-helices wrap around the outside of this N-helix coiled-coil along conserved, hydrophobic grooves. This structure likely corresponds to the core of the fusion-active state of gp41 (discussed in D. C. Chan, D. Fass, J. M. Berger, P. S. Kim, Cell, 89:263 (1997), and D. C. Chan and Peter S. Kim, Cell, 93:681 (1998)) and shows similarity to the proposed fusogenic structures of envelope fusion proteins from influenza (P. A. Bullough, F. M. Hughson, J. J. Skehel, D. C. Wiley, Nature, 371:37 (1994)), Moloney Murine Leukemia Virus (D. Fass, S. C. Harrison, P. S. Kim, Nat. Struct. Biol., 3:465 (1996)), and simian immunodeficiency virus (SIV). (V. N. Malashkevich, D. C. Chan, C. T. Chutkowski, P. S. Kim, Proc. Natl. Acad. Sci. USA, 95:9134 (1998), M. Caffrey et al., EMBO J., 17:4572 (1998)), and Ebola virus (W. Weissenhorn et al., Mol. Cell 2:605 (1998), V. N. Malashkevich et al., Proc. Natl. Acad. Sci. USA, 96:2662 (1999).)

Synthetic C-peptides (peptides corresponding to the C-helix), such as DP178 and C34, are potent inhibitors of HIV-1 membrane fusion and are effective against both laboratory-adapted strains and primary isolates (V. N. Malashkevich, D. C. Chan, C. T. Chutkowski, P. S. Kim, Proc. Natl. Acad. Sci. USA, 95:9134 (1998), DP178 corresponds to residues 638-673 of HIV-1 gp41 and is acetylated at the amino terminus and amidated at the carboxy terminus (C. T. Wild, D. C. Shugars, T. K. Greenwell, C. B. McDanal, T. J. Matthews, Proc. Natl. Acad. Sci. USA, 91:9770 (1994), S. Jiang, K. Lin, N. Strick, A. R. Neurath, Nature, 365:113 (1993)). A Phase I clinical trial with the C-peptide DP 178 (also called T-20) indicates that it has antiviral activity in vivo, resulting in reduced viral loads (M. Saag, et al., abstract #771 presented at the Infectious Disease Society of America 35th Annual Meeting, San Francisco, Calif., 16 Sep. 1997; Kilby, J. M. et al. Nature Med. 4:1302-1307 (1998)). Based on the structural features of the gp41 core, these peptides are thought to act through a dominant-negative mechanism, in which exogenous C-peptides bind to the central coiled-coil of gp41 and lead to its inactivation (D. C. Chan and P. S. Kim, Cell, 93:681 (1998); R. A. Furuta et al., Nat. Struct. Biol., 5:276 (1998); D. C. Chan, D. Fass, J. M. Berger, P. S. Kim, Cell, 89:263 (1997), W. Weissenhorn, A. Dessen, S. C. Harrison, J. J. Skehel, D. C. Wiley, Nature, 387:426 (1997); K. Tan, J. Liu, J. Wang, S. Shen, M. Lu, Proc. Natl. Acad. Sci. USA, 94:12303 (1997), M. Lu, S. C. Blacklow, P. S. Kim, Nat. Struct. Biol., 2:1075 (1995) and C. H. Chen, T. J. Matthews, C. B. McDanal, D. P. Bolognesi, M. L. Greenberg, J. Virol., 69:3771 (1995)). These peptides likely act on a pre-hairpin intermediate of gp41 that forms when the native gp41 structure (i.e., the nonfusogenic conformation present on free virions) is perturbed by gp120/CD4/coreceptor interactions. This pre-hairpin intermediate is proposed to have an exposed N-coiled-coil, thereby allowing C-peptides to bind and inactivate gp41 prior to the formation of the fusion-active hairpin structure (D. C. Chan, P. S. Kim, Cell, 93:681 (1998)). This model is further supported by immunoprecipitation experiments indicating that the C-peptide DP178 binds to gp41 (R. A. Furuta, C. T. Wild, Y. Weng, C. D. Weiss, Nat. Struct. Biol., 5:276 (1998)). In addition, viruses escaping DP178 inhibition show mutations in the central coiled-coil region of gp41 (L. T. Rimsky, D. C. Shugars, T. J. Matthews, J. Virol., 72:986 (1998)).

Recent crystallographic studies of gp41 facilitate the development of small-molecule peptidomimetic drugs which, in contrast to C-peptides, have the potential to be orally administered. Within each coiled-coil interface is a deep cavity, formed by a cluster of residues in the N-helix coiled-coil, that is an attractive target for the development of antiviral compounds. Three residues from the C-helix ($Trp^{628}$, $Trp^{631}$, and $Ile^{635}$) insert into this cavity and make extensive hydrophobic contacts. Mutational analysis indicates that two of the N-helix residues ($Leu^{568}$ and $Trp^{571}$) comprising this cavity are critical for membrane fusion activity (J. Cao, et al., J. virol., 67:2747 (1993)). Therefore, it is reasonable to expect that compounds that bind with high affinity to this cavity and prevent normal N- and C-helix pairing will be effective HIV-1 inhibitors. In addition, residues in the cavity are highly conserved among diverse HIV-1 isolates. Because of the high structural conservation, drugs targeting this site would have broad activity against diverse HIV-1 isolates, and possibly HIV-2 isolates.

Although this hypothesis is tempting, until now, it had not been demonstrated that these cavity contacts are important for the potency of the C34 inhibitor. In fact, some C-peptides that lack the cavity-binding residues, such as DP178 (C. T. Wild, D. C. Shugars, T. K. Greenwell, C. B. McDanal, T. J. Matthews, ibid, 91:9770 (1994); Kilby, J. M. et al., Nature Med., 4:1302 (1998)), are highly effective inhibitors of HIV-1 membrane fusion. These concerns emphasize the need for systematic structure-function analysis to identify determinants of C-peptide activity.

To determine the role of cavity-contacts in inhibitory activity, structure-based mutagenesis was performed on C34. The core of the gp41 ectodomain (FIG. 1) was reconstituted with two synthetic peptides called N36 and C34 (M. Lu, P. S. Kim, J. Biomol. Struct. Dyn., 15:465 (1997), D. C. Chan, D. Fass, J. M. Berger, P. S. Kim, Cell, 89:263 (1997)). Variants of the C34 peptide with single alanine substitutions were synthesized, and the helical content and thermal stability of mutant N36/C34 complexes were quantitated by circular dichroism. As expected, mutation of C34 residues ($Met^{629}$, $Arg^{633}$) that do not contact the N36 coiled-coil had little effect on mean residue ellipticity at 222 nm (a measure of helical content) or stability of N36/C34 complexes (Table 1). However, mutation of the three residues ($Trp^{628} \rightarrow Ala$, $Trp^{631} \rightarrow Ala$ or $Ile^{635} \rightarrow Ala$) that project into the N36 coiled-coil cavity resulted in N36/C34 complexes with substantially decreased mean ellipticity and stability (Table 1). The greatest destabilization was observed with the mutant $Trp^{631}$ Ala, which formed N36/C34 complexes with an apparent melting temperature ($T_m$) of 37° C., compared to 66° C. for wildtype. These results demonstrate that C34 residues making hydrophobic contacts with the N36 coiled-coil cavity are important for stabilizing the helical-hairpin structure of the gp41 ectodomain core.

To determine the importance of these residues in the ability of C34 to inhibit membrane fusion, the activity of C34 peptides was tested in HIV-1 viral entry and syncytium assays (Table 1). Mutations ($Met^{629} \rightarrow Ala$ and $Arg^{633} \rightarrow Ala$) that had little effect on the stability of the N36/C34 complex also had little effect on the inhibitory activity of wildtype C34 ($IC_{50}$ ~2.1 nM and ~0.55 nM for viral entry and syncytium formation, respectively). However, mutation of the strictly conserved Trp$^{628}$ or Trp$^{631}$ to alanine resulted in a substantial decrease in activity of ~5 fold and ~30-fold, respectively (Table 1). Mutation of the less well-conserved Ile$^{635}$ resulted in only a ~2-fold decrease in inhibitory activity. These results demonstrate for the first time, the C34 residues which make contact with gp41 pocket are important for the inhibitory potency of C34.

The relationship between the potency of mutant C34 peptides and the stability of mutant N36/C34 complexes was clarified by taking advantage of the greatly destabilizing effect of the Trp$^{631}$ mutation to construct a series of N36/C34 complexes with a gradation of stabilities. The Trp$^{631}$ position was used as a "guest site" and the tryptophan was substituted with natural and artificial amino acids representing a broad range of hydrophobic bulk. In order of increasing hydrophobic bulk, the substitutions were: glycine (Gly), alanine (Ala), L-α-aminobutyric acid (Abu), valine (Val), leucine (Leu), phenylalanine (Phe), the wildtype residue tryptophan (Trp), and L-β-(1-naphthyl)alanine (Nal). This approach resulted in a set of C34 peptides that form N36/C34 complexes with $T_m$s ranging from 37° C. to 66° C. The $T_m$s and $[\theta]_{222}$ ($10^3$ deg cm$^2$ dmol$^{-1}$) for the N36/C34 variants (with IC$_{50}$ values (nanomolar) for virus entry and cell fusion, respectively, in parentheses) are: Trp$^{631}$→Gly, 35° C., 17.1 (38±6.1, 25±3.8); Trp$^{631}$→Ala, 37° C., −24.9 (40±4.3, 15±0.8); Trp$^{631}$→Abu, 43° C.; −23.2 (16±4.8, 6.9±0.4); Trp$^{631}$→Val, 43° C., −23.9 (13±2.8, 4.5±0.09); Trp$^{631}$→Leu, 50° C., −26.7 (5.3±1.0, 3.2±0.1); Trp$^{631}$→Phe, 59° C., −26.3 (3.6±0.8, 1.6±0.05); wildtype, 66° C., −31.7 (1.5±0.2, 0.55±0.03); Trp$^{631}$-Nal, 62° C., −32.0 (1.4±0.3, 0.79±0.08). The concentration of the Trp$^{631}$-Nal peptide was measured by NaI absorbance using the extinction coefficient ε=6900 at 282 nm (J. Blake, C. H. Li, J. Med. Chem., 18:423-426 (1975)). In HIV-1 infection and syncytium assays, this series of peptides showed potencies that closely correlated with the $T_m$ of the corresponding N36/C34 complex (FIG. 2). The potency order of these mutants is wt~Nal>Phe>Leu>Val~Abu>Ala~Gly, in close agreement with the hydrophobic bulk of the substitution and the stability of N36/C34 complexes. There is a striking linear relationship when the IC$_{50}$ is plotted on a logarithimic scale as a function of the $T_m$ (FIG. 2). Since ΔG=−RTlnK (ΔG, change in free energy; R, gas constant; T, absolute temperature; and K, equilibrium constant) and $\Delta T_m$ ($T_{m, \ wildtype \ complex} - T_{m, \ mutant \ complex}$) is proportional to Δ(ΔG) ($\Delta G_{wildtype \ complex} - \Delta G_{mutant \ complex}$) (W. J. Becktel, J. A. Schellman, Biopolymers, 26:1859 (1987)), the observed linear relationship strongly suggests that the potency of the C34 variants is directly related to their affinity for the N-helix coiled-coil, as predicted by a dominant-negative mode of inhibition. These results provide strong support for the proposal that the coiled-coil cavity in the gp41 core is an attractive drug target. Conserved residues projecting into the hydrophobic cavity clearly play a major role in the ability of C34 to inhibit HIV-1 infection, indicating that this inhibitor works by forming a high-affinity complex with the N-helix coiled-coil. Moving beyond traditional peptides, mirror-image phage display techniques (T. N. Schumacher, et al., Science, 271:1854 (1996)), selection-reflection aptamer techniques (K. P. Williams et al., PNAS, 94:11285 (1997); S. Kluβmann et al., Nat. Biotech., 4:1112 (1996); A. Nolte et al., Nat. Biotech., 14:1116 (1996), combinatorial chemistry (A. Borchardt, S. D. Liberles, S. R. Biggar, G. R. Crabtree, S. L. Schreiber, Chem. Biol., 4:961 (1997); J. C. Chabala, Curr. Opin. Biotechnol., 6:632 (1995)) and computational approaches in structure-based drug design (H. Kubinyi, Curr. Opin. Drug Discov. Develop., 1:16 (1998)), can be used to identify D-peptides, peptidomimetics, and small molecules that bind with high affinity to the coiled-coil cavity. The close correlation between N36/C34 stability and C34 inhibitory potency suggests that the effectiveness of such compounds will depend critically on the strength of their cavity-contacts. These results suggest that candidate compounds can be tested for the ability to form a stable complex with N36, thereby providing a basis for rapid, quantitative screens to identify and evaluate potential inhibitors of HIV-1 entry.

Small-molecule inhibitors directed against the cavity of the central coiled-coil target one of the most highly conserved regions of the HIV-1 envelope proteins. The analogous cavity in the SIV gp41 core has an essentially identical structure, with conservation of side chain conformations (V. N. Malashkevich, D. C. Chan, C. T. Chutkowski, P. S. Kim, Proc. Natl. Acad. Sci. USA, 95:9134 (1998)). This high degree of structural conservation explains the broad neutralizing activity of C-peptides, which are effective against laboratory-adapted strains as well as primary isolates (C. T. Wild, D. C. Shugars, T. K. Greenwell, C. B. McDanal, T. J. Matthews, Proc. Natl. Acad. Sci. USA, 91:9770 (1994), S. Jiang, K. Lin, N. Strick, A. R. Neurath, Nature, 365:113 (1993)). Remarkably, SIV C34 peptide is nearly as effective as HIV-1 C34 in inhibiting HIV-1 infection (V. N. Malashkevich, D. C. Chan, C. T. Chutkowski, P. S. Kim, Proc. Natl. Acad. Sci. USA, 95:9134 (1998)). In addition, a C-peptide (T649) containing the cavity-binding region is much less susceptible to the evolution of resistant virus (L. T. Rimsky, D. C. Shugars, T. J. Matthews, J. Virol., 72:986 (1998)) than DP178 (also called T-20), which lacks this region. These observations are evidence that high-affinity ligands targeting the coiled-coil surface, particularly its cavity, will have broad activity against diverse HIV isolates (including HIV-2) and will be less likely to be bypassed by drug-escape mutants.

These studies on the mechanism of C-peptide action also support the hypothesis that the trimeric hairpin structure of the gp41 core (Chan, D. C. et al., Cell, 89:263 (1997); Weissenhorn, W. et al., Nature, 387:426 (1997); Tan, K. et al., Proc. Natl. Acad. Sci. USA, 94:12303 (1997)) corresponds to the fusion-active state of gp41. The work described herein shows that the inhibitory potency of C34 depends on its ability to bind to the N-coiled-coil of gp41. Since the hairpin structure of gp41 is extremely stable (with a melting temperature in excess of 90° C.) (Lu, M. et al., Nat. Struct. Biol., 2:1075 (1995)), it is unlikely that nanomolar concentrations of C34 can disrupt this structure once it has formed, especially given the high effective concentration of the N- and C-helices within an intact gp41 molecule. Rather, C-peptides likely act prior to the formation of the gp41 hairpin by binding to a transient pre-hairpin intermediate, in which the central coiled-coil is exposed. Binding of C-peptides to this pre-hairpin intermediate inactivates gp41 and prevents its conversion to the fusion-active hairpin structure (D. C. Chan, P. S. Kim, Cell, 93:681 (1998)).

As described herein, the pocket on the surface of the N-helix coiled-coil of HIV-1 envelope protein gp41 subunit is a drug target. Similarly, cavities on other pathogens (e.g., HIV-2) which can cause AIDS or on pathogens which cause AIDS-like conditions in nonhuman mammals (e.g., SIV) are also drug targets. As described herein, available methods (e.g., mirror image phage display methods, combinational chemistry, computational approaches and other drug screening and medicinal chemistry methods) can be used to identify peptides, D-peptides, peptidomimetics and small molecules that bind the coiled-coil cavity of HIV-1 (and/or HIV-2) with sufficient affinity to interfere with viral entry into cells and, thus, inhibit viral infection. As further described herein (Example 3), mirror image phage display has been used to identify D-peptides which bind to a cavity on the surface of the N-helix coiled-coil of HIV-1 gp41.

As a result of the work described herein, screening assays which identify molecules or compounds (agents or drugs) that prevent C34/N36 complex formation and/or disrupt the complex once it has formed are available, as are methods of identifying molecules or compounds (agents or drugs) which bind the N-helix coiled-coil pocket of HIV gp41. Such drugs or agents are useful to inhibit (totally or partially) HIV entry into cells and, thus, infection by HIV.

Methods of screening for compounds or molecules (referred to as drugs or agents) that interfere with formation of a stable complex between C34 and N36 or disrupt a complex between the two and methods of screening for compounds or molecules that bind the N-helix coiled-coil pocket of HIV gp41 are a subject of the present invention.

In one embodiment of a screening method of the present invention, drugs which interfere with formation of a complex between C34 peptide and N36 peptide are identified by combining a candidate drug (a compound or molecule to be assessed for its ability to interfere with formation of a complex between C34 and N36) with C34 and N36, thus forming a test sample, under conditions appropriate for formation of a complex between C34 and N36 and determining whether formation of C34/N36 complex is inhibited (partially or totally) in the test sample. Results of this assessment can be compared with the results of an appropriate control, which is the same combination as the test sample, except that the candidate drug is not present; the control is subjected to the same conditions as is the test sample. If C34/N36 complex is not formed or is formed to a lesser extent in the presence of the candidate drug (in the test sample) than in its absence, the candidate drug is a drug that interferes with formation of a stable complex between C34 and N36. Such a drug is also referred to herein as an inhibitor of C34/N36 complex formation. Inhibition of complex formation can be assessed by determining the extent to which binding of the two members of the complex occurs, such as by means of a fluorescence assay (e.g., FRET), in which C34 and N36 are each labeled by a member of a pair of donor-acceptor molecules or one end of one of the peptides (e.g., the N-terminus of C34) is labeled with one member of such a pair (EDANS) and the natural fluorophore tryptophan, present in the N36 peptide, is the other member of the donor/acceptor pair. Binding of the C34 and N36 is assessed by the extent to which light emission (FRET) occurs from the acceptor model and/or the wavelength spectrum of the light emitted is altered. Prevention of binding by the candidate drug alters the extent to which light is emitted and/or prevents the shift in wavelength that would occur if binding of C34 and N36 occurred. Alternatively, C34 can be labeled with a detectable label, such as a radiolabel (e.g., by synthesizing a variant C34 with a kinase recognition site that can be labeled with a kinase and radioactive ATP). The radiolabeled C34 and the candidate drug are combined with N36 immobilized to, for example, a solid surface (e.g., a bead or a plastic well), thus producing a test sample. The extent to which binding of labeled C34 with immobilized N36 occurs is determined and compared with the extent to which binding of labeled C34 to immobilized N36 occurs under the same conditions to which the test sample is subjected, but in the absence of the candidate drug (in a control sample). Typically, this assessment is carried out after the sample has been maintained for sufficient time and under appropriate conditions for C34/N36 binding to occur and a subsequent wash to remove any unbound C34 and candidate drug. If binding occurs in the test sample to a lesser extent than in the control sample, as evidenced by less radiolabel bound to the immobilized N36 in the test sample than in the control sample, the candidate drug is an inhibitor of binding of C34 and N36. Alternatively, the label or tag on C34 can be a member of a binding pair, the other member of which is used to detect binding to N36. For example, C34 can be tagged with biotin (through standard solid-state peptide synthesis, for example) and combined with N36, which can be in solution or bound to a solid surface, such as a bead, well or flat/planar surface, along with the candidate drug (test sample) or in the absence or the candidate drug (control sample). Binding of C34 to N36 is assessed by detecting the presence of biotin associated with N36, such as through the use of labeled streptavidin (e.g., streptavidin—HRP, streptavidin—AP or iodinated streptavidin), which binds the biotin on C34 and is then itself detected through its label. If binding occurs less in the presence of the candidate drug (in the test sample) than in the absence of the candidate drug (in the control sample), as indicated by the presence of less biotin detected on N36 in the test sample than in the control sample, the candidate drug is an inhibitor of C34/N36 binding. The candidate drugs can be obtained, for example, from a library of synthetic organic compounds or random peptide sequences, which can be generated synthetically or through recombinant technology.

In a similar fashion, the ability of a candidate drug to disrupt C34/N36 binding can be assessed, to identify inhibitors of C34/N36 and, thus, of HIV infection. In this embodiment, preformed C34/N36 complex is combined with a candidate drug, which is to be assessed for its ability to disrupt the complex, thus producing a test sample. The control sample is the same as the test sample, except that the control sample does not contain the candidate drug; it is treated in the same manner as the test sample. If C34/N36 binding is disrupted in the presence of the candidate drug and not in the control sample or if disruption of the complex occurs to a greater extent in the test sample than in the control sample, the candidate drug is an inhibitor (disrupter) of C34/N36. Detection of disruption of binding can be carried out as described above for detection of/prevention of/interference with binding of C34/N36 (e.g., by FRET or a fluorescence assay, by detecting a radiolabel or other detectable label, such as biotin.)

Results described herein demonstrate that hybrids (i.e., fusion proteins) can be made between a trimeric version of the coiled-coil region of a protein (such as GCN4) and the N-helix coiled-coil of HIV gp41, and that such hybrids are trimeric (i.e., not aggregated) and 100% helical. Results described herein also clearly indicate that such fusion proteins do not disrupt or alter the structure of the N-peptide large cavity (i.e., hydrophobic pocket), which is essentially the same in IQN17 (ligand-free and in complex with D10pep1; see Example 5) as it is in N36 (i.e., in complex with C34; Chan D. C. et al. *Cell*, 89, 263 (1997)).

Figure 5B:
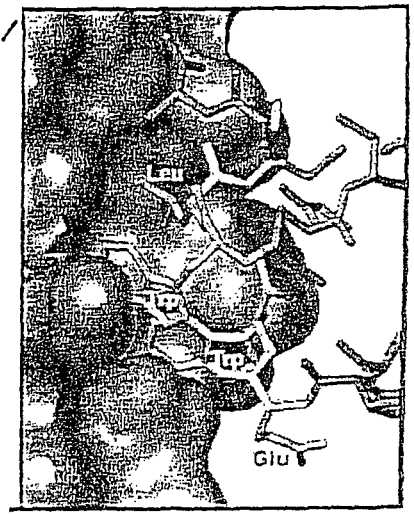
Figure 8A:
Figure 8B:
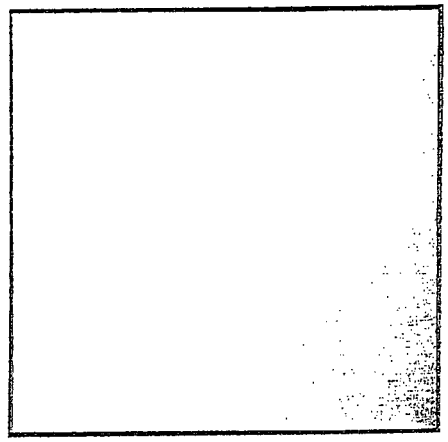

FIGS. 5A, 5B and 6 present results of assessment of peptides described herein. In FIG. 5A-5B, the IQN17 crystal structure is shown to be a continuous, three-stranded coiled-coil; the 17 residues derived from HIV gp41 form a hydrophobic pocket very similar to that found in the crystal structure of gp41. As shown, D10pep1 is bound to this pocket and the residues of D10pep1 that correspond to the conserved residues (leucine, tryptophan, tryptophan) found in all of the D-peptide inhibitors described herein are packed into this pocket, clearly indicating that other D-peptide inhibitors which comprise these conserved residues would bind to IQN17 in the same manner. FIG. 6 shows results of syncytia assays carried out according to the method described by Chan et al. (Chan, D. C. et al. *Proc. Natl. Acad. Sci.*, 95: 15613-

15617 (1998)). In the experiments whose results are represented in FIG. 6, D-peptides identified as described herein were used. In each instance, a blocking group (e.g., an acetyl group) was present at the N terminus and a CONH$_2$ (amide) was present at the C-terminus. Results of these assays showed a range of IC$_{50}$ concentrations, where IC$_{50}$ is the concentration at which one half of the number of syncytia are observed, compared to the control, in which no peptide is included. For example, D10pep5 with two lysines at the N-terminus has an IC$_{50}$ of approximately 6 µM.

In another embodiment, the invention relates to a method of identifying a drug that binds the N-helix coiled-coil cavity of HIV gp41. Here, too, the assay is based on assessing loss or decrease in binding, but unlike the C34/N36 complex assay described above, which is a more general assay in that it covers or detects interaction with any portion of the groove formed by the N-helical region of HIV gp41, this embodiment focuses on the HIV gp41 hydrophobic pocket (the N-helix coiled-coil cavity). In this embodiment, the method comprises combining a candidate drug to be assessed for its ability to bind the N-helix coiled-coil cavity of HIV gp41 with a fusion protein that comprises a trimeric version of the coiled-coil region of a protein and a sufficient portion of the N-peptide of HIV gp41 to include the HIV gp41 cavity, under conditions appropriate for presentation of the HIV gp41 cavity for binding by a peptide or other molecule and determining (e.g., in a high throughput screen) whether the candidate drug binds the fusion protein. If binding occurs, the candidate drug is a "hit" that may be a drug that binds the N-helix coiled-coil cavity of HIV gp41. If binding occurs, the candidate drug has bound the N-helix coiled coil and it can be determined if it binds to the coiled-coil cavity. Such "hits" can then be screened in secondary assays, such as the cell/cell fusion assay and HIV infectivity assay to determine if the candidate drug is a drug. Alternatively, or in addition, such "hits" can be assessed further by use of a counterscreen with other fusion proteins (or peptides), to which pocket-binding molecules will not bind. For example, GCN4-pI$_Q$I (with the same three surface mutations as in IQN17) or a version of IQN17 with a point mutation in the hydrophobic pocket, IQN17(G39W), in which glycine 39 is mutated to tryptophan, resulting in a large protrusion into the pocket, can be used in a counterscreen. In this example, a candidate drug that binds to IQN17 but not to GCN4-pI$_Q$I (with the same three surface mutations as in IQN17) or IQN17(G39W) is a drug that binds the N-helix coiled-coil cavity of HIV gp41.

In a further embodiment, a competitive assay is carried out. In this embodiment, a peptide or protein that binds the N-helix coiled-coil cavity of HIV gp41 is combined with the candidate drug and the fusion protein and whether the candidate drug binds the HIV gp41 cavity is determined in the presence of the peptide that binds the N-helix coiled cavity of HIV gp41. If the candidate drug binds the fusion protein, it is a drug that binds the HIV gp41 cavity. For example, a fusion protein which comprises a trimeric version of the coiled-coil region of GCN4 and the C-terminus of the N peptide of HIV gp41 that includes the N-helix coiled-coil cavity (IQN17) is combined with a "reference" D-peptide (e.g., any of the D-peptides described herein or variants thereof) that binds the N-helix coiled-coil cavity and a candidate drug to be assessed for its ability to bind the N-helix coiled-coil cavity of HIV gp41, thus producing a test sample, which is maintained under conditions appropriate for binding of the D-peptide to bind to the cavity. A control sample, which includes the same components as the test sample, except for the candidate drug, and is handled in the same manner as the test sample, is also assessed. In both samples, binding of the reference D-peptide is assessed. If binding of the reference D-peptide occurs to a lesser extent in the presence of the candidate drug (in the test sample) than in its absence (in the control sample), the candidate drug is a drug that binds the N-helix coiled-coil cavity of HIV gp41. Detection of binding is assessed, for example, in a similar manner as described above for the C34/N36 embodiment of the invention. For example, the D-peptide is labeled with a detectable label, such as a radiolabel or a first member of a binding pair (e.g., biotin), and the extent to which the N-helix coiled-coil cavity bears the label (after the samples have been maintained under conditions appropriate for binding of the reference D-peptide to the cavity) is determined. In the case in which radiolabeling is used, the extent to which the fusion protein bears the radiolabel is assessed in the test sample and compared with the extent to which the fusion protein bears the radiolabel in the control sample. If the detectable label is a first member of a binding pair (e.g. biotin), the second member of the pair (a binding partner) is added to the samples in order to detect the extent to which the fusion protein is bound by the reference D-peptide. This can be done directly or indirectly (e.g., by adding a molecule, such as an antibody or other moiety which binds the second member of the binding pair). Less of the label will be present on the fusion protein (N-helix coiled-coil cavity) if the candidate drug has inhibited (totally or partially) binding of the D-peptide to the cavity. If binding occurs to a lesser extent in the test sample (in the presence of the candidate drug) than in the control sample (in the absence of the candidate drug), then the candidate drug is a drug that binds the N-helix coiled-coil cavity of HIV gp41.

IQN17, or a variant thereof, in the D-enantiomer, is useful to identify molecules or compounds which are members of a library or collection and bind the N-helix coiled-coil of gp41. For example, a library or collection of molecules or compounds, such as a phage display library, can be screened with IQN17 in the D-enantiomer to identify members that bind the pocket. This has been carried out successfully, as described herein. The mirror image of IQN17, or a variant thereof, is used as the target molecule. As used herein, the terms "D-enantiomer of a polypeptide" and "D-peptide" refer to the exact mirror image of the molecule in the natural handedness. Thus, for amino acid residues that contain a second chiral center, such as Ile and Thr, the exact mirror image of the naturally-occurring amino acid residue is used to create the D version of the polypeptide. Also as used herein, the terms "D-amino acids" and "L-amino acids" are both meant to include the non-chiral amino acid glycine. D-IQN17 can be immobilized to a solid surface, such as by addition of one member of a binding pair (e.g., biotin) to it and addition of the other member of the pair (e.g., streptavidin) to the solid surface. Binding of the two members results in immobilization of D-IQN17 on the solid surface, such as for phage panning. A linker which is an enzyme recognition site (e.g., an amino acid linker such as Gly-Lys-Gly, in which an L-lysine residue is used) can be placed between the D-IQN17 sequence and the binding pair member (between the biotin and D-IQN17) to provide an enzyme recognition site (here, a trypsin recognition site), so that bound phage can be eluted by a trypsin digestion, rather than by non-specific elution, such as acid addition. The phage display library can be a library of L-amino acid peptides of any appropriate length fused to an appropriate phage gene. In one embodiment, it is a phage display library of L-amino acid peptides fused to the gIII gene of M13 phage. The peptides, in one embodiment, comprise 10 randomly encoded amino acid residues flanked by either a cysteine or a serine on both sides. Typically, several rounds of panning are carried out. D-IQN17-specific binding phage are identified. Phage that bind only the gp41 region of D-IQN17 can be identified by post-panning assessment, such as by screening against wells that lack the antigen and then further testing against a panel of molecules. For example, specific pocket-binding phage include those that bind D-IQN17 but not D-GCN4-pI$_Q$I (with the same three surface mutations as in IQN17) or a version of D-IQN17 with a point mutation in the hydrophobic pocket, D-IQN17(G39W), in which glycine 39 is mutated to tryptophan, resulting in a large protrusion into the pocket. D-peptides identified in this manner can be assessed for their ability to inhibit HIV gp41, using known assays, such as the cell/cell fusion assay and HIV infectivity assay. The mirror-image phage display method described herein has demonstrated the value of IQN17 and IQN17 (G39W), and their D-enantiomers in identifying inhibitors of HIV-1 entry that bind the gp41 pocket. Of nine specific pocket-binding phage sequences identified (phage that bind to D-IQN17 but not to D-IQN17(G39W), eight contain a consensus EWXWL sequence and inhibit HIV-1 gp41-induced syncytia formation when tested as D-peptides. The ninth peptide was toxic to cells and was not investigated further.

The D-versions of IQN17 and IQN17(G39W) can be used in a similar manner with other biologically encoded libraries, to discover other pocket-binding molecules that are not subject to enzymatic degradation by natural enzymes. For example, other phage-display libraries can be used to identify new D-peptide inhibitors (e.g., with a different number of residues between the flanking Cys residues and/or with randomly encoded amino acid residues outside the regions flanked by cysteine residues and/or with more than two cysteine residues). Strategies for encoding peptide libraries without phage (e.g., in which the encoding mRNA is attached to the peptide) can be used to identify D-peptide inhibitors. RNA or DNA libraries can be used (e.g., with SELEX methods) to identify L-ribose- or L-deoxyribose-based RNA or DNA aptamers, respectively, that bind to the hydrophobic pocket and are not substrates for natural nucleases (see e.g., Williams et al., *PNAS,* 74:11285 (1997)).

Although the versions of IQN17 and IQN17(G39W) of natural L-handedness can also be used in similar manner with biologically encoded libraries, the most likely applications will be with other, non-biologically encoded libraries. For example, chemical combinatorial libraries on beads (of the one-bead, one-compound variety) can be screened with labeled IQN17 (e.g., radioactive or with a chromophore) to identify beads containing molecules that bind to IQN17. In this example, IQN17(G39W) can be used as a counterscreen to determine if the molecules on the bead bind to the pocket of IQN17. (If they bind to IQN17(G39W), then they are not likely to be pocket-binding molecules.) As another example, beads to which IQN17 had been previously attached can be incubated with a mixture of potential pocket-binding molecules (e.g., a mixture of chemicals, or a natural product extract). IQN17 (bound to the beads) can then be separated from the mixture, washed, and then subjected to conditions (e.g., organic solvent, low pH, high temperature) that elute molecules bound to the IQN17 on the beads. The eluted molecules (i.e., potential pocket-binding molecules) could be identified by analytical chemistry methods (e.g., HPLC, mass spectrometry). A counterscreen with IQN17(G39W) is useful to help to identify true pocket-binding molecules.

Drugs identified by the methods described above are then further tested for their ability to inhibit (totally or partially) HIV gp41 function (membrane fusion) and, thus entry into cells, using further in vitro assays, such as the syncytium assays and/or infectivity assays described herein or others known to those of skill in the art, and/or in vivo assays in appropriate animal models or in humans.

One embodiment of the present invention is a method of identifying a drug that binds the N-helix coiled-coil of HIV gp41, particularly the N-helix coiled-coil pocket. The method comprises combining a candidate drug to be assessed for its ability to bind the N-helix coiled-coil pocket of HIV gp41 and peptide which comprises a soluble, trimeric coiled-coil and a sufficient portion of the N-peptide of HIV gp41 to include the HIV gp41 pocket, under conditions appropriate for presentation of the HIV gp41 pocket for binding by a molecule or compound (e.g., a drug) and determining whether the candidate drug binds the HIV gp41 pocket. If binding of the candidate drug with the HIV gp41 pocket occurs, the candidate drug is a drug which binds the N-helix coiled-coil pocket of HIV gp41. Optionally, binding of the candidate drug can be assessed in the assay as described above, except that a peptide that binds the N-helix coiled-coil pocket (a peptide previously identified as one which binds the pocket) is combined with the candidate drug and the peptide. In this competitive assay, binding of the candidate drug to the N-helix coiled-coil pocket is assessed in the presence of a known binding moiety (a molecule or compound which binds the pocket). If binding of the candidate drug occurs in the presence of the known binding moiety, the candidate drug is a drug which binds the N-helix coiled-coil pocket with sufficient affinity to successfully compete with the known binding moiety. The fusion protein used in this embodiment comprises a soluble, trimeric version of a coiled-coil, such as a soluble, trimeric version of the coiled-coil region of a protein (e.g., a non-HIV protein, such as that of GCN4 or GCN4-pI$_Q$I, although an HIV protein can be used) and a sufficient portion of the N-peptide of HIV gp41 to include the HIV gp41 cavity. For example, this portion can comprise SEQ ID NO.: 20 or a sufficient portion to comprise the cavity and, when present in an appropriate fusion protein or other soluble model, present the cavity in such a manner that it is available for binding. Alternatively, a variant of the HIV gp41 sequence present herein, a sequence from another strain of the human virus (e.g., HIV-2) or a sequence from another species (e.g., SIV, feline immunodeficiency virus, Visna virus (M. Singh et al., *J. Mol. Biol.,* 290:1031 (1999)) can be used in the fusion protein or soluble model. The fusion protein can comprise a soluble, trimeric version of the coiled-coil of any protein, provided that when it is in the fusion protein with the HIV component, the HIV cavity is presented in such a manner that it is available for binding. It can be, for example, that of GCN4-pI$_Q$I, GCN4-pII, Moloney Murine Leukemia Virus (Mo-MLV) or the ABC heterotrimer. In one embodiment, the fusion protein is IQN17 in the D-form. In another embodiment, the fusion protein is IQN17 in the natural L-handedness.

In the competitive assay format, any peptide known to bind the N-helix coiled-coil cavity can be used as the known binding moiety. For example, any of the peptides described herein (SEQ ID NOS.: 3-12, 15, 17-19, 23, 24) or a variant or portion thereof can be used. Also, any non-peptide pocket-binding molecule can be used in the competitive assay format. The competitive assay can be performed in solution, on a bead, or on a solid surface.

In one embodiment, the candidate drug is detectably labeled and binding of the candidate drug to the HIV gp41 N-helix coiled-coil is determined by detecting the presence of the detectable label on the HIV gp41 N-helix coiled-coil (as a result of binding of the labeled candidate drug to the N-helix coiled-coil). Detection of the label on the helix coiled-coil pocket of the soluble model is indicative of binding of the candidate drug to the N-helix coiled-coil pocket and demonstrates that the candidate drug is a drug which binds the N-helix coiled-coil pocket. If the labeled candidate drug is detected on the fusion protein, the candidate drug is a drug which binds the N-helix coiled-coil cavity.

In another embodiment of the method of identifying a drug that binds the N-helix coiled-coil pocket of the HIV gp41, a soluble model that presents the pocket in such a manner that it is available for binding by a drug is combined with a candidate drug and whether binding of the candidate drug with the N-helix coiled-coil of the soluble model occurs is determined. If binding occurs, the candidate drug is a drug which binds the pocket. Here, too, a competitive assay format can be used. The components of the competition assay (e.g., IQN17 and a D-peptide) can be labeled, with any of a variety of detectable labels, including fluorophore/quencher combinations. The candidate drug can be labeled, as described above, with any of a variety of detectable labels. The components of the soluble model (fusion protein) used in this embodiment and the competing moiety which is used in a competitive assay format can also be as described above.

The present invention also relates to a method of producing a drug that binds the N-helix coiled-coil pocket of HIV gp41. In one embodiment, the method is carried out as follows: A soluble model that presents the N-helix coiled-coil pocket of HIV gp41 or a fusion protein which comprises a soluble, trimeric coiled-coil (e.g., of a protein, such as a non-HIV protein, such as GCN4-pI$_Q$I, GCN4-pII, Mo-MLV, ABC heterotrimer or an HIV protein) is combined with a candidate drug to be assessed for its ability to bind the N-helix coiled-coil pocket of HIV gp41 and inhibit entry into cells, under conditions appropriate for presentation of the HIV gp41 pocket for binding by a drug. Whether the candidate drug binds the HIV gp41 pocket is determined, wherein if binding of the candidate drug to the N-helix coiled-coil pocket of HIV gp41 occurs, the candidate drug is a drug which binds the N-helix coiled-coil cavity of HIV gp41. In this embodiment, the fusion protein comprises a soluble, trimeric coiled-coil (e.g., of a protein such as a non-HIV protein, such as a soluble, trimeric coiled coil of GCN4, GCN4-pI$_Q$I, GCN4-pII, Mo-MLV, ABC heterotrimer or an HIV protein) and a sufficient portion of the N-peptide of HIV gp41 to include the HIV gp41 N-helix coiled-coil pocket (e.g., all or a portion of SEQ ID NO.: 20, a variant or modification thereof or a sequence from another strain or species). IQN17, described herein, can be used in this method; the D enantiomer of IQN17 can also be used (e.g., in mirror-image phage applications). The ability of the drug produced to inhibit HIV entry into cells is assessed, for example, in a syncytium assay and/or an infectivity assay, as described herein. It can be further assessed in an appropriate animal model or in humans.

The invention also relates to a method of producing a drug that binds the N-helix coiled-coil pocket of HIV gp41. The method comprises: producing or obtaining a soluble model of the N-helix coiled-coil pocket of HIV gp41 (e.g., a fusion protein as described herein and particularly IQN17 or a variant thereof); combining a candidate drug (a molecule or compound) to be assessed for it ability to bind the N-helix coiled-coil pocket of HIV gp41 and the soluble model of the N-helix coiled-coil pocket of HIV gp41 and determining whether the candidate drug binds the N-helix coiled-coil pocket of HIV gp41. If the candidate drug binds the N-helix coiled-coil pocket of HIV gp41, the candidate drug is a drug which binds the N-helix coiled-coil pocket of HIV gp41; as a result, a drug which binds the N-helix coiled-coil cavity of HIV gp41 is produced. The fusion protein used in this embodiment is described herein and can be, for example, IQN17, the D enantiomer of IQN17, or variants thereof. Alternatively, a drug that binds the N-helix coiled-coil pocket of HIV gp41 and inhibits entry of HIV into cells can be produced by a method comprising: producing or obtaining a soluble model of the N-helix coiled-coil pocket of HIV gp41, as described herein; combining the soluble model and a candidate drug to be assessed for its ability to bind the N-helix coiled-coil pocket of HIV gp41; determining whether the candidate drug binds the N-helix coiled-coil pocket of the soluble model (fusion protein), wherein if binding occurs, the candidate drug is a drug which binds the N-helix coiled-coil of HIV gp41; and assessing the ability of the drug which binds the N-helix coiled-coil to inhibit HIV entry into cells, wherein if the drug inhibits HIV entry into cells, it is a drug which binds the N-helix coiled-coil pocket of HIV gp41 and inhibits HIV entry into cells. Its ability to inhibit HIV entry into cells can be assessed in vitro (e.g., in a syncytium assay, an infectivity assay) or in vivo (e.g. in an appropriate animal model or in humans). The soluble model can be a peptide which comprises a soluble, trimeric coiled-coil, such as that of a protein (e.g., GCN4-pI$_Q$I) and a sufficient portion of the N-peptide of HIV gp41 to include the HIV gp41 pocket.

Drugs identified or produced by the methods described herein, as well as by other methods, which bind the N-helix coiled-coil pocket of HIV gp41 and inhibit HIV entry into cells are also the subject of this invention.

Drugs identified or produced by the methods described herein, as well as by other methods, which bind to more than one N-helix coiled-coil pocket of HIV gp41 and inhibit HIV entry into cells are also the subject of this invention. Such drugs can be obtained, for example, by linking two or more pocket-binding molecules (drugs) via an appropriate linker (e.g., a linker of amino aicd residues or other chemical moieties) to increase the effectiveness of inhibition. The pocket-binding molecules that are linked can be the same or different. Drugs identified or produced by the methods described herein or by other methods which bind to the N-helix coiled-coil pocket of HIV gp41, in addition to binding to HIV gp120, CD4, CCR5, CXCR4, or a non-pocket region of HIV gp41 are also the subject of this invention.

Drugs which inhibit HIV gp41 can also be designed or improved with reference to the X-ray crystal structure of the complex between IQN17 and a D-peptide which binds the N-helix coiled-coil cavity presented by IQN17, such as with reference to the X-ray structure of the complex between IQN17 and D10pep1, presented herein. Alternatively, or in addition, drugs which inhibit HIV gp41 can also be designed or improved with reference to the X-ray crystal structure of free IQN17, presented herein.

Compounds and molecules (drugs) identified as described herein inhibit (partially or totally) entry of HIV into cells, and thus are useful therapeutically in uninfected individuals (humans) and infected individuals (e.g., to prevent or reduce infection in an uninfected individual, to reduce or prevent further infection in an infected individual) and as research reagents both to study the mechanism of gp41 induced membrane fusion and to assess the rate of viral clearance by an individual and as reagents to discover or develop other compounds and molecules (drugs) that inhibit entry of HIV into cells. D-peptides described herein (e.g., D10pep5, D10pep1) have been shown, using the infectivity assay described herein, to inhibit infection of cells. Other D-peptides can be similarly assessed for their ability to inhibit infectivity.

The drugs can be administered by a variety of route(s), such as orally, nasally, intraperitoneally, intramuscularly, vaginally or rectally. In each embodiment, the drug is provided in an appropriate carrier or pharmaceutical composition. For example, a cavity-binding drug can be administered in an appropriate buffer, saline, water, gel, foam, cream or other appropriate carrier. A pharmaceutical composition comprising the drug and, generally, an appropriate carrier and optional components, such as stabilizers, absorption or uptake enhancers, flavorings and/or emulsifying agents, can be formulated and administered in therapeutically effective dose(s) to an individual (uninfected or infected with HIV). In one embodiment, drugs which bind the N-helix coiled-coil of gp41 (e.g., those described herein, DP178 (C. T. Wild, D. C. Shugars, T. K. Greenwell, C. B. McDanal, T. J. Matthews, ibid, 91:9770 (1994)), T649 which corresponds to residues 117-152 of HIV-1 gp41 (HXB2 strain) and is acetylated at the amino terminus and amidated at the carboxy terminus) (L. T. Rimsky, D. C. Shugars, T. J. Matthews, *J. Virol.*, 72:986 (1998), are administered (or applied) as microbicidal agents and interfere with viral entry into cells. For example, a drug or drugs which bind(s) the HIV cavity can be included in a composition which is applied to or contacted with a mucosal surface, such as the vaginal, rectal or oral mucosa. The composition comprises, in addition to the drug, a carrier or base (e.g., a cream, foam, gel, other substance sufficiently viscous to retain the drug, water, buffer) appropriate for application to a mucosal surface or to the surface of a contraceptive device (e.g., condom, cervical cap, diaphragm). The drug can be applied to a mucosal surface, such as by application of a foam, gel, cream, water or other carrier containing the drug. Alternatively, it can be applied by means of a vaginal or rectal suppository which is a carrier or base which contains the drug or drugs and is made of a material which releases or delivers the drug (e.g., by degradation, dissolution, other means of release) under the conditions of use (e.g., vaginal or rectal temperature, pH, moisture conditions). Such compositions can also be administered orally (e.g., swallowed in capsule, pill, liquid or other form) and pass into an individual's blood stream. In all embodiments, controlled or time release (gradual release, release at a particular time after administration or insertion) of the drug can be effected by, for example, incorporating the drug into a composition which releases the drug gradually or after a defined period of time. Alternatively, the drug can be incorporated into a composition which releases the drug immediately or soon after its administration or application (e.g., into the vagina, mouth or rectum). Combined release (e.g., release of some of the drug immediately or soon after insertion, and over time or at a particular time after insertion) can also be effective (e.g., by producing a composition which is comprised of two or more materials: one from which release or delivery occurs immediately or soon after insertion and/or one from which release or delivery is gradual and/or one from which release occurs after a specified period). For example, a drug or drugs which bind the HIV cavity can be incorporated into a sustained release composition such as that taught in U.S. Pat. No. 4,707,362. The cream, foam, gel or suppository can be one also used for birth control purposes (e.g., containing a spermicide or other contraceptive agent), although that is not necessary (e.g., it can be used solely to deliver the anti-HIV drug, alone or in combination with another non-contraceptive agent, such as an antibacterial or antifungal drug or a lubricating agent). An anti-HIV drug of the present invention can also be administered to an individual through the use of a contraceptive device (e.g., condom, cervical cap, diaphragm) which is coated with or has incorporated therein in a manner which permits release under conditions of use a drug or drugs which bind the HIV gp41 N-helix coiled coil. Release of the drug(s) can occur immediately, gradually or at a specified time, as described above. As a result, they make contact with and bind HIV and reduce or prevent viral entry into cells.

In another embodiment, a drug which interferes with HIV entry into cells by a mechanism other than binding to the gp41 N-helix coiled-coil cavity (e.g., a drug which interferes with viral entry by interfering with gp120 binding at the CD4 stage) is administered or applied to a mucosal surface as described above for drugs which bind to the gp41 N-helix coiled coil.

Fusion proteins of the present invention comprise a soluble, trimeric form or version of a coiled-coil, such as a soluble, trimeric form or version of a coiled-coil region of a protein (of non-HIV origin or of HIV origin) and a sufficient portion of the C-terminal end of the N peptide of HIV gp41 to include (comprise) the HIV coiled-coil cavity or hydrophobic pocket (the pocket-comprising residues of the N-peptide). The N peptide of HIV gp41 can be that of HIV-1, HIV-2, another HIV strain or a strain from another species (e.g., simian immunodeficiency virus (SIV), feline immunodeficiency virus or Visna virus). For example, HIV-2 sequence LLRLTVWGTKNLQARVT (SEQ ID NO: 26), SIV sequence LLRLTVWGTKNLQTRVT (SEQ ID NO: 27) or a sequence comprising invariant residues in HIV-1, HIV-2 and SIV (represented LLXLTVWGXKXLQXRXX (SEQ ID NO: 42), wherein amino acid residues L, T, V, W, G, K, Q, and R are the single letter code used for amino acid residues and X can be any amino acid residue). Also the subject of this invention is a soluble trimeric model of the HIV gp41 hydrophobic pocket, which can be a D-peptide or an L-peptide and comprises a soluble trimeric coiled coil and a sufficient portion of the N peptide region of HIV gp41 to comprise the amino aicd residues which form the pocket of the N-helix coiled-coil region of HIV gp41. The D- or L-peptide can comprise as the soluble, trimeric coiled coil the coiled coil of GCN4-pI$_Q$I, of GCN4-pII, of Moloney Murine Leukemia Virus or of the ABC heterotrimer. The component which is a sufficient portion of the N peptide of HIV gp41 to comprise the amino acid residues of the pocket can comprise, for example: LLQLTVWGIKQLQARIL of HIV-1 (SEQ ID NO: 20); LLRLTVWGTKNLQARVT of HIV-2 (SEQ ID NO: 26); LLRLTVWGTKNLQTRVT of SIV (SEQ ID NO: 27) or the invariant residues of these, which are: LLXLTVWGXKXLQXRXX (SEQ ID NO: 42).

One embodiment of the instant invention are fusion proteins between a trimeric version of the coiled-coil region of a protein (such as GCN4-pI$_Q$I) and the N-helix coiled-coil of HIV gp41 that include all, part or none of the N-helix cavity. That is, a fusion protein of the present invention can comprise a trimeric form of the coiled-coil region of GCN4-pI$_Q$I and a portion of the N-peptide of HIV-1 gp41, wherein the portion of the N-peptide of gp41 comprises part, or all, or none of the N-helix cavity of HIV-1 gp41. For example, a fusion protein can be made that contains residues from GCN4-pI$_Q$I and residues from N36. The fusion protein, denoted IQN24n, contains 29 residues of GCN4-pI$_Q$I, including three mutations for increased solubility, and 24 residues from the N-terminal end of N36 (SGIVQQQNNLLRAIEAQQHLLQLT) (SEQ ID NO 21); for recombinant expression in *E. coli*, an extra Met residue is included at the N-terminus. For example, a fusion protein can comprise a portion of the N-peptide of HIV gp41 comprising the amino acid sequence of (SEQ ID.: 21). The sequence of IQN24n is: MRMKQIEDKIEEIESKQKKIENE-IARIKKLISGIVQQQNNLLRAIEAQQHLLQLT (SEQ ID.: 22). This fusion protein can be made by a variety of methods, including chemical synthesis or recombinant DNA methods or by recombinant expression in *E. coli*, in which case the N- and C-termini are not blocked. Because the superhelix parameters of the GCN4-pI$_Q$I coiled coil are nearly identical to the HIV gp41 N-helix coiled coil, the resulting fusion protein molecule (IQN24n) is predicted to form a long trimeric coiled coil, which presents part of the gp41 N-helix coiled coil as a trimer (not aggregated).

An alternative embodiment of the instant invention provides a method of eliciting an immune response in an individual. The strategy used to create a soluble, trimeric model for part of the gp41 N-terminal region coiled coil is also helpful to develop HIV vaccine candidates. One goal for a potential HIV vaccine is to elicit a neutralizing antibody response that binds to the "pre-hairpin" intermediate of the HIV-1 gp120/gp41 envelope protein complex. In this transient form, the N-helix region of gp41 is exposed, but the C-helix region is not. Although it seems reasonable to use an N-peptide (such as N36, N51 or DP-107) as an immunogen to elicit an antibody response against the N-helix region of gp41, the isolated N-peptides are aggregated and do not properly present the gp41 N-helix coiled-coil trimer. Accordingly, the same strategy described herein to solve this problem for the gp41 hydrophobic pocket can be applied towards the development of soluble, trimeric models of the gp41 N-helix coiled-coil region, in general. Such trimeric models (including IQN17, but also including, for example, peptides that do not contain the pocket residues of gp41) can be used as immunogens to elicit an antibody response to the pre-hairpin intermediate, thereby inhibiting HIV-1 infection. For example, an individual to be immunized can be administered a fusion protein comprising a trimeric form of a coiled-coil region of a protein and a portion of an N-peptide from HIV-1 gp41, wherein the portion from gp41 comprises part of, all of, or none of the N-helix coiled-coil cavity in a pharmaceutically acceptable carrier. For example, IQN24n can be used, either alone or in combination with other materials, in a vaccine, which will elicit the production of antibodies that bind to the coiled coil in the individual to whom it is administered (the vaccinee), and thereby offer protection against infection and/or disease. IQN24n can also be used to identify (from humans, other animals or antibody libraries) and/or raise antibodies (monoclonal and/or polyclonal) that bind to the N-helix coiled coil. This provides the basis for a diagnostic method in which IQN24n (or IQN17 or other soluble trimeric model) is used to assess the presence/absence/level of antibodies that bind the N-helix coiled coil in a biological sample (e.g., blood).

Any of a wide variety of variations can be made in the GCN4-pI$_Q$I component of fusion proteins described herein (e.g., IQN17 or IQN24n) and used in the method, provided that these changes do not alter the trimeric state of the coiled-coil. Changes can also be made in the amino acid composition of the fusion protein component which is the portion from the HIV gp41 N36 peptide, to produce variants (e.g., variants of IQN17 or IQN24n). There is no limit to the number or types of amino acid residue changes possible, provided that the trimeric state of the coiled-coil and the structure of the surface of the fusion protein corresponding to the N-peptide coiled coil of HIV gp41 are maintained. The fusion protein component which is the portion of the HIV gp41 N-peptide can include all, part, or none of the N-helix cavity. For example, other parts of N51, N36, DP-107, or other regions of the HIV gp41 N-helix region can be fused to GCN4-pI$_Q$I (or another trimeric version of the coiled-coil region of a protein) to generate trimeric (not aggregated) helical coiled-coil fusion proteins and used in the method. There is no limit to the number or types of fusion proteins that can be designed and generated, provided that the trimeric state of the coiled-coil and the structure of the surface of the fusion protein corresponding to the N-peptide coiled coil of HIV gp41 are maintained. Such fusion proteins can be designed and generated using methods known to those of skill in the art, such as evaluating heptad-repeat positions or superhelix parameters of coiled coils.

Described herein are peptides, which can be D-peptides or L-peptides, which bind to a cavity on the surface of the N-helix coiled-coil of HIV envelope glycoprotein gp41 (e.g., HIV-1, HIV-2). Such peptides can be of any length, provided that they are of sufficient length to bind the cavity in such a manner that they interfere with the interaction of the N-helix coiled-coil cavity and amino acid residues of the C-peptide region of HIV gp41 and prevent HIV entry into the cells. For example, D- or L-peptides comprise at least two amino acid residues and generally will be from about two to about 21 amino acid residues. That is, they can comprise any number of amino acid residues from about two to about 21. The amino acid residues can be naturally occurring or non-naturally occurring or modified, as described below. The peptides can be linear or circular.

Examples of D-peptides, identified as described herein, are shown in FIG. 3. Because of library design, each peptide, in addition to the amino acid residues shown, is flanked by GA on the N-terminus and AA on the C-terminus. N-terminal lysine residues were added to improve water solubility.

In one embodiment, the present invention provides compounds which inhibit the binding of the N-helix coiled coil to the C-helix of HIV-1 gp41 envelope protein. Such compounds are of use in a method of treating a patient infected by, or potentially subject to infection by, HIV. These compounds are also of use in a method of assessing the ability of a second compound to bind to the N-helix coiled coil cavity.

In one embodiment, the compounds which inhibit the binding of the N-helix coiled coil to the C-helix of HIV-1 gp41 envelope protein are of Formula I, 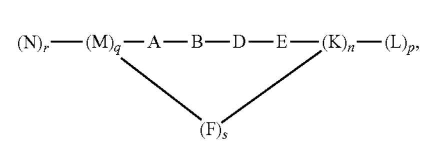 (I)

wherein A, B, D and E are each, independently, a D-amino acid residue, an L-amino acid residue, or an N-substituted glycyl residue. Natural or nonnatural amino acid residues can be used. K, L, M and N are each, independently, an amino acid residue or a polypeptide group of from 2 to about 6 amino acid residues which can be the same or different, and n, p, q and r are each, independently, 0 or 1. F is a direct bond or a difunctional linking group and s is 0 or 1.

In one subset of the compounds of Formula I, A is a D-amino acid residue, an L-amino acid residue or an N-substituted glycyl residue of the formula 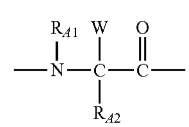 where one of $R_{A1}$ and $R_{A2}$ is a substituted or unsubstituted aryl, heteroaryl, arylmethyl, heteroarylmethyl, benzo-fused aryl, benzo-fused heteroaryl, benzo-fused arylmethyl, benzo-fused heteroarylmethyl, cycloalkyl or bicycloalkyl; and the other is hydrogen. W is hydrogen, methyl, trifluoromethyl or halogen, for example, fluorine, chlorine, bromine or iodine.

B is a glycyl residue or D-amino acid or N-substituted glycyl residue of the formula

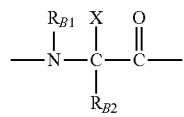

where one of $R_{B1}$ and $R_{B2}$ is a substituted or unsubstituted linear, branched or cyclic alkyl, aryl, arylalkyl, heteroaryl or heteroarylalkyl group; and the other is hydrogen. X is hydrogen, methyl, trifluoromethyl or halogen, such as fluorine, chlorine, bromine or iodine.

D is a D-amino acid residue or N-substituted glycyl residue of the formula

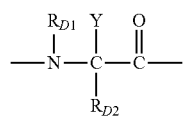

where one of $R_{D1}$ and $R_{D2}$ is a substituted or unsubstituted aryl, heteroaryl, arylmethyl, heteroarylmethyl, benzo-fused aryl, benzo-fused heteroaryl, benzo-fused arylmethyl; benzo-fused heteroarylmethyl, cycloalkyl or bicycloalkyl; and the other is hydrogen. Y is hydrogen, methyl, trifluoromethyl or halogen, such as fluorine, chlorine, bromine or iodine.

E is a D-amino acid residue or N-substituted glycyl residue of the formula

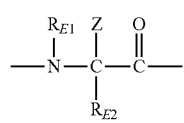

where one of $R_{E1}$ and $R_{E2}$ is a substituted or unsubstituted, linear, branched or cyclic alkyl, aryl or arylalkyl group; and the other is hydrogen. Z is hydrogen, methyl, trifluoromethyl or halogen, such as fluorine, chlorine, bromine or iodine.

K, L, M and N are each, independently, composed of from 1 to about 6 (which can be the same or different), D-amino acid residues, L-amino acid residues, N-substituted glycyl residues or a combination thereof. Natural or nonnatural amino acid residues can be used. One or more of the amino acid residues or N-substiuted glylcyl residues can, optionally, be substituted at the α-carbon by a methyl or trifluoromethyl group, or a halogen, such as a fluorine, chlorine, bromine or iodine atom.

In a preferred embodiment, one of $R_{A1}$ and $R_{A2}$ and one of $R_{D1}$ and $R_{D2}$ are, independently, a phenyl, substituted phenyl, naphthyl, substituted naphthyl, naphthylmethyl, substituted naphthylmethyl, benzyl or substituted benzyl group, or a group of the formula

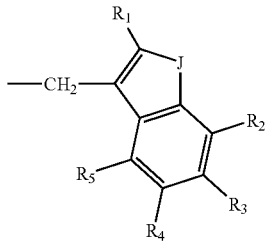

where J is O, S or NR, where R is H or linear, branched or cyclic $C_1$-$C_6$-alkyl, preferably methyl. $R_1$, $R_2$, $R_3$, $R_4$ and $R_5$ are independently selected from the group consisting of hydrogen, halogen and alkyl, preferably, linear, branched or cyclic $C_1$-$C_4$-alkyl, such as methyl. Suitable phenyl, naphthyl, naphthylmethyl and benzyl substituents include alkyl, preferably linear, branched or cyclic $C_1$-$C_4$-alkyl, such as methyl; and halogen, such as flourine, chlorine, bromine or iodine. More preferably, $R_{A1}$ and $R_{D1}$ are both hydrogen, and $R_{A2}$ and $R_{D2}$ are each, ndependently, one of the foregoing groups.

Preferably, one of $R_{B1}$ and $R_{B2}$ is hydrogen, substituted or unsubstituted linear, branched or cyclic $C_1$-$C_4$-alkyl, phenyl, benzyl, naphthyl or naphthylmethyl. Suitable substituents include linear, branched or cyclic $C_1$-$C_4$-alkyl groups and halogens, such as fluorine, chlorine, bromine or iodine. More preferably, $R_{B1}$ is hydrogen and $R_{B2}$ is one of the foregoing groups.

Preferably, one of $R_{E1}$ and $R_{E2}$ is a substituted or unsubstituted, linear, branched or cyclic $C_1$-$C_6$-alkyl group or a substituted or unsubstituted phenyl or naphthyl group. Suitable substituents include linear, branched or cyclic $C_1$-$C_4$-alkyl groups, such as methyl, and halogens, such as fluorine, chlorine, bromine and iodine. More preferably, $R_{E1}$ is hydrogen and $R_{E2}$ is one of the foregoing groups.

In a preferred subset of the compounds of formula I, A and D are each a D-tryptophan residue and E is a D-leucine residue.

Preferably, K is a D-amino acid residue or an N-substituted glycyl residue comprising an amino-, carboxyl- or sulfhydryl substituted side chain, such as a cysteine, glutamic acid, aspartic acid or lysine residue, and L is a polypeptide comprising 2 or 3 D-amino acid residues, L-amino acid residues (the D- or L-amino acid residues can be the same or different) or N-substituted glycine residues. For example, in one embodiment, L comprises 2 or 3 residues selected from among D-glycine, D-alanine or D-α-$C_1$-$C_4$-alkylglycine.

Preferably, M is a polypeptide group comprising from 2 to about 8 D-amino acid residues, of which at least one comprises an amino-, carboxy- or sulfhydryl substituted side chain, such as a cysteine, glutamic acid, aspartic acid or lysine residue. N is, preferably, a polypeptide group comprising from 1 to about 6 amino acid residues, of which at least one is a lysine residue.

The identity of divalent linking group F is not critical, as long as it is of a suitable length to position residues A to E to interact with the N-helix coiled coil cavity (J. R. Morphy, Curr. Op. Drug Discov. Develop., 1:59-65 (1998)). For example, F preferably has a length from about 2 to about 40 atoms. In one embodiment, F is a direct bond or a polypeptide linking group of the formula —$P_n$—, wherein n is 1 to about 12 and each P is independently an L- or D-amino acid or N-substituted glycyl resdiue residue, a glycyl residue or an N-substituted glycyl derivative.

In another embodiment, F is a substituted or unsubstituted $C_4$-$C_{40}$-alkylene group, such as a polymethylene group of the formula —$(CH_2)_m$—, wherein m is from about 4 to about 40; an alkylene group which is interrupted at one or more points by a heteroatom, such as a nitrogen, oxygen or sulfur atom. For example, F can be a group $(CH_2CH_2O)_q$—, wherein q is from 1 to about 20. F can also be an alkylene group which is interrupted at one or more points by a phenylene or heteroarylene group, or a polysaccharide group, for example, a glycoside or poly(glycoside) group comprising one or more glycoside groups, for example, from 1 to about 10 glycoside groups. Suitable glycosides include glucoside, lactoside, mannoside, galactoside, fucoside, fructoside, guloside, alloside, altroside, taloside, idoside and others, such as pyranosides and furanosides, which are known in the art.

In compounds of Formula I having a C-terminal amino acid residue, the C-terminal residue can be, for example, in the form of an amide, an N-substituted amide or a carboxylic acid protecting group, as is known in the art. The nitrogen atom of an N-terminal residue can be acylated, for example, acetylated, or substituted with an amino protecting group, as is known in the art.

The term "D-amino acid residue", as used herein, refers to an α-amino acid residue having the same absolute configuration as D-glyceraldehyde. When the amino acid residue includes a first non-hydrogen α substituent and a second α substituent selected from methyl and halogen, the absolute configuration is the same as that of D-glyceraldehyde with the second α substituent taking the place of the hydrogen atom at the glyceraldehyde α-carbon.

The peptides, portions of the peptides, variations/derivatives of the peptides or portions of the variations/derivatives described herein can be used as inhibitors of HIV entry into cells. The peptides represented in FIG. 3 or a portion of a peptide sufficient to fit into the hydrophobic pocket at the C-terminal end of the coiled-coil and prevent interaction of the C-peptide region with the N-peptide region of gp41 are useful to inhibit HIV infection. A portion of any of the peptides represented or of a derivative thereof can be from 2 to 20 (any number of residues from 2 to 20) amino acid residues in size. D-peptides which comprise the consensus sequence tryptophan-tryptophan-leucine or the sequence tryptophan-tryptophan-leucine-glutamate, described herein, and additional residues, can be used; the other residues present in such D-peptides and the size of the D-peptides can be selected with reference to peptides described herein or can be designed independent of those peptides, provided that these three or four residues are positioned in such a manner that the peptide can fit into the hydrophobic pocket and act as an inhibitor. Additional amino acid residues can also be present at the N-terminus, the C-terminus or both of the D-peptides described herein, thus producing a larger peptide. Alternatively, there can be other amino acid residues selected, for example, to enhance binding affinity. Alternatively, a peptide which comprises the conserved amino acid residues of the D-peptides of FIG. 3 can be used. For example, such a peptide can be 16 amino acid residues in size and include the conserved amino acid residues, which can be at the same positions as those at which they occur in the peptides shown in FIG. 3. The intervening amino acid residues can be different from the amino acid residues at these positions in any of the peptides shown in FIG. 3 (e.g., can be isoleucine or asparagine or other amino acid residue which does not appear in the peptides represented in FIG. 3) or can be substituted for or replaced by an amino acid residue represented at a specific position in another peptide shown in FIG. 3 (e.g., the aspartic acid residue in D10pep1 can be replaced by a serine residue).

Amino acid residues other than the D-versions of the 20 L-amino acids found in natural proteins can be used. Such changes can be made, for example, to enhance bioavailability, binding affinity or other characteristic of the peptide. A D-peptide can comprise the conserved amino acid residues present in the peptides shown in FIG. 3, but they can be separated by fewer (or more) amino acid residues than the number of intervening amino acid residues shown in FIG. 3. For example, fewer than five amino acid residues (e.g., Tarrago-Litvak, L. et al., *FASEB, J.*, 8:497 (1994); Tucker, T. J. et al., *Methods Enzymol.*, 275:440 (1996), Tarrago-Litvak, L. et al., *FASEB, J.*, 8:497 (1994); Tucker, T. J. et al., *Methods Enzymol.*, 275:440 (1996)), can be present between the first cysteine and the glutamic acid in the consensus sequence shown in FIG. 3. Alternatively, these two residues can be separated by more than five amino acid residues. Internal modifications can also be made (e.g., to enhance binding or increase solubility of a peptide). For example, the first tryptophan of D10pep5 can be replaced by an arginine to increase solubility. A D-peptide can have additional moieties or amino acids at its N-terminus. For example, a moiety which blocks the N terminus or gets rid of the charge otherwise present at the N-terminus can be added. The moiety can be, for example, a blocking moiety, such as an acetyl group linked directly to the glycine (G), or an acetyl group linked to one or more additional amino acid residues linked to the N-terminal of G, such as an acetyl group linked to one or more lysine residues, which, in turn, are linked to the N terminal G. In one embodiment, two lysine residues are linked to the N-terminal G (KKGAC . . . ), for example to increase the solubility of the peptide; a blocking moiety, such as an acetyl group, can be linked to the terminal lysine (acetyl group KKGAC . . . ). In another embodiment, four lysine residues are linked to the N-terminal G. In addition, a D-peptide can have additional and/or altered moieties or amino acids at its C-terminus. For example, one or both of the alanine residues at the C-terminus can be altered and/or one or more residues can be added at the C-terminus, for example to enhance binding. Alternatively, functional (chemical) groups other than amino acid residues can be included to produce an inhibitor of the present invention. For example, these additional chemical groups can be present at the N-terminus, the C-terminus, both termini or internally. In addition, two or more D-peptides can be linked via an appropriate linker (e.g., a linker of amino acid residues or other chemical moieties) to increase the effectiveness of inhibition. Alternatively, one or more D-peptides can be linked via an appropriate linker to a molecule (drug) that binds to HIV gp120, CD4, CCR5, CXCR4, or a non-pocket region of HIV gp41 to increase the effectiveness of inhibition.

The D-peptides (or L-peptides or peptides with both D- and L-amino acids) can be produced using known methods, such as chemical methods or recombinant technology. The polypeptide backbone can be altered (e.g., N-methylation) or replaced with alternative scaffolds (e.g., peptoids) at one or more positions of the peptides. Additional components can be included in the peptides, such as, for example, linkers (chemical, amino acid) which are positioned between amino acids or amino acid portions of the peptide (e.g., to provide greater flexibility or to provide greater rigidity). As described herein, the D-peptides of the present invention are flanked by GA at the N-terminus and AA at the C-terminus, due to the design of the library used in identifying the D-peptides. Some or all of these four amino acid residues may be altered, replaced or deleted in order to produce D-peptides with, for example, altered absorption, distribution, metabolism and/or excretion. In one embodiment, the C-terminus is modified by the addition of a glycine residue immediately before the C-terminal amide. In another embodiment, the most C-terminal A is altered/modified or replaced by a different amino acid residue or deleted.

D-peptides, which are of the opposite handedness from the handedness of naturally-occurring peptides, do not serve as efficient substrates for enzymes, such as proteases, and, therefore, are not as readily degraded as L-peptides. In addition, there is no effective immune response which targets D-peptides and therefore, they do not elicit an immune response comparable to that elicited by L amino acid peptides.

The present invention is illustrated by the following examples, which are not intended to be limiting in any way.

Example 1

Synthesis of Variants of the C34 Peptide

Mutant peptides were synthesized by solid-phase FMOC peptide chemistry and have an acetylated amino terminus and an amidated carboxy terminus. After cleavage from the resin, peptides were desalted with a Sephadex G-25 column (Pharmacia), and then purified by reverse-phase high-performance liquid chromatography (Waters, Inc.) on a Vydac C18 preparative column using a linear water-acetonitrile gradient and 0.1% trifluoroacetic acid. Peptide identities were verified by MALDI mass spectrometry (Voyager Elite, PerSeptive Biosystems). Peptide concentrations were measured by tryptophan and tyrosine absorbance in 6 M GuHCl [H. Edelhoch, *Biochemistry*, 6:1948 (1967)].

Example 2

Quantitation of Helical Content and Thermal Stability of Mutant N36/C34 Complexes CD measurements were performed in phosphate-buffered saline (50 mM sodium phosphate, 150 mM NaCl, pH 7.0) with an Aviv Model 62DS spectrometer as previously described (M. Lu, S. C. Blacklow, P. S. Kim, *Nat. Struct. Biol.*, 2:1075 (1995)). The apparent melting temperature of each complex was estimated from the maximum of the first derivative of $[\theta]_{222}$ with respect to temperature.

The mean residue ellipticities ($[\theta]_{222}$, $10^3$ deg cm$^2$ dmol$^{-1}$) at 0° C. were as follows: wildtype, −31.7; Met$^{629}$→Ala; −32.0; Arg$^{633}$→Ala, −30.7; Ile$^{635}$→Ala, −25.9; Trp$^{628}$→Ala, −27.0; Trp$^{631}$→Ala, −24.9. In the case of the Trp$^{628}$→Ala and Trp$^{631}$→Ala mutations, the decrease in $[\theta]_{222}$ is likely to overestimate the actual reduction in helical content. The removal of tryptophan residues from model helices has been reported to significantly reduce the absolute value of $[\theta]_{222}$ even when there is little change in helical content (A. Chakrabartty, T. Kortemme, S. Padmanabhan, R. L. Baldwin, *Biochemistry*, 32:5560 (1993)).

Example 3

Identification of Peptides Which Bind to a Pocket on the Surface of the N-helix Coiled-Coil of HIV-1 gp41

Methods are available to identify D-peptides which bind to a cavity on the surface of the N-helix coiled-coil of HIV envelope glycoprotein gp41. As described in detail below, D-peptides which bind to a cavity on the surface of the N-helix coiled-coil of HIV-1 envelope glycoprotein gp41 were identified by mirror-image phage display. This method involves the identification of ligands composed of D-amino acids by screening a phage display library. D-amino acid containing ligands have a chiral specificity for substrates and inhibitors that is the opposite of that of the naturally occurring L-amino ligands. The phage display library has been used to identify D-amino acid peptide ligands which bind a target or desired L-amino acid peptide (Schumacher et al. *Science*, 271:1854-1857 (1996)).

D-peptides that bind to the hydrophobic pocket of gp41 were identified using a target that is an enantiomer of IQN17, a hybrid molecule containing 29 residues of GCN4-pI$_Q$I on the N-terminal end and 17 residues of gp41 on the C-terminus. The phage library used for selection is described in U.S. Pat. No. 5,780,221 and Schumacher et al. *Science*, 271:1854-1857 (1996). The complexity of the library is greater than $10^8$ different sequences. The sequences are flanked on either end by either a cysteine or a serine, with ten random residues in the middle. These sequences are located in the pIII gene of the phage, a coat protein that is expressed as approximately five copies on the outer surface of the phage.

The following experimental procedures were used in the examples described herein.

Phage Display

Neutravidin (Pierce, 10 μg in 100 μL of 100 mM NaHCO$_3$) was added to individual wells of a 96-well high-binding styrene plate (Costar) and incubated overnight on a rocking platform at 4° C. The neutravidin was removed and the wells were washed four times with a TBS/Tween solution. Biotinylated D-IQN17 (100 μL of a 10 μL peptide solution in 100 mM NaHCO$_3$) was added to the wells and incubated for one hour at 25° C. The biotinylated target was removed and a blocking solution (30 mg/ml nonfat dried milk in 100 mM NaHCO$_3$) was added to the wells and incubated for two hours, with rocking, at 4° C. The blocking solution was removed and the wells were coated again with the biotinylated target as above. The target was removed and the unliganded neutravidin was blocked by the addition of the blocking solution with 5 mM biotin. After removing the biotin, the wells were washed six times with the TBS/Tween solution. The phage stock was then added to the wells (50 μL of phage stock plus 50 μL of phage-binding buffer: TBS, 0.1% Tween-20, 1 mg/ml milk, 0.05% sodium azide). The incubation time of the phage stock in the wells decreased in increasing rounds of selection. After incubation, the phage solution was removed and the wells were washed twelve times with TBS/Tween to remove the unbound phage. Odd numbered washes were performed quickly, with no incubation time; even numbered washes were incubated for increasing amounts of time each round of phage selection. The phage were eluted by the addition of two micrograms of trypsin in 100 μL of phage-binding buffer and 2.5 mM CaCl$_2$ with an hour incubation at 37° C. To determine recovery, a dilution of the eluted phage was used to infect K 91 kan cells. After a one hour incubation, 100 μL of cells were removed and 1:10, 1:100, and 1:100 dilutions in LB were plated on LB/tetracycline plates. Phage recovery was determined as a ratio of transducing units recovered (the titer of the eluted phage) to the input number of transducing units (the titer of the phage stock used that round). Transducing units were determined by counting the number of tetracycline-resistant colonies on the LB/tetracycline plates. Non-specific phage recovery generally has a ratio in the order of magnitude of $10^{-8}$ to $10^{-9}$, whereas specifically amplified phage have a ratio $10^{-7}$ or greater. Individual clones were amplified and sequenced. They were assayed in the binding assay to determine binding specificity.

D10pep7 was identified after five rounds of phage selection. D10pep1, D10pep3, D10pep4, D10pep5, and D10pep6 were identified after seven rounds of phage selection. The phage selection was performed again, with shorter incubation times and longer washes, and D10pep10 and D10pep12 were identified after three rounds of selection. (A ninth D-peptide was identified but was not further investigated once it was shown to be toxic to cells.)

To test the specificity of binding of identified phage clones to the pocket of D-IQN17, the phage clones were added to wells of 96-well plates coated as above with D-INQ17, D-GCN4-pI$_Q$I (with the three mutations), D-IQN17 (G39W=glycine36 substituted with tryptophan), or wells with no target. The phage were incubated on the plates and washed for the same lengths of time as in the round from which they were identified. Eluted phage were used to infect K91 kan cells and the recovered transducing units were determined as above. These sequences bound specifically to the wells with D-IQN17.

Peptide Purification

IQN17 and the D10 peptides were synthesized by FMOC peptide chemistry. They have an acetylated N-terminus and a C-terminal amide. IQN17 contains 29 residues derived from GCN4-pI$_Q$I on the N-terminus and 17 residues from the C-terminus of N36 on the C-terminus. There is one residue overlap between GCN4-pI$_Q$I and the N36 region, making the peptide 45 residues long. To improve solubility, three amino-acid substitutions were made in the GCN4-pI$_Q$I region of IQN17, as compared to the original GCN4-pI$_Q$I sequence (Eckert, D. M. et al., *J. Mol. Biol.*, 284:859-865 1998). These substitutions are L13E, Y17K, and H18K. Thus, the sequence of IQN7 is:

```
                                          (SEQ ID NO: 1)
ac-RMKQIEDKIEEIESKQKKIENEIARIKKLLQLTVWGIKQLQARIL-
am
```

(ac-represents an N-terminal acetyl group and -am represents a C-terminal amide), with the HIV portion underlined. For mirror-image phage display, IQN17 was synthesized using D-amino acids (for amino acid residues that contain a second chiral center, such as Ile and Thr, the exact mirror image of the naturally occurring amino acid residue is used to create the D-version of the target). In addition, the N-terminus of the peptide was biotinylated using NHS-LC-biotin II (Pierce, catalog #21336). Between the biotin and the IQN17 sequence was a three amino acid linker of GKG, with the lysine in the naturally-occurring L-form. This lysine was inserted as a trypsin recognition site.

The sequences of the D-peptides are as follows (with all amino acids in the D-enantiomer, using the exact mirror image of naturally occurring amino acid residues for Ile and Thr, which contain a second chiral center):

```
D10pep1:
  Ac-GACEARHREWAWLCAA-CONH2;    (SEQ ID NO: 34)

D10pep3:
  Ac-KKGACGLGQEEWFWLCAA-CONH2;  (SEQ ID NO: 64)

D10pep4:
  Ac-GACDLKAKEWFWLCAA-CONH2;    (SEQ ID NO: 35)

D10pep5:
  Ac-KKGACELLGWEWAWLCAA-CONH2;  (SEQ ID NO: 65)

D10pep6:
  Ac-GACSRSQPEWEWLCAA-CONH2;    (SEQ ID NO: 36)

D10pep7:
  Ac-GACLLRAPEWGWLCAA-CONH2;    (SEQ ID NO: 37)

D10pep10:
  Ac-KKGACMRGEWEWSWLCAA-CONH2;  (SEQ ID NO: 67)
and

D10pep12:
  Ac-KKGACPPLNKEWAWLCAA-CONH2.  (SEQ ID NO: 68)
```

After cleavage from the resin, the peptides were desalted on a Sephadex G-25 column (Pharmacia) and lyophilized. The lyophilized peptides were purified by reverse-phase high performance liquid chromatography (Waters, Inc.) on a Vydac C18 preparative column. The D-peptides were then air-oxidized by dissolving the lyophilized powder in 20 mM Tris, pH 8.2, and stirring at room temperature for several days. The oxidized peptides were HPLC purified as before. The expected molecular weights of the peptides were verified using MALDI-TOF mass spectrometry (PerSeptive Biosystems). Peptide concentrations were determined using tyrosine, tryptophan and cysteine absorbance at 280 nm in six molar GuHCl (Edelhoch, 1967). Peptide stock solutions were prepared in DMSO.

The N-terminal lysines on D10pep3, D10pep5, D10pep7a, D10pep10 and D10pep12 were added to increase the water solubility of the peptides. To investigate the effect of the added lysines on the inhibitory activity of the peptides, D10pep1 was synthesized with two N-terminal lysines (denoted D10pep1a) and compared to D10pep1 without lysines: D10pep1a was found to have an IC$_{50}$ for inhibition of syncytia formation approximately 2-fold higher than D10pep1 (i.e., without lysines). In addition, D10pep5 was synthesized with two additional N-terminal lysines (for a total of four lysines to generate a peptide denoted D10pep5a). The IC$_{50}$ for inhibition of syncytia formation of D10pep5a was approximately 2-fold higher than D10pep5. The addition of N-terminal lysine residues to the D-peptides results in only a modest decrease of inhibitory activity.

D-peptides that had additional D-Lys residues added to the N-termini, that were synthesized for study are indicated with the addition of "a" to the peptide name and include the following:

```
D10pep1a:
  Ac-KKGACEARHREWAWLCAA-CONH2;   (SEQ ID NO: 38)

D10pep4a:
  Ac-KKGACDLKAKEWFWLCAA-CONH2;   (SEQ ID NO: 39)

D10pep5a:
  Ac-KKKKGACELLGWEWAWLCAA-CONH2; (SEQ ID NO: 66)

D10pep6a:
  Ac-KKGACSRSQPEWEWLCAA-CONH2;   (SEQ ID NO: 40)
and

D10pep7a:
  Ac-KKGACLLRAPEWGWLCAA-CONH2.   (SEQ ID NO: 41)
```

These sequences are also represented in FIG. 3. The 12 amino acid "core" of each D-peptide (which, in turn comprises a 10-mer and the consensus sequences described herein) are as follows:

```
       CDLKAKEWFWLC       (SEQ ID NO: 3)

CEARHREWAWLC       (SEQ ID NO: 4)
```

-continued

```
CELLGWEWAWLC      (SEQ ID NO: 5)

CLLRAPEWGWLC      (SEQ ID NO: 6)

CSRSQPEWEWLC      (SEQ ID NO: 7)

CGLGQEEWFWLC      (SEQ ID NO: 8)

CMRGEWEWSWLC      (SEQ ID NO: 9)

CPPLNKEWAWLC      (SEQ ID NO: 10)

CVLKAKEWFWLC.     (SEQ ID NO: 11)
is an alternative sequence for
peptide SEQ ID NO: 3.
```

It is readily apparent that there is a highly conserved consensus sequence in these peptides. The 12 amino acid peptide represented in FIG. 3 can be represented as: CXXXXXEWX-WLC (SEQ ID NO: 12), where amino acid residues common to the peptides are shown and X represents an amino acid residue which is not conserved among the peptides.

Example 4

Assessment of Activity of C34 Peptides and D-Peptides

The potency of C34 peptides in inhibiting viral infection and the HIV-1 infection inhibitory activity of the D-peptides were assayed using recombinant luciferase-expressing HIV-1 (Chen, B. K. et al., *J. Virol.*, 68:654 (1994); Malashkevich, V. N., et al. *Proc. Natl. Acad. Sci., USA*, 95:9134 (1998)). The virus was produced by co-transfecting an envelope-deficient HIV genome NL43LucR-E- (Chen, B. K. et al., *J. Virol.*, 68:654 (1994) and the HXB2 gp160 expression vector pCMVHXB2gp160 (see Chan, D. C. et al., *Proc. Natl. Acad. Sci.*, 95:11513 (1998)) into 293T cells. Low-speed centrifugation was used to clear the viral supernatants of cellular debris. The supernatant was used to infect HOS-CD4/Fusion cells (N. Landau, NIH AIDS Reagent Program) in the presence of the D-peptides, with concentrations ranging from 0 to 500 µM. Cells were harvested 48 hours post-infection, and luciferase activity was monitored in a Wallac AutoLumat LB953 luminometer (Gaithersburg, Md.). The $IC_{50}$ is the peptide concentration that results in a 50% decrease in activity relative to control samples lacking peptide. The $IC_{50}$ was calculated from fitting the data to a Langmuir equation [y=k/(1+([peptide]/$IC_{50}$)+x], where y=luciferase activity and k and x are scaling constants.

Cell/Cell Fusion Assay

Inhibition of cell/cell fusion (i.e., syncytia formation) was assayed by co-culturing Chinese hamster ovary cell expressing HXB2 envelope (K. Kozarsky, et al., *J. Acquir. Immune. Defic. Syndr.*, 2:163 (1989) and the HeLa-CD4-LTR-Beta-gal cells (M. Emerman, NIH AIDS Reagent program) in the presence of varying concentration of peptide. When mixed, these cells form syncytia, or multi-nucleated cells, which express β-galactosidase. Approximately twenty hours after co-culturing the cells, the monolayers were stained with 5-bromo-4-chloro-3-indolyl-β-D-galactoside to visualize the syncytia. The syncytia are visualized with a microscope and counted manually (a syncytia is scored as a fused cell containing three or more nuclei). The $IC_{50}$ was calculated from fitting the data to a Langmuir equation [y=k/(1+[peptide]/$IC_{50}$)+x], where y=number of syncytia and k and x are scaling constants.

TABLE 1

Stability of mutant N36/C34 complexes and the inhibitory potency of C34 mutants.

| Peptide | $T_m$ (° C.) | $IC_{50}$ (nM) viral entry | $IC_{50}$ (nM) cell fusion |
|---|---|---|---|
| Wildtype Cavity-binding | 66 | 2.1 ± 0.31 | 0.55 ± 0.03 |
| Trp$^{628}$→Ala | 53 | 10 ± 2.0 | 3.8 ± 0.33 |
| Trp$^{631}$→Ala | 37 | 61 ± 16 | 15 ± 0.82 |
| Ile$^{635}$→Ala | 55 | 4.1 ± 0.91 | 0.96 ± 0.12 |
| Control residues | | | |
| Met$^{629}$→Ala | 66 | 2.0 ± 0.27 | 0.74 ± 0.03 |
| Arg$^{633}$→Ala | 65 | 2.6 ± 0.89 | 0.76 ± 0.07 |

Mutant C34 peptides (10 µM) were complexed with the N36 peptide (10 µM) in phosphate-buffered saline (pH 7.0) for circular dichroism (CD) measurements. The apparent melting temperatures ($T_m$) were estimated from the thermal dependence of the CD signal at 222 nm. Inhibition of viral entry was measured in a cell-culture infection assay using recombinant luciferase-expressing HIV-1. Inhibition of cell-cell fusion was measured in a syncytium assay. The means and standard errors are from triplicate trials.

Similarly, the activity of the D-peptides described was assessed using the two assays described above. Results are shown in FIGS. 6A-6B and 8A-8B.

Example 5

Crystallization of the IQ17/D10pep1 Complex and Ligand-Free IQN17

Peptide Purification, Crystallization

Peptides IQN17 and D10pep1 were synthesized by FMOC peptide chemistry, as described above.

A 10 mg/ml stock of a mixture of IQN17 and b 10pep1 was prepared in water. The final concentration of IQN17 was about 1.37 nM, and the final concentration of D10pep1 was about 1.51 mM. Initial crystallization conditions were found using Crystal Kits I and II (Hampton Research), and then optimized. To grow the best diffracting crystals, one microliter of this stock was added to one microliter of the reservoir buffer (10% PEG 4000, 0.1 M NaCl pH 5.6, 20% 2-propanol) and allowed to equilibrate against the reservoir buffer. Crystals belong to a space group P321 (a=b=41.83 Å, c=84.82 Å, α=β=90°, γ=120°) and contain one IQN17/D10pep1 monomer in the asymmetric unit. A useful osmium derivative was produced by increasing the concentration of PEG 4000 in the reservoir solution by 4%, adding $(NH_4)_2OsCl_6$ to the reservoir solution to a final concentration of 5 mM and adding five microliters of the resulting solution to the drop containing the protein crystal. Prior to data collection native and heavy-atom derivative crystals were transferred into cryosolution containing 20% PEG 4000, 0.1 M NaCl PH 5.6, 20% 2-Propanol and flash-frozen using X-stream cryogenic crystal cooler (Molecular Structure Corporation).

The best diffracting crystals of ligand-free IQN17 were grown with a similar technique as above: on microliter of a 10 mg/ml solution of IQN17 in water was added to one microliter of the reservoir buffer (1.0 M K,Na Tartrate, 0.1 M NaHEPES pH 7.0) and allowed to equilibrate against the reservoir buffer. Before flash freezing, the crystals were transferred into buffers consisting of the reservoir solution with increasing amounts of glycerol, up to a final concentration of 23% glycerol. Crystals belong to the space group C222₁ (a=57.94 Å, b=121.96 Å, c=73.67 Å; α=β=γ=90°) and contain one IQN17 trimer in the asymmetric unit.

X-Ray Data Collection and Processing

Initial data were collected on a Rigaku RU300 rotating-anode x-ray generator mounted to an R-axis IV area detector (Molecular Structure Corporation). Diffraction data for IQN17 were collected at 100 K using a Quantum-4 CCD detector and the 5.0.2 beamline at the Advanced Light Source (Berkeley, ISA). Final native and multiwavelength anomalous diffraction (MAD) data for IQN17/D10pep1 were collected at the Howard Hughes Medical Institute Beamline X4A at Brookhaven National Laboratory using a Raxis-IV detector. For MAD data, four wavelengths near the osmium L-III absorption edge were selected based on the fluorescence spectrum of the Os derivative crystal (Table 2). The four wavelengths were: 1.1398 Å, 1.1403 Å, 1.1393 Å, 1.1197 Å. Data sets were collected in 20° batches, allowing the same batch to be collected at each wavelength before moving to the next batch, in order to minimize the crystal decay between data sets. Reflections were integrated and scaled with the programs DENZO and SCALEPACK (Otwinowski, Z., (1993) in *Data Collection and Processing*, eds. Sawer, L., Isaacs, N. & Bailey, S. (SERC, Daresbury Laboratory, Warrington, England), pp. 55-62).

Further diffraction data processing, phase determination and map calculations were performed using the CCP4 suite of programs (CCP4, *Acta Cryst.* D50:760-763 (1994)). Intensities were reduced to amplitudes with the program TRUNCATE, and the data sets for the wavelengths closest to the Os L-III absorption edge ($\lambda 1$, $\lambda 2$, $\lambda 3$) were scaled with SCALEIT to the remote wavelength ($\lambda 4$) data set (Table 2).

Phase Determination and Crystallographic Refinement

Initially, phase determination for IQN17/D10pep1 crystals was attempted with the molecular replacement technique using the theoretical model of IQN17 build from the published GCN4-pI$_Q$I and HIV gp41 structures (Eckert, D. M., et al. (1998) *J. Mol. Biol.* 284:859-865; Chan, D. C., et al. (1997) *Cell* 89, 263-273) with sidechains truncated to a polyserine chain. The resulting molecular replacement solutions were ambiguous and the electron density map did not reveal conformation of the D10pep1 peptide. The molecular replacement phases were good enough, however, for determining the coordinates of a single Os atom in the corresponding derivative using difference and anomalous fourier maps. The heavy atom binds on the cryallographic three-fold axis (0.333, 0.667, 0.047). MAD phases were then generated with the program MLPHARE (Table 2) and extended to higher resolution with the program DM. The quality of MAD electron density map at 1.5 Å resolution was exceptional, and revealed structural details of IQN17 and D10pep1 peptide with clarity. Electron density map interpretation and model building was done with the program O (Jones, T. A. et al. (1991) *Acta Crystallogr.* D47, 110-119). The structure of IQN17-D10pep1 complex was refined using the program CNS (Brünger, A. T. et al., *Acta Crystallogr.* D54, 905-921 (1998)). The correctness of the structure was checked with simulated annealing omit maps and with the program WHAT CHECK (Hoff, R. W W. et al., *Nature* 381: 272 (1996)). All residues of IQN17 and the D10pep1 peptide (when converted into its mirror image) occupy most preferred areas of the Ramachandran plot. The conformations of the majority of the residues are well defined except for the two most N-terminal residues of IQN17 and the side chains of Arg-6 and Arg-8 of the D10pep1 peptide.

The structure of ligand-free IQN17 was solved by molecular replacement using the program AMORE (Navaza, J. (1994) *Acta Crystallogr.* A50, 157-163) and the IQN17 part of the refined IQN17/D10pep1 structure as a test model. Threefold noncrystallographic averaging, solvent flattening and histogram matching with the program DM was used for phase improvement. Electron density map interpretation and model building was done with the program O (Jones et al., *Acta Crystallogr.* D54, 905-921 (1991). The structure of the IQN17/D10pep1 complex was refined using the program CNS (Brunger, A. T. et al., *Acta Crystallogr.* D54, 905-921 (1998)).

The crystal structure can be used to design more effective and/or new D-peptides, peptidomemetics or other small molecules that inhibit HIV infectivity.

Example 6

Nuclear Magnetic Resonance (NMR) Methods for Identifying Compounds Which Bind to the N-Helix Hydrophobic Pocket of gp41

A. Assaying Specific Binding Between the IQN17 Hydrophobic Pocket and D-Peptides NMR experiments were used to assay the binding of each D-peptide to IQN17. The single tryptophan residue of IQN17 (denoted Trp-571) provides an excellent probe of specific binding to the hydrophobic pocket of gp41. In deuterium oxide (deuterated water) buffers, the simple homonuclear one-dimensional ¹H NMR spectrum of IQN17 (FIG. 9A, middle) shows five signals from the Trp-571 indole, extremely well-resolved from all other signals in the molecule. To test a compound for binding to the gp41 pocket, two one-dimensional ¹H NMR measurements were made on samples in deuterated buffers. First, a reference (control) spectrum of IQN17 was taken, identifying the Trp571 chemical shifts in the unbound form. A second spectrum was acquired on a sample containing both IQN17 and the compound in question. An optional third spectrum of the D-peptide (or other small molecule, or mix of molecules) was also taken. ¹H NMR experiments were performed on a Bruker AMX 500 spectrometer. Data was processed in Felix 98.0 (MSI) on Silicon Graphics computers, and all spectra were referenced to DSS. All experiments were performed at 25° C. in 100 mM NaCl, 50 mM sodium phosphate (pH 7.5). All buffers used were >99.7% D₂O, to remove overlapping resonances from exchangeable backbone and side chain protons. Solute concentrations ranged from 0.3-1.0 mM for individual peptides, 0.8-1.0 mM for 1:1 commmplexes of IQN17 with each D-peptide.

Figure 9A:
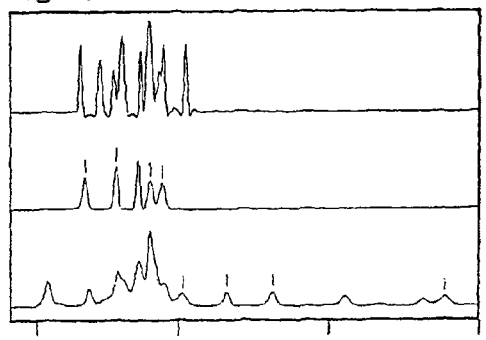
Figure 9B:
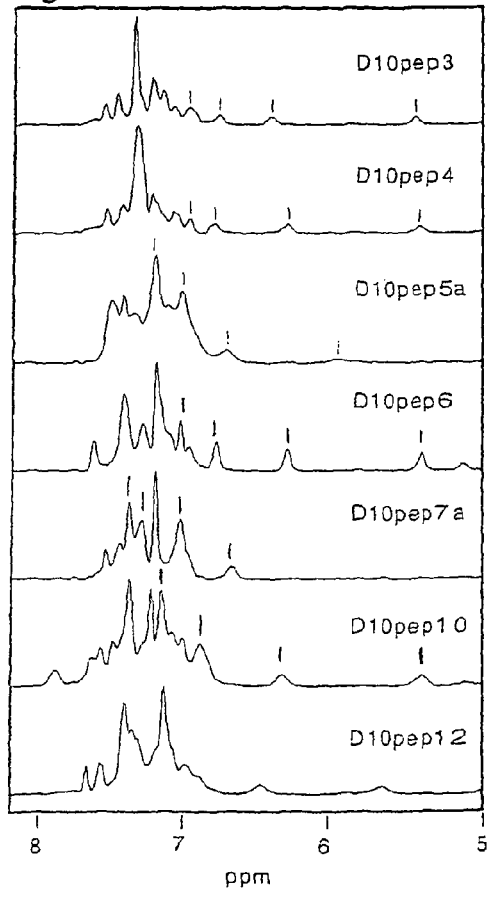

Simple binding of two or more components is expected to result both in broader peaks (due to the increased size of the complex) and in changes in chemical shifts (due to the different chemical environments experienced by nuclei in free and bound forms). Specific binding to the hydrophobic pocket is indicated by a change in the Trp-571 chemical shifts, as well as by a broadening of peaks. Binding can also be indicated by similar changes in the chemical shifts and peak widths of the molecule (peptides and small organic molecules, for example) assayed. FIG. 9A shows an example of these effects: the NMR spectrum of the IQN17/D10pep1a complex displays broader peaks and dramatically different chemical shifts than the spectra for either of the two separate components. All IQN17/D-peptide complexes studied gave similar results, though varying in the degree of chemical shift dispersion (FIG. 9B). Thus, binding was indicated in all cases.

The x-ray crystallographic finding that the two conserved Trp residues, and the conserved Leu residue, in D10pep1 are directly involved in the binding of the IQN17 pocket, strongly suggests that these conserved residues participate in a similar manner when the other D-peptides bind the pocket. These conserved trypophan residues, and Trp-571 of IQN17, provide an opportunity to study the binding interfaces in greater detail. In the IQN17/D10pep1 crystal structure, the Trp-571 sidechain of IQN17 is in close contact with Trp-10 of D10pep1, with several protons of Trp-571 ($H_{\zeta 2}$, $H_{\eta 2}$, $H_{\zeta 3}$, $H_{\epsilon 3}$; the four scalar-coupled protons of the aromatic ring) above the plane of the Trp-10 indole group. In this position, aromatic ring current interactions (F. A. Bovey, *Nuclear Magnetic Resonance Spectroscopy* (1988)) are expected to alter the chemical shifts of some of those protons, moving peaks upfield in the manner seen (FIG. 9A, bottom). Use of the structure-based chemical shift prediction program SHIFTS (version 3.0b2, K. Osapay, D. Sitkoff, D. Case) also predicted that only protons from Trp-571 will experience a large upfield shift, expecially the $H_{\zeta 3}$ proton. If the other D-peptides bind to the IQN17 pocket in the same fashion as D10pep1, a similar juxtaposition of Trp-571 and Trp-10 should occur, resulting in upfield-shifted peaks. All of the D-peptide/ IQN17 complexes studied displayed such peaks, though varying in the extent of the shift (FIG. 9B). The D10pep1 complex showed the most extreme upfield shifts, and the D10pep7a complex the least. The magnitude of these changes is very large, ranging from roughly 0.5 to 2 ppm for the most upfield-shifted proton ($H_{\zeta 3}$, in all cases where it could be assigned). In comparison, chemical shift differences often used to detect binding in SAR by NMR experiments (Shuker, S. B., Hajduk, P. J., Meadows, R. P., Fesik, S. W., *Science* 274:1531-1534 (1996)) are frequently in the range of 0.05 to 0.2 ppm.) Though a broad range of upfield chemical shifts was observed, ring-current effects can be highly sensitive to distance and orientation, so that small structural differences may give rise to substantial variations in chemical shift. (All of the upfield shifts observed are consistent with the approximate orientation of Trp side chains expected from the x-ray crystal structure.) Also, the upfield-shifted peaks are somewhat broadened compared to others in these NMR spectra (most likely due to some type of exchange process) an effect particularly pronounced for the complexes with D10pep5a and with D10pep7a.

Figure 9C:
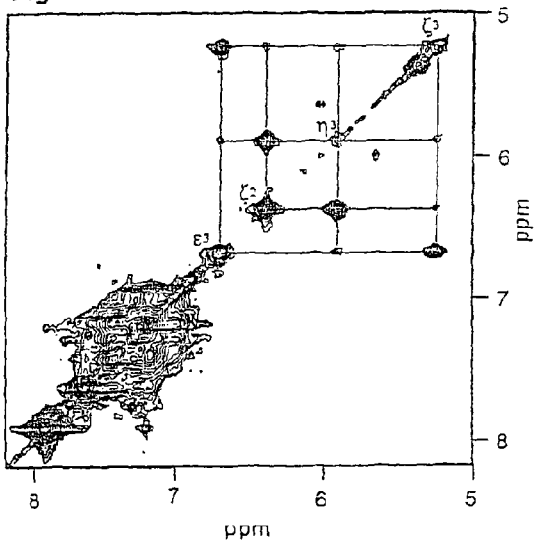

To confirm that the strongly upfield-shifted peaks all correspond to a single sidechain (almost certainly Trp-571), two-dimensional NMR (TOCSY) experiments were performed on each of the IQN17/D-peptide complexes. As expected, the TOCSY experiments indicate that in each complex, the strongly upfield-shifted resonances all belong to the same aromatic side chain, identified as a group of four scalar-coupled protons. One example TOCSY spectrum is shown in FIG. 9C. For several of the complexes studied, NOESY experiments also indicate contact between this sidechain and other (unassigned) aromatic groups, as expected from the IQN17/D10pep1 structure. Not all of the potential NOE crosspeaks could be resolved, due to intense spectral overlap in the 6.8-7.6 ppm region. 2D NOESY and TOCSY experiments as described in J. Cavanaugh, W. J. Fairbrother, A. G. Palmer, N. J. Skelton, *Protein NMR Spectroscopy: Principles and Practice* (1996) were performed on samples of IQN17 and of each complex, with mixing times ranging between 30-90 ms (NOESY) and 30-70 ms (TOCSY). Spectral widths of 11,111 Hz and 5555 Hz were used in the acquisition ($t_2$) and indirect ($t_1$) dimensions, respectively. TOCSY experiments employed the DIPSI-2rc mixing sequence (J. Cavanaugh, M. Rance, *J. Magn. Reson. Serv. A.*, 105:328 (1993)).

We conclude that all D-peptides assayed clearly bind the hydrophobic pocket of IQN17. Additionally, in the majority of these IQN17 complexes (i.e., D10pep1, D10pep3, D10pep4, D10pep6, D10pep10, and D10pep12) the D-peptides contact the pocket with very similar binding interfaces, bringing Trp-571 in close contact with the aromatic ring of Trp-10. In the cases of complexes with D10pep5a and D10pep7a this conclusion also seems very likely, although the more limited chemical shift dispersion and broader peaks raise a remote possibility of some other mode of binding.

The binding assay employed here can also be employed to assay binding of other molecules to the hydrophobic pocket of gp41 (e.g., such as found in IQN17). The assay is especially easy to interpret in a case where an aromatic group binds the pocket, as with the set of D-peptides described above. However, any pocket-binding molecules should also perturb the chemical shifts of Trp-571, an easily noticeable effect. In addition, new NMR signals generated by the small molecules themselves upon binding, are also indicative of binding.

The use of one-dimensional homonuclear $^1H$ NMR provides significant advantages over multidimensional heteronuclear NMR to determine specific binding: (1) Sensitivity is higher, allowing samples to be assayed more quickly; alternately the higher sensitivity makes possible the use of lower concentrations of IQN17 and of putative binding agents, allowing screening for higher-affinity compounds, and more of them simultaneously. (2) Non-isotopically labeled proteins are simpler to produce, and more cost-effective. However, two-dimensional NMR experiments, either homonuclear or heteronuclear (with $^{15}N$ and/or $^{13}C$ isotopic labeling) could also be employed.

B. Screening Chemical Libraries

The binding assay described in (A) above can be used to screen large numbers of compounds present in a chemical library. Simple one-dimensional homonuclear $^1H$ NMR experiments are sufficient to assess binding, with no requirement for isotopic labeling. Two-dimensional NMR experiments, either homonuclear or heteronuclear (with $^{15}N$ and/or $^{13}C$ isotopic labeling) could also be employed. Single compounds can be screened one at a time in this process. However, multiple compounds can also be combined in the same assay with IQN17 (or any representation of the gp41 N-helix coiled coil) and screened simultaneously. Binding to the pocket by any component of the mixture is indicated by a change in the Trp-571 chemical shifts. NMR signals from a large number of compounds together have the potential to obscure signals from Trp-571; these signals from unbound molecules can be eliminated using pulsed field gradient techniques well known in the art. With use of these techniques and a commercially available NMR tube sample changer, the automated screening of large numbers of compounds is straightforward.

C. Evaluating the Products of Multiple Combinatorial Syntheses

The screening process described in (B) above can also be extended to take advantage of combinatorial organic synthetic methods. Such methods are currently being used to generate whole families of compounds, with each family containing a diverse number of chemically related compounds. By the simple assay described above, the products of an entire combinatorial synthesis can be screened simultaneously. If no binding is indicated, then there is no need to invest further attention in any member of that family of compounds. If binding is indicated, then a particular family of promising compounds can be targeted for more detailed investigation. Simple one-dimensional homonuclear $^1H$ NMR experiments are sufficient to assess binding, with no requirement for isotopic labeling. Two-dimensional NMR experiments, either homonuclear or heteronuclear (with $^{15}N$ and/or $^{13}C$ isotopic labeling) could also be employed.

TABLE 2

| Data collection | | | | |
|---|---|---|---|---|
| Crystal | λ (Å) | Completeness (%) | $R_{sym}^1$ (%) | Resolution (Å) |
| IQN17 | 1.0000 | 89.5 | 3.7 | 2.1 |
| IQN17/D10 | 1.1197 | 93.8 | 4.8 | 1.5 |
| Os λ1 | 1.1403 | 98.6 | 6.3 | 2.0 |
| Os λ2 | 1.1399 | 96.8 | 9.7 | 2.0 |
| Os λ3 | 1.1393 | 96.9 | 7.9 | 2.0 |
| Os λ4 | 1.1197 | 97.0 | 8.4 | 2.0 |

| MAD phasing statistics (22.0-2.0 Å) | | | | | | | | |
|---|---|---|---|---|---|---|---|---|
| Derivative | $R_{iso}^2$ (%) | $R_{cullis}^3$ Acentric | $R_{cullis}^3$ Centric | $R_{cullis}^3$ Anom. | Ph. Power$^4$ Acentric | Ph. Power$^4$ Centric | Occ.$^5$ | Anom. Occ.$^5$ |
| Os λ1 vs. λ4 | 7.3 | 0.75 | 0.61 | 0.47 | 1.41 | 1.21 | −0.039 | 0.337 |
| Os λ2 vs. λ4 | 5.2 | 0.83 | 0.71 | 0.44 | 1.04 | 1.15 | −0.027 | 0.533 |
| Os λ3 vs. λ4 | 3.3 | 0.97 | 0.97 | 0.49 | 0.35 | 0.28 | −0.005 | 0.295 |

| Refinement statistics | | | | | | | | | |
|---|---|---|---|---|---|---|---|---|---|
| Crystal | Non-hydrogen protein atoms | Waters | Ions | Resolution (Å) | Reflections total | $R_{cryst}^6$ | $R_{free}^6$ | R.m.s. deviations bonds (Å) | angles (°) |
| IQN17/D10 | 516 | 150 | 1 | 10.0-1.5 | 13549 | 0.214 | 0.245 | 0.012 | 1.498 |
| IQN17 | 1143 | 160 | 1 | 5.0-2.5 | 7541 | 0.282 | 0.352 | 0.009 | 1.252 |

Overall figure of merit (before solvent flattening): 0.68

$^1R_{sym} = \Sigma\Sigma_j ||_j − <i>| / \Sigma\Sigma_j|<i>|$, where $l_j$ is the recorded intensity of the reflection j and <i> is the mean recorded intensity over multiple recordings.
$^2R_{iso} = \rho||F_{(\lambda,i)} − f_{(\lambda 4)}| − |F_{(\lambda,i)}|| / \Sigma|F_{(\lambda 4)}|$, where $F_{(\lambda,i)}$ is the structure factor at wavelength λi and $F_{(\lambda 4)}$ is the structure factor at the reference wavelength λ4.
$^3R_{cullis} = \Sigma||F_{(\lambda,i)} − F_{(\lambda 4)}| − |F_{h(\lambda,i),c}||/\Sigma|F_{(\lambda,i)} \pm F_{(\lambda 4)}|$, where $F_{h(\lambda,i),c}$ is the calculated heavy atom structure factor.
$^4$Phase power = $<F_{h(\lambda,i)}>/E$, where $<F_{h(\lambda,i)}>$ is the root-mean-square heavy atom structure factor and E is the residual lack of closure error.
$^5$Occupancies are values output from MLPHARE.
$^6R_{cryst,free} = \Sigma||F_{obs}| − |F_{calc}||/|F_{obs}|$, where the crystallographic and free R factors are calculated using the working and test sets, respectively. Test set contained 10% of reflections.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated soluble, non-aggregating trimeric peptide that presents the hydrophobic pocket of HIV gp41 in such a manner that it is available for binding by ligand, the peptide comprising a soluble, trimeric form of a coiled-coil and an amino acid sequence comprising: LLXLTVWGXKX-LQXRXX (SEQ ID NO: 42), which forms the pocket of the N-helix coiled-coil of HIV gp41, wherein L, T, V, W, G, K, Q and R are amino acid residues represented by the single letter amino acid code and X is any amino acid residue.

2. The peptide of claim 1 wherein the peptide is a D-peptide.

3. The D-peptide of claim 2 wherein the coiled coil is selected from the group consisting of:

(a) the coiled coil of GCN4-pI$_Q$I;

(b) the coiled coil of GCN4-pII;

(c) the coiled coil of Moloney Murine Leukemia Virus; and
(d) the coiled coil of ABC heterotrimer.

4. The peptide of claim 1 wherein the peptide is an L-peptide.

5. The L-peptide of claim 4 wherein the soluble, trimeric coiled-coil is selected from the group consisting of:
(a) the coiled coil of GCN4-pI$_Q$I;
(b) the coiled coil of GCN4-pII;
(c) the coiled coil of Moloney Murine Leukemia Virus; and
(d) the coiled coil of ABC heterotrimer.

6. The peptide of claim 1, wherein the amino acid sequence of the coiled-coil comprises: RMKQIEDKIEEIESKQKKIENEIARIKK (SEQ ID NO: 25).

7. The peptide of claim 1, wherein the amino acid sequence that forms the pocket of the N-helix coiled-coil of HIV gp41 is selected from the group consisting of SEQ ID NO: 13, SEQ ID NO: 20, SEQ ID NO: 26 and SEQ ID NO: 27.

8. An isolated fusion protein that presents the hydrophobic pocket of HIV gp41 in such a manner that it is available for binding by ligand, the fusion protein comprising a soluble trimeric coiled-coil and a portion of the N-peptide region of HIV gp41, wherein the portion comprises the amino acid sequence:
SGIVQQQNNLLRAIEAQQHLLQLTVWGIKQLQARIL (SEQ ID NO: 13).

9. The fusion protein of claim 8, wherein the coiled-coil is a coiled-coil region of GCN4, a yeast transcriptional activator.

10. An isolated fusion protein comprising a soluble, non-aggregating trimeric peptide that presents the hydrophobic pocket of HIV gp41 in such a manner that it is available for binding by ligand, the fusion protein comprising a soluble, trimeric form of a coiled-coil and an amino acid sequence comprising:
LLXLTVWGXKXLQXRXX (SEQ ID NO: 42), which forms the pocket of the N-helix coiled-coil of HIV gp41, wherein L, T, V, W, G, K, Q and R are amino acid residues represented by the single letter amino acid code and X is any amino acid residue.

11. The fusion protein of claim 10, wherein the amino acid sequence that forms the pocket of the N-helix coiled-coil of HIV gp41 is selected from the group consisting of SEQ ID NO: 13, SEQ ID NO: 20, SEQ ID NO: 26 and SEQ ID NO: 27.

12. The fusion protein of claim 10, wherein the amino acid sequence of the coiled-coil comprises: RMKQIEDKIEEIESKQKKIENEIARIKK (SEQ ID NO: 25).

* * * * *

```
                        SEQUENCE LISTING

<160> NUMBER OF SEQ ID NOS: 71

<210> SEQ ID NO 1
<211> LENGTH: 33
<212> TYPE: PRT
<213> ORGANISM: Artificial Sequence
<220> FEATURE:
<223> OTHER INFORMATION: GCN4-PIQI
<220> FEATURE:
<221> NAME/KEY: ACETYLATION
<222> LOCATION: 1

<400> SEQUENCE: 1

Arg Met Lys Gln Ile Glu Asp Lys Ile Glu Glu Ile Leu Ser Lys Gln
1               5                   10                  15

Tyr His Ile Glu Asn Glu Ile Ala Arg Ile Lys Lys Leu Ile Gly Glu
            20                  25                  30

Arg

<210> SEQ ID NO 2
<211> LENGTH: 45
<212> TYPE: PRT
<213> ORGANISM: Artificial Sequence
<220> FEATURE:
<223> OTHER INFORMATION: IQN17
<220> FEATURE:
<221> NAME/KEY: ACETYLATION
<222> LOCATION: 1
```

```
<220> FEATURE:
<221> NAME/KEY: AMIDATION
<222> LOCATION: 45

<400> SEQUENCE: 2

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Leu Leu Gln Leu
            20                  25                  30

Thr Val Trp Gly Ile Lys Gln Leu Gln Ala Arg Ile Leu
            35                  40              45

<210> SEQ ID NO 3
<211> LENGTH: 12
<212> TYPE: PRT
<213> ORGANISM: Artificial Sequence
<220> FEATURE:
<223> OTHER INFORMATION: D-peptide

<400> SEQUENCE: 3

Cys Asp Leu Lys Ala Lys Glu Trp Phe Trp Leu Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: D-peptide

<400> SEQUENCE: 4

Cys Glu Ala Arg His Arg Glu Trp Ala Trp Leu Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: D-peptide

<400> SEQUENCE: 5

Cys Glu Leu Leu Gly Trp Glu Trp Ala Trp Leu Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: D-peptide

<400> SEQUENCE: 6

Cys Leu Leu Arg Ala Pro Glu Trp Gly Trp Leu Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: D-peptide

<400> SEQUENCE: 7

Cys Ser Arg Ser Gln Pro Glu Trp Glu Trp Leu Cys
1               5                   10
```

```
<210> SEQ ID NO 8
<211> LENGTH: 12
<212> TYPE: PRT
<213> ORGANISM: Artificial Sequence
<220> FEATURE:
<223> OTHER INFORMATION: D-peptide

<400> SEQUENCE: 8

Cys Gly Leu Gly Gln Glu Glu Trp Phe Trp Leu Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: D-peptide

<400> SEQUENCE: 9

Cys Met Arg Gly Glu Trp Glu Trp Ser Trp Leu Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: D-peptide

<400> SEQUENCE: 10

Cys Pro Pro Leu Asn Lys Glu Trp Ala Trp Leu Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: D-peptide

<400> SEQUENCE: 11

Cys Val Leu Lys Ala Lys Glu Trp Phe Trp Leu Cys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 2, 3, 4, 5, 6, 9
<223> OTHER INFORMATION: Xaa = Any Amino Acid

<400> SEQUENCE: 12

Cys Xaa Xaa Xaa Xaa Xaa Glu Trp Xaa Trp Leu
1               5                   10

<210> SEQ ID NO 13
<211> LENGTH: 36
<212> TYPE: PRT
<213> ORGANISM: Artificial Sequence
<220> FEATURE:
<223> OTHER INFORMATION: N36

<400> SEQUENCE: 13

Ser Gly Ile Val Gln Gln Gln Asn Asn Leu Leu Arg Ala Ile Glu Ala
```

-continued

```
                1               5                  10                  15
Gln Gln His Leu Leu Gln Leu Thr Val Trp Gly Ile Lys Gln Leu Gln
                        20                  25                  30

Ala Arg Ile Leu
            35

<210> SEQ ID NO 14
<211> LENGTH: 34
<212> TYPE: PRT
<213> ORGANISM: Artificial Sequence
<220> FEATURE:
<223> OTHER INFORMATION: C34

<400> SEQUENCE: 14

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
                20                  25                  30

Leu Leu

<210> SEQ ID NO 15
<211> LENGTH: 16
<212> TYPE: PRT
<213> ORGANISM: Artificial Sequence
<220> FEATURE:
<223> OTHER INFORMATION: D-peptide

<400> SEQUENCE: 15

Lys Lys Gly Ala Cys Gly Leu Gly Gln Glu Glu Trp Phe Trp Leu Cys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: D-peptide

<400> SEQUENCE: 16

Lys Lys Gly Ala Cys Glu Leu Leu Gly Trp Glu Trp Ala Trp Leu Cys
1               5                   10                  15

<210> SEQ ID NO 17
<211> LENGTH: 18
<212> TYPE: PRT
<213> ORGANISM: Artificial Sequence
<220> FEATURE:
<223> OTHER INFORMATION: D-peptide

<400> SEQUENCE: 17

Lys Lys Lys Lys Gly Ala Cys Glu Leu Leu Gly Trp Glu Trp Ala Trp
1               5                   10                  15

Leu Cys

<210> SEQ ID NO 18
<211> LENGTH: 16
<212> TYPE: PRT
<213> ORGANISM: Artificial Sequence
<220> FEATURE:
<223> OTHER INFORMATION: D-peptide

<400> SEQUENCE: 18

Lys Lys Gly Ala Cys Met Arg Gly Glu Trp Glu Trp Ser Trp Leu Cys
1               5                   10                  15
```

```
<210> SEQ ID NO 19
<211> LENGTH: 18
<212> TYPE: PRT
<213> ORGANISM: Artificial Sequence
<220> FEATURE:
<223> OTHER INFORMATION: D-peptide

<400> SEQUENCE: 19

Lys Lys Gly Ala Cys Pro Pro Leu Asn Lys Glu Trp Ala Trp Leu Cys
1               5                   10                  15

Ala Ala

<210> SEQ ID NO 20
<211> LENGTH: 17
<212> TYPE: PRT
<213> ORGANISM: Artificial Sequence
<220> FEATURE:
<223> OTHER INFORMATION: portion of N-peptide region of HIV gp41

<400> SEQUENCE: 20

Leu Leu Gln Leu Thr Val Trp Gly Ile Lys Gln Leu Gln Ala Arg Ile
1               5                   10                  15

Leu

<210> SEQ ID NO 21
<211> LENGTH: 24
<212> TYPE: PRT
<213> ORGANISM: Artificial Sequence
<220> FEATURE:
<223> OTHER INFORMATION: 24 Resides from the N- Terminal of N26

<400> SEQUENCE: 21

Ser Gly Ile Val Gln Gln Gln Asn Asn Leu Leu Arg Ala Ile Glu Ala
1               5                   10                  15

Gln Gln His Leu Leu Gln Leu Thr
            20

<210> SEQ ID NO 22
<211> LENGTH: 55
<212> TYPE: PRT
<213> ORGANISM: Artificial Sequence
<220> FEATURE:
<223> OTHER INFORMATION: IQN24n

<400> SEQUENCE: 22

Met Arg Met Lys Gln Ile Glu Asp Lys Ile Glu Glu Ile Glu Ser Lys
1               5                   10                  15

Gln Lys Lys Ile Glu Asn Glu Ile Ala Arg Ile Lys Lys Leu Ile Ser
            20                  25                  30

Gly Ile Val Gln Gln Gln Asn Asn Leu Leu Arg Ala Ile Glu Ala Gln
        35                  40                  45

Gln His Leu Leu Gln Leu Thr
    50                  55

<210> SEQ ID NO 23
<211> LENGTH: 4
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 2
<223> OTHER INFORMATION: Xaa = Any Amino Acid
```

-continued

```
<400> SEQUENCE: 23

Trp Xaa Trp Leu
1

<210> SEQ ID NO 24
<211> LENGTH: 5
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 3
<223> OTHER INFORMATION: Xaa = Any Amino Acid

<400> SEQUENCE: 24

Glu Trp Xaa Trp Leu
1               5

<210> SEQ ID NO 25
<211> LENGTH: 28
<212> TYPE: PRT
<213> ORGANISM: Artificial Sequence
<220> FEATURE:
<223> OTHER INFORMATION: Soluble, Trimerica Coiled Coil Region of GCN4

<400> SEQUENCE: 25

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys
            20                  25

<210> SEQ ID NO 26
<211> LENGTH: 17
<212> TYPE: PRT
<213> ORGANISM: Artificial Sequence
<220> FEATURE:
<223> OTHER INFORMATION: portion of HIV-2 Sequence

<400> SEQUENCE: 26

Leu Leu Arg Leu Thr Val Trp Gly Thr Lys Asn Leu Gln Ala Arg Val
1               5                   10                  15

Thr

<210> SEQ ID NO 27
<211> LENGTH: 17
<212> TYPE: PRT
<213> ORGANISM: Artificial Sequence
<220> FEATURE:
<223> OTHER INFORMATION: portion of SIV Sequence

<400> SEQUENCE: 27

Leu Leu Arg Leu Thr Val Trp Gly Thr Lys Asn Leu Gln Thr Arg Val
1               5                   10                  15

Thr

<210> SEQ ID NO 28
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 1, 2, 4, 5, 6, 7, 8, 11, 15, 16
<223> OTHER INFORMATION: Xaa = Any Amino Acid
<220> FEATURE:
```

```
<221> NAME/KEY: ACETYLATION
<222> LOCATION: 1
<220> FEATURE:
<221> NAME/KEY: AMIDATION
<222> LOCATION: 16

<400> SEQUENCE: 28

Xaa Xaa Cys Xaa Xaa Xaa Xaa Xaa Glu Trp Xaa Trp Leu Cys Xaa Xaa
1               5                   10                  15

<210> SEQ ID NO 29
<211> LENGTH: 18
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 3, 4, 6, 7, 8, 9, 10, 13, 17, 18
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 29

Lys Lys Xaa Xaa Cys Xaa Xaa Xaa Xaa Xaa Glu Trp Xaa Trp Leu Cys
1               5                   10                  15

Xaa Xaa

<210> SEQ ID NO 30
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 5, 6, 8, 9, 10, 11, 12, 15, 19, 20
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 30

Lys Lys Lys Lys Xaa Xaa Cys Xaa Xaa Xaa Xaa Xaa Glu Trp Xaa Trp
1               5                   10                  15

Leu Cys Xaa Xaa
            20

<210> SEQ ID NO 31
<211> LENGTH: 17
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 1, 2, 4, 5, 6, 7, 8, 11, 15, 16, 17
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 17
```

-continued

```
<400> SEQUENCE: 31

Xaa Xaa Cys Xaa Xaa Xaa Xaa Xaa Glu Trp Xaa Trp Leu Cys Xaa Xaa
1               5                   10                  15

Xaa

<210> SEQ ID NO 32
<211> LENGTH: 19
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 3, 4, 6, 7, 8, 9, 10, 13, 17, 18, 19
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 19

<400> SEQUENCE: 32

Lys Lys Xaa Xaa Cys Xaa Xaa Xaa Xaa Xaa Glu Trp Xaa Trp Leu Cys
1               5                   10                  15

Xaa Xaa Xaa

<210> SEQ ID NO 33
<211> LENGTH: 21
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 5, 6, 8, 9, 10, 11, 12, 15, 19, 20, 21
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 21

<400> SEQUENCE: 33

Lys Lys Lys Lys Xaa Xaa Cys Xaa Xaa Xaa Xaa Xaa Glu Trp Xaa Trp
1               5                   10                  15

Leu Cys Xaa Xaa Xaa
            20

<210> SEQ ID NO 34
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 34

Gly Ala Cys Glu Ala Arg His Arg Glu Trp Ala Trp Leu Cys Ala Ala
1               5                   10                  15

<210> SEQ ID NO 35
<211> LENGTH: 16
```

```
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 35

Gly Ala Cys Asp Leu Lys Ala Lys Glu Trp Phe Trp Leu Cys Ala Ala
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 36

Gly Ala Cys Ser Arg Ser Gln Pro Glu Trp Glu Trp Leu Cys Ala Ala
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 37

Gly Ala Cys Leu Leu Arg Ala Pro Glu Trp Gly Trp Leu Cys Ala Ala
1               5                   10                  15

<210> SEQ ID NO 38
<211> LENGTH: 18
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 38

Lys Lys Gly Ala Cys Glu Ala Arg His Arg Glu Trp Ala Trp Leu Cys
1               5                   10                  15

Ala Ala

<210> SEQ ID NO 39
<211> LENGTH: 18
<212> TYPE: PRT
<213> ORGANISM: Artificial Sequence
```

```
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 39

Lys Lys Gly Ala Cys Asp Leu Lys Ala Lys Glu Trp Phe Trp Leu Cys
1               5                   10                  15

Ala Ala

<210> SEQ ID NO 40
<211> LENGTH: 18
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 40

Lys Lys Gly Ala Cys Ser Arg Ser Gln Pro Glu Trp Glu Trp Leu Cys
1               5                   10                  15

Ala Ala

<210> SEQ ID NO 41
<211> LENGTH: 18
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 41

Lys Lys Gly Ala Cys Leu Leu Arg Ala Pro Glu Trp Gly Trp Leu Cys
1               5                   10                  15

Ala Ala

<210> SEQ ID NO 42
<211> LENGTH: 17
<212> TYPE: PRT
<213> ORGANISM: Artificial Sequence
<220> FEATURE:
<223> OTHER INFORMATION: Invariant Residues in HIV-1, HIV-2 and SIV
<220> FEATURE:
<221> NAME/KEY: VARIANT
<222> LOCATION: (0)...(0)
<220> FEATURE:
<221> NAME/KEY: VARIANT
<222> LOCATION: 3, 9, 11, 14, 16, 17
<223> OTHER INFORMATION: Xaa = Any Amino Acid

<400> SEQUENCE: 42

Leu Leu Xaa Leu Thr Val Trp Gly Xaa Lys Xaa Leu Gln Xaa Arg Xaa
1               5                   10                  15

Xaa
```

```
<210> SEQ ID NO 43
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 43

Lys Lys Lys Lys Gly Ala Cys Glu Ala Arg His Arg Glu Trp Ala Trp
1               5                   10                  15

Leu Cys Ala Ala
            20

<210> SEQ ID NO 44
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 44

Gly Ala Cys Gly Leu Gly Gln Glu Glu Trp Phe Trp Leu Cys Ala Ala
1               5                   10                  15

<210> SEQ ID NO 45
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 45

Lys Lys Lys Lys Gly Ala Cys Gly Leu Gly Gln Glu Glu Trp Phe Trp
1               5                   10                  15

Leu Cys Ala Ala
            20

<210> SEQ ID NO 46
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 46

Lys Lys Lys Lys Gly Ala Cys Asp Leu Lys Ala Lys Glu Trp Phe Trp
```

```
1               5                   10                  15
Leu Cys Ala Ala
            20

<210> SEQ ID NO 47
<211> LENGTH: 15
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 15

<400> SEQUENCE: 47

Gly Ala Cys Glu Leu Leu Gly Trp Glu Trp Ala Trp Leu Cys Cys
1               5                   10                  15

<210> SEQ ID NO 48
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 48

Lys Lys Lys Lys Gly Ala Cys Ser Arg Ser Gln Pro Glu Trp Glu Trp
1               5                   10                  15
Leu Cys Ala Ala
            20

<210> SEQ ID NO 49
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 49

Lys Lys Lys Lys Gly Ala Cys Leu Leu Arg Ala Pro Glu Trp Gly Trp
1               5                   10                  15
Leu Cys Ala Ala
            20

<210> SEQ ID NO 50
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
```

```
<222> LOCATION: 20

<400> SEQUENCE: 50

Gly Ala Cys Met Arg Gly Glu Trp Glu Trp Ser Trp Leu Cys Ala Ala
1               5                   10                  15

<210> SEQ ID NO 51
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 51

Lys Lys Lys Lys Gly Ala Cys Met Arg Gly Glu Trp Glu Trp Ser Trp
1               5                   10                  15

Leu Cys Ala Ala
            20

<210> SEQ ID NO 52
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 16

<400> SEQUENCE: 52

Gly Ala Cys Pro Pro Leu Asn Lys Glu Trp Ala Trp Leu Cys Ala Ala
1               5                   10                  15

<210> SEQ ID NO 53
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 53

Lys Lys Lys Lys Gly Ala Cys Pro Pro Leu Asn Lys Glu Trp Ala Trp
1               5                   10                  15

Leu Cys Ala Ala
            20

<210> SEQ ID NO 54
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 4, 5, 6, 7, 8, 11
```

```
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 54

Gly Ala Cys Xaa Xaa Xaa Xaa Xaa Glu Trp Xaa Trp Leu Cys Ala Ala
1               5                   10                  15

<210> SEQ ID NO 55
<211> LENGTH: 18
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 6, 7, 8, 9, 10, 13
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 55

Lys Lys Gly Ala Cys Xaa Xaa Xaa Xaa Xaa Glu Trp Xaa Trp Leu Cys
1               5                   10                  15

Ala Ala

<210> SEQ ID NO 56
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 8, 9, 10, 11, 12, 15
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 56

Lys Lys Lys Lys Gly Ala Cys Xaa Xaa Xaa Xaa Xaa Glu Trp Xaa Trp
1               5                   10                  15

Leu Cys Ala Ala
            20

<210> SEQ ID NO 57
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 1, 2, 4, 5, 6, 7, 8, 11, 15, 16
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
```

```
<222> LOCATION: 16

<400> SEQUENCE: 57

Xaa Xaa Cys Xaa Xaa Xaa Xaa Xaa Glu Trp Xaa Trp Leu Cys Xaa Xaa
1               5                   10                  15

<210> SEQ ID NO 58
<211> LENGTH: 18
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 3, 4, 6, 7, 8, 9, 10, 13, 18
<223> OTHER INFORMATION: Xaa = Any Amino Acid
<220> FEATURE:
<221> NAME/KEY: ACETYLATION
<222> LOCATION: (0)...(0)
<220> FEATURE:
<221> NAME/KEY: AMIDATION
<222> LOCATION: 18
<220> FEATURE:
<221> NAME/KEY: VARIANT
<222> LOCATION: 3, 4, 6, 7, 8, 9, 10, 13, 17, 18
<223> OTHER INFORMATION: Xaa = Any Amino Acid

<400> SEQUENCE: 58

Lys Lys Xaa Xaa Cys Xaa Xaa Xaa Xaa Xaa Glu Trp Xaa Trp Leu Cys
1               5                   10                  15

Xaa Xaa

<210> SEQ ID NO 59
<211> LENGTH: 20
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 5, 6, 8, 9, 10, 11, 12, 15, 19, 20
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 59

Lys Lys Lys Lys Xaa Xaa Cys Xaa Xaa Xaa Xaa Xaa Glu Trp Xaa Trp
1               5                   10                  15

Leu Cys Xaa Xaa
            20

<210> SEQ ID NO 60
<211> LENGTH: 17
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 1, 2, 4, 5, 6, 7, 8, 11, 15, 16, 17
<220> FEATURE:
<221> NAME/KEY: ACETYLATION
<222> LOCATION: 1
<220> FEATURE:
<221> NAME/KEY: AMIDATION
<222> LOCATION: 17
<220> FEATURE:
<221> NAME/KEY: VARIANT
```

<222> LOCATION: 1, 2, 4, 5, 6, 7, 8, 11, 15, 16, 17
<223> OTHER INFORMATION: Xaa = Any Amino Acid

<400> SEQUENCE: 60

Xaa Xaa Cys Xaa Xaa Xaa Xaa Xaa Glu Trp Xaa Trp Leu Cys Xaa Xaa
1               5                   10                  15

Xaa

<210> SEQ ID NO 61
<211> LENGTH: 19
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 3, 4, 6, 7, 8, 9, 10, 13, 17, 18, 19
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 19

<400> SEQUENCE: 61

Lys Lys Xaa Xaa Cys Xaa Xaa Xaa Xaa Xaa Glu Trp Xaa Trp Leu Cys
1               5                   10                  15

Xaa Xaa Xaa

<210> SEQ ID NO 62
<211> LENGTH: 21
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 5, 6, 8, 9, 10, 11, 12, 15, 19, 20, 21
<223> OTHER INFORMATION: Xaa = Any Amino Acid
<220> FEATURE:
<221> NAME/KEY: ACETYLATION
<222> LOCATION: 1
<220> FEATURE:
<221> NAME/KEY: AMIDATION
<222> LOCATION: 21

<400> SEQUENCE: 62

Lys Lys Lys Lys Xaa Xaa Cys Xaa Xaa Xaa Xaa Xaa Glu Trp Xaa Trp
1               5                   10                  15

Leu Cys Xaa Xaa Xaa
            20

<210> SEQ ID NO 63
<211> LENGTH: 12
<212> TYPE: PRT
<213> ORGANISM: Artificial Sequence
<220> FEATURE:
<223> OTHER INFORMATION: Sequence Pattern in C-Terminal Residues in
      D-peptides
<220> FEATURE:
<221> NAME/KEY: VARIANT
<222> LOCATION: 2, 3, 4, 5, 6, 9
<223> OTHER INFORMATION: Xaa = Any Amino Acid

<400> SEQUENCE: 63

Cys Xaa Xaa Xaa Xaa Xaa Glu Trp Xaa Trp Leu Cys
1               5                   10

```
<210> SEQ ID NO 64
<211> LENGTH: 16
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 64

Lys Lys Gly Ala Cys Gly Leu Gly Gln Glu Glu Trp Phe Trp Leu Cys
1               5                   10                  15

<210> SEQ ID NO 65
<211> LENGTH: 18
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 65

Lys Lys Gly Ala Cys Glu Leu Leu Gly Trp Glu Trp Ala Trp Leu Cys
1               5                   10                  15

Ala Ala

<210> SEQ ID NO 66
<211> LENGTH: 20
<212> TYPE: PRT
<213> ORGANISM: Artificial Sequence
<220> FEATURE:
<223> OTHER INFORMATION: Synethtic

<400> SEQUENCE: 66

Lys Lys Lys Lys Gly Ala Cys Glu Leu Leu Gly Trp Glu Trp Ala Trp
1               5                   10                  15

Leu Cys Ala Ala
            20

<210> SEQ ID NO 67
<211> LENGTH: 18
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 20

<400> SEQUENCE: 67

Lys Lys Gly Ala Cys Met Arg Gly Glu Trp Glu Trp Ser Trp Leu Cys
1               5                   10                  15

Ala Ala

<210> SEQ ID NO 68
<211> LENGTH: 18
<212> TYPE: PRT
```

```
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1
<220> FEATURE:
<221> NAME/KEY: AMIDATION
<222> LOCATION: 18

<400> SEQUENCE: 68

Lys Lys Gly Ala Cys Pro Pro Leu Asn Lys Glu Trp Ala Trp Leu Cys
1               5                   10                  15
Ala Ala

<210> SEQ ID NO 69
<211> LENGTH: 14
<212> TYPE: PRT
<213> ORGANISM: Artificial Sequence
<220> FEATURE:
<223> OTHER INFORMATION: D-peptide
<220> FEATURE:
<221> NAME/KEY: VARIANT
<222> LOCATION: 2, 3, 4, 5, 6, 9
<223> OTHER INFORMATION: Xaa = Any Amino Acid
<220> FEATURE:
<221> NAME/KEY: AMIDATION
<222> LOCATION: 14

<400> SEQUENCE: 69

Cys Xaa Xaa Xaa Xaa Xaa Glu Trp Xaa Trp Leu Cys Ala Ala
1               5                   10

<210> SEQ ID NO 70
<211> LENGTH: 4
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1

<400> SEQUENCE: 70

Lys Lys Gly Ala
1

<210> SEQ ID NO 71
<211> LENGTH: 6
<212> TYPE: PRT
<213> ORGANISM: Artificial Sequence
<220> FEATURE:
<223> OTHER INFORMATION: D-peptide
<220> FEATURE:
<221> NAME/KEY: ACETYLATION
<222> LOCATION: 1

<400> SEQUENCE: 71

Lys Lys Lys Lys Gly Ala
1               5
```